(12) United States Patent
Cha et al.

(10) Patent No.: US 11,459,290 B2
(45) Date of Patent: Oct. 4, 2022

(54) COMPOUND AND ORGANIC LIGHT EMITTING DEVICE USING THE SAME

(71) Applicant: LG CHEM, LTD., Seoul (KR)

(72) Inventors: Yong Bum Cha, Daejeon (KR); Sung Jae Lee, Daejeon (KR); Yeon Hwan Kim, Daejeon (KR); Sang Young Jeon, Daejeon (KR); Su Jin Han, Daejeon (KR)

(73) Assignee: LG CHEM, LTD., Seoul (KR)

( * ) Notice: Subject to any disclaimer, the term of this patent is extended or adjusted under 35 U.S.C. 154(b) by 307 days.

(21) Appl. No.: 16/487,404

(22) PCT Filed: Apr. 11, 2018

(86) PCT No.: PCT/KR2018/004249
§ 371 (c)(1),
(2) Date: Aug. 20, 2019

(87) PCT Pub. No.: WO2018/216903
PCT Pub. Date: Nov. 29, 2018

(65) Prior Publication Data
US 2020/0131112 A1    Apr. 30, 2020

(30) Foreign Application Priority Data

May 22, 2017   (KR) .................. 10-2017-0063091
Jan. 8, 2018   (KR) .................. 10-2018-0002356

(51) Int. Cl.
*C07C 211/54*   (2006.01)
*C07D 209/82*   (2006.01)
(Continued)

(52) U.S. Cl.
CPC .......... *C07C 211/54* (2013.01); *C07D 209/82* (2013.01); *C07D 307/91* (2013.01);
(Continued)

(58) Field of Classification Search
CPC ................. C07C 211/54; C07C 211/58; C07C 211/61; C07C 255/50; C07C 2603/16;
(Continued)

(56) References Cited

U.S. PATENT DOCUMENTS 7,507,485 B2 *  3/2009  Oh .................... C09B 15/00
                                                    313/506
10,158,083 B2   12/2018 Stoessel et al.
(Continued)

FOREIGN PATENT DOCUMENTS

CN    106588674 A    4/2017
CN    106612616 A    5/2017
(Continued)

OTHER PUBLICATIONS

Machine translation for CN 106588674 A (publication date: Apr. 2017). (Year: 2017).*

(Continued)

*Primary Examiner* — Dawn L Garrett
(74) *Attorney, Agent, or Firm* — Dentons US LLP

(57) ABSTRACT

The present disclosure relates to a novel compound represented by Chemical Formula 1 and an organic light emitting device using the same. The compound is used as a material of an organic material layer of the organic light emitting device.

(Continued)

[Chemical Formula 1]

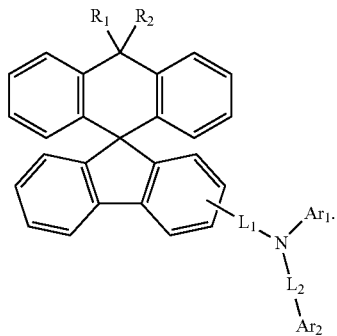

10 Claims, 1 Drawing Sheet

(51) Int. Cl.
  C07D 307/91 (2006.01)
  C07D 333/76 (2006.01)
  C07D 407/12 (2006.01)
  C07D 409/12 (2006.01)
  C07F 7/08 (2006.01)
  H01L 51/00 (2006.01)
  H01L 51/50 (2006.01)

(52) U.S. Cl.
  CPC ......... C07D 333/76 (2013.01); C07D 407/12 (2013.01); C07D 409/12 (2013.01); C07F 7/081 (2013.01); C07F 7/0812 (2013.01); H01L 51/006 (2013.01); H01L 51/0054 (2013.01); H01L 51/0072 (2013.01); H01L 51/0073 (2013.01); H01L 51/0074 (2013.01); H01L 51/0094 (2013.01); H01L 51/5056 (2013.01); H01L 51/5092 (2013.01); H01L 51/5096 (2013.01)

(58) Field of Classification Search
  CPC ............ C07C 2603/66; C07C 2603/86; C07C 2603/90; C07D 209/82; C07D 209/86; C07D 307/91; C07D 333/76; C07D 407/12; C07D 409/12; C07F 7/0805; C07F 7/081; C07F 7/0812; C07F 7/10; C09K 11/06; H01L 51/00; H01L 51/0054; H01L 51/006; H01L 51/0072; H01L 51/0073; H01L 51/0074; H01L 51/0094; H01L 51/50; H01L 51/5056; H01L 51/5092; H01L 51/5096
  See application file for complete search history.

(56) References Cited

U.S. PATENT DOCUMENTS

| 2003/0168970 A1* | 9/2003 | Tominaga ............. C07F 7/0814 556/415 |
| 2015/0295181 A1 | 10/2015 | Mujica-Fernaud et al. |
| 2016/0351817 A1 | 12/2016 | Kim et al. |
| 2021/0147336 A1 | 5/2021 | Sim et al. |

FOREIGN PATENT DOCUMENTS

| CN | 110785401 A | 2/2020 |
| JP | 2009-191232 A | 8/2009 |
| JP | 2017-502007 A | 1/2017 |
| JP | 2020-097525 A | 6/2020 |
| KR | 0169570 B1 | 1/1999 |
| KR | 10-2000-0051826 A | 8/2000 |
| KR | 10-2013-0140303 A | 12/2013 |
| KR | 10-2015-0083917 A | 7/2015 |
| KR | 10-2016-0102949 A | 8/2016 |
| KR | 10-2016-0131887 A | 11/2016 |
| KR | 10-2016-0141361 A | 12/2016 |
| KR | 10-1695270 B1 | 1/2017 |
| KR | 10-2018-0136218 A | 12/2018 |
| TW | I560171 B | 12/2016 |
| WO | 2003/012890 A2 | 2/2003 |
| WO | 2016/182270 A1 | 11/2016 |
| WO | 2018-0164265 A1 | 9/2018 |

OTHER PUBLICATIONS

Chem. Rev. (2007), vol. 107, pp. 1011-1065. (Year: 2007).*
International Search Report from PCT/KR2018/004249, dated Aug. 10, 2018.
Written Opinion of the ISA from PCT/KR2018/004249, dated Aug. 10, 2018.
Notice of Allowance of Japanese Patent Office in Appl'n No. 2019-546159, dated Dec. 1, 2020.
Office Action of Chinese Patent Office in Appl'n No. 201880012821. 3, dated Dec. 8, 2021.

* cited by examiner

[FIG. 1]
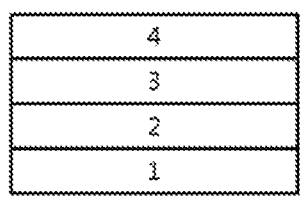
[FIG. 2]
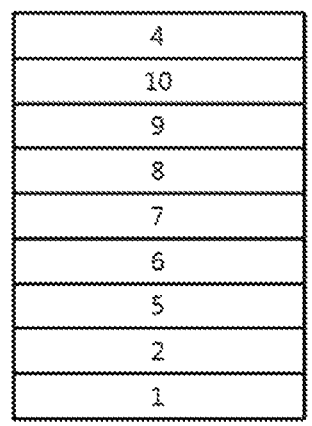

COMPOUND AND ORGANIC LIGHT EMITTING DEVICE USING THE SAME

CROSS-REFERENCE TO RELATED APPLICATION(S)

This application is a National Phase entry pursuant to 35 U.S.C. § 371 of PCT/KR2018/004249 filed on Apr. 11, 2018, and claims the benefit of priority from Korean Patent Application No. 10-2017-0063091 filed on May 22, 2017 and Korean Patent Application No. 10-2018-0002356 filed on Jan. 8, 2018, the full disclosures of which are incorporated herein by reference.

TECHNICAL FIELD

The present disclosure relates to a novel compound and an organic light emitting device comprising the same.

BACKGROUND ART

In general, an organic light emitting phenomenon refers to a phenomenon where electric energy is converted into light energy by using an organic material. The organic light emitting device using the organic light emitting phenomenon has characteristics such as a wide viewing angle, an excellent contrast, a fast response time, an excellent luminance, driving voltage and response speed, and thus many studies have proceeded.

The organic light emitting device generally has a structure which comprises an anode, a cathode, and an organic material layer interposed between the anode and the cathode. The organic material layer frequently have a multilayered structure that comprises different materials in order to enhance efficiency and stability of the organic light emitting device, and for example, the organic material layer may be formed of a hole injection layer, a hole transport layer, a light emitting layer, an electron transport layer, an electron injection layer and the like. In the structure of the organic light emitting device, if a voltage is applied between two electrodes, the holes are injected from an anode into the organic material layer and the electrons are injected from the cathode into the organic material layer, and when the injected holes and the electrons meet each other, an exciton is formed, and light is emitted when the exciton falls to a ground state again.

There is a continuing need for the development of new materials for the organic materials used in such organic light emitting devices.

PRIOR ART LITERATURE

Patent Literature
(Patent Literature 0001) Korean Patent Laid-open Publication No. 10-2000-0051826

DETAILED DESCRIPTION OF THE DISCLOSURE

Technical Problem

It is an object of the present disclosure to provide a novel compound and an organic light emitting device comprising the same.

Technical Solution

In order to achieve the above object, the present disclosure provides a compound represented by the following Chemical Formula 1:

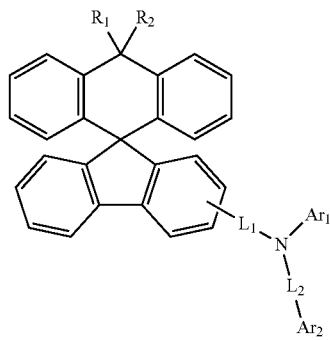

[Chemical Formula 1]

in Chemical Formula 1,
$R_1$ and $R_2$ are each independently methyl, or phenyl,
$L_1$ and $L_2$ are each independently a bond; or substituted or unsubstituted $C_{6-60}$ arylene, and
$Ar_1$ and $Ar_2$ are each independently substituted or unsubstituted $C_{6-60}$ aryl; or $C_{2-60}$ heteroaryl containing O or S.

The present disclosure also provides an organic light emitting device comprising a first electrode; a second electrode provided at a side opposite to the first electrode; and at least one layer of the organic material layers provided between the first electrode and the second electrode, wherein the at least one layer of the organic material layers comprises a compound represented by the Chemical Formula 1.

Advantageous Effects

The compound represented by the Chemical Formula 1 described above can be used as a material of an organic material layer of an organic light emitting device, and can allow improvement of the efficiency, low driving voltage and/or improvement of the lifetime characteristic when applied to the organic light emitting device. In particular, the compound represented by the Chemical Formula 1 can be used as hole injection, hole transport, hole injection and transport, light emission, electron transport, or electron injection materials.

BRIEF DESCRIPTION OF DRAWINGS

FIG. 1 shows an example of an organic light emitting device comprising a substrate 1, an anode 2, an organic material layer 3, and a cathode 4.

FIG. 2 shows an example of an organic light emitting device comprising a substrate 1, an anode 2, a hole injection layer 5, a hole transport layer 6, an electron blocking layer 7, a light emitting layer 8, an electron transport layer 9, an electron injection layer 10, and a cathode 4.

DETAILED DESCRIPTION OF THE EMBODIMENTS

Hereinafter, the present disclosure will be described in more detail in order to aid in understanding the disclosure.

The present disclosure provides a compound represented by the Chemical Formula 1.

In the present specification, ⊹ means a bond connected to another substituent group.

As used herein, the term "substituted or unsubstituted" means that substitution is performed by one or more substituent groups selected from the group consisting of deuterium; a halogen group; a nitrile group; a nitro group; a hydroxyl group; a carbonyl group; an ester group; an imide group; an amino group; a phosphine oxide group; an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl group; an aralkenyl group; an alkylaryl group; an alkylamine group; an aralkylamine group; a heteroarylamine group; an arylamine group; an arylphosphine group; or a heterocyclic group containing at least one of N, O, and S atoms, or there is no substituent group, or substitution is performed by a substituent group where two or more substituent groups of the exemplified substituent groups are linked or there is no substituent group. For example, the term "substituent group where two or more substituent groups are linked" may be a biphenyl group. That is, the biphenyl group may be an aryl group, or may be interpreted as a substituent group where two phenyl groups are linked.

In the present specification, the number of carbon atoms in a carbonyl group is not particularly limited, but is preferably 1 to 40. Specifically, the carbonyl group may be compounds having the following structures, but is not limited thereto.

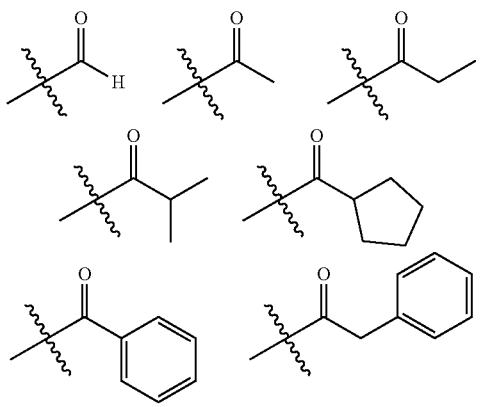

In the present specification, the ester group may have a structure in which oxygen of the ester group may be substituted by a straight-chain, branched-chain, or cyclic alkyl group having 1 to 25 carbon atoms, or an aryl group having 6 to 25 carbon atoms. Specifically, the ester group may be compounds having the following structures, but is not limited thereto.

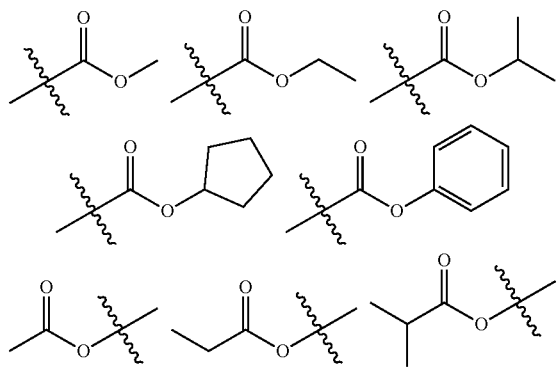

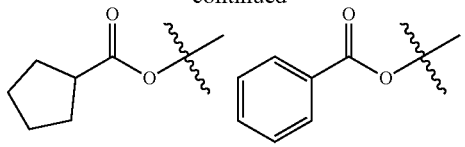

In the present specification, the number of carbon atoms in an imide group is not particularly limited, but is preferably 1 to 25. Specifically, the imide group may be compounds having the following structures, but is not limited thereto.

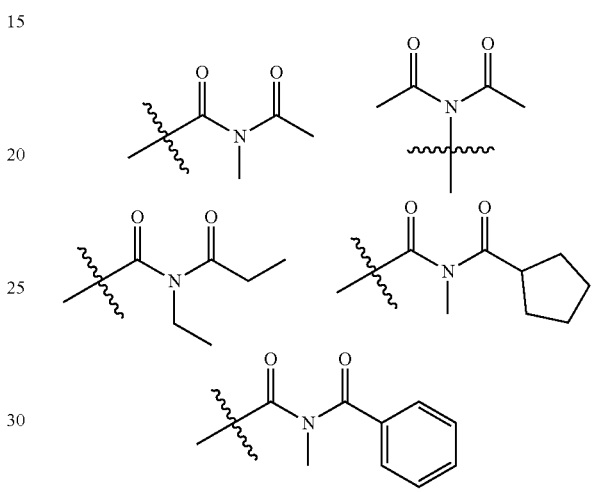

In the present specification, the silyl group specifically includes a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, and the like, but is not limited thereto.

In the present specification, the boron group specifically includes a trimethylboron group, a triethylboron group, a t-butyldimethylboron group, a triphenylboron group, a phenylboron group, and the like, but is not limited thereto.

In the present specification, examples of a halogen group include fluorine, chlorine, bromine, or iodine.

In the present specification, the alkyl group may be a straight chain or a branched chain, and the number of carbon atoms thereof is not particularly limited, but is preferably 1 to 40. According to one embodiment, the alkyl group has 1 to 20 carbon atoms. According to another embodiment, the alkyl group has 1 to 10 carbon atoms. According to still another embodiment, the alkyl group has 1 to 6 carbon atoms. Specific examples of the alkyl group include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethylpropyl, isohexyl, 2-methylpentyl, 4-methylhexyl, 5-methylhexyl, and the like, but are not limited thereto.

In the present specification, the alkenyl group may be a straight chain or a branched chain, and the number of carbon atoms thereof is not particularly limited, but is preferably 2 to 40. According to one embodiment, the alkenyl group has 2 to 20 carbon atoms. According to another embodiment, the alkenyl group has 2 to 10 carbon atoms. According to still another embodiment, the alkenyl group has 2 to 6 carbon atoms. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenyl-vinyl-1-yl, 2-phenyl-2-(naphthyl-1-yl)vinyl-1-yl, 2,2-bis(di-phenyl-1-yl)vinyl-1-yl, a stilbenyl group, a styrenyl group, and the like, but are not limited thereto.

In the present specification, the cycloalkyl group is not particularly limited, but the number of carbon atoms thereof is preferably 3 to 60. According to one embodiment, the cycloalkyl group has 3 to 30 carbon atoms. According to another embodiment, the cycloalkyl group has 3 to 20 carbon atoms. According to another embodiment, the cycloalkyl group has 3 to 6 carbon atoms. Specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcy-clohexyl, 3,4,5-trimethylcyclohexyl, 4-tert-butylcyclohexyl, cycloheptyl, cyclooctyl, and the like, but are not limited thereto.

In the present specification, the aryl group is not particularly limited, but preferably has 6 to 60 carbon atoms, and may be a monocyclic aryl group or a polycyclic aryl group. According to one embodiment, the aryl group has 6 to 30 carbon atoms. According to one embodiment, the aryl group has 6 to 20 carbon atoms. The aryl group may be a phenyl group, a biphenyl group, a terphenyl group or the like as the monocyclic aryl group, but is not limited thereto. Examples of the polycyclic aryl group include a naphthyl group, an anthracenyl group, a phenanthryl group, a pyrenyl group, a perylenyl group, a chrycenyl group, a fluorenyl group or the like, but is not limited thereto.

In the present specification, a fluorenyl group may be substituted, and two substituent groups may be linked with each other to form a spiro structure. In the case where the fluorenyl group is substituted,

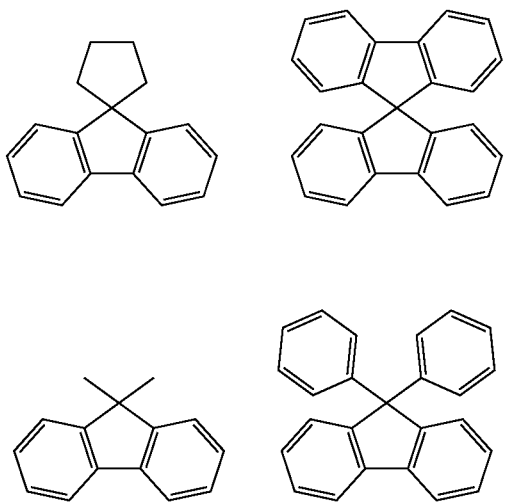

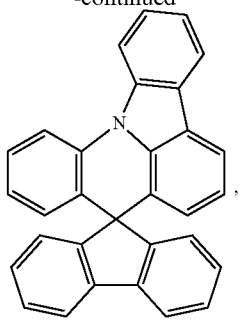

and the like can be formed. However, the structure is not limited thereto.

In the present specification, the heterocyclic group is a heterocyclic group containing at least one of O, N, Si and S as a heteroatom, and the number of carbon atoms thereof is not particularly limited, but is preferably 2 to 60. Examples of the heterocyclic group include a thiophene group, a furan group, a pyrrole group, an imidazole group, a thiazole group, an oxazole group, an oxadiazole group, a triazole group, a pyridyl group, a bipyridyl group, a pyrimidyl group, a triazine group, an acridyl group, a pyridazine group, a pyrazinyl group, a quinolinyl group, a quinazoline group, a quinoxalinyl group, a phthalazinyl group, a pyridopyrimidi-nyl group, a pyridopyrazinyl group, a pyrazinopyrazinyl group, an isoquinoline group, an indole group, a carbazole group, a benzoxazole group, a benzimidazole group, a benzothiazole group, a benzocarbazole group, a benzothi-ophene group, a dibenzothiophene group, a benzofuranyl group, a phenanthroline group, an isoxazolyl group, a thia-diazolyl group, a phenothiazinyl group, a dibenzofuranyl group, and the like, but are not limited thereto.

In the present specification, the aryl group in the aralkyl group, the aralkenyl group, the alkylaryl group, and the arylamine group is the same as the aforementioned examples of the aryl group. In the present specification, the alkyl group in the aralkyl group, the alkylaryl group and the alkylamine group is the same as the aforementioned examples of the alkyl group. In the present specification, the heteroaryl in the heteroarylamine can be applied to the aforementioned description of the heterocyclic group. In the present specification, the alkenyl group in the aralkenyl group is the same as the aforementioned examples of the alkenyl group. In the present specification, the aforementioned description of the aryl group may be applied except that the arylene is a divalent group. In the present specification, the aforementioned description of the heterocyclic group can be applied except that the heteroarylene is a divalent group. In the present specification, the aforementioned description of the aryl group or cycloalkyl group can be applied except that the hydrocarbon ring is not a monovalent group but formed by combining two substituent groups. In the present specification, the aforementioned description of the heterocyclic group can be applied, except that the heterocycle is not a monovalent group but formed by combining two substituent groups.

In the Chemical Formula 1, depending on the position of attachment, the Chemical Formula 1 may be represented by any one of the following Chemical Formulas 1-1 to 1-3:

[Chemical Formula 1-1]

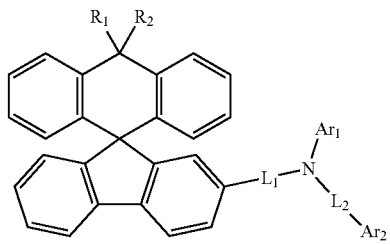

[Chemical Formula 1-2]

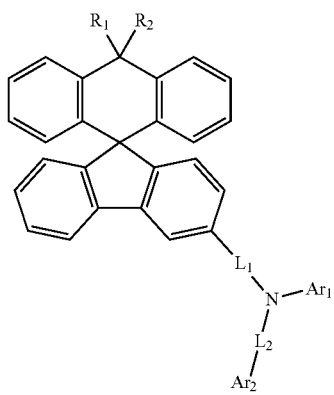

[Chemical Formula 1-3]

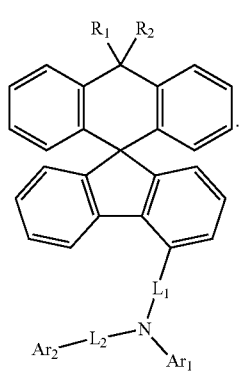

Preferably, both $R_1$ and $R_2$ are methyl, or both are phenyl.

Preferably, $L_1$ and $L_2$ are each independently a bond, phenylene, biphenyldiyl, terphenyldiyl, quarterphenyldiyl, naphthalenediyl, anthracenediyl, dimethylfluorenediyl, phenanthrendiyl, pyrenediyl, or triphenylenediyl. More preferably, $L_1$ is a bond, and $L_2$ is a bond, or phenylene.

Preferably, $Ar_1$ and $Ar_2$ are each independently phenyl unsubstituted or substituted with any one substituent selected from the group consisting of $C_{1-4}$ alkyl, halogen, cyano, and tri($C_{1-4}$ alkyl)silyl; biphenylyl; terphenylyl; quaterphenylyl; naphthyl; anthracenyl; phenanthrenyl; triphenylenyl; dimethylfluorenyl; diphenylfluorenyl; dibenzofuranyl; or dibenzothiophenyl.

Representative examples of the compound represented by the Chemical Formula 1 are as follows:

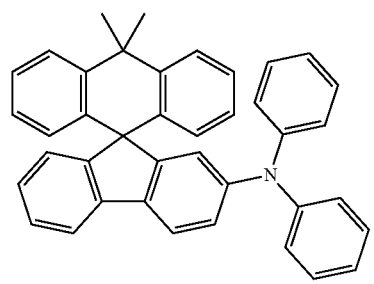

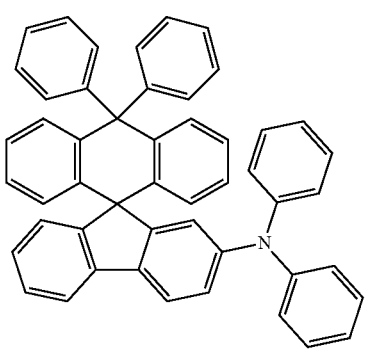

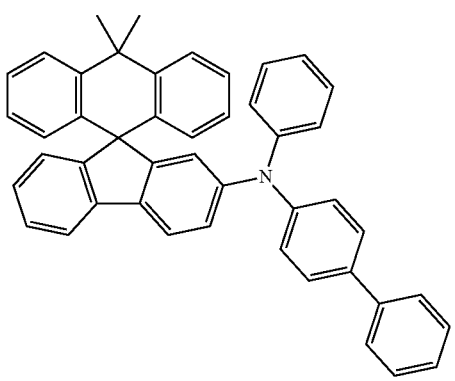

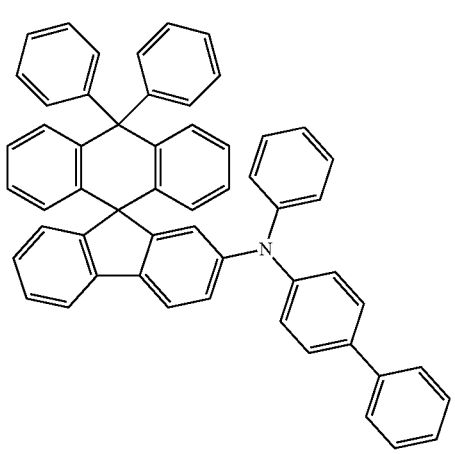

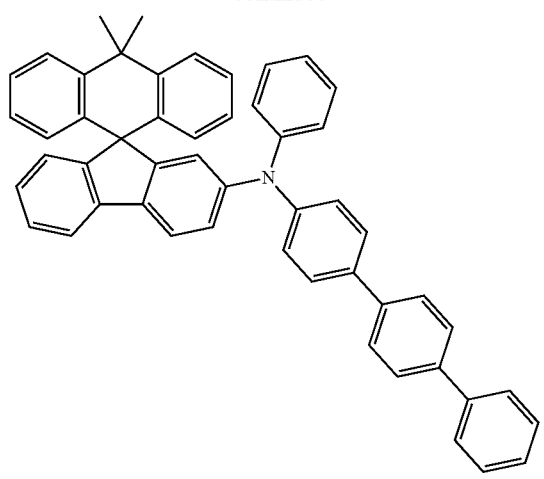
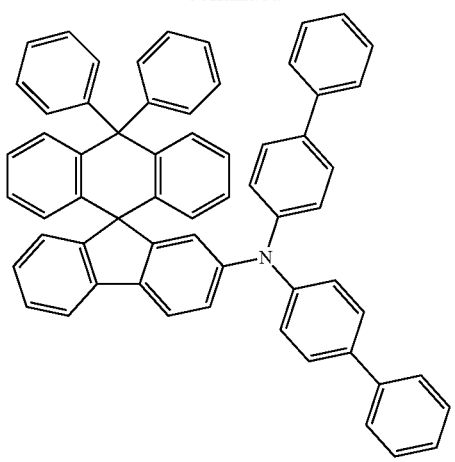
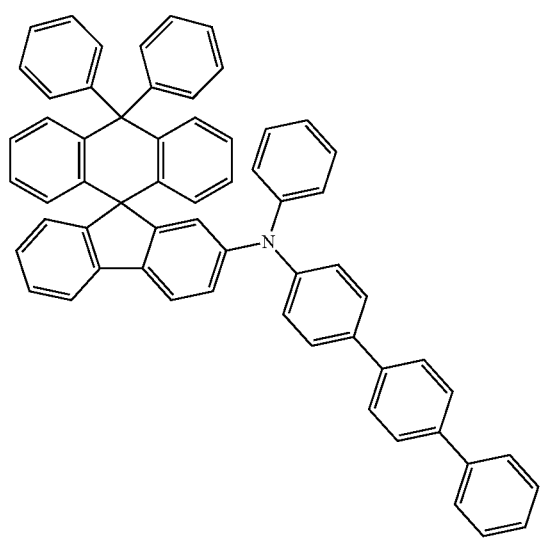
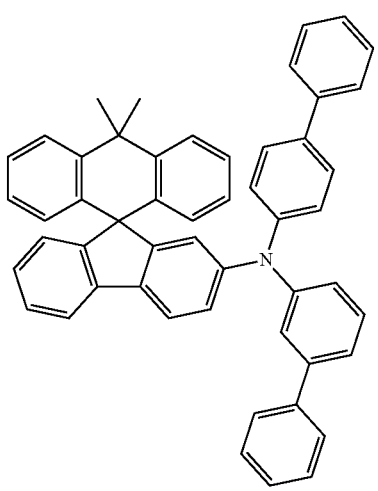
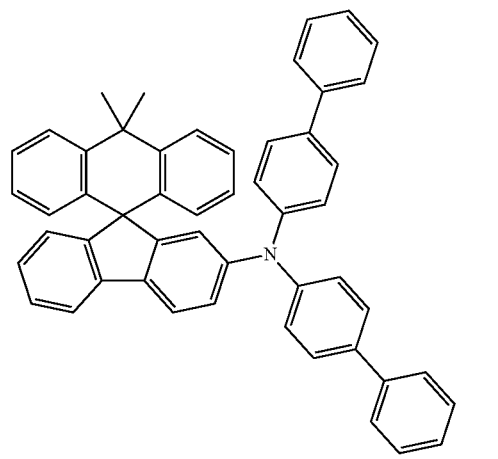
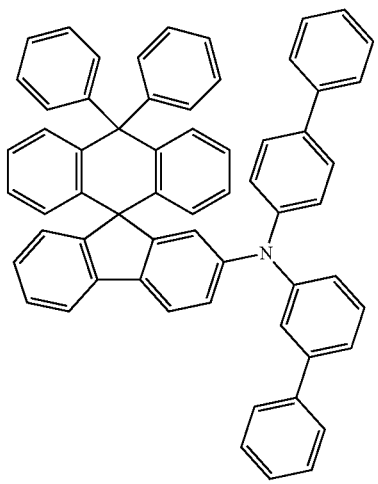

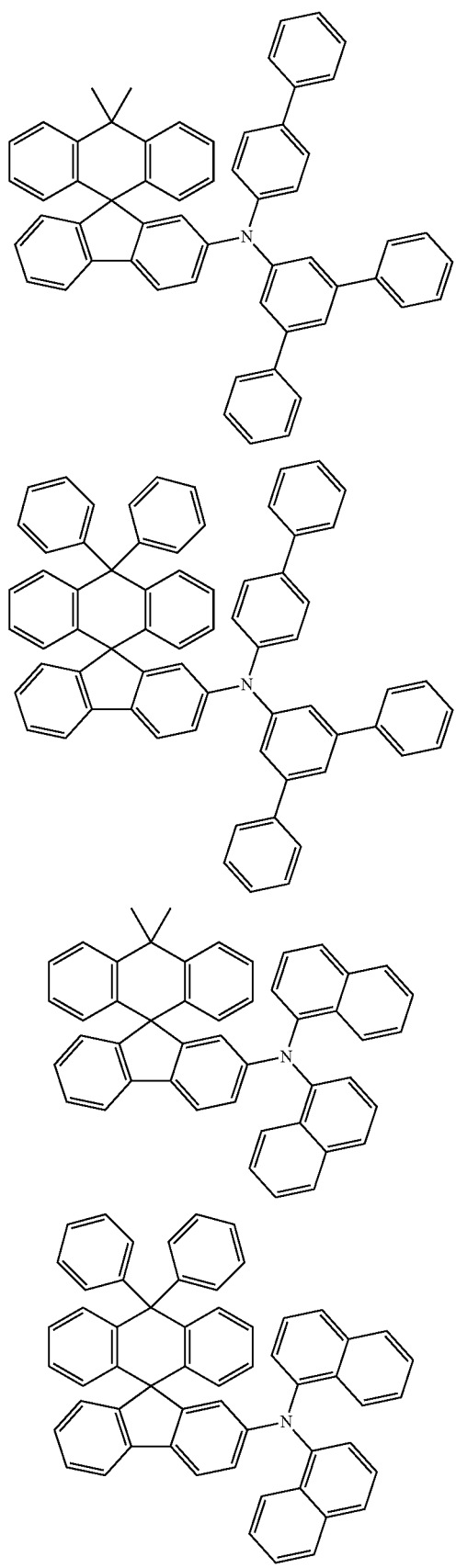
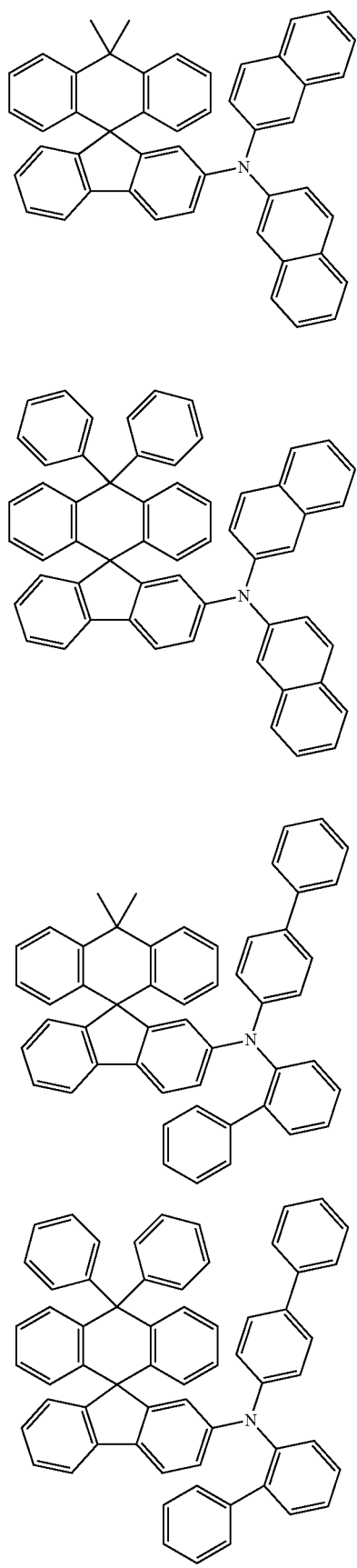

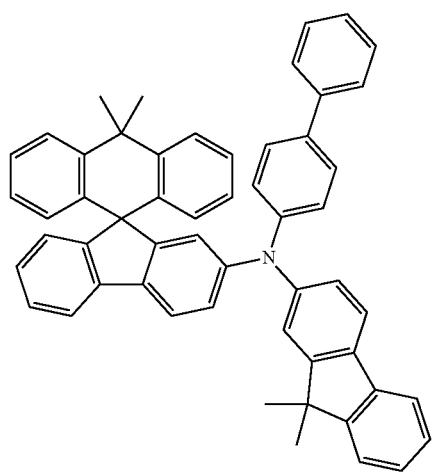
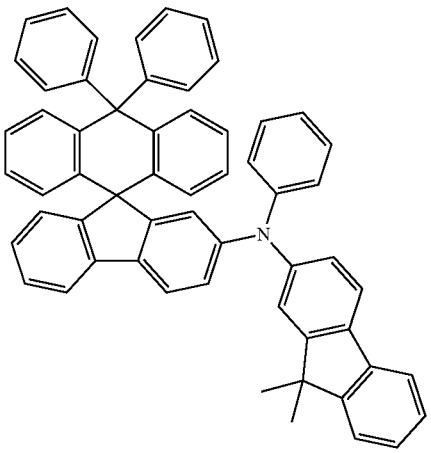
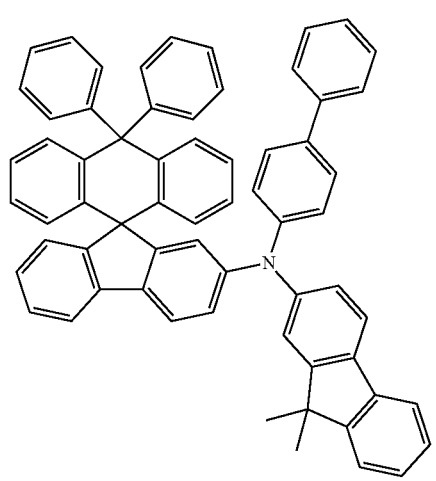
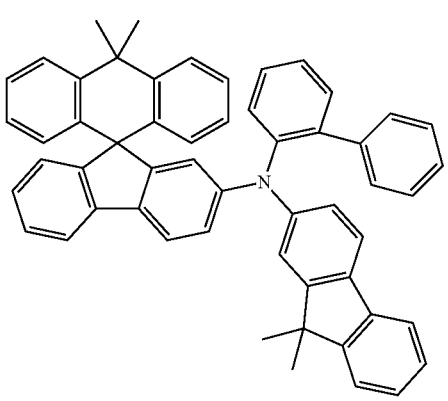
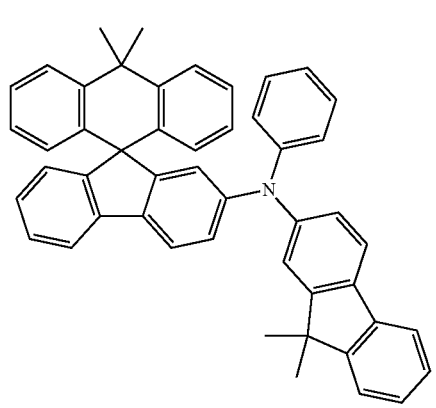
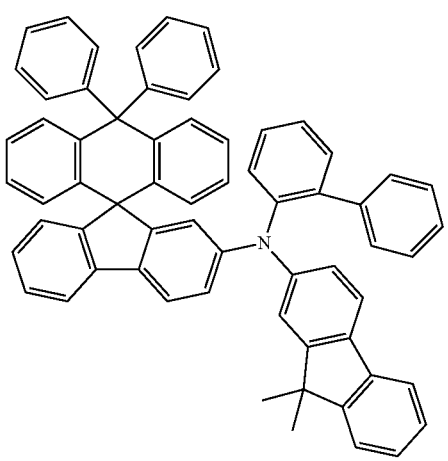

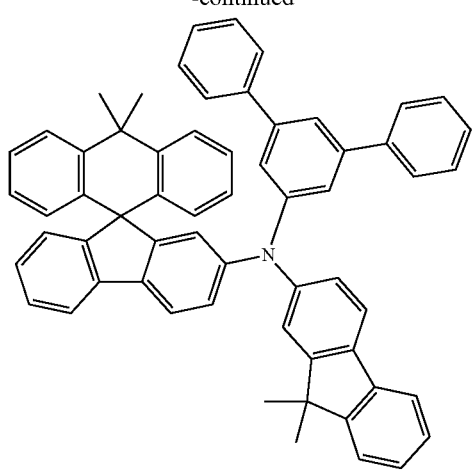
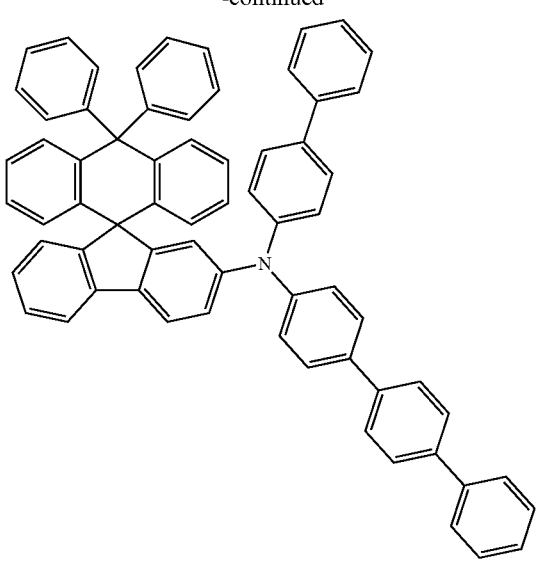
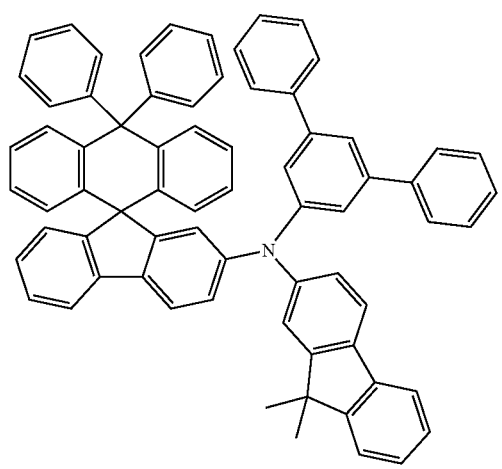
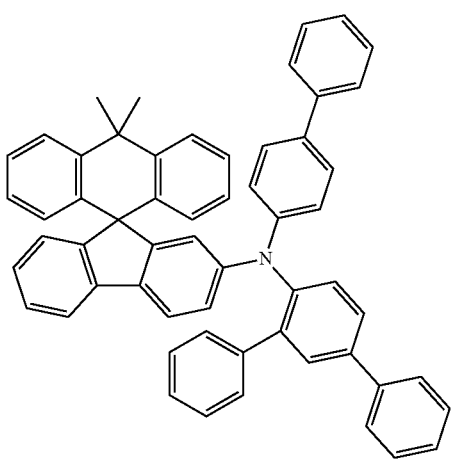
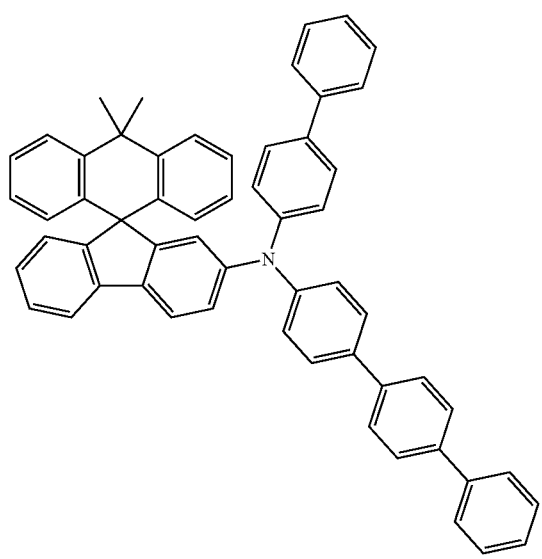
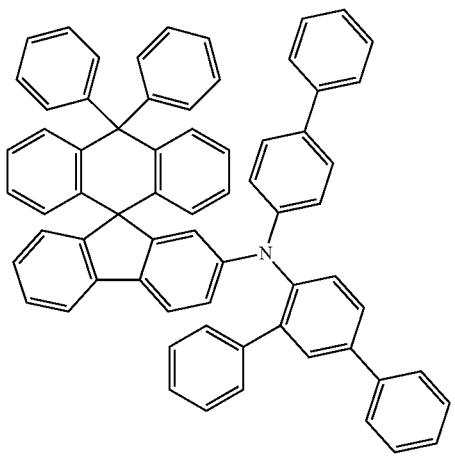

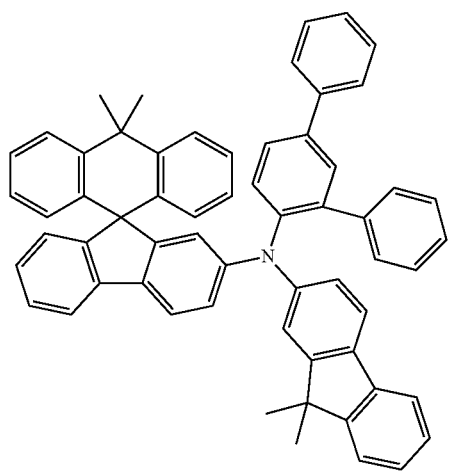
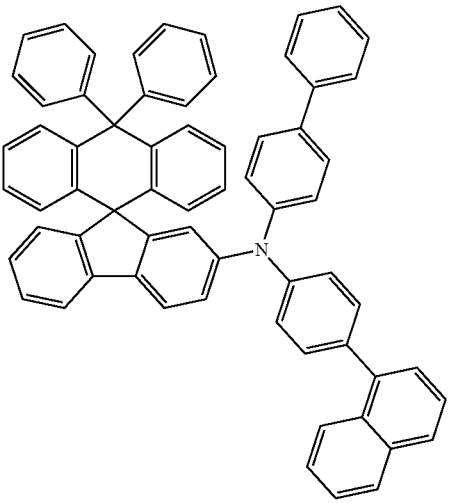
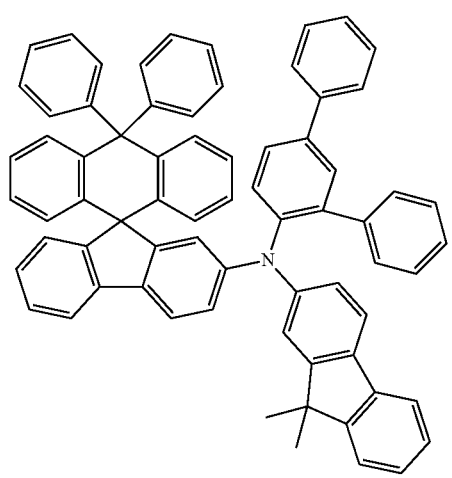
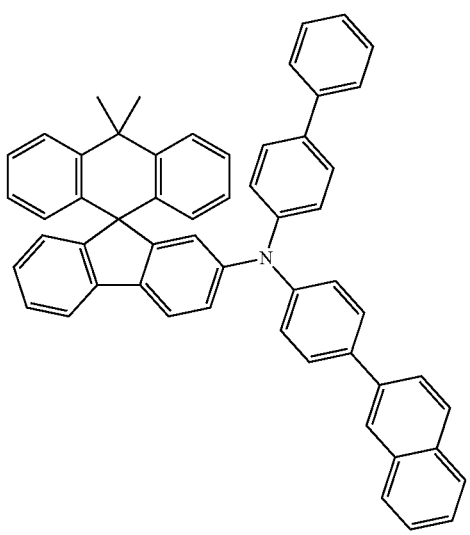
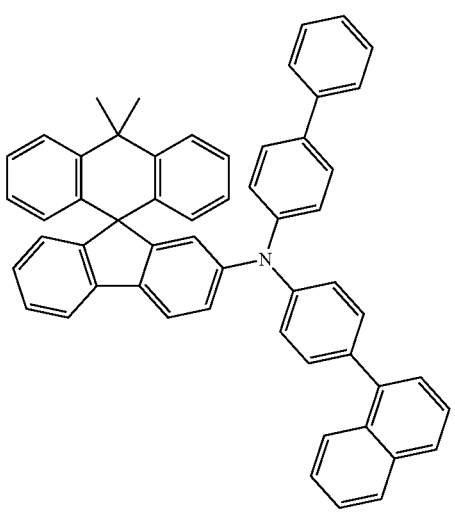

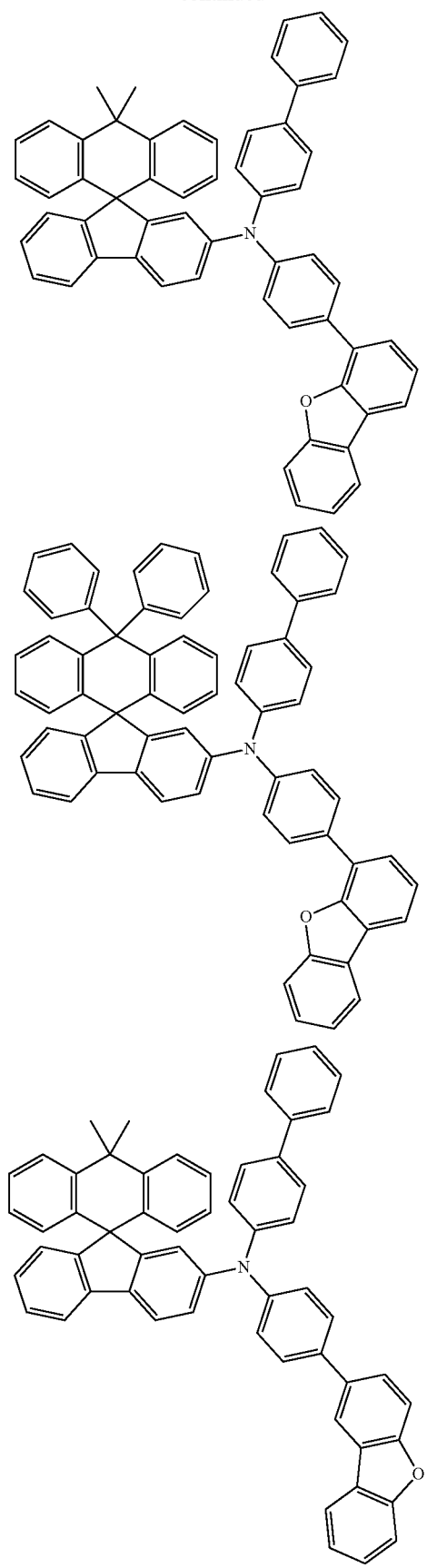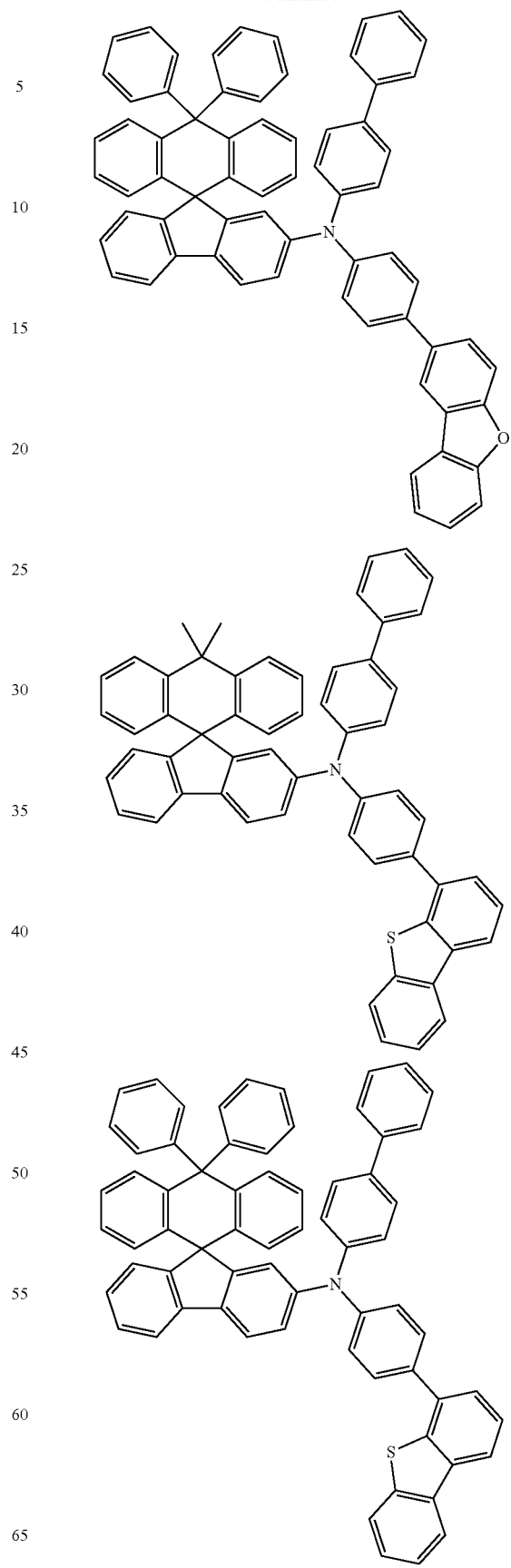

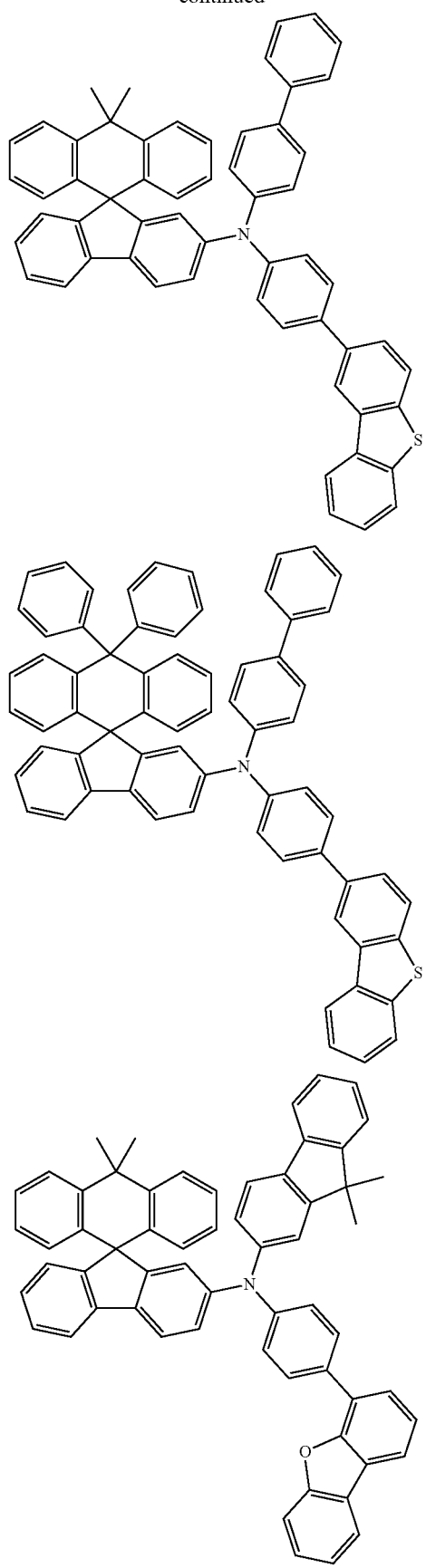
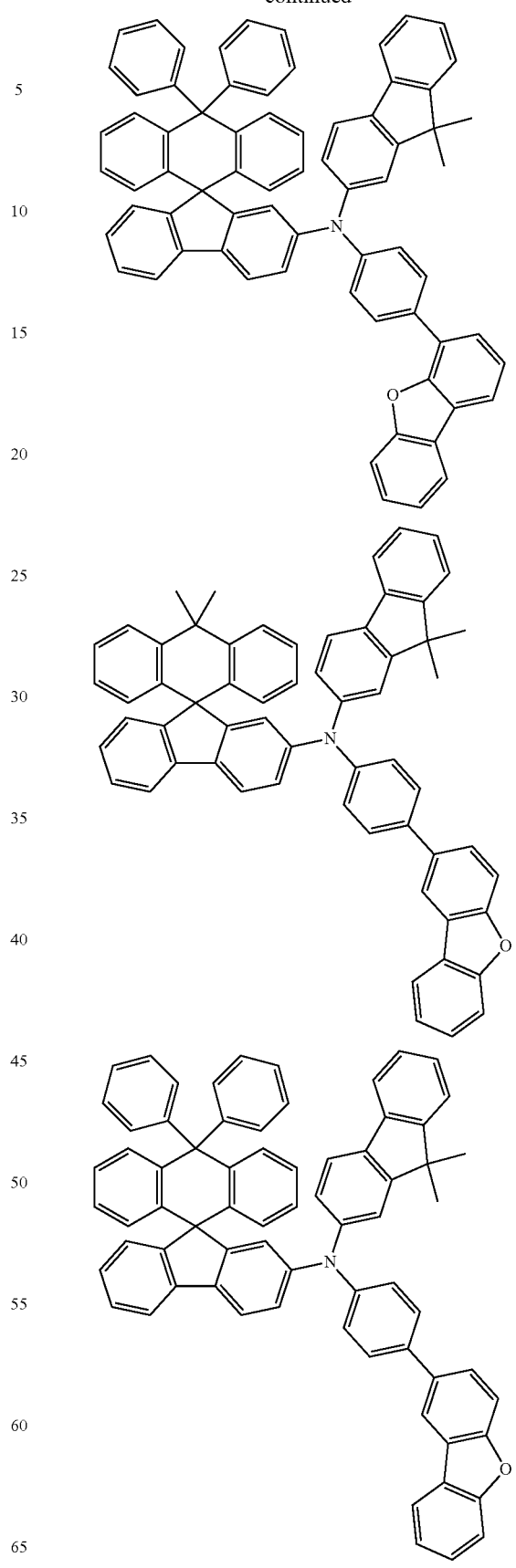

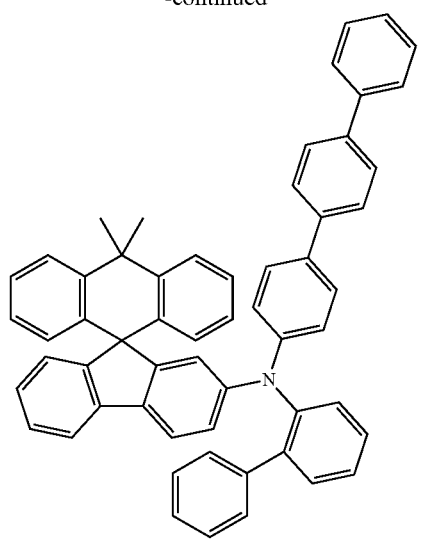
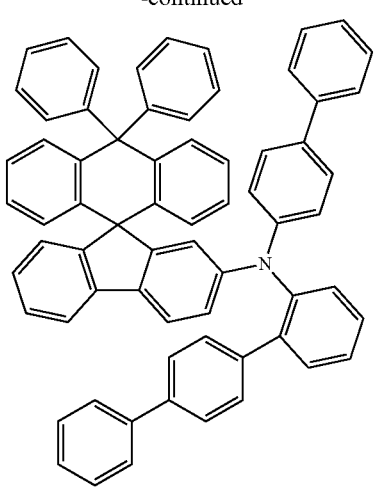
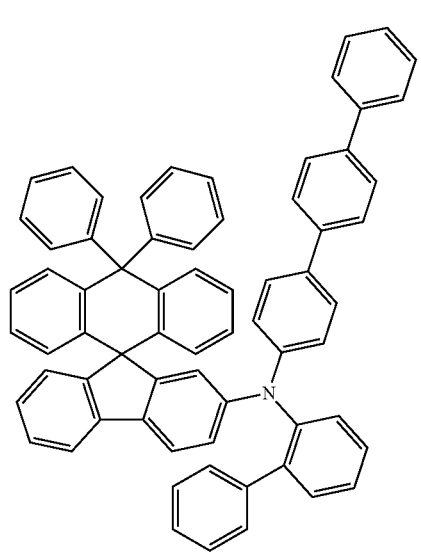
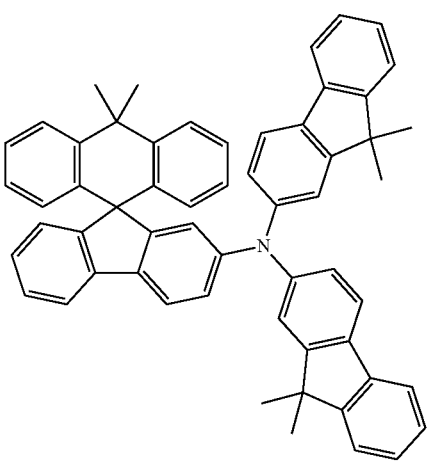
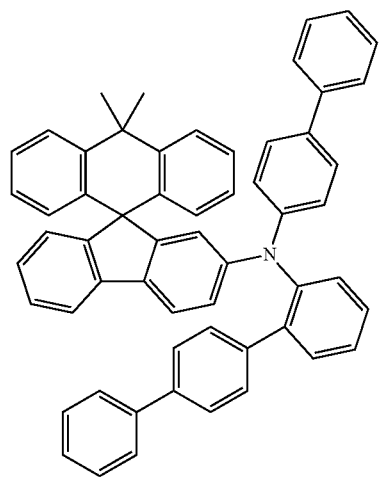
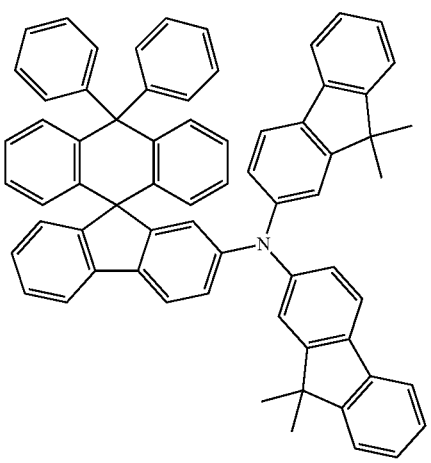

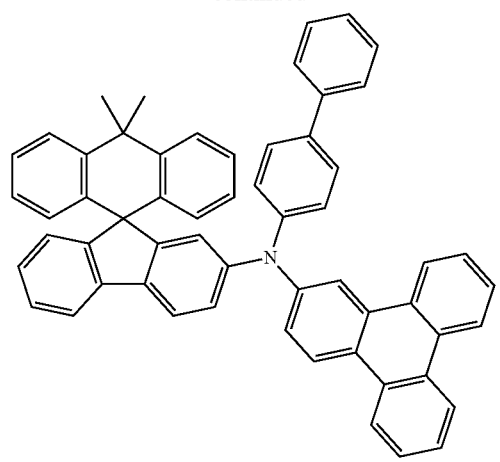
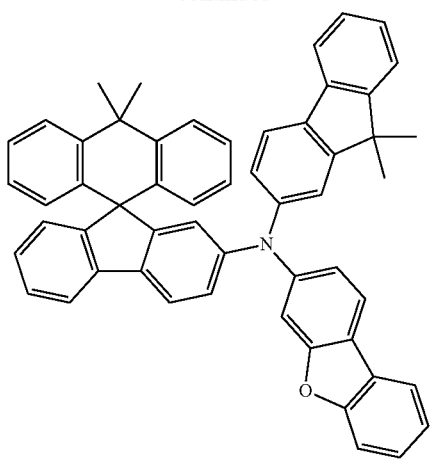
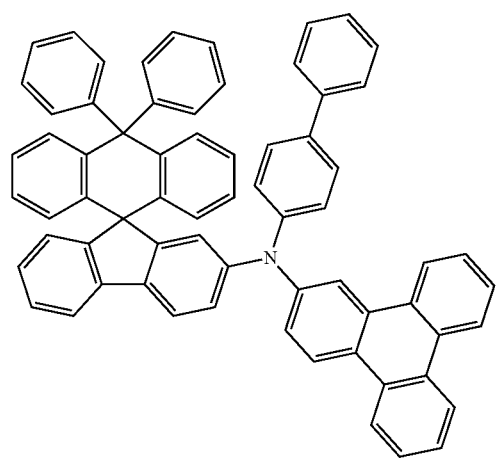
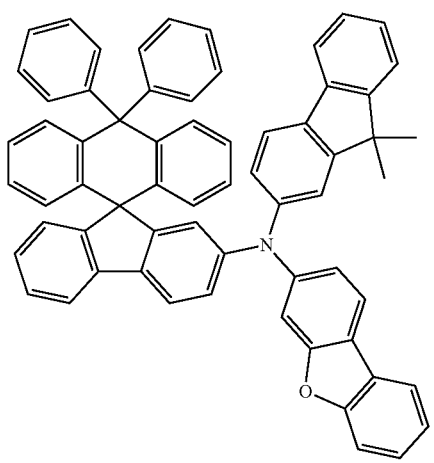

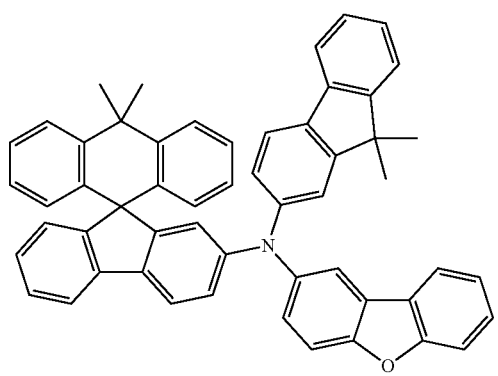
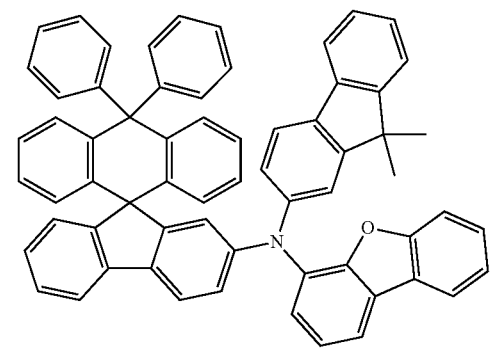
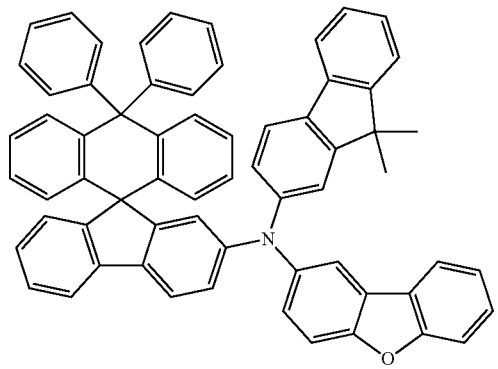

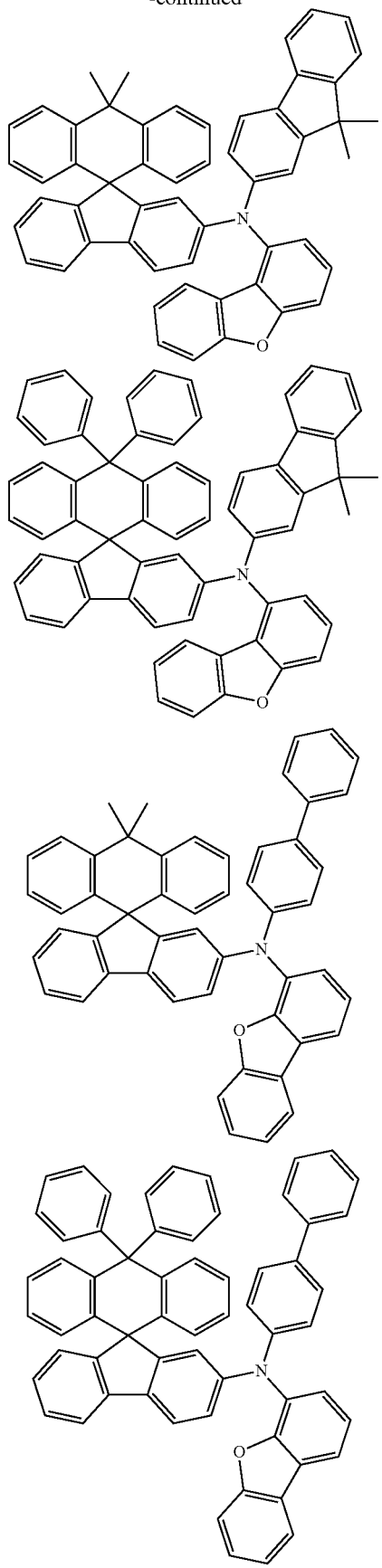
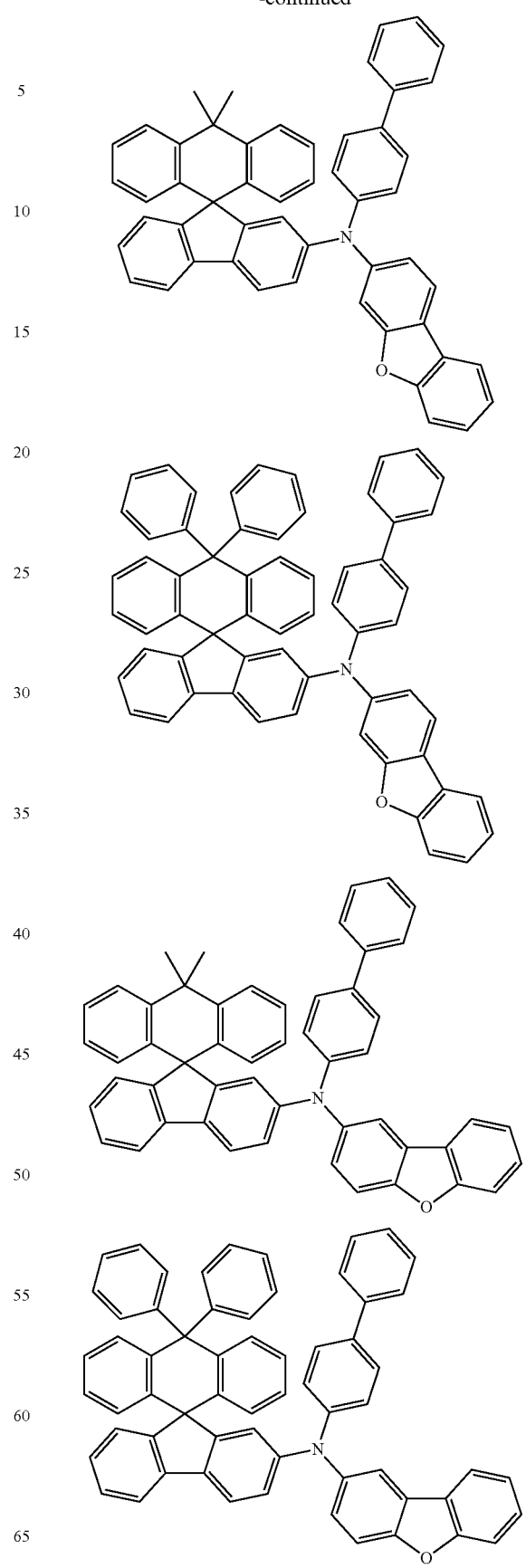

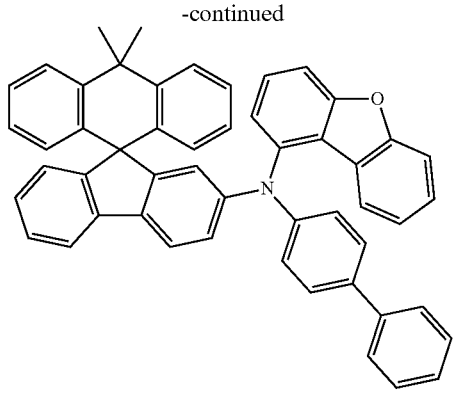
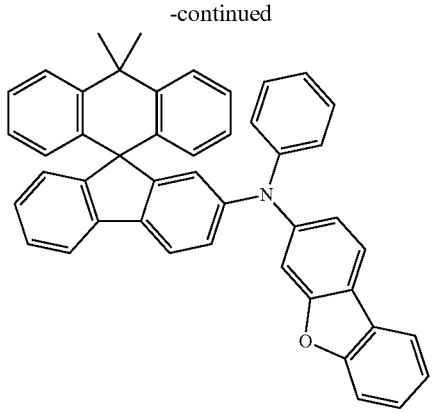
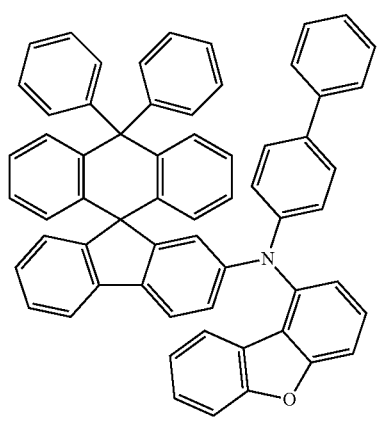
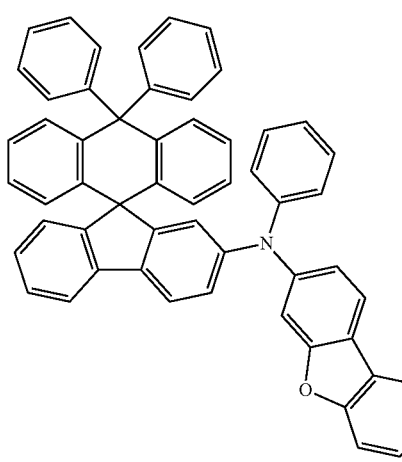
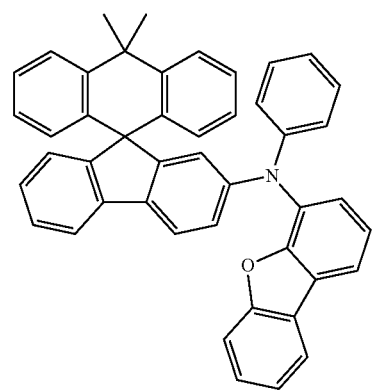
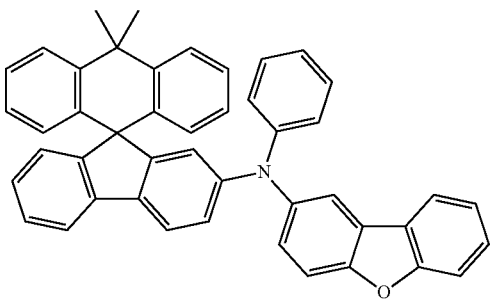
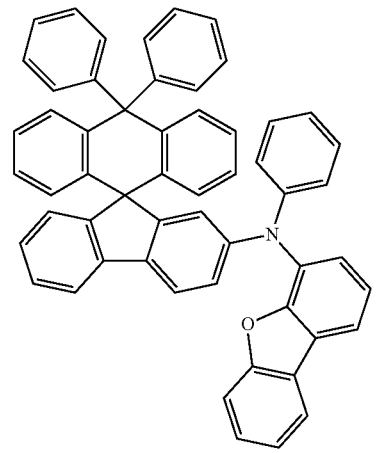
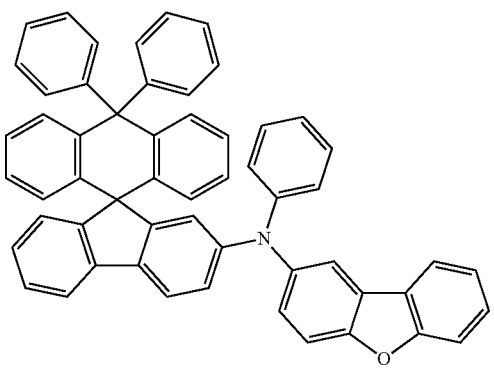

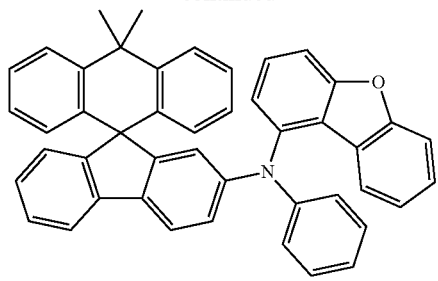
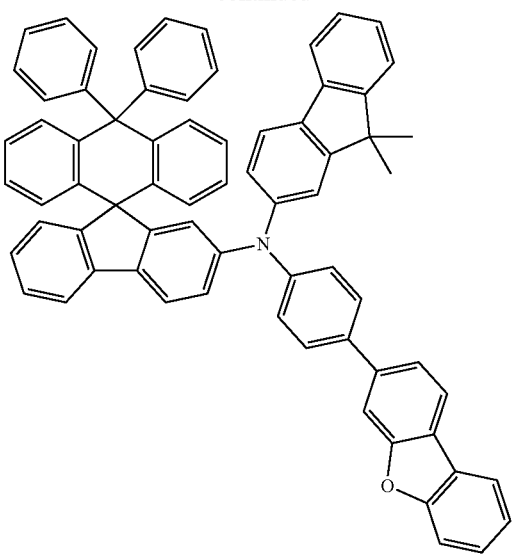
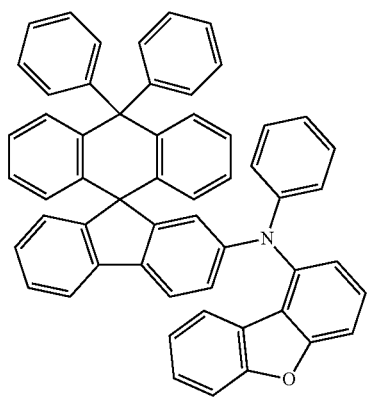
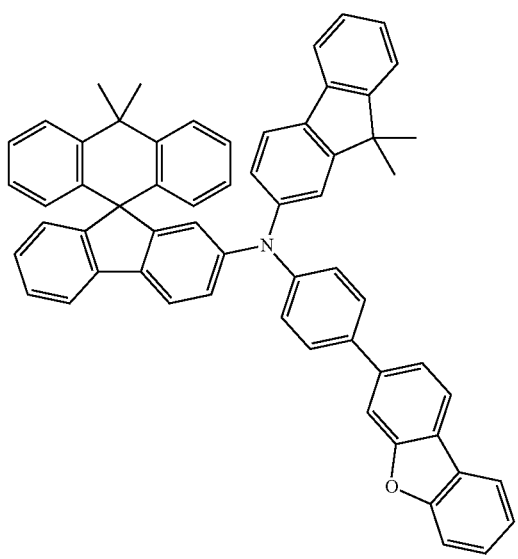

-continued
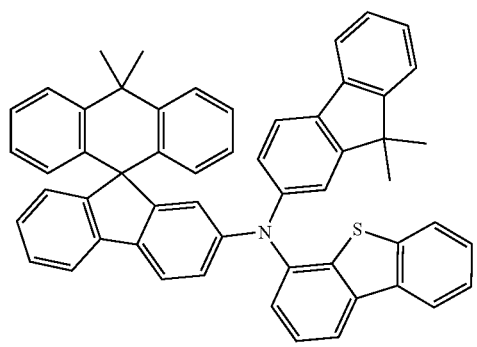
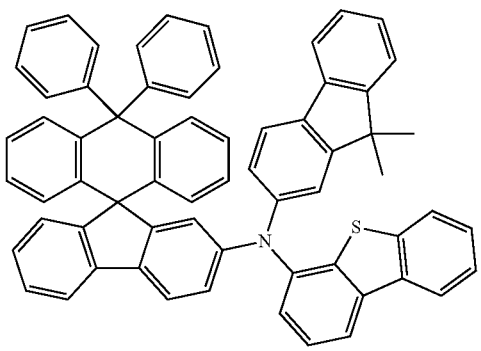
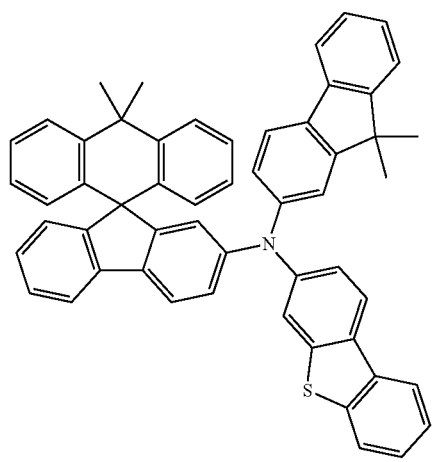
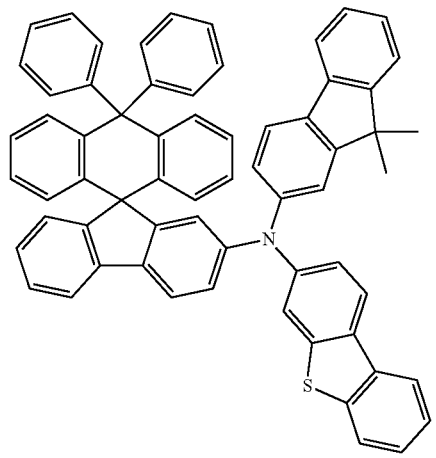
-continued
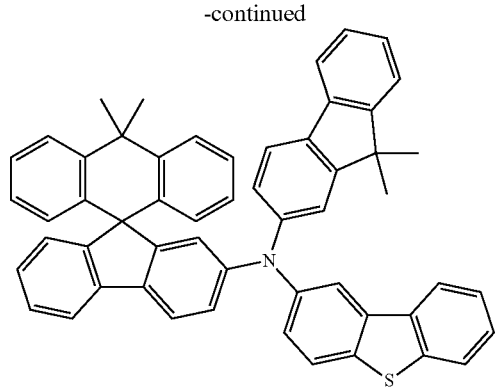
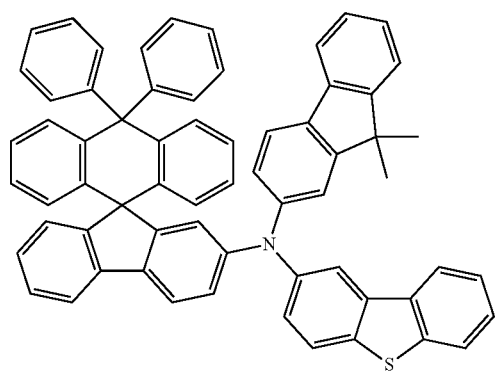
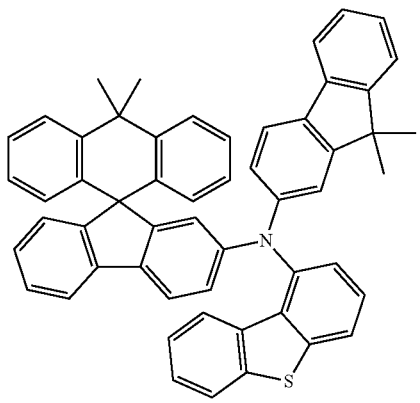
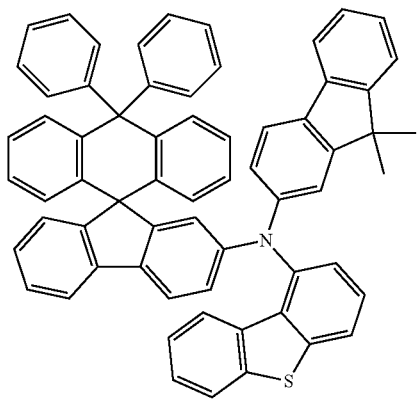

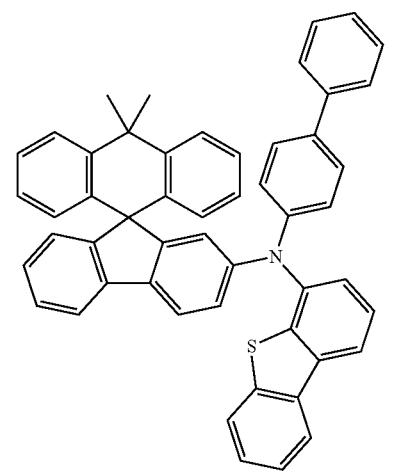
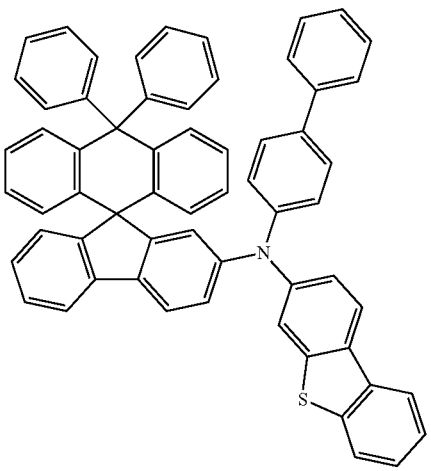
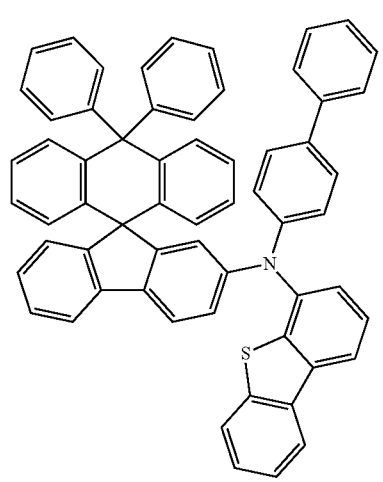
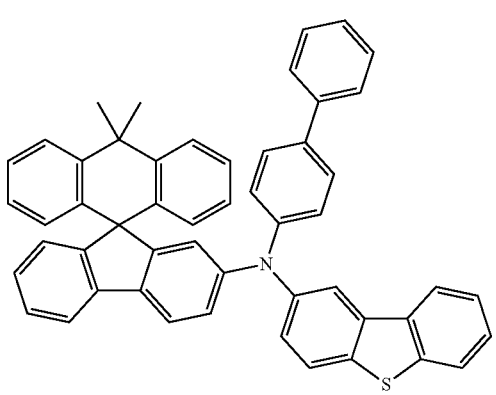
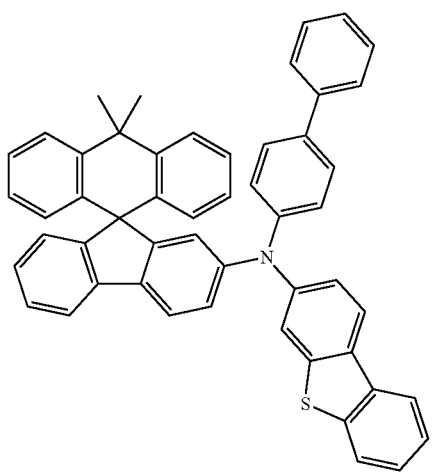
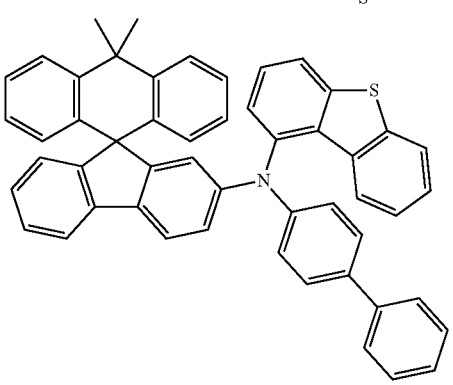

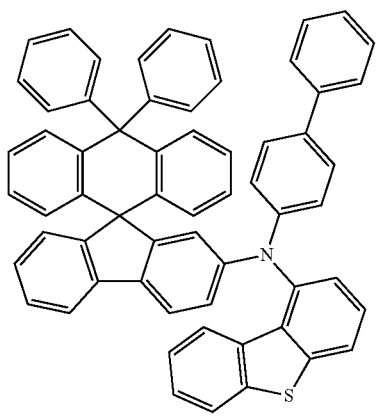
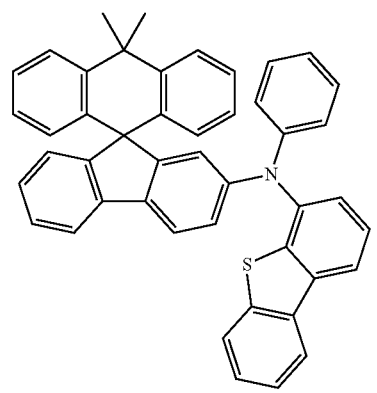
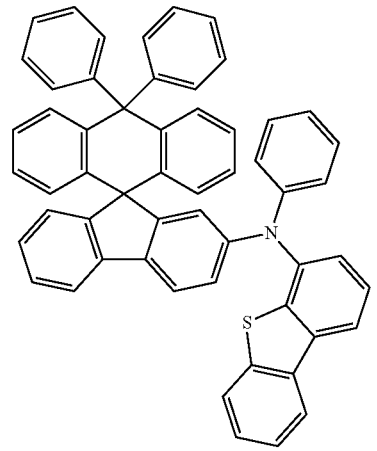
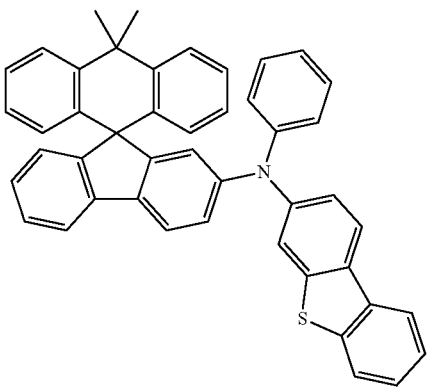
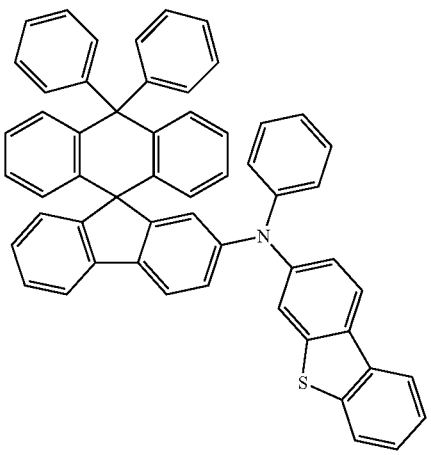
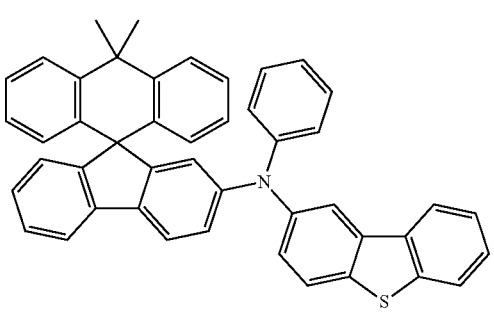
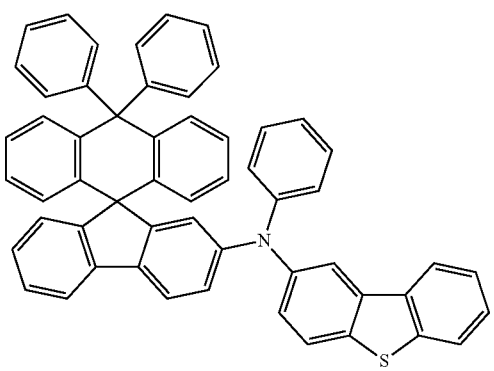
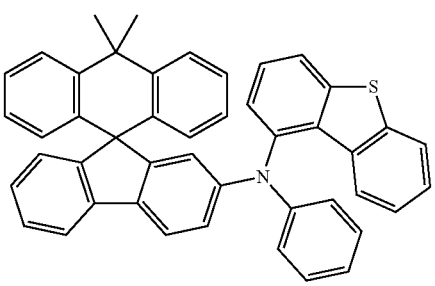

39
-continued
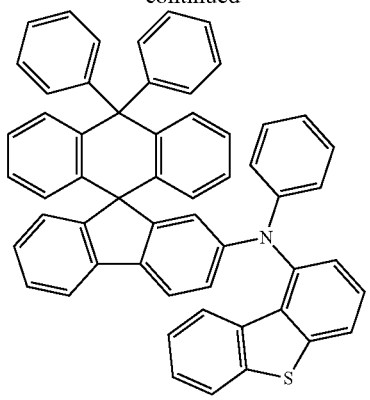
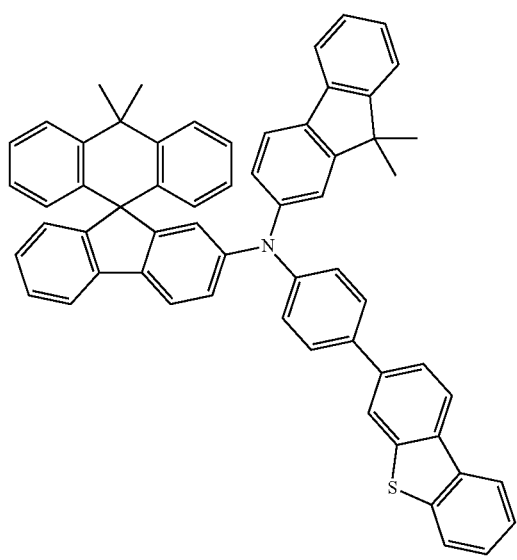
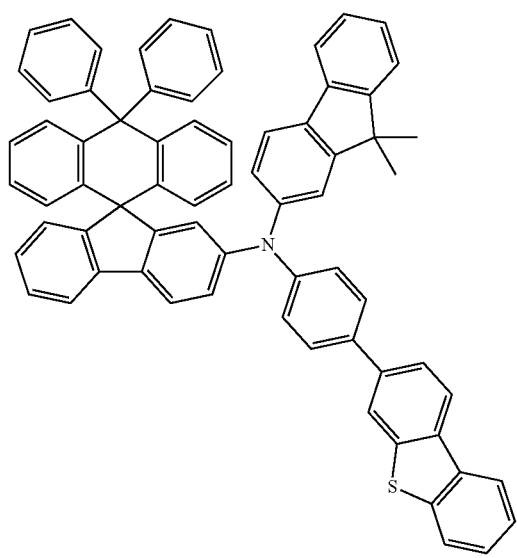
40
-continued
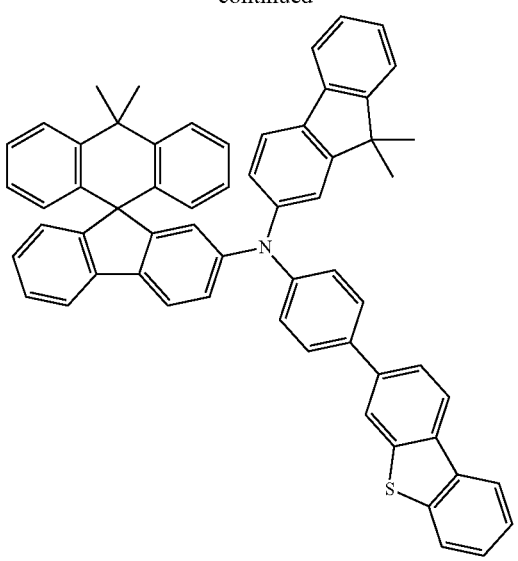
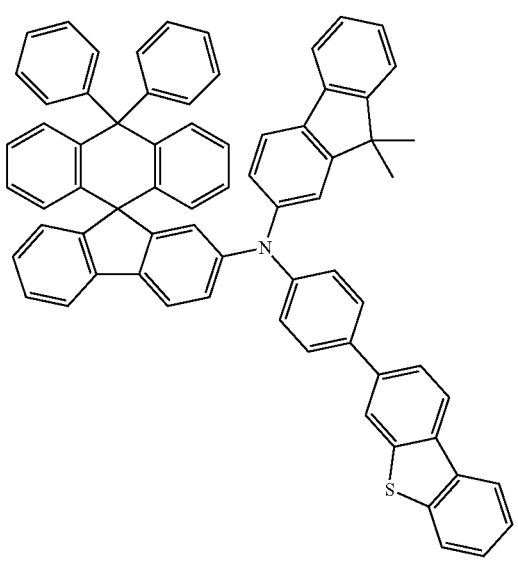
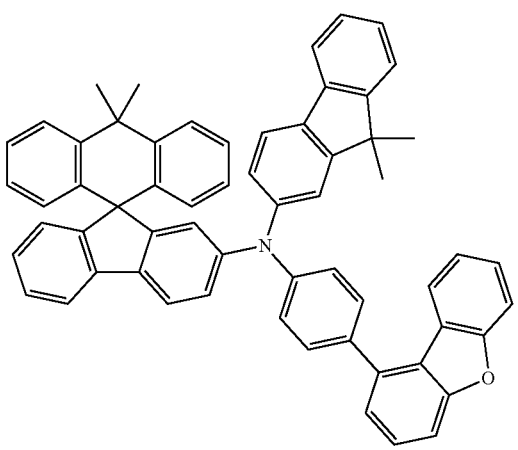

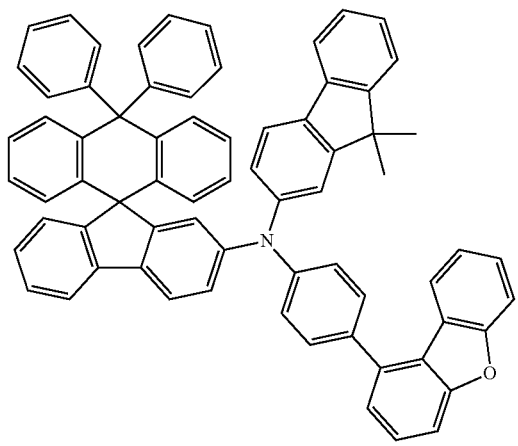
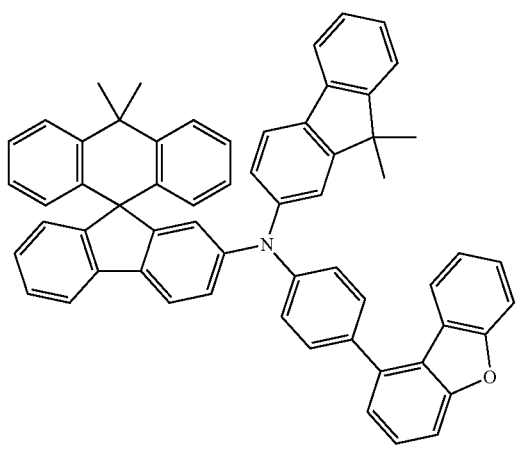
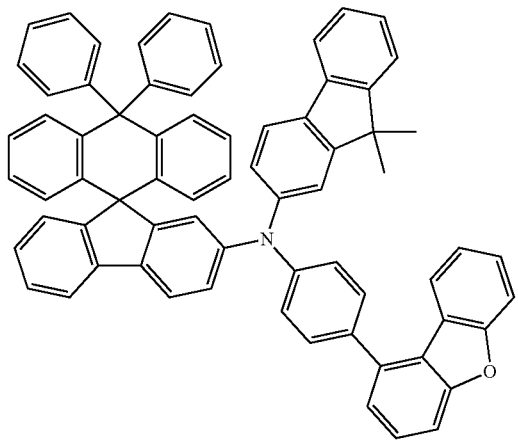
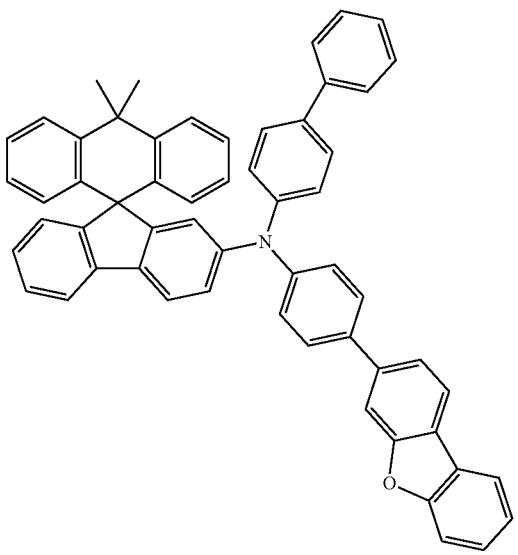
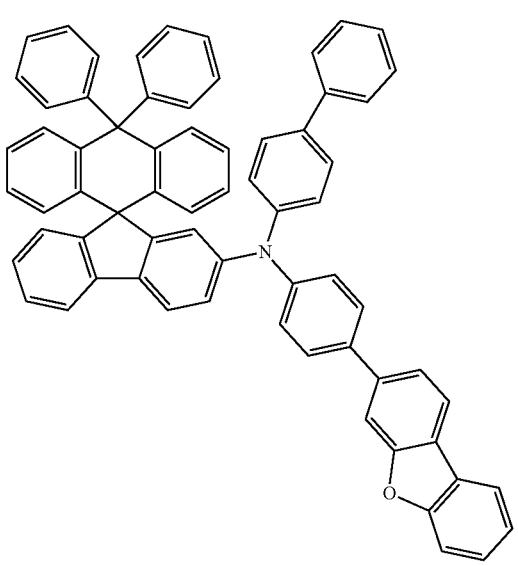
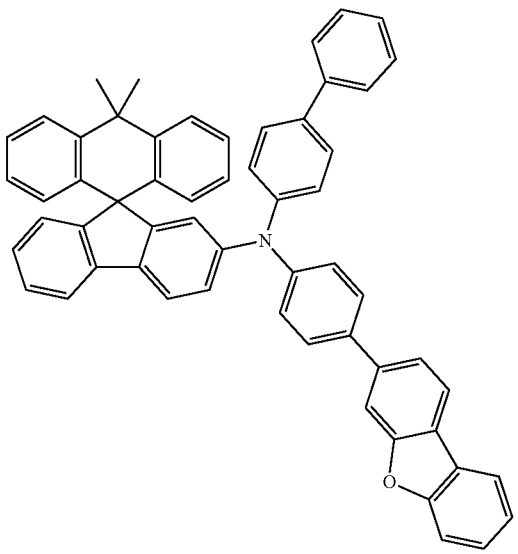

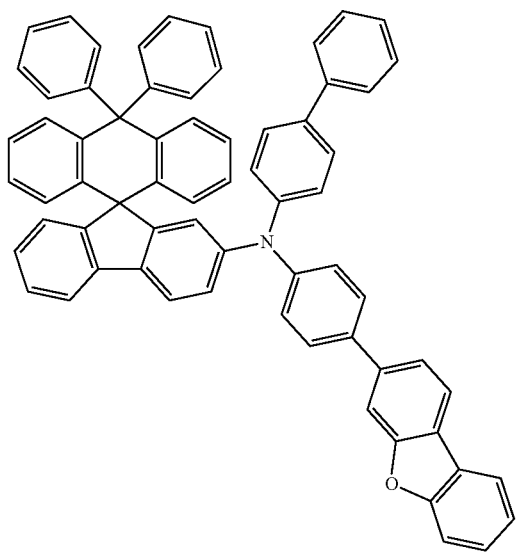
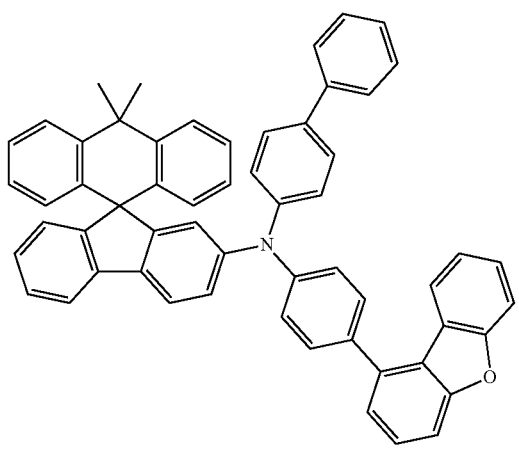
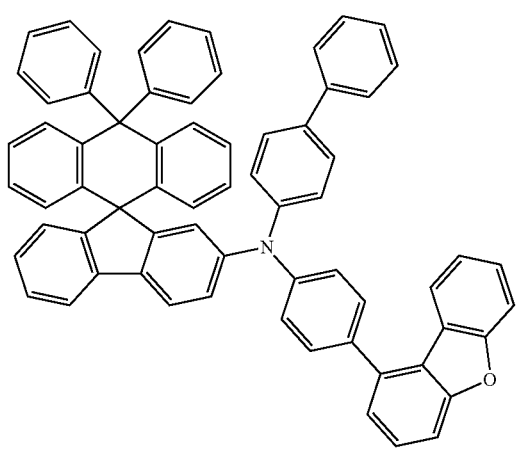
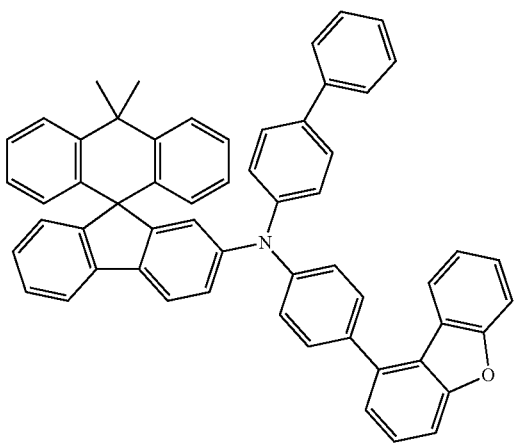
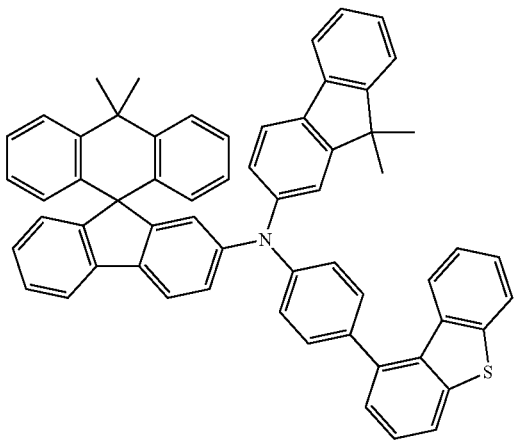

45
-continued
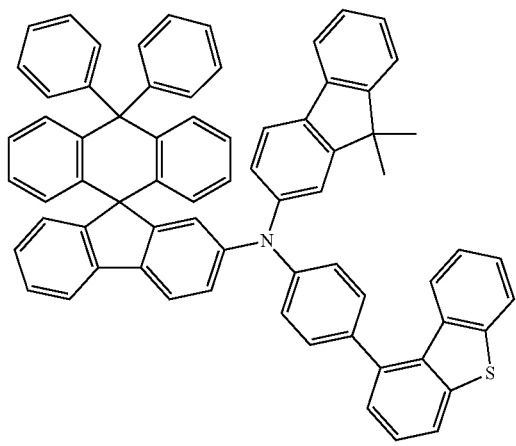
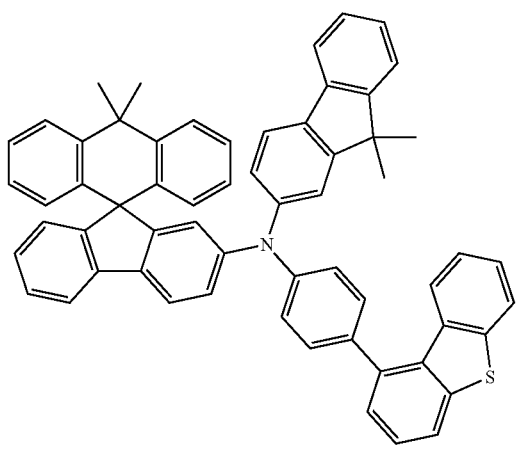
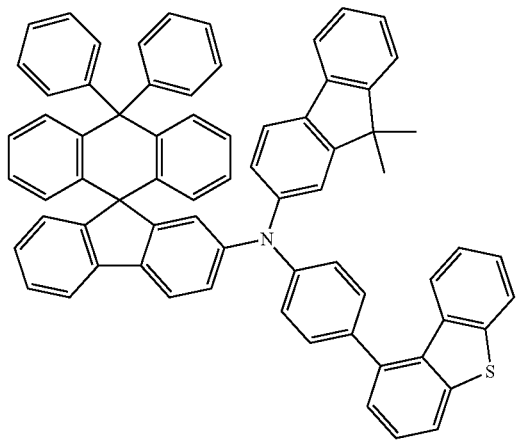
46
-continued
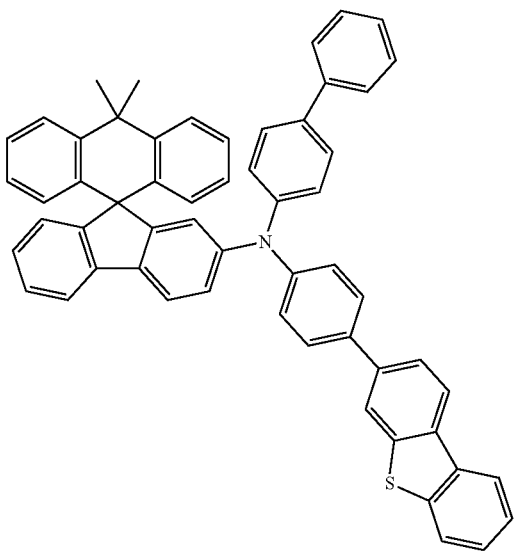
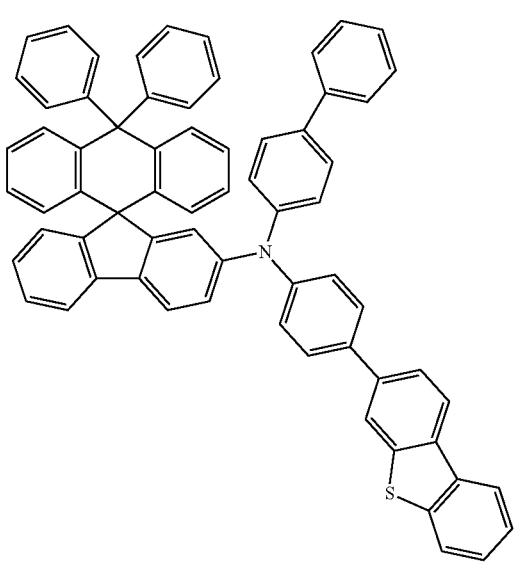
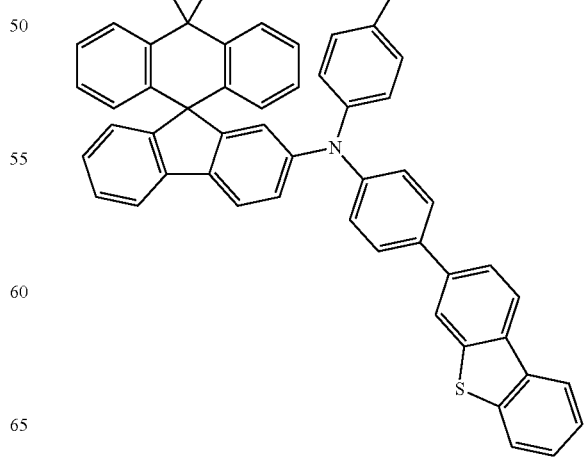

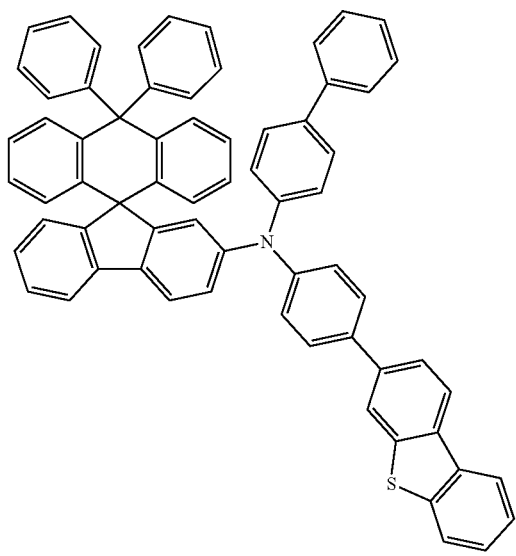
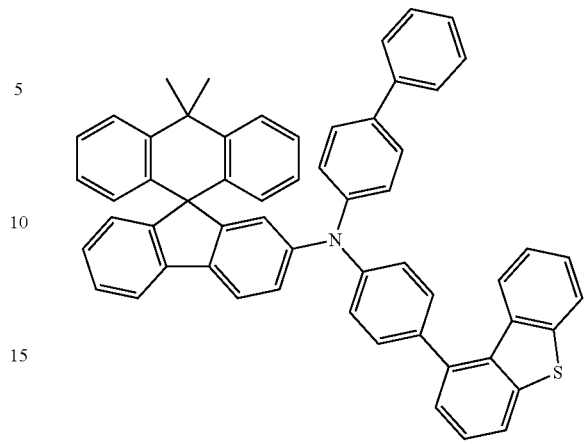
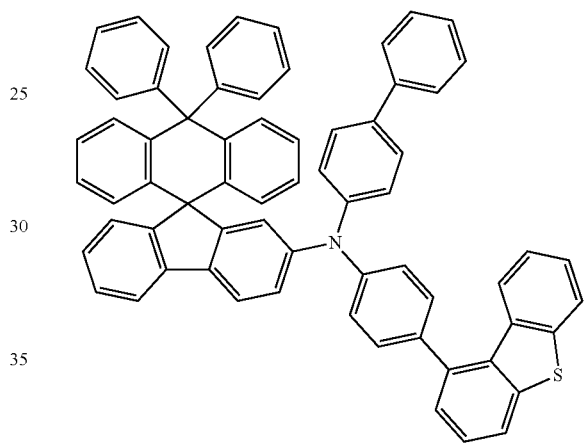
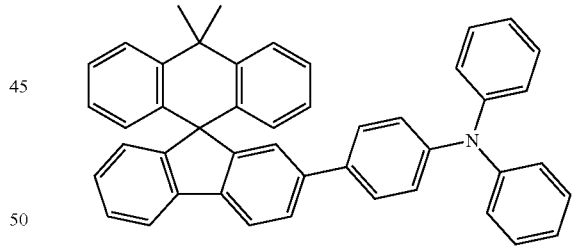
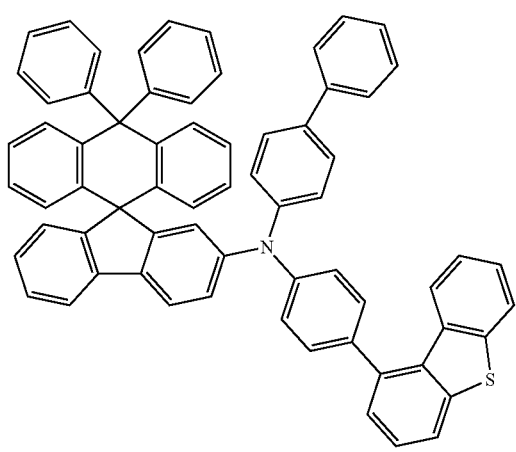
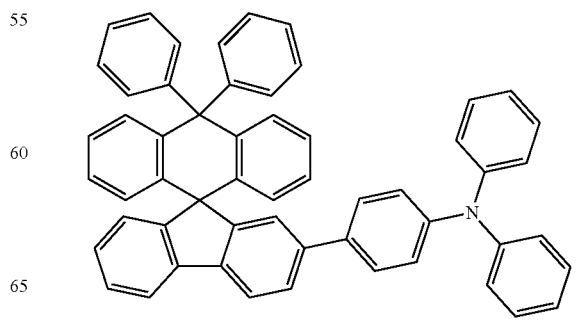

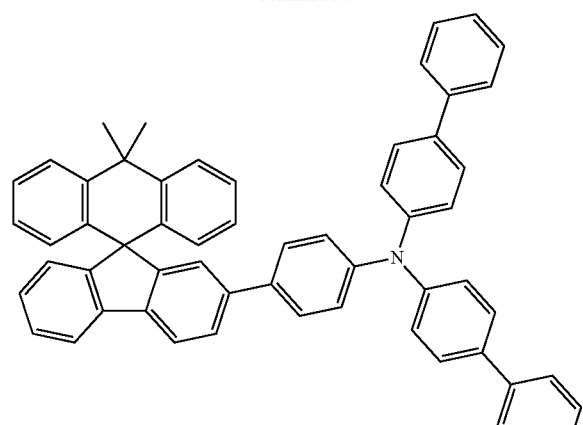
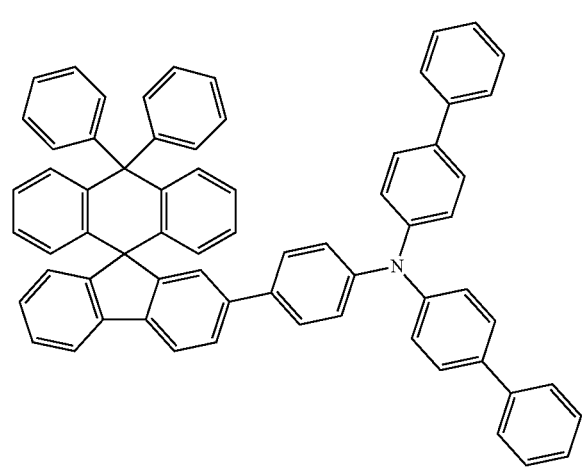
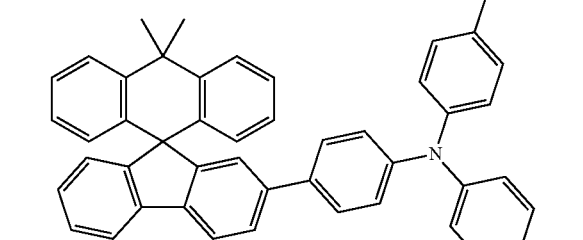
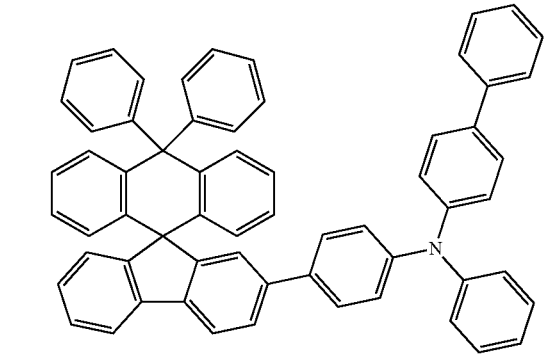
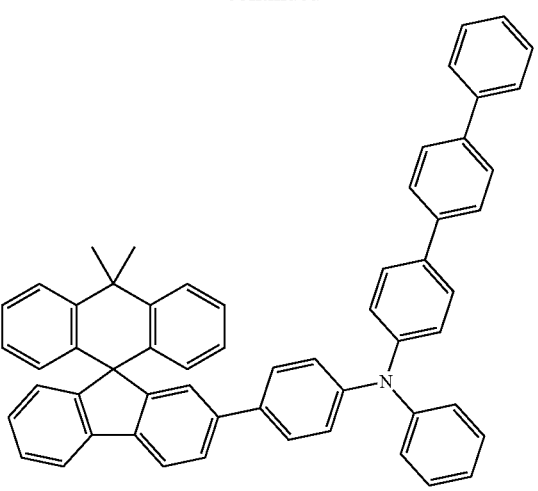

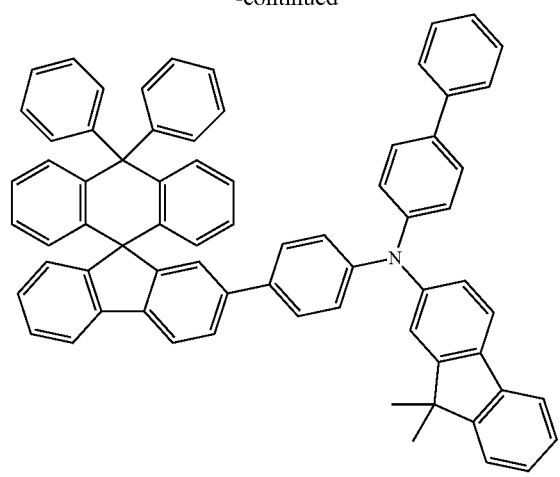
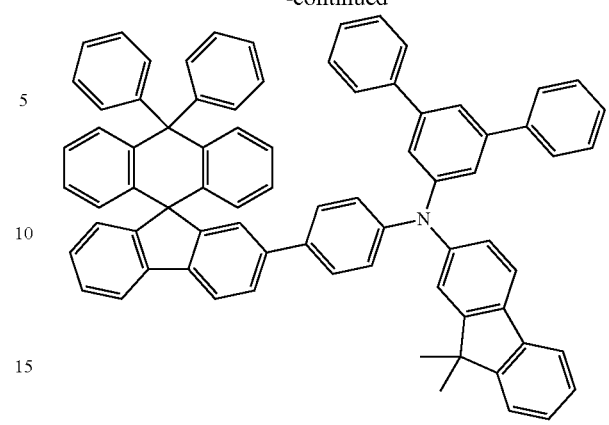
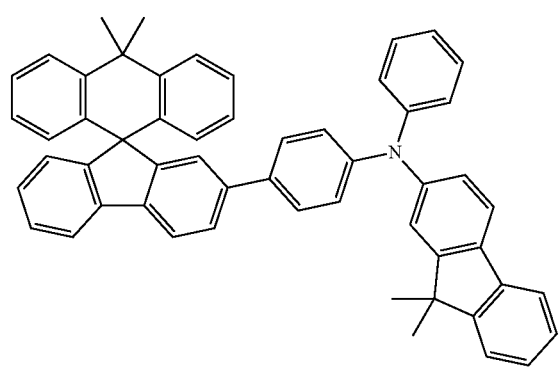
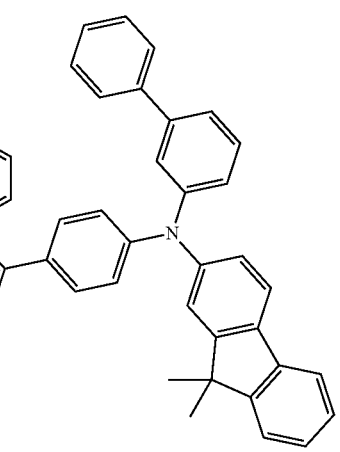
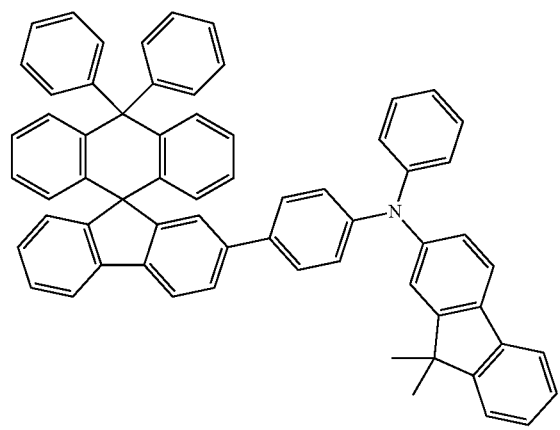
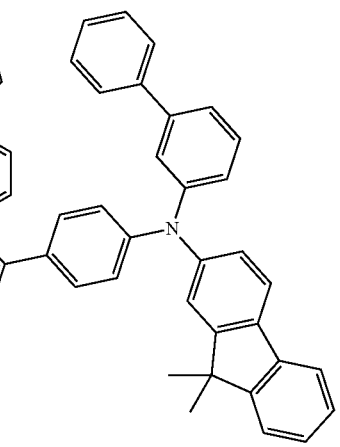
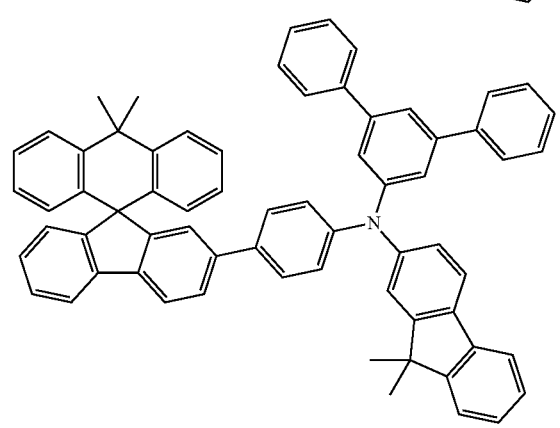
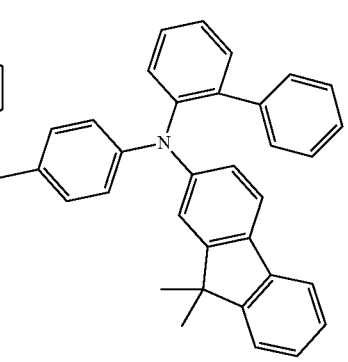

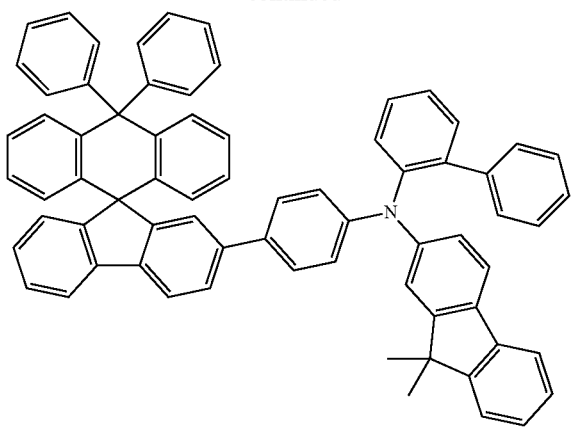
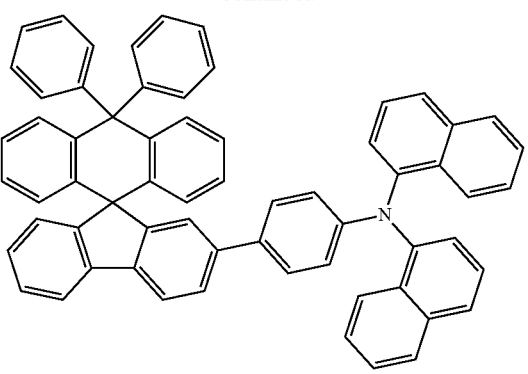
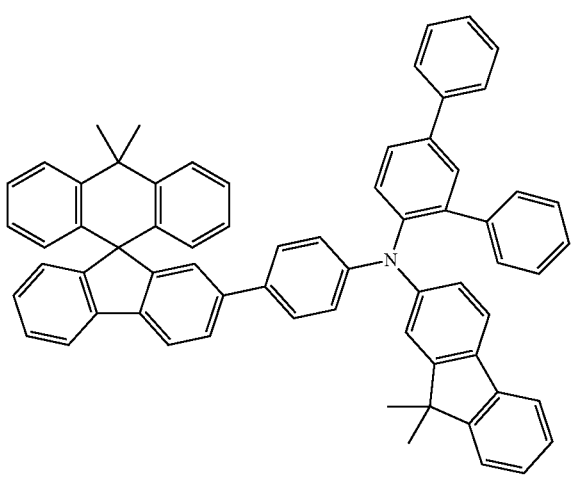
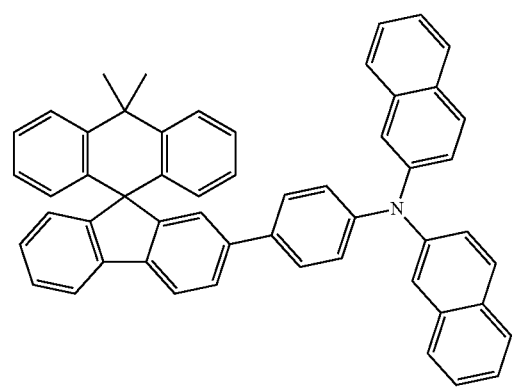
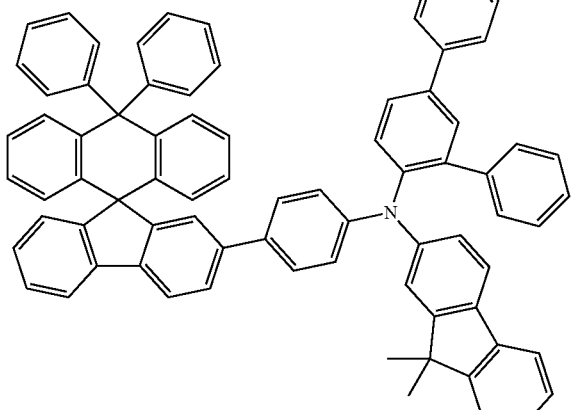
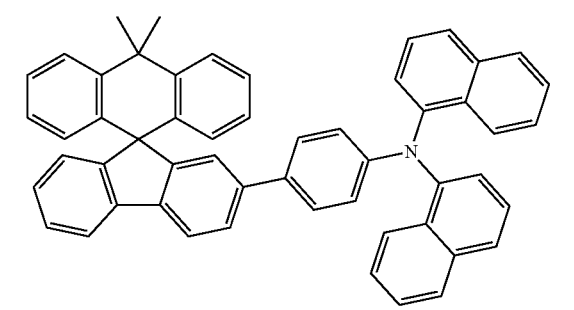
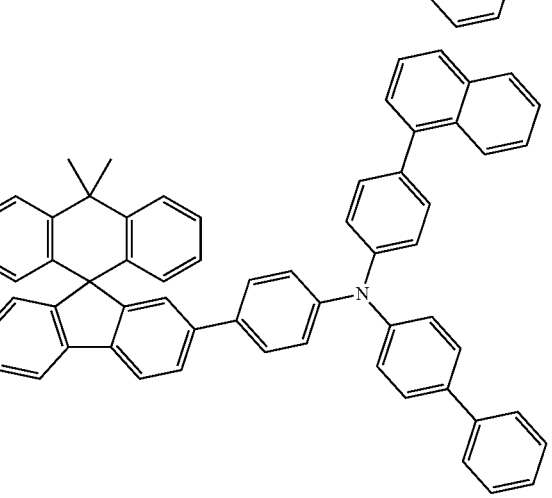

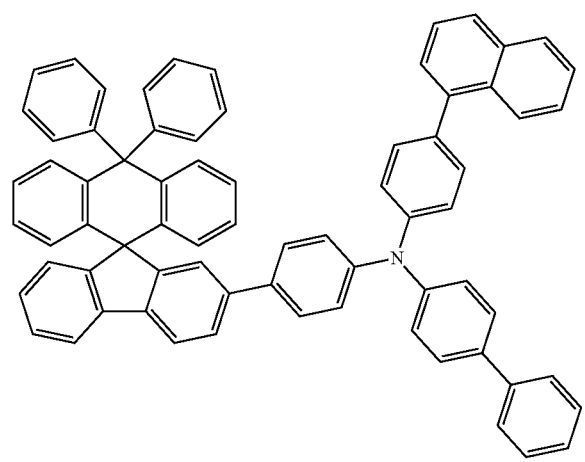
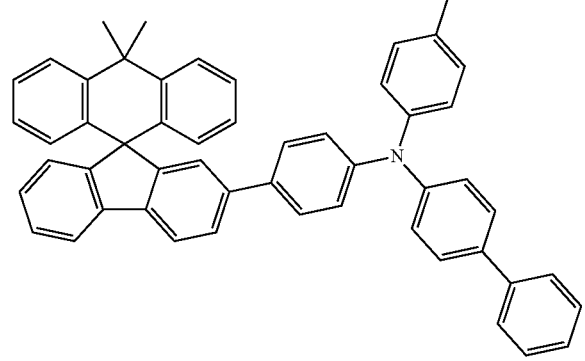
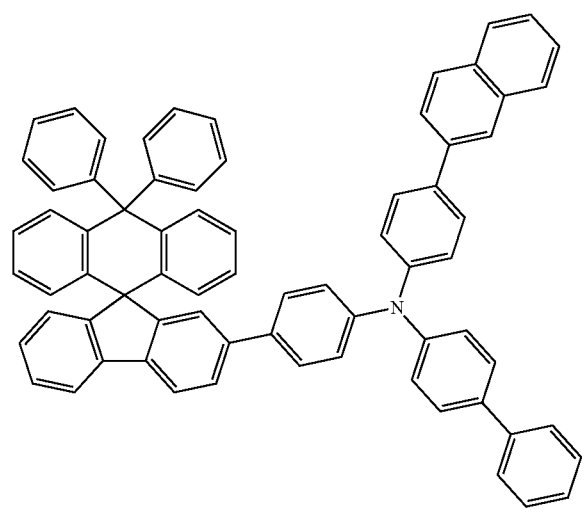
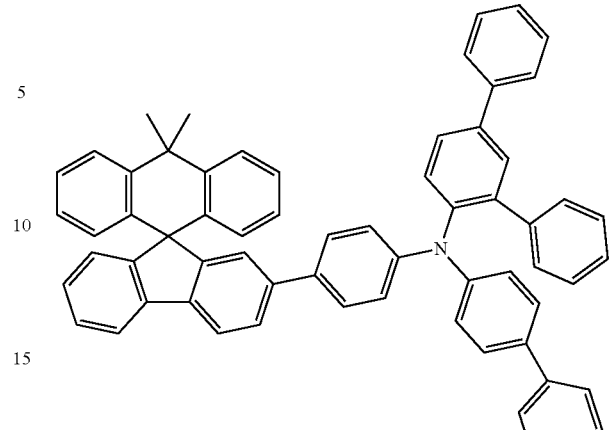
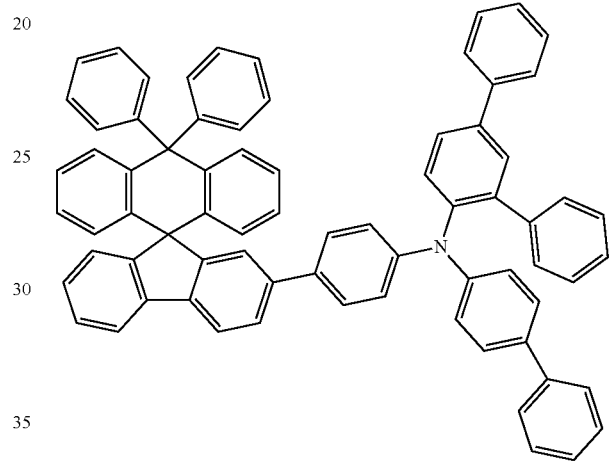
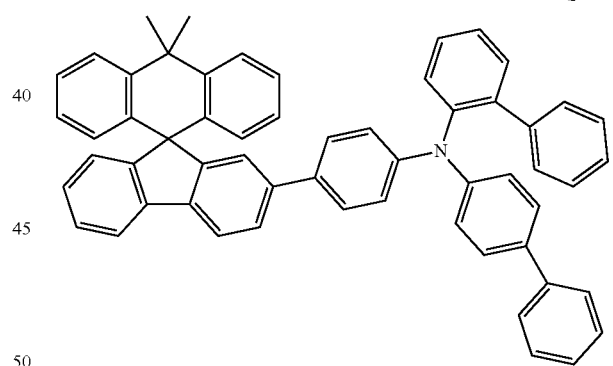
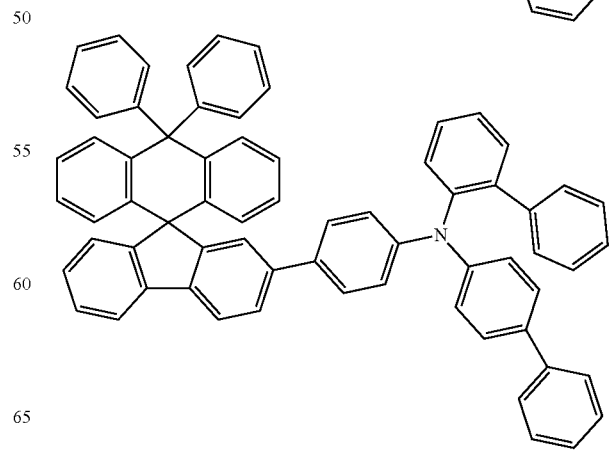

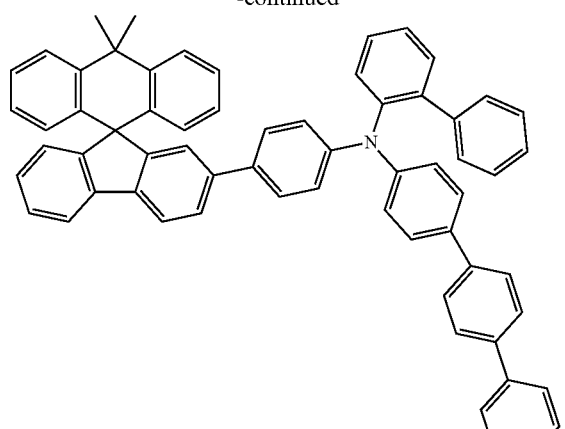
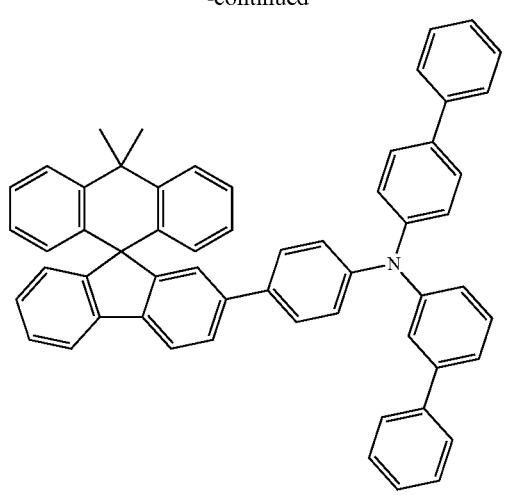
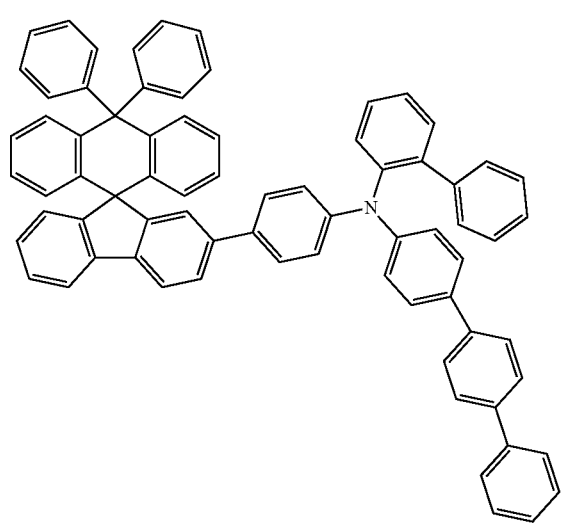
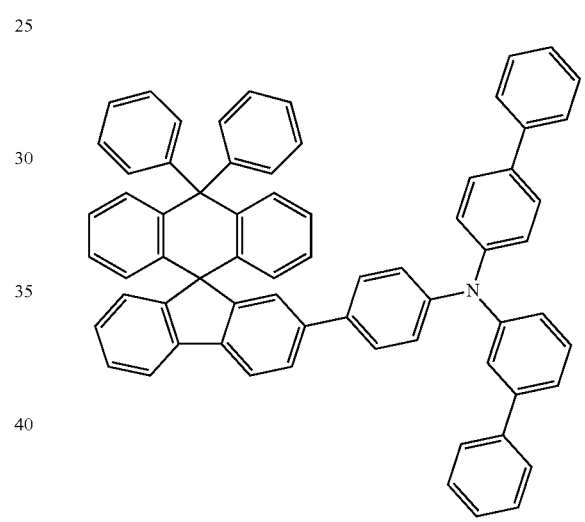
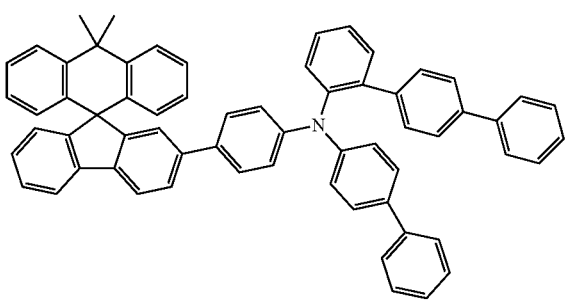
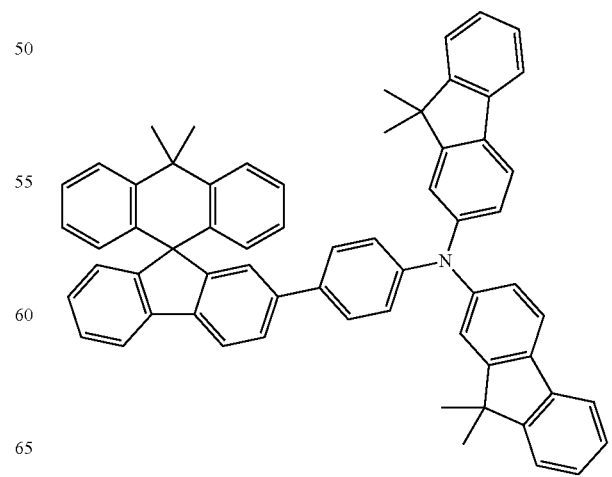

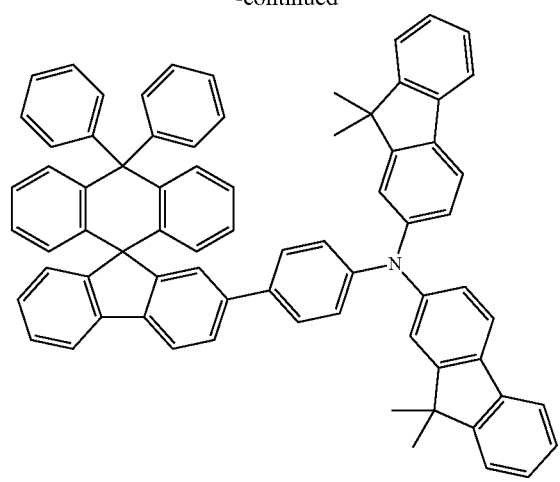
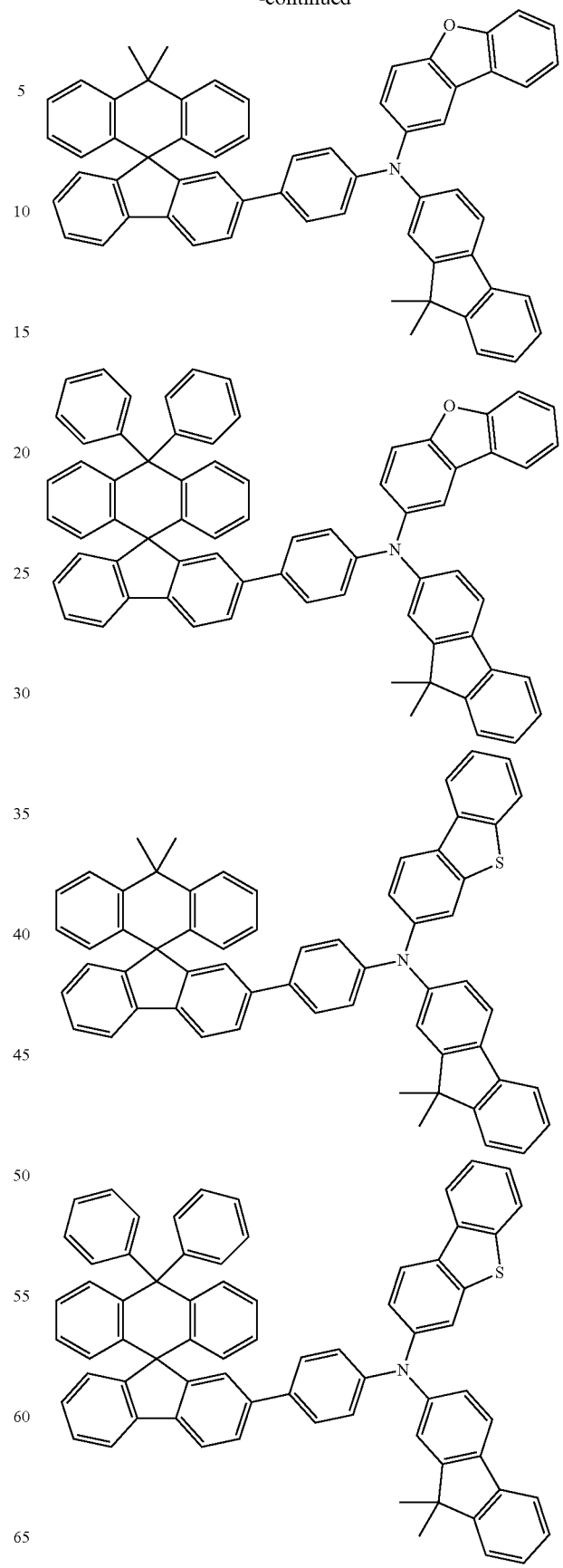

61
-continued
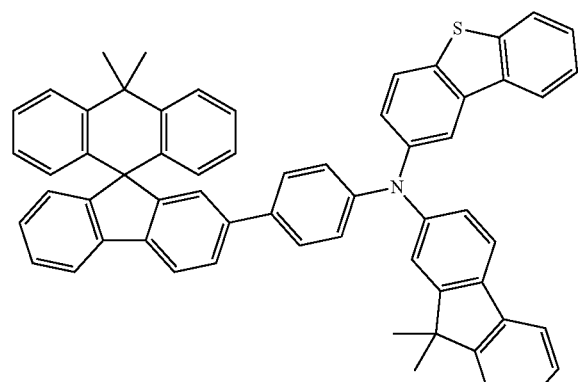
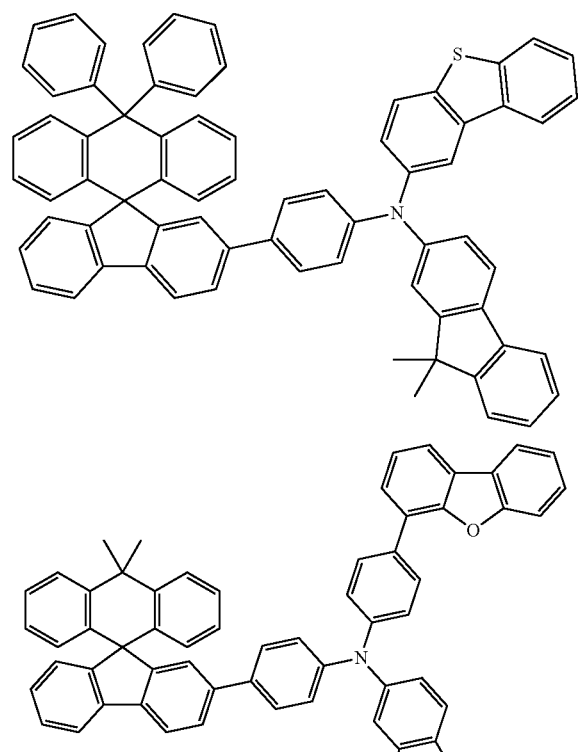
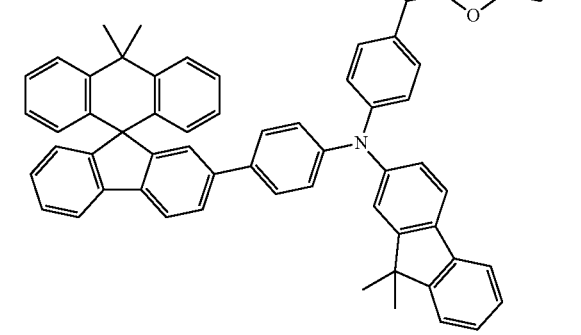
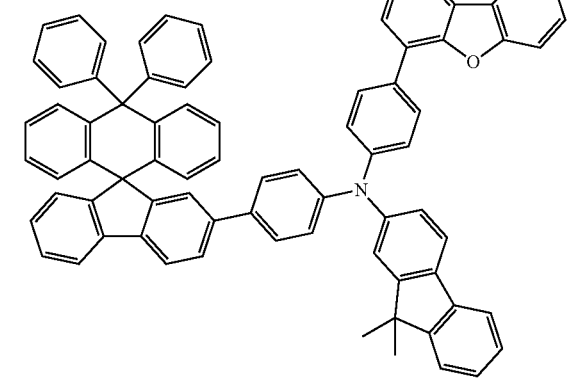
62
-continued
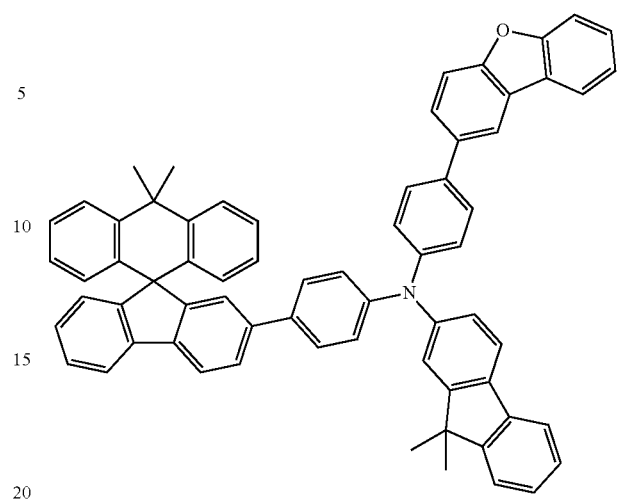
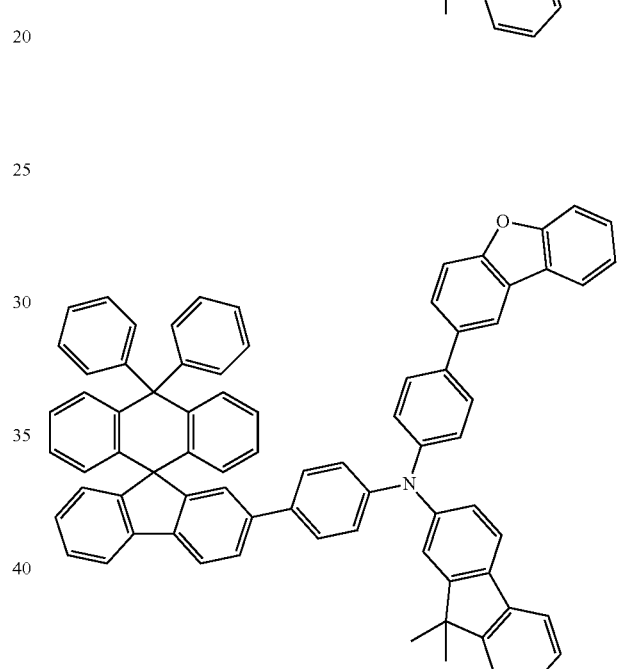
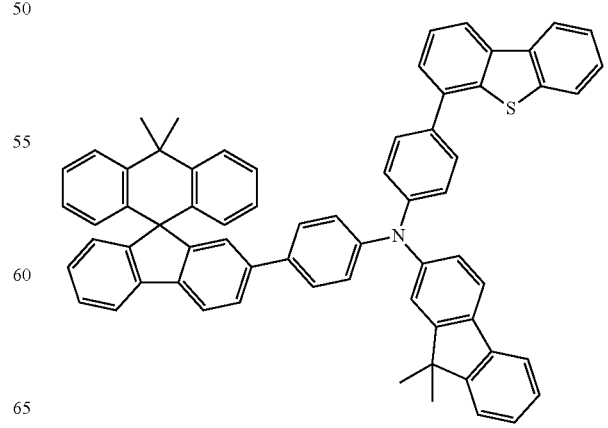

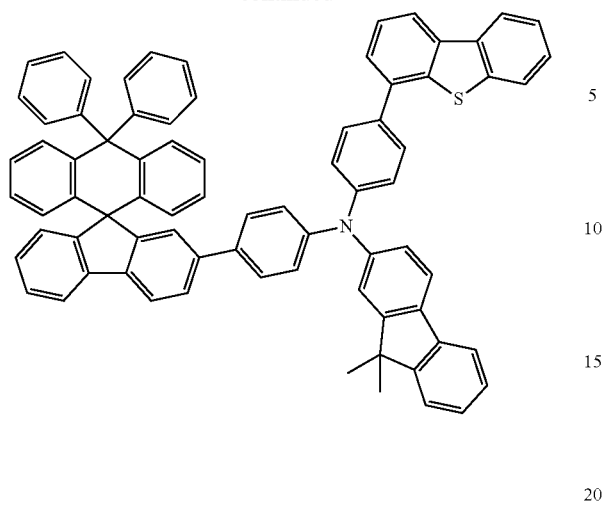
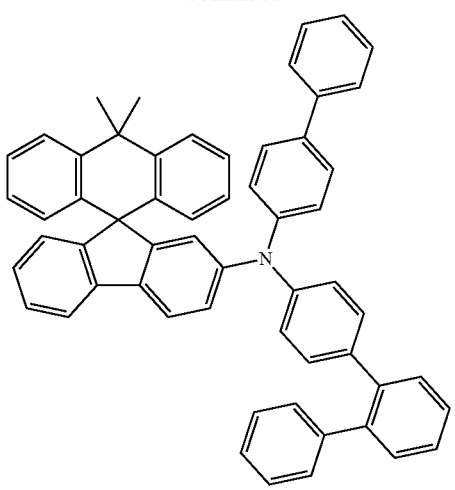
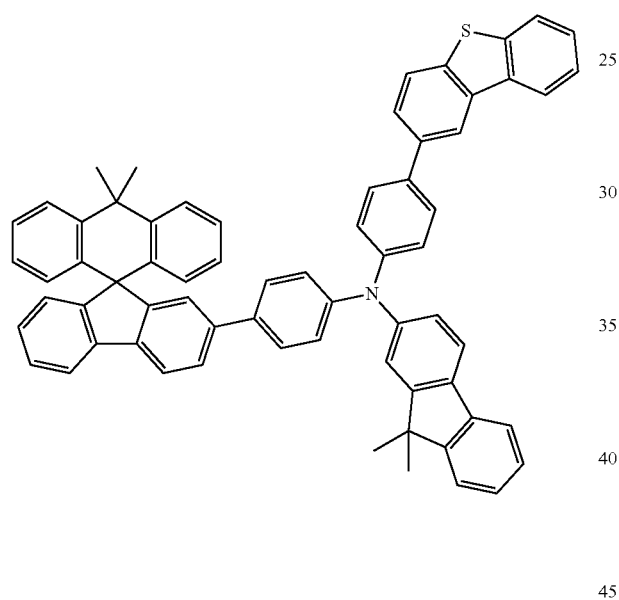
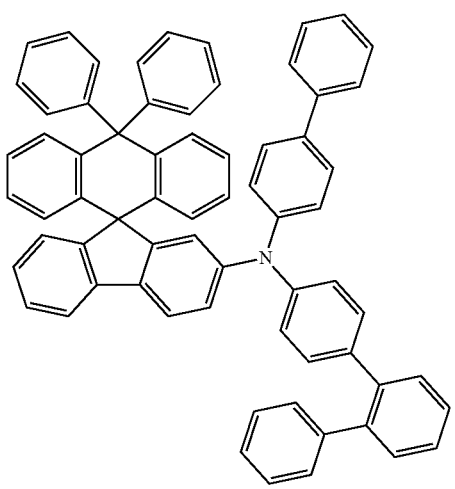
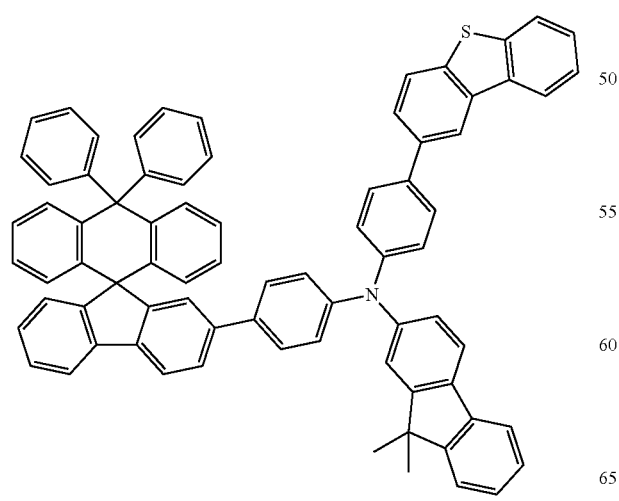
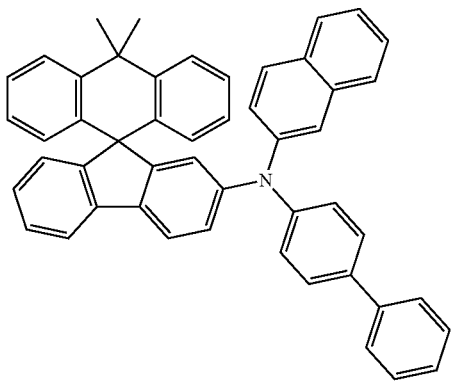

65
-continued
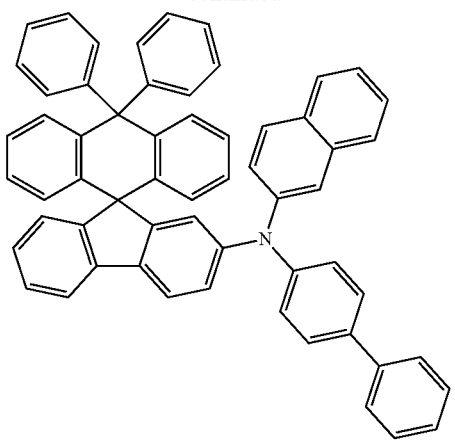
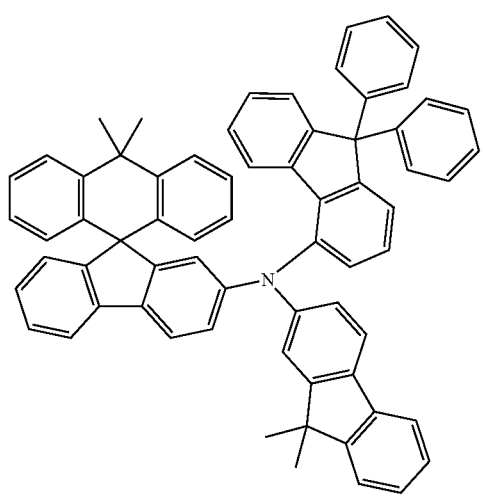
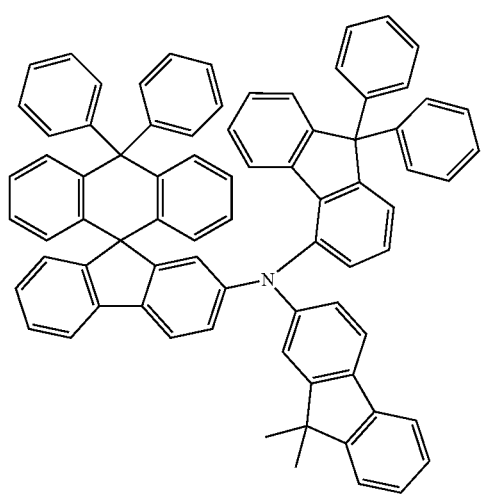
66
-continued
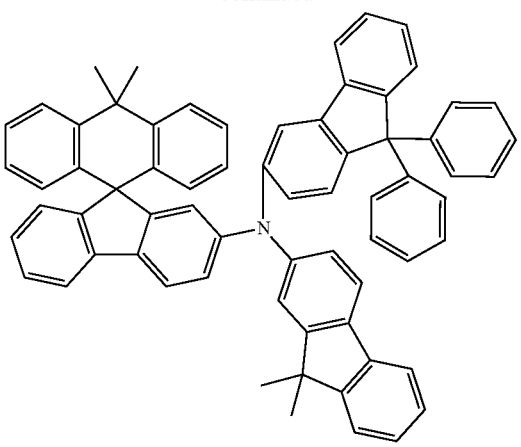
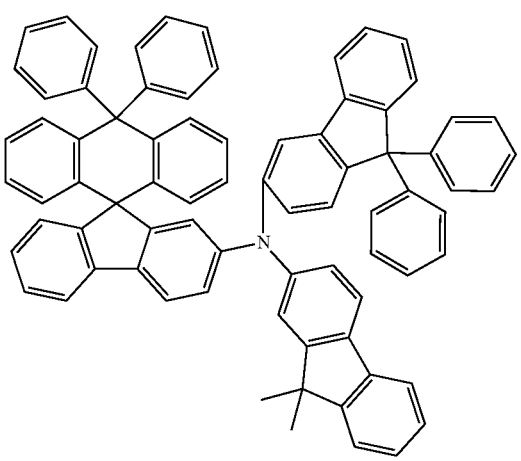
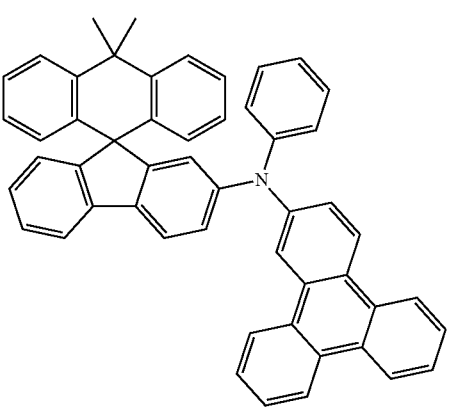

67
-continued
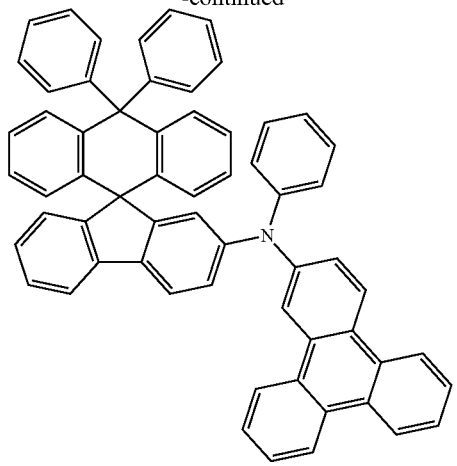
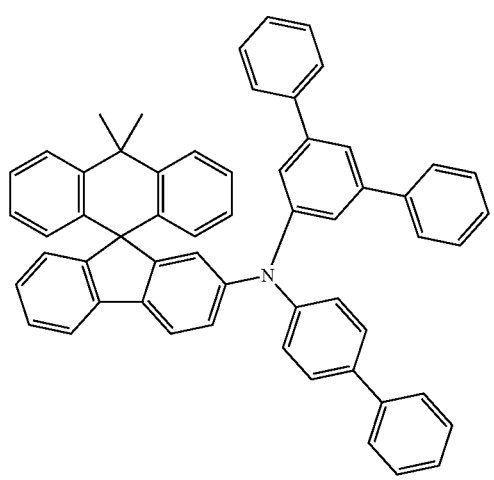
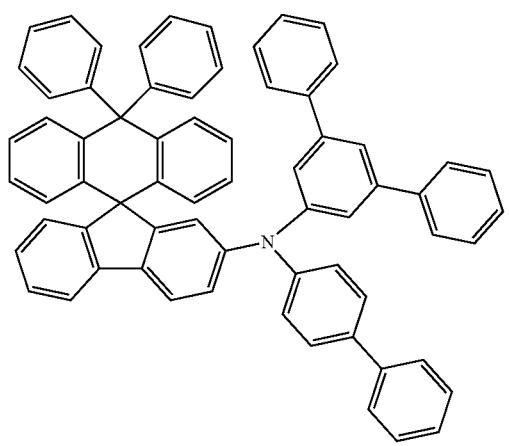
68
-continued
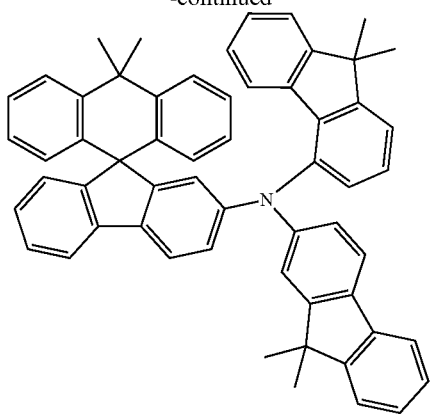
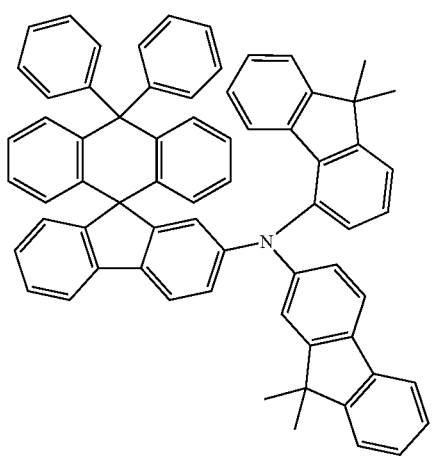
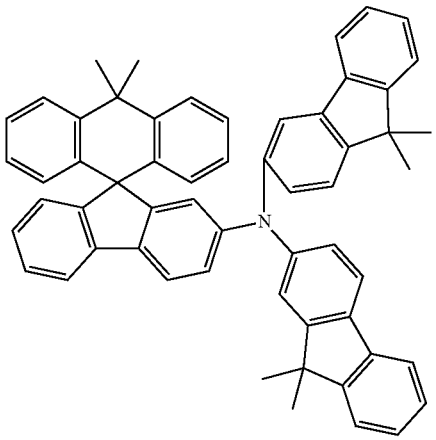

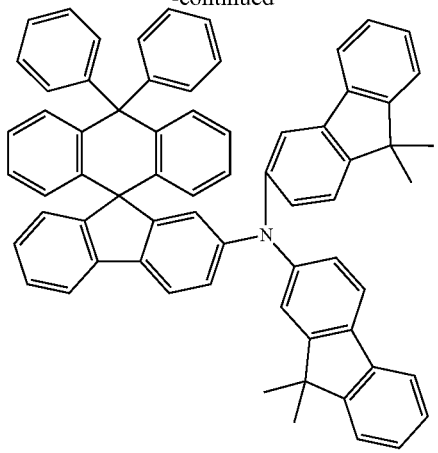
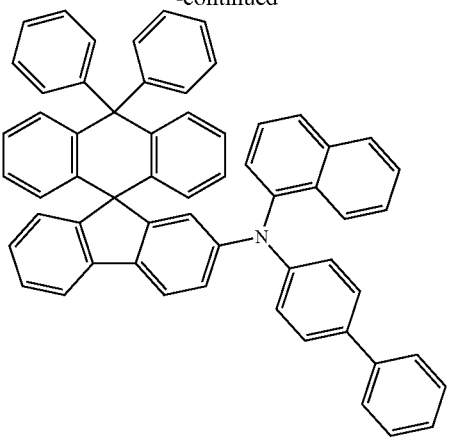
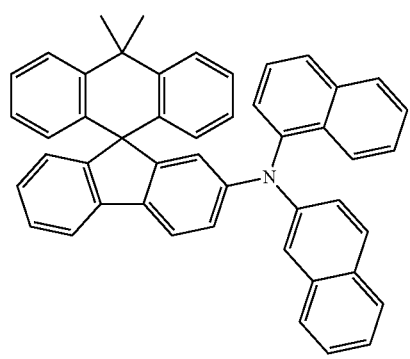
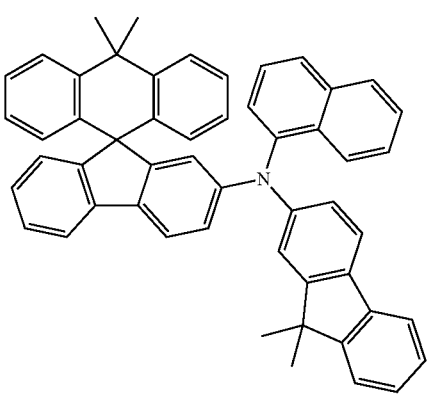
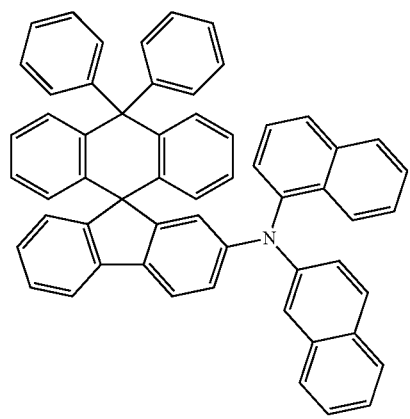
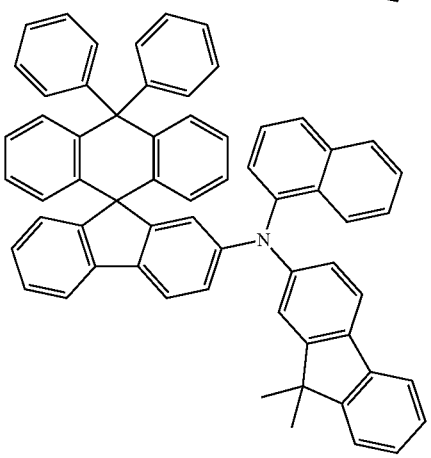
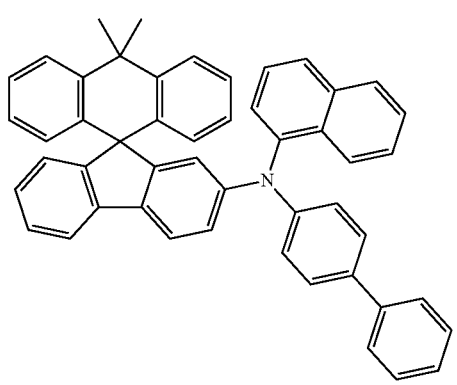
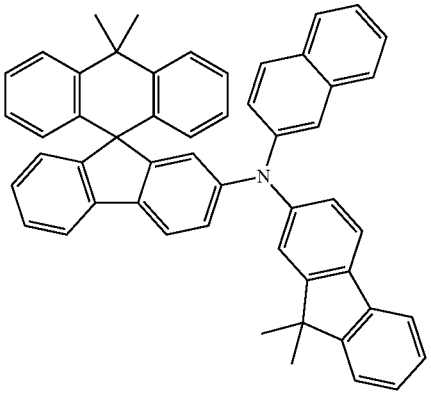

-continued
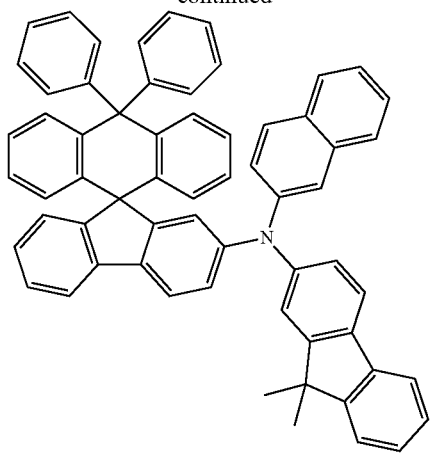
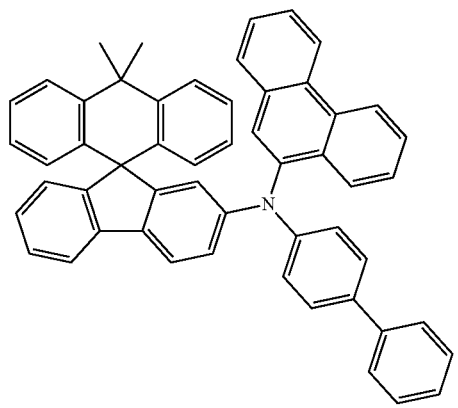
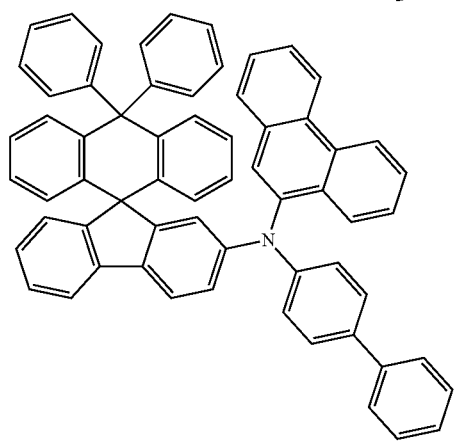
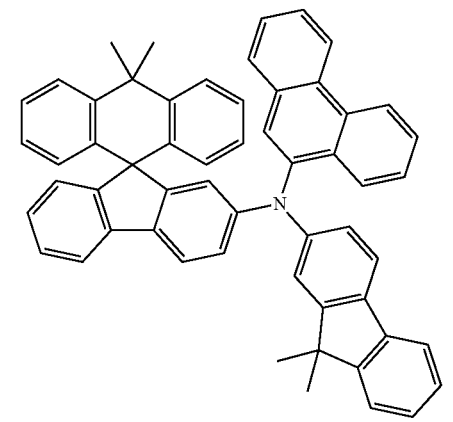
-continued
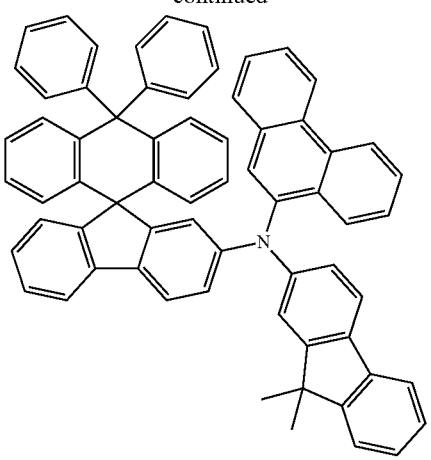
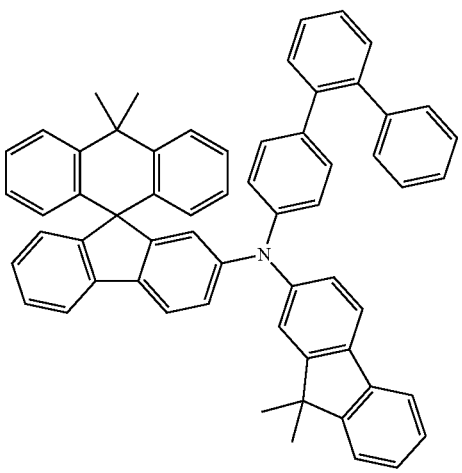
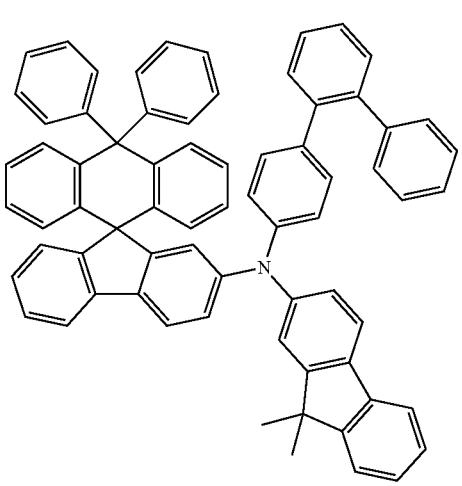

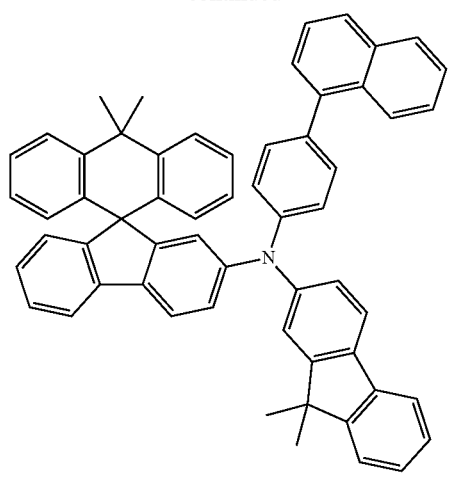
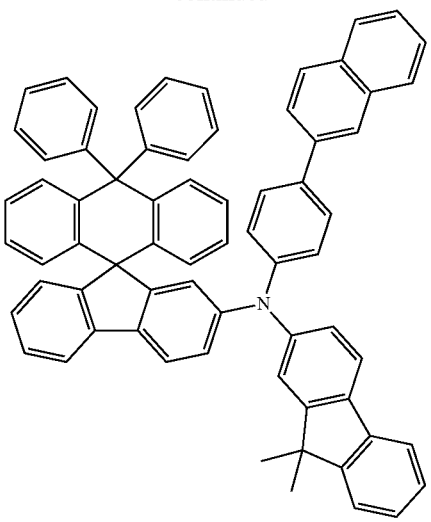
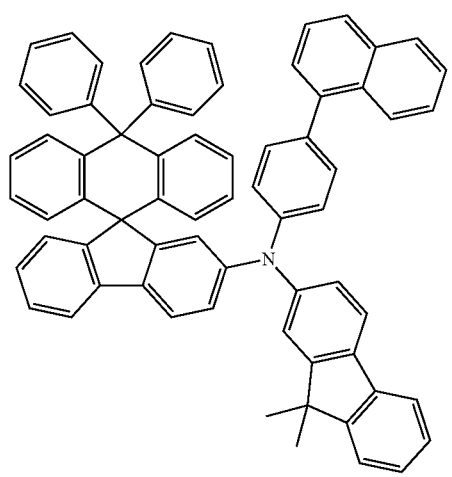
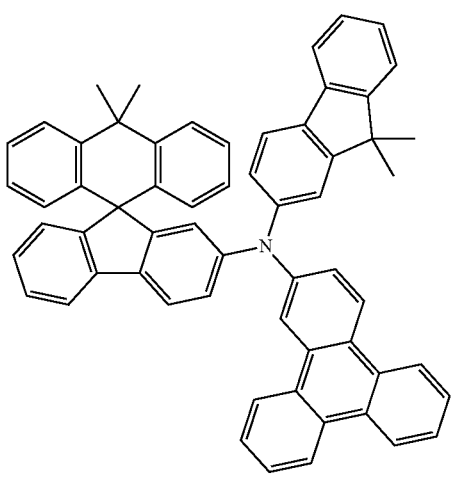
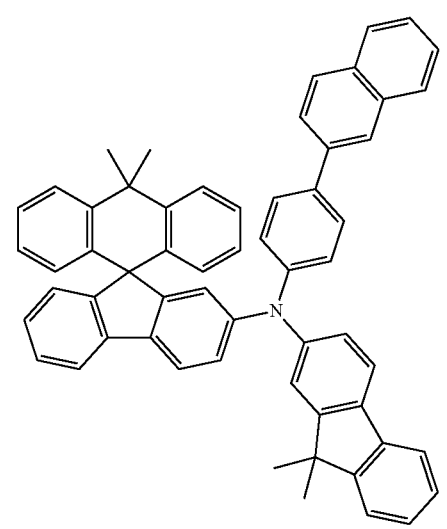
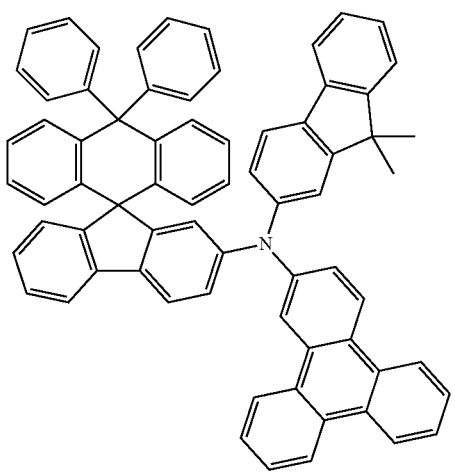

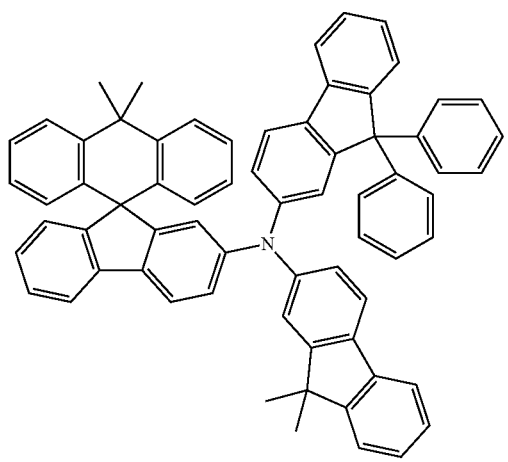
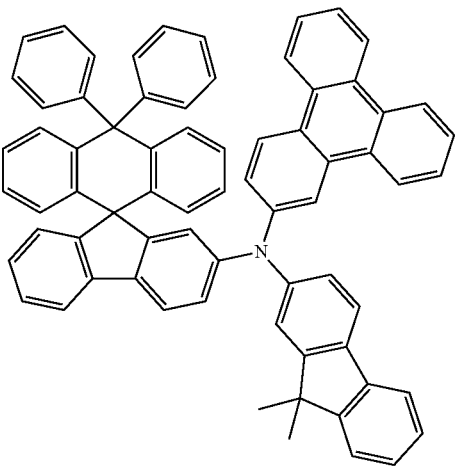
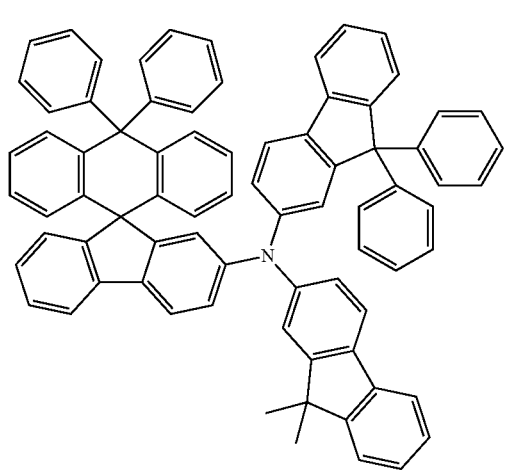
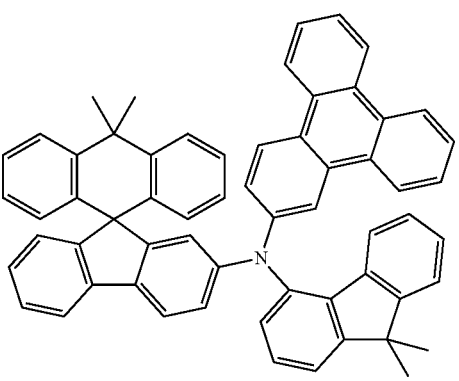
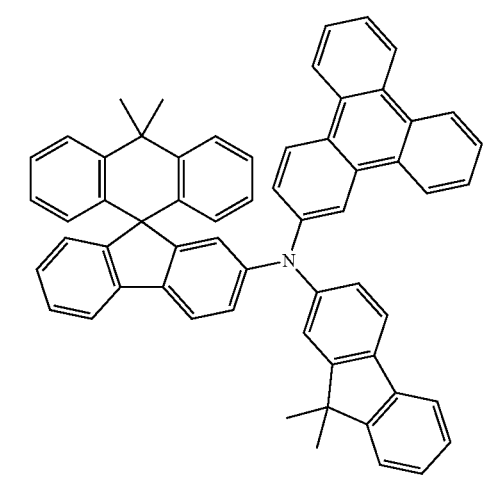
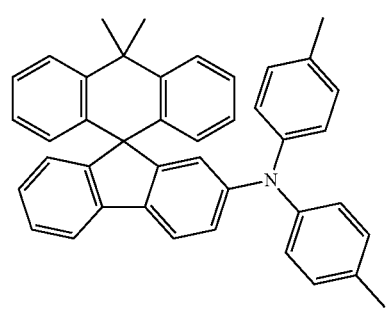

-continued
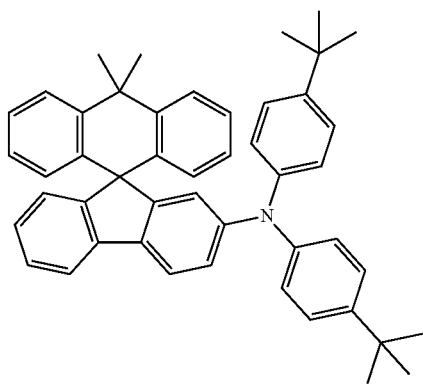
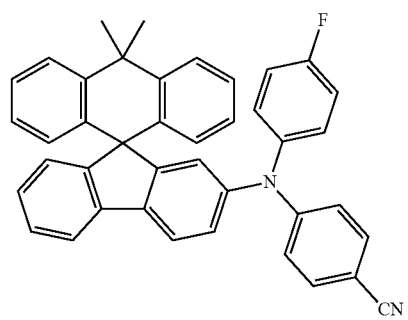
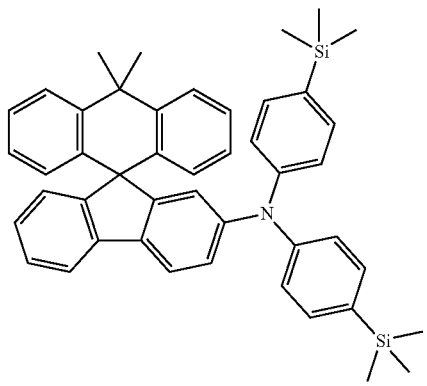
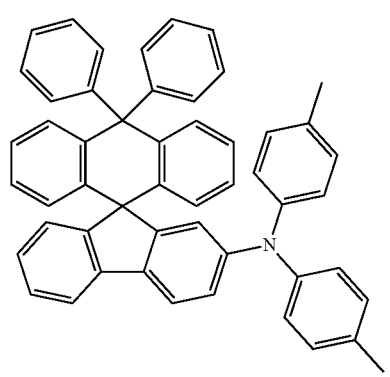
-continued
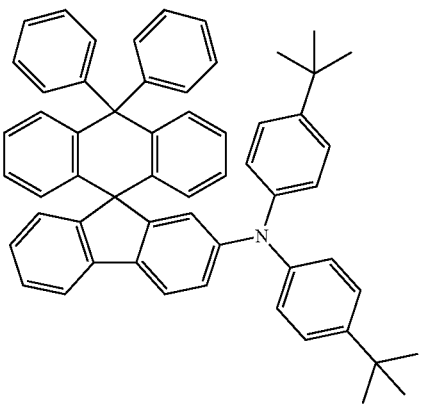
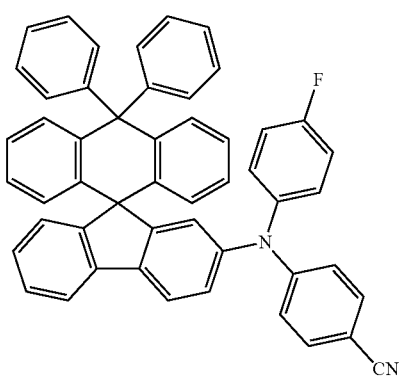
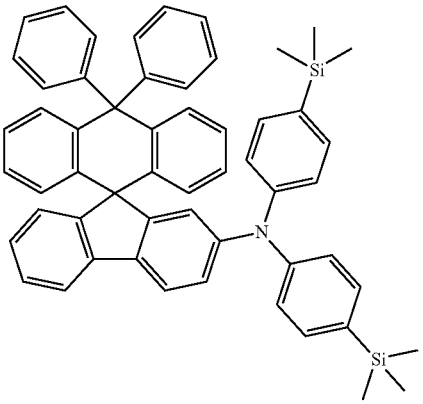
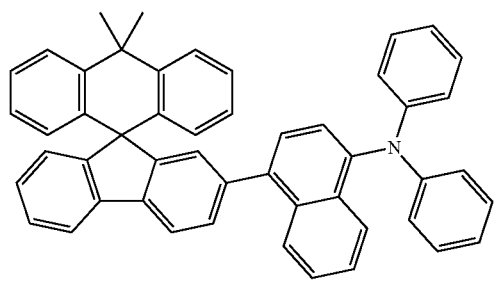

79
-continued
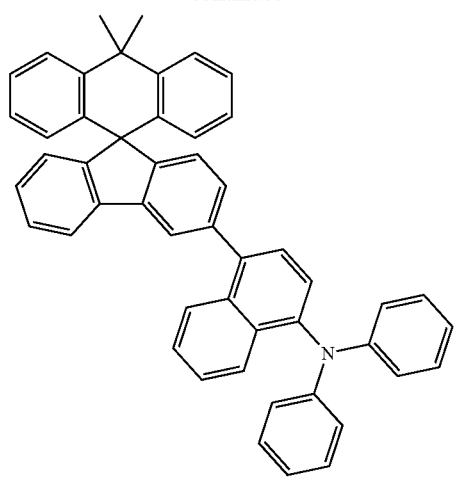
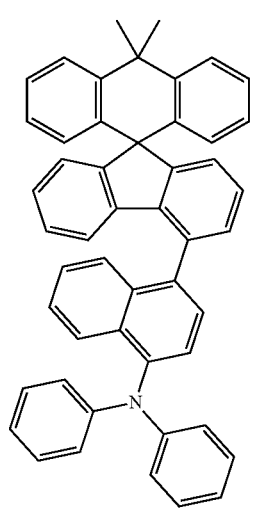
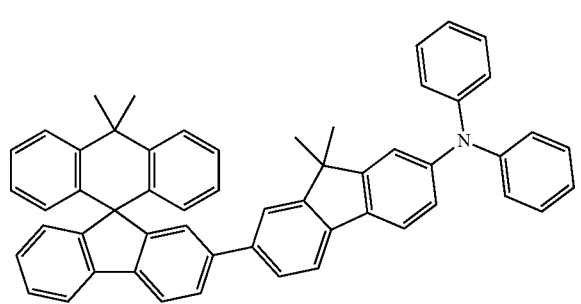
80
-continued
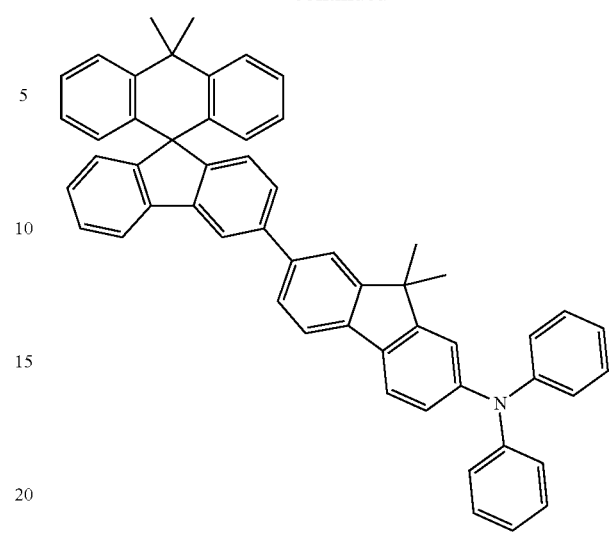
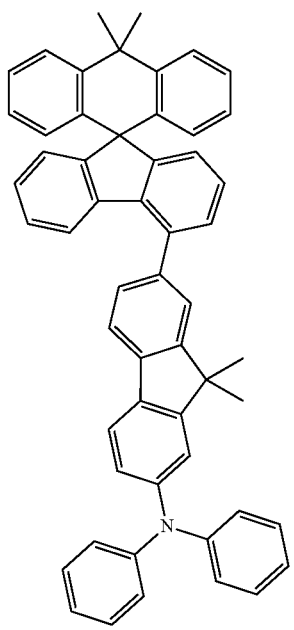
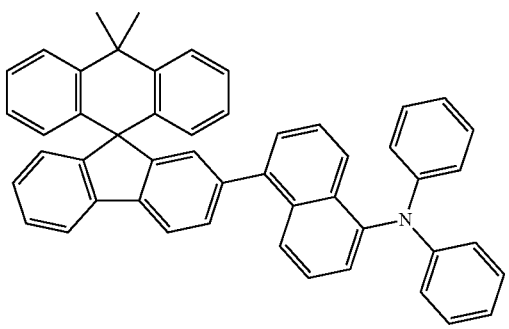

81
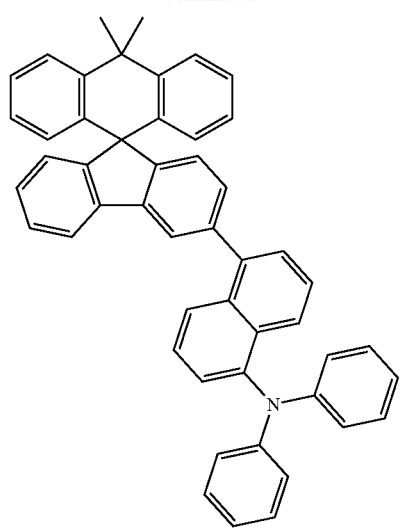
82
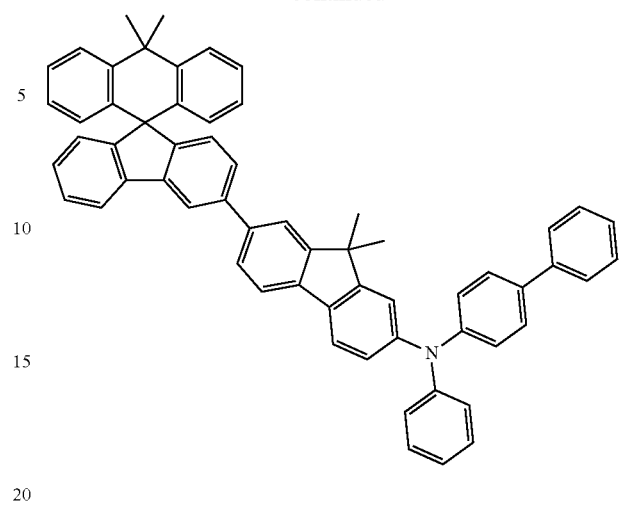
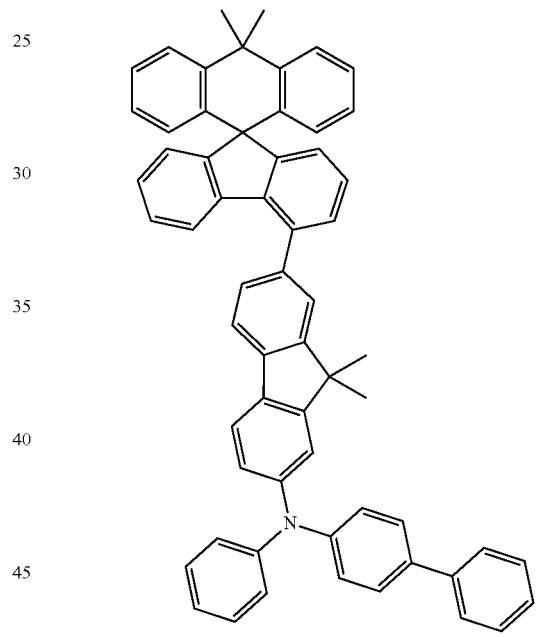
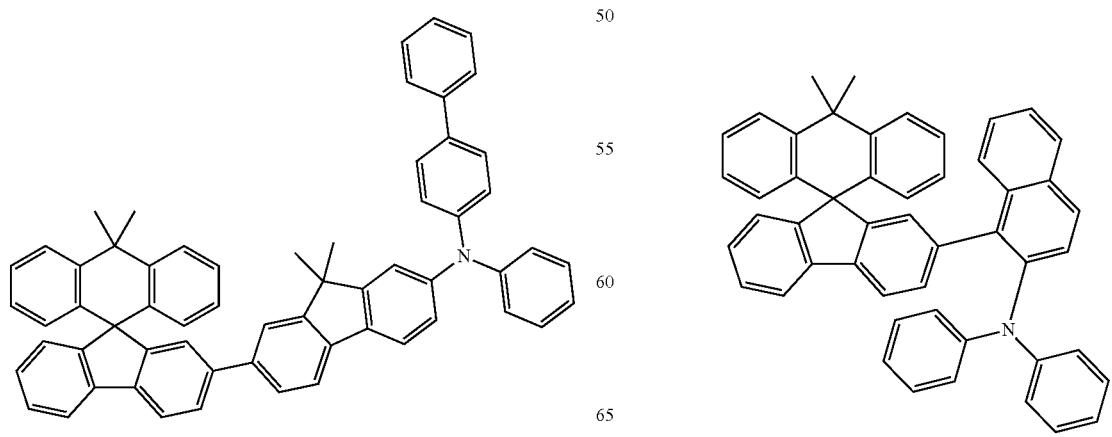

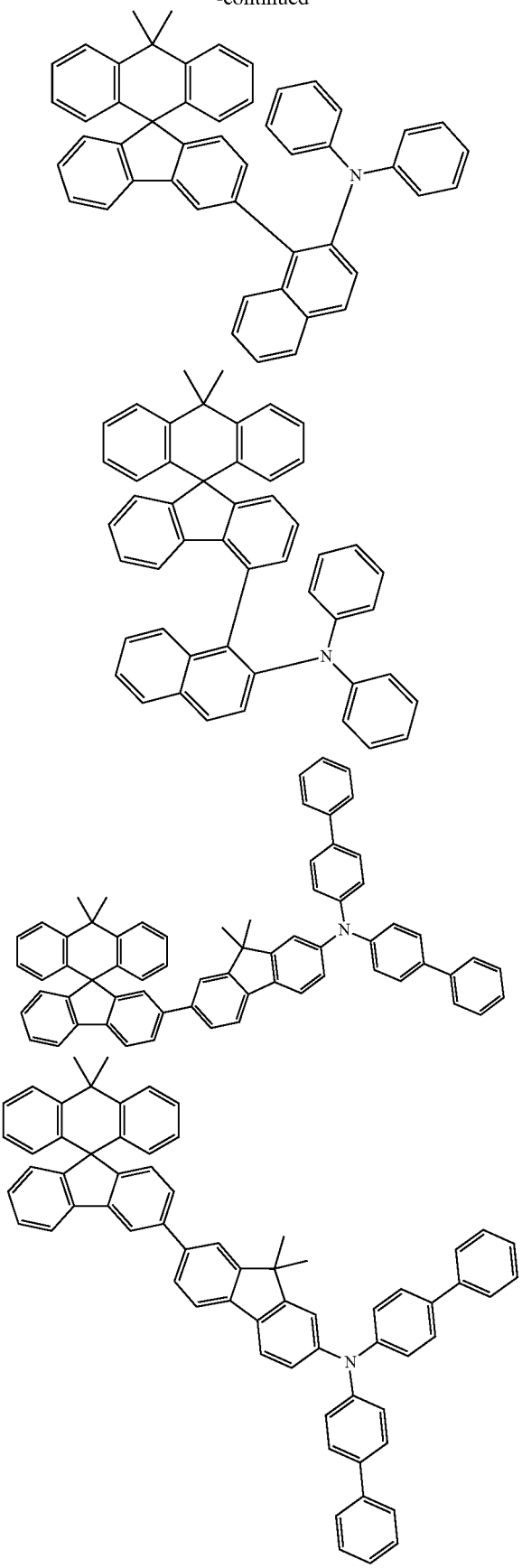
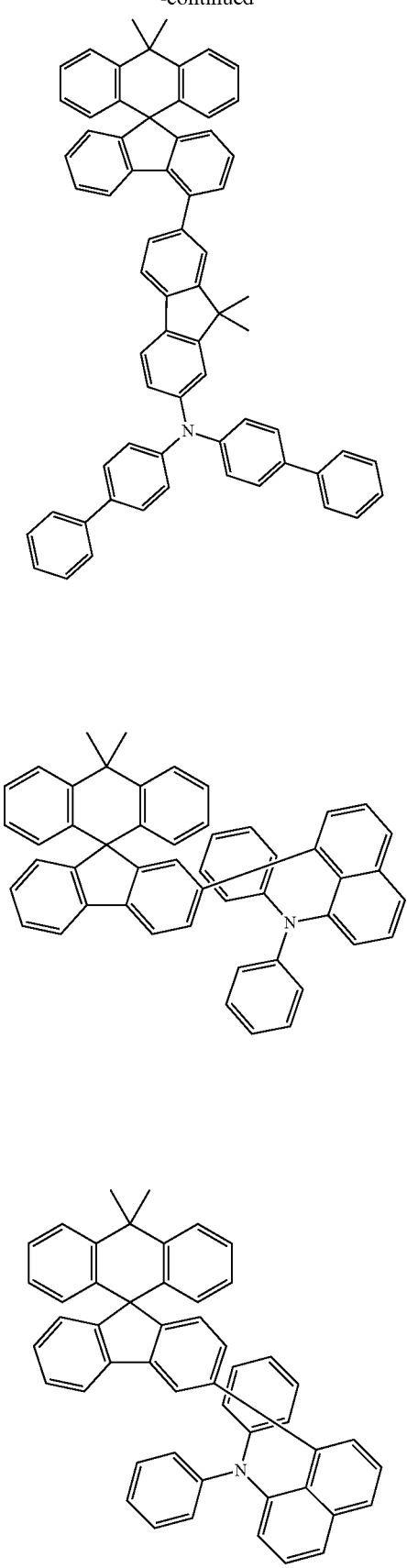

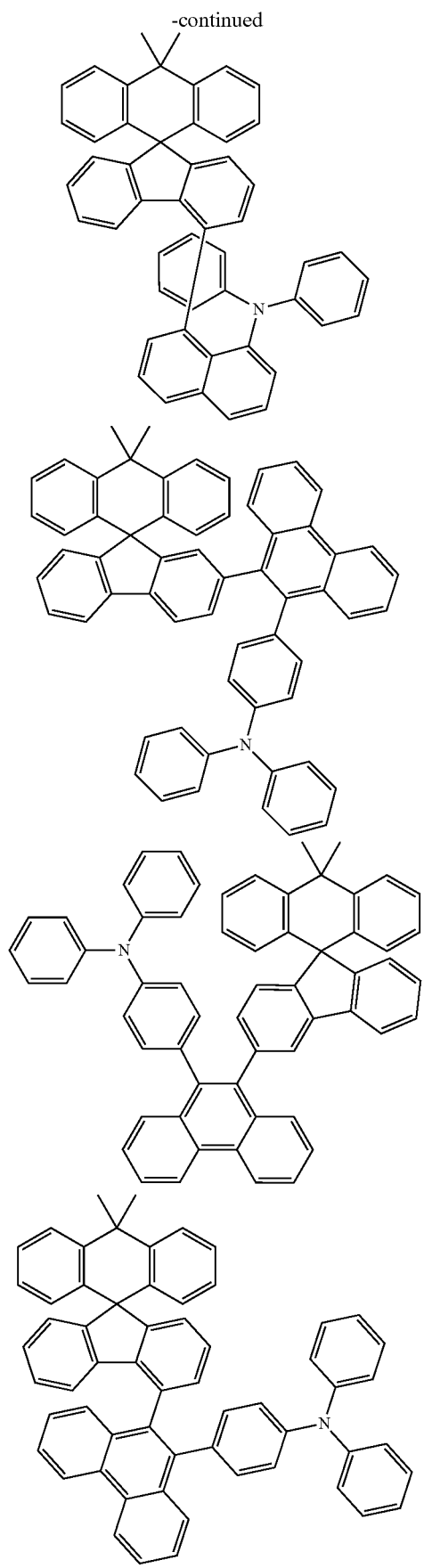
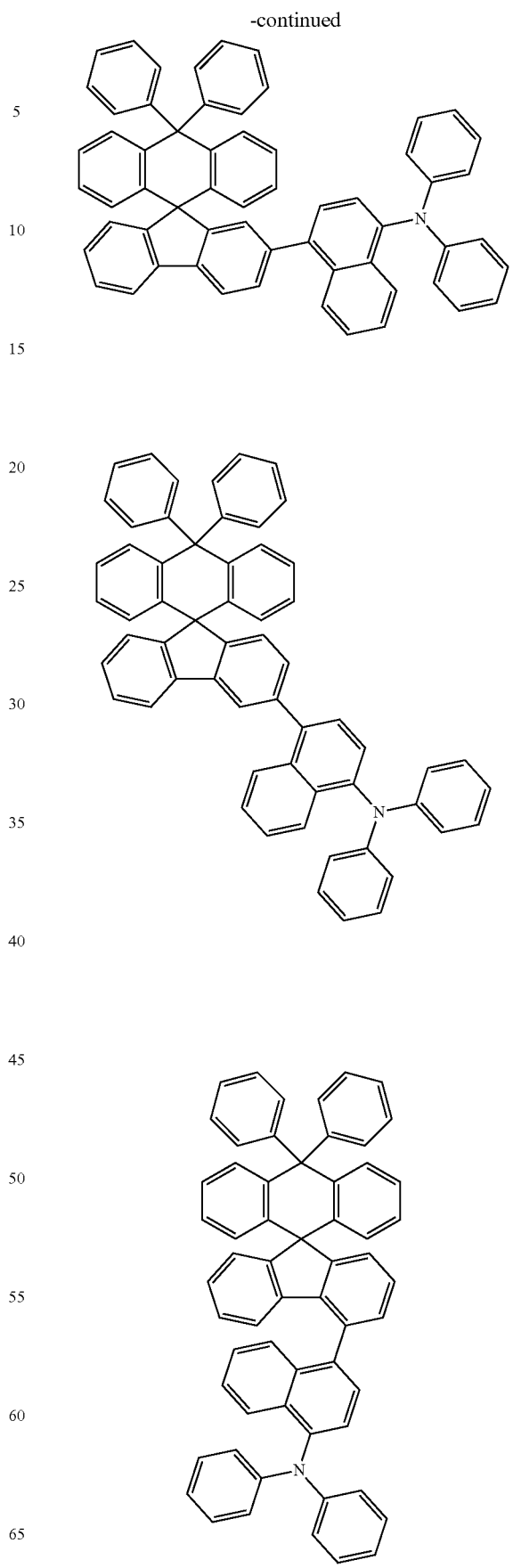

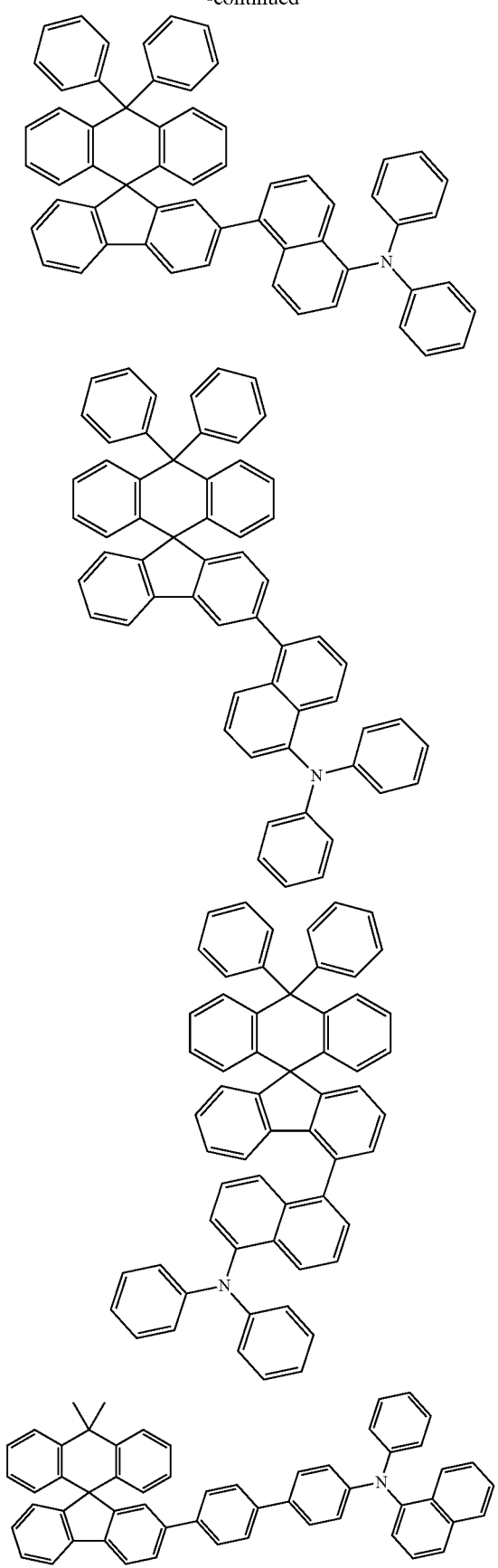
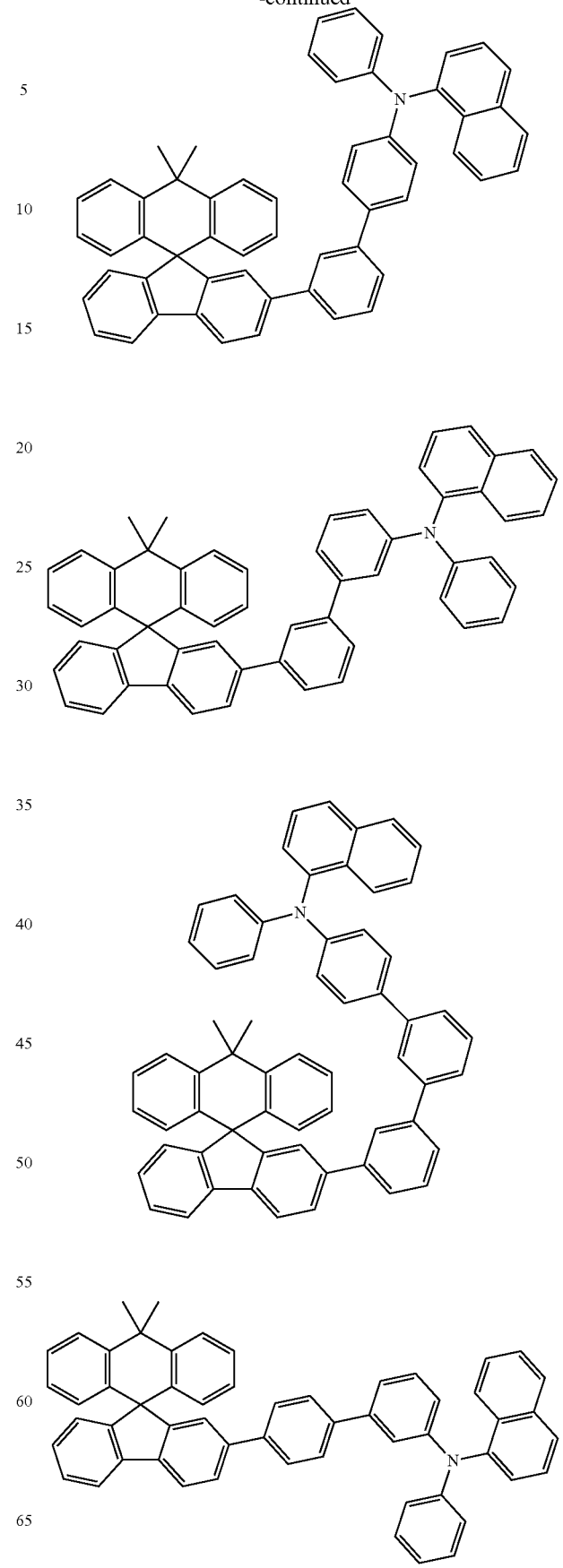

-continued
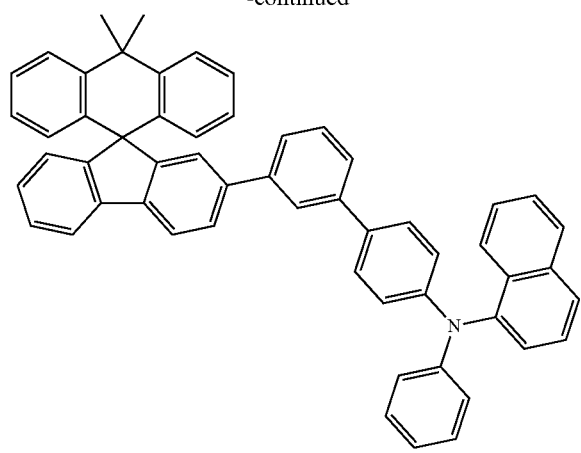
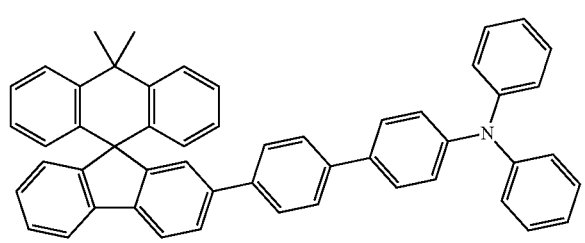
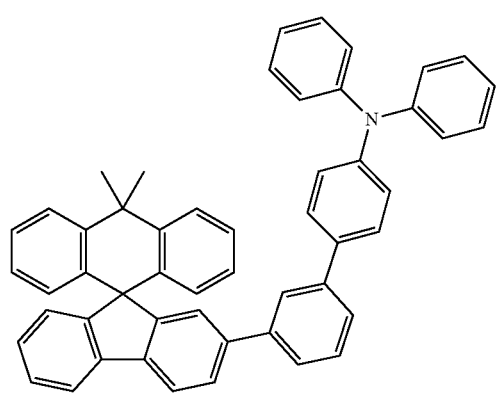
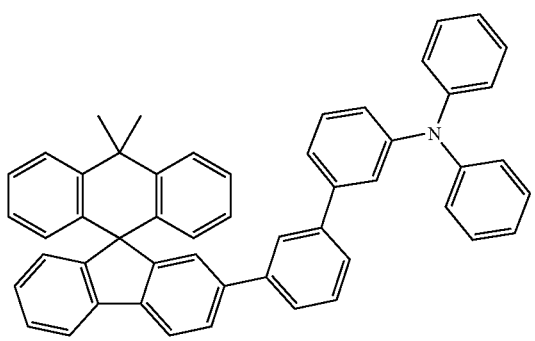
-continued
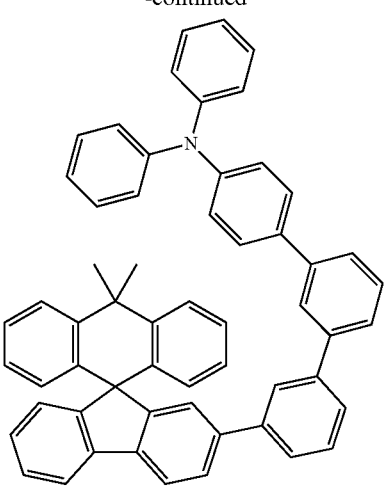
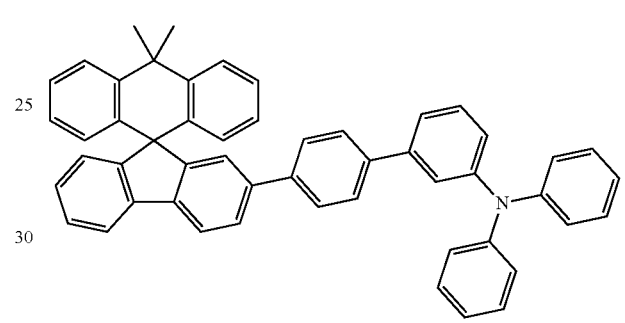
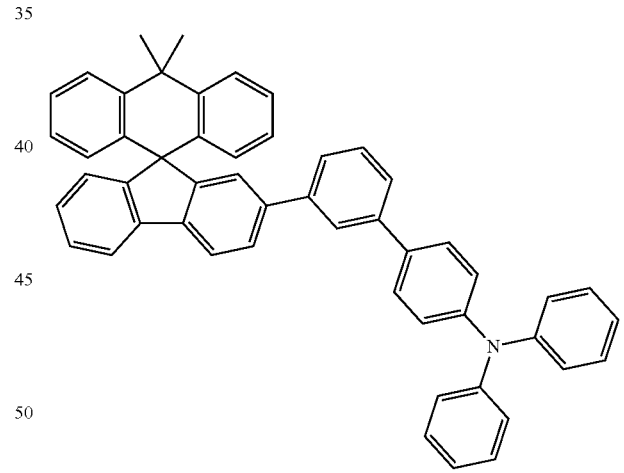
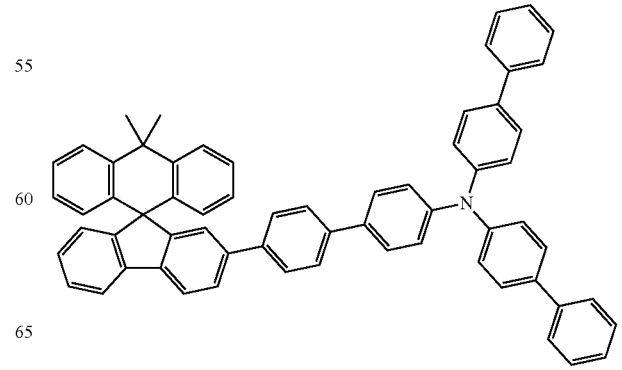

91
-continued
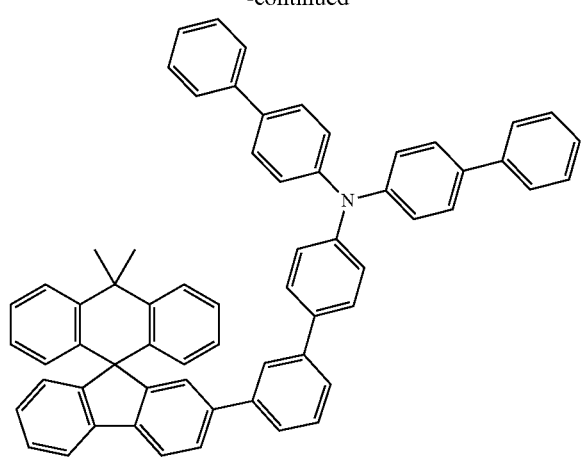
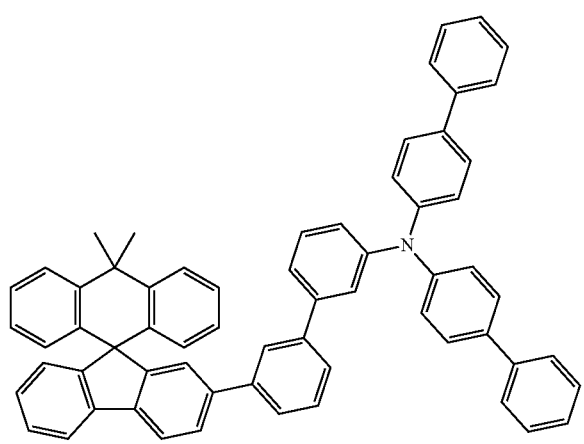
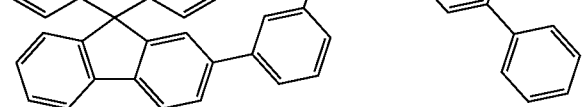
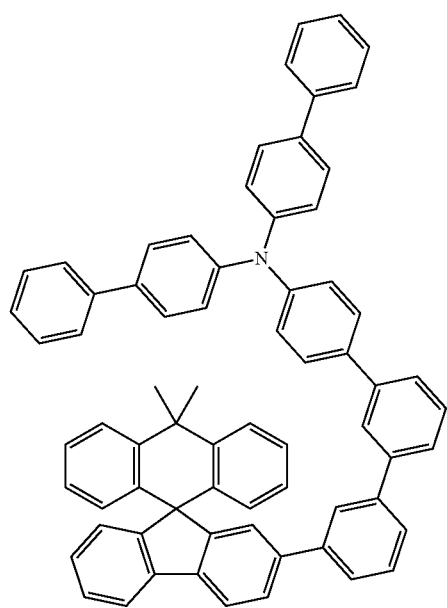
92
-continued
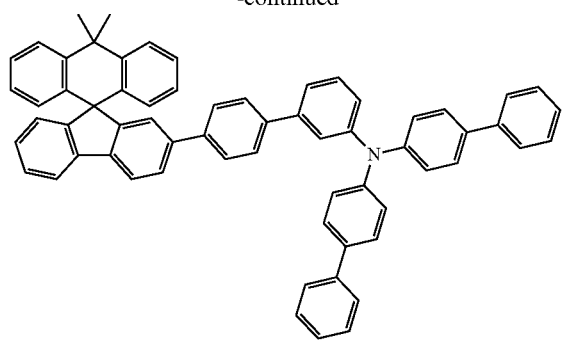
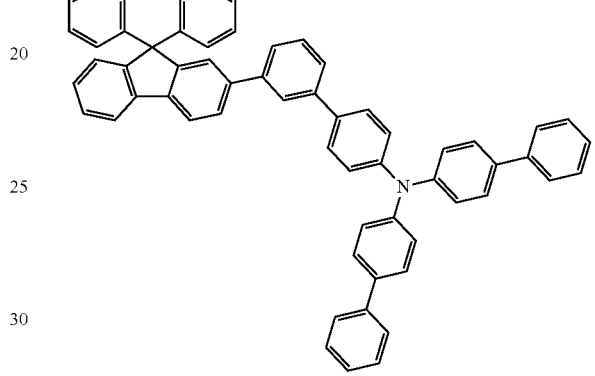
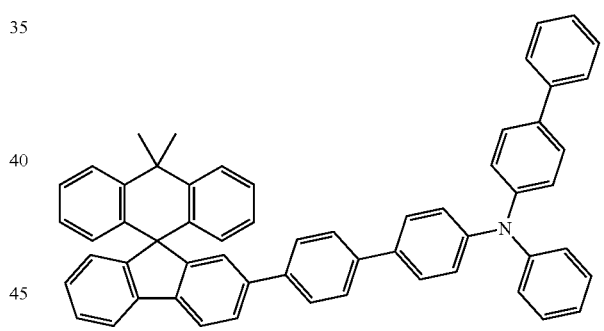
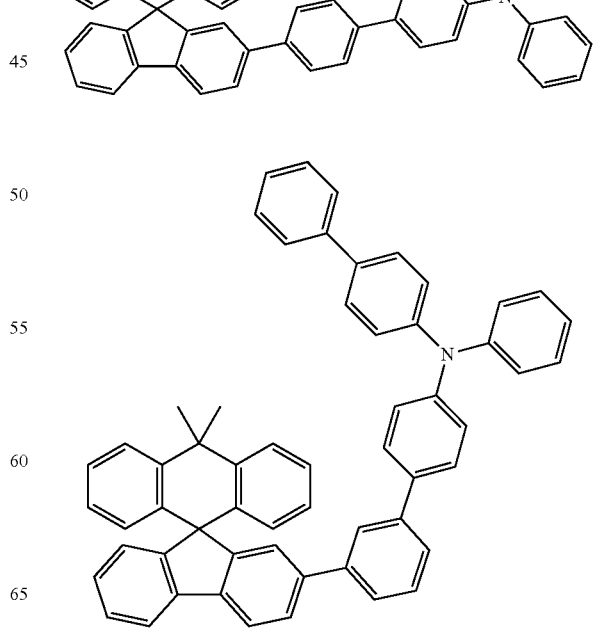

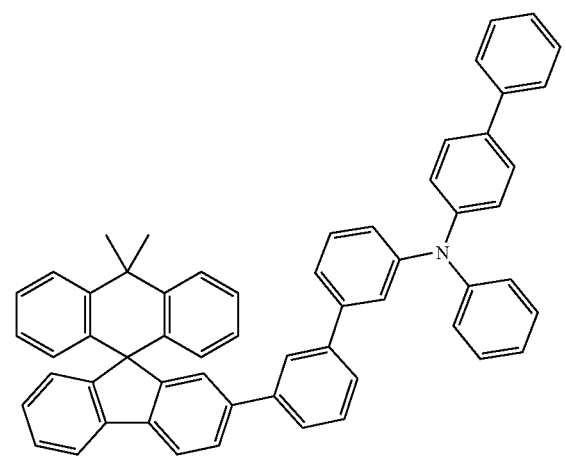
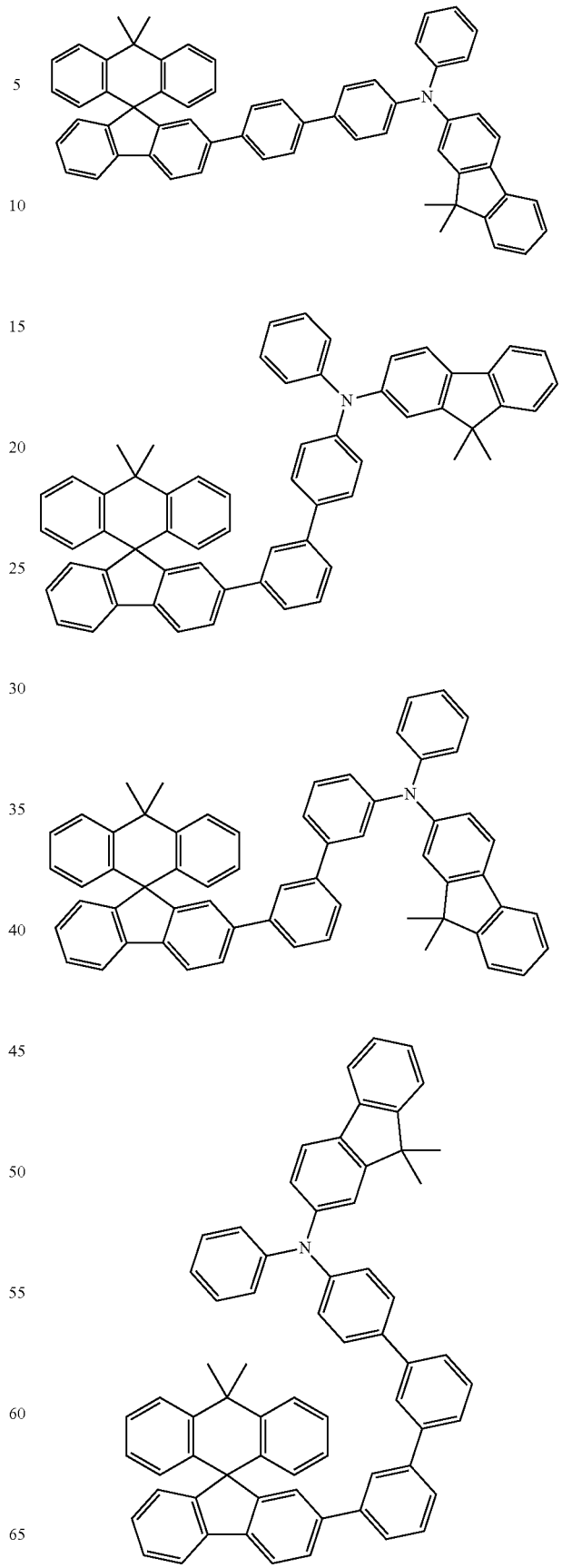

95
-continued
96
-continued
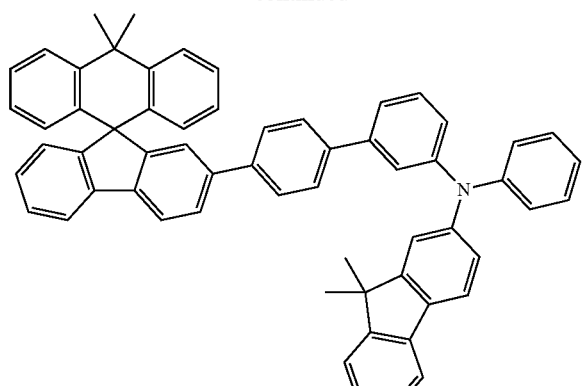
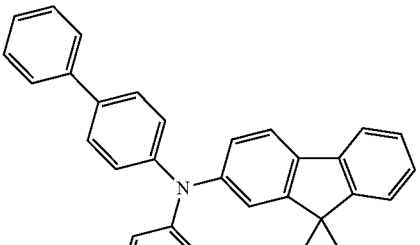
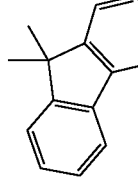
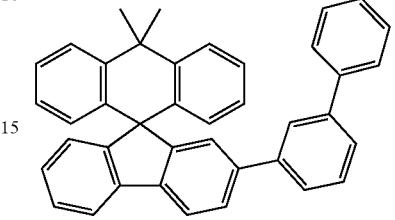
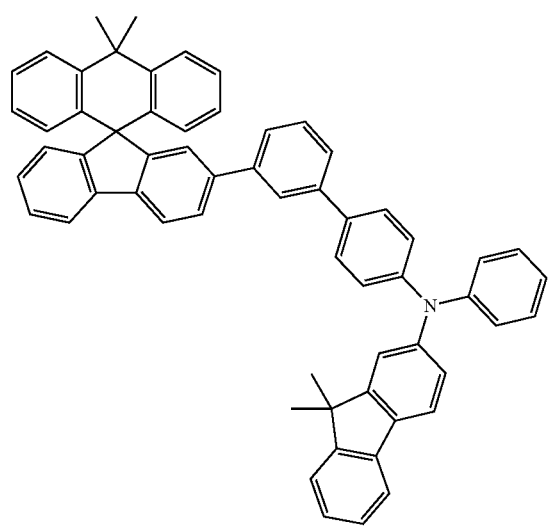
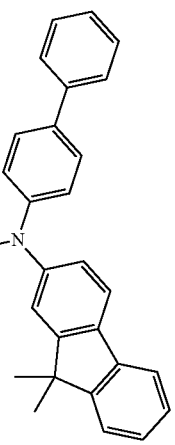
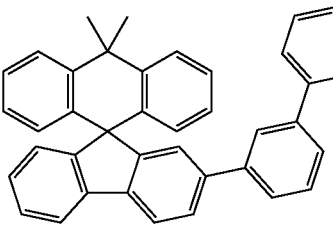
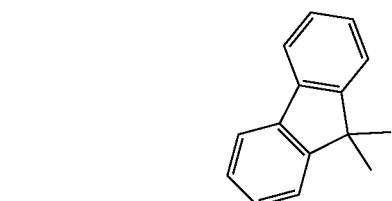
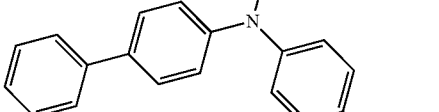
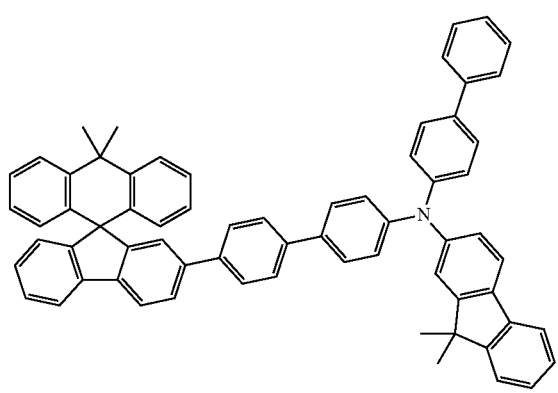
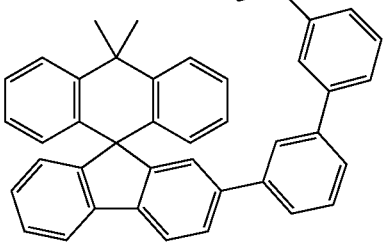

97
-continued
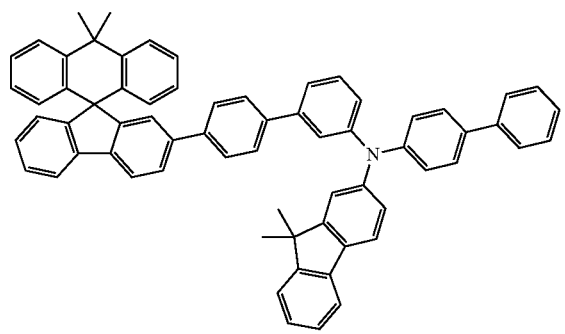
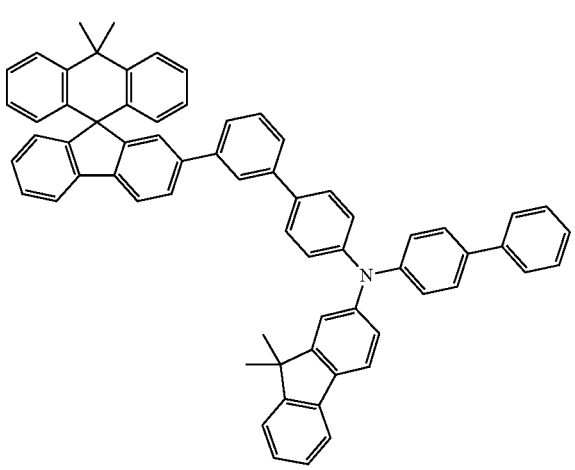
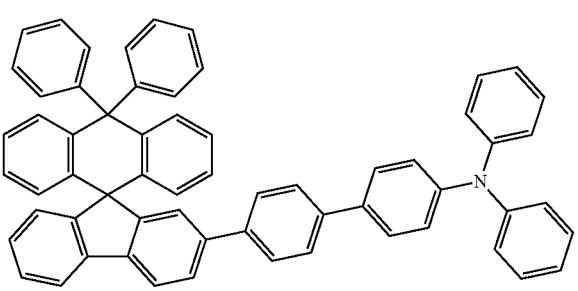
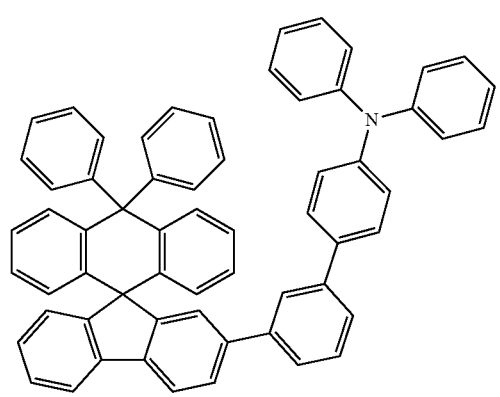
98
-continued
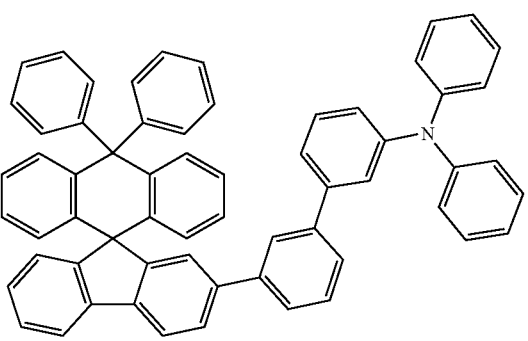
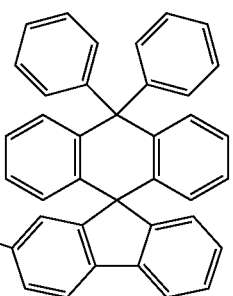
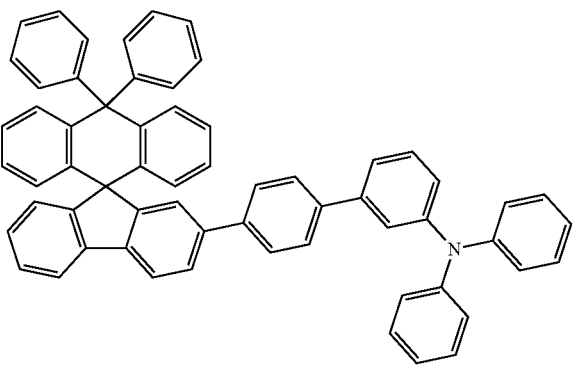

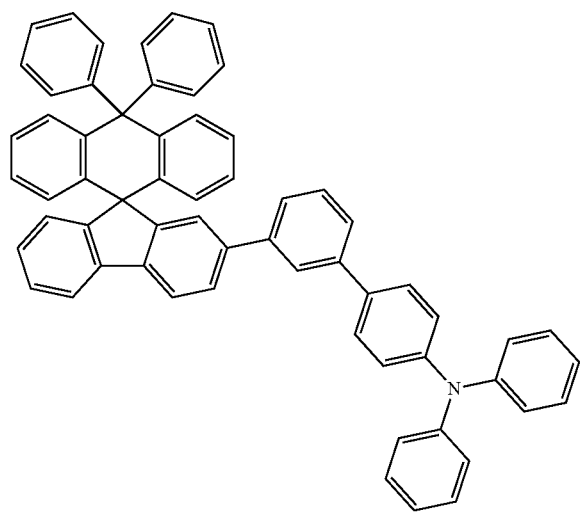
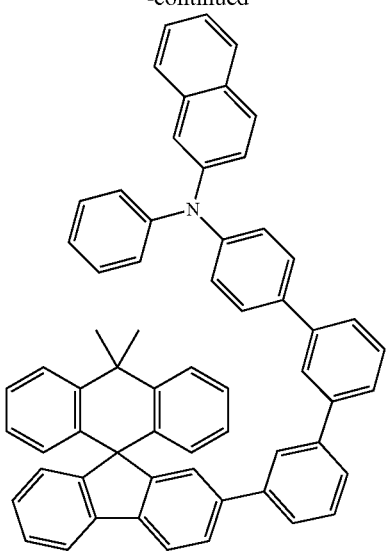
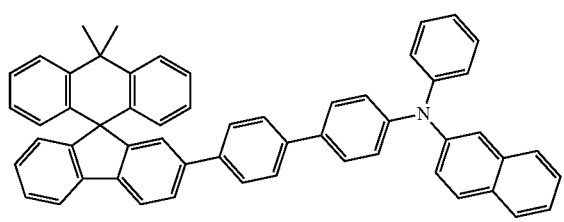
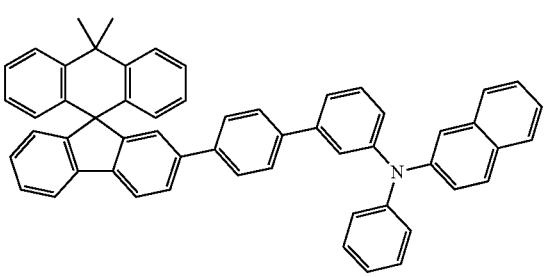
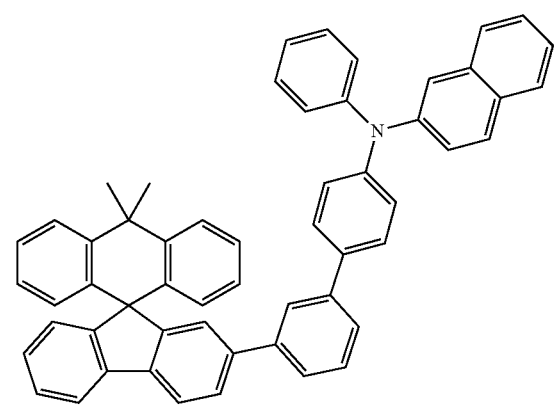
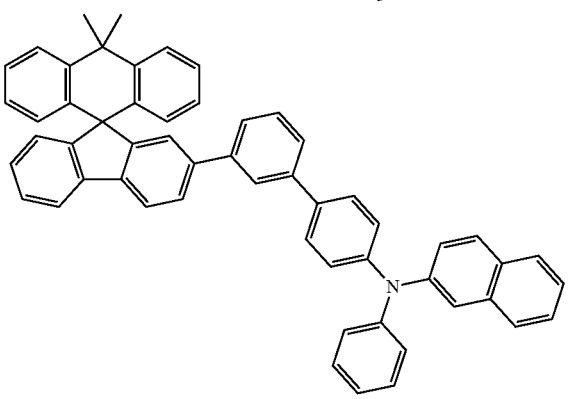
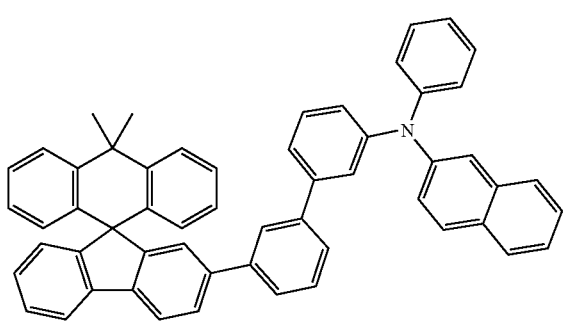
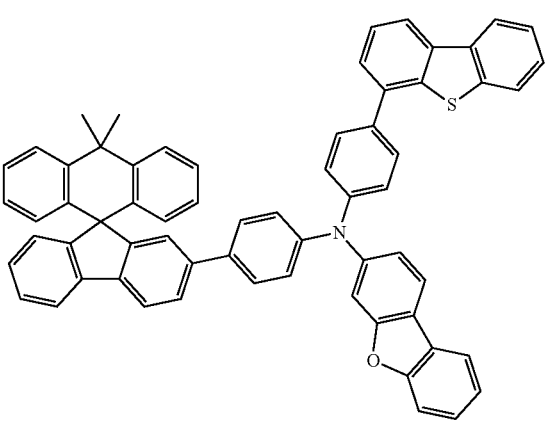

101
-continued
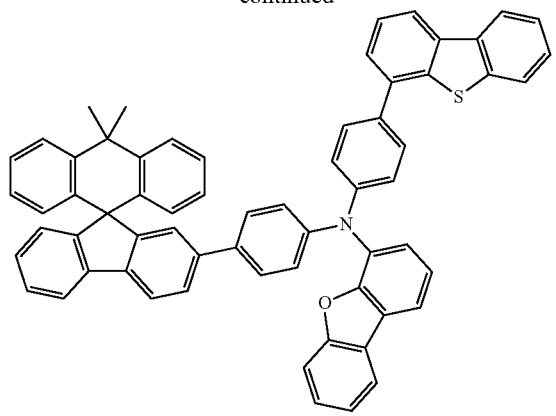
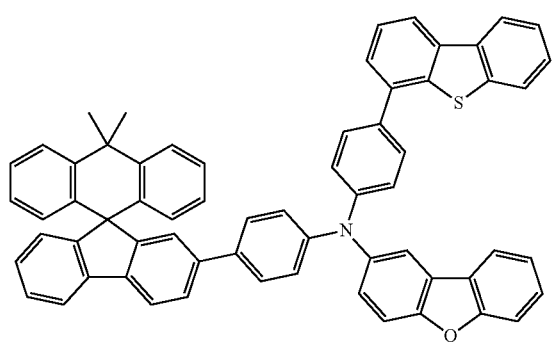
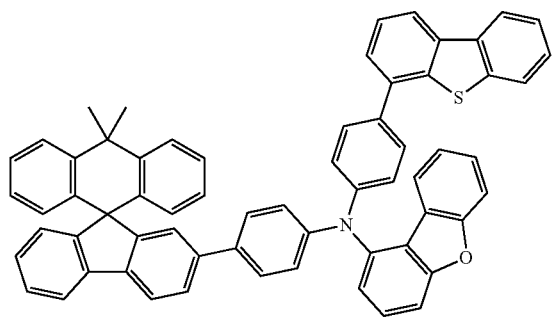
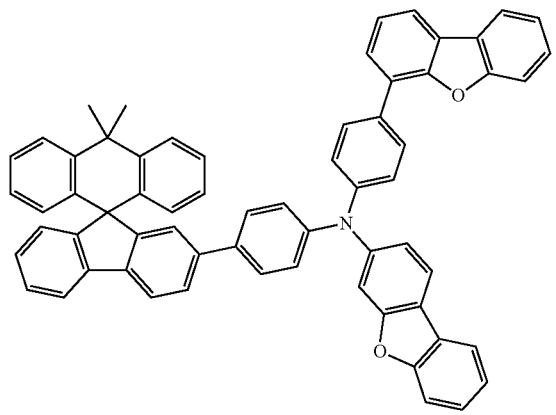
102
-continued
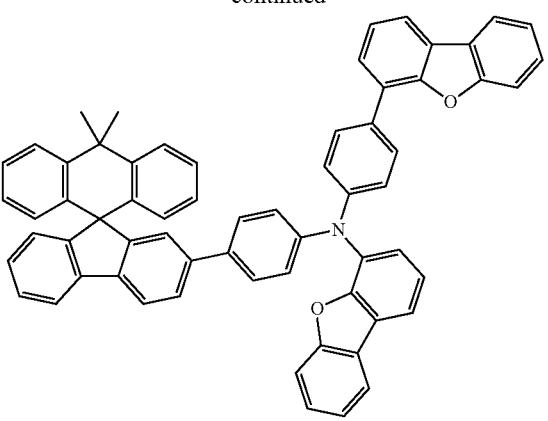
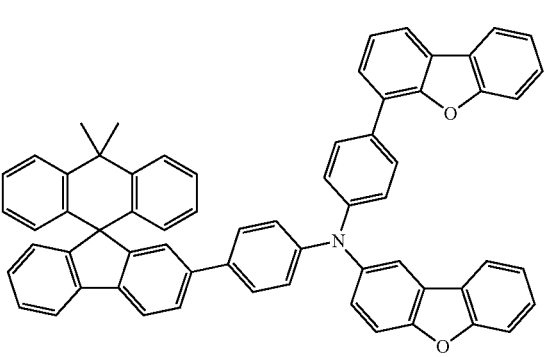
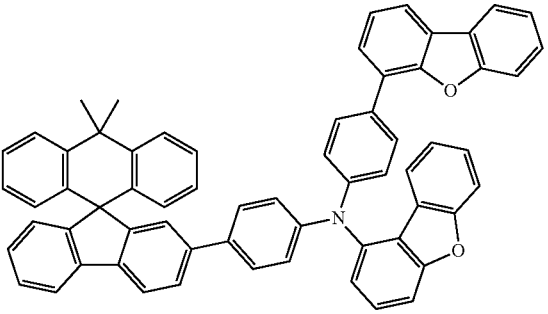
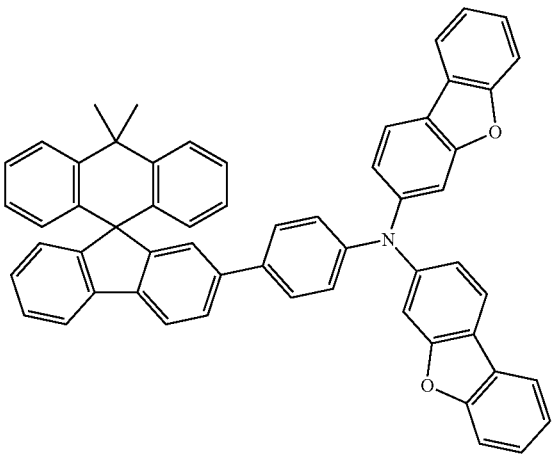

103
-continued
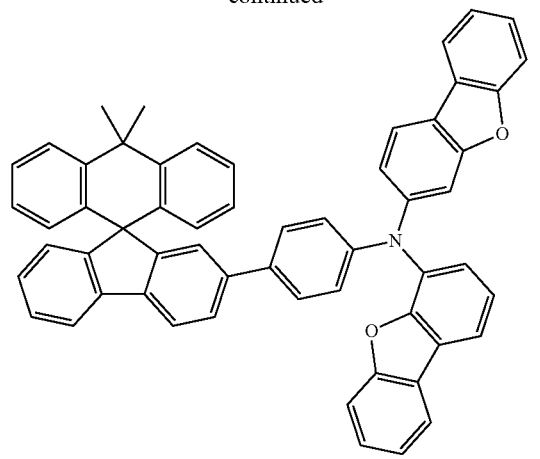
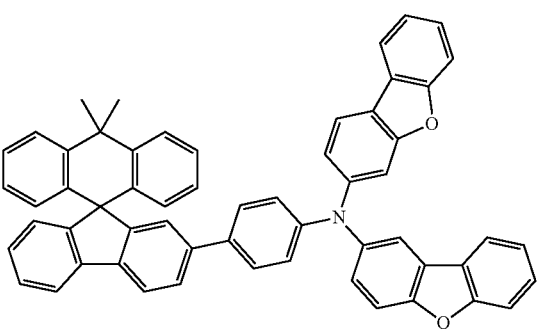
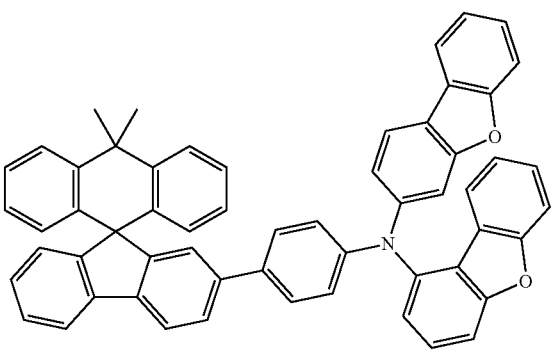
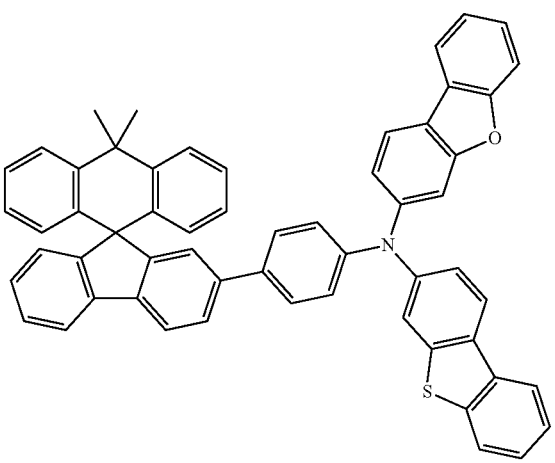
104
-continued
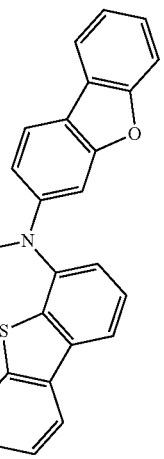
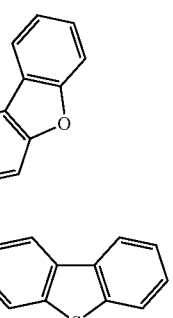
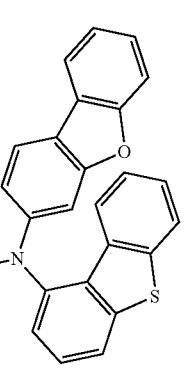
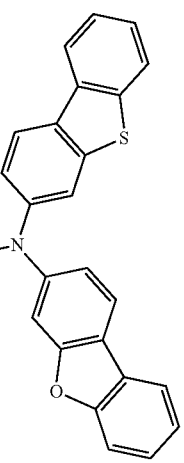

| 105 | 106 |
|---|---|
| -continued | -continued |
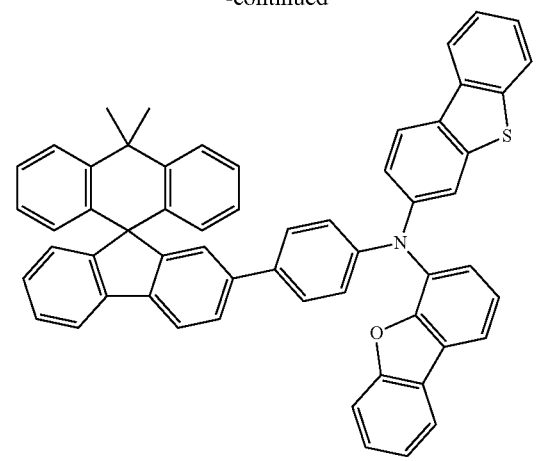
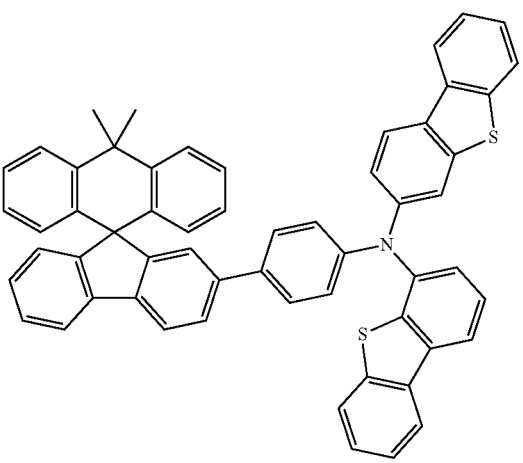
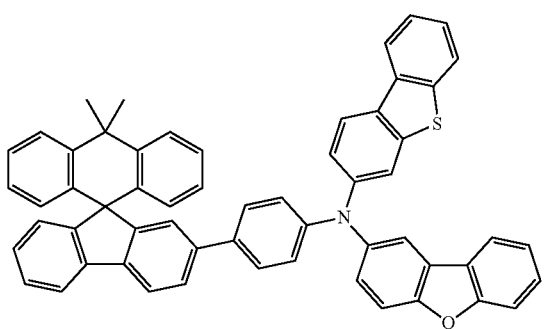
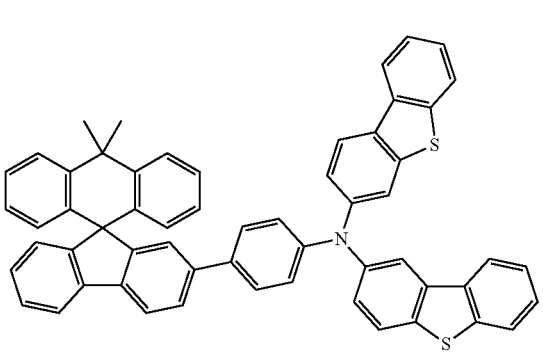
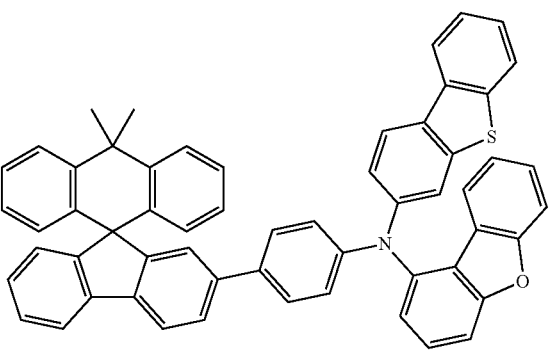
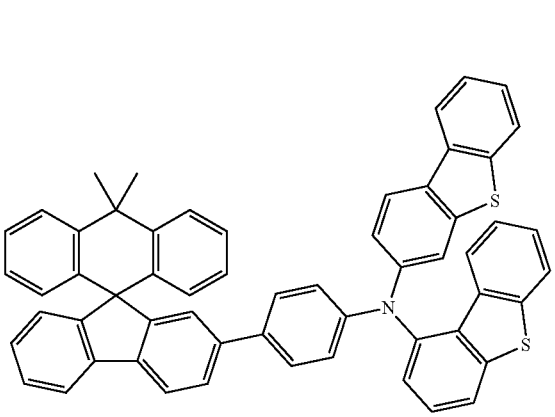
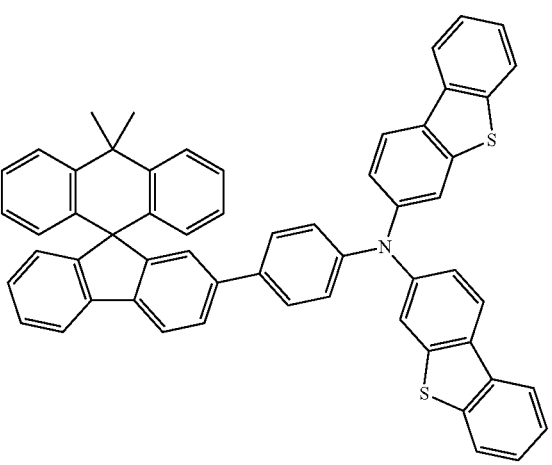
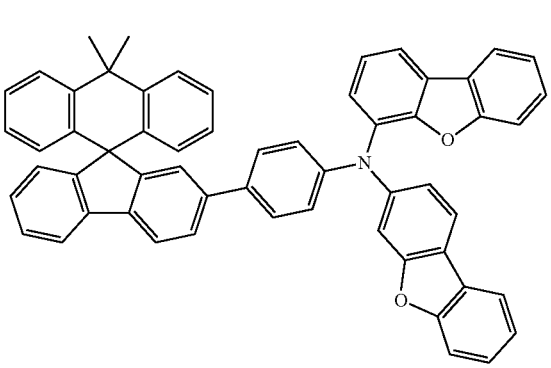

107
-continued
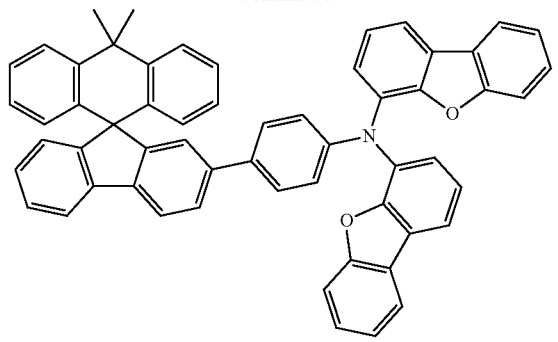
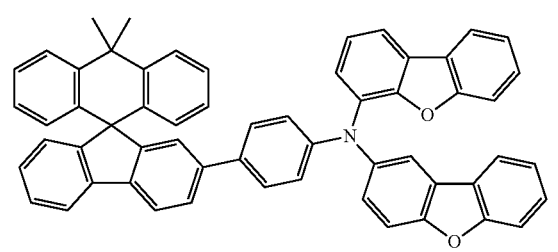
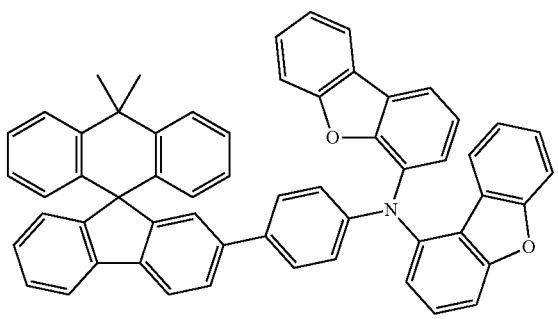
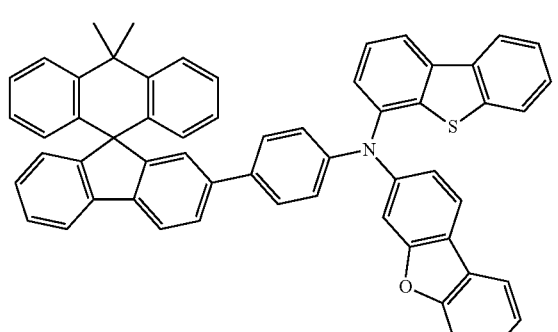
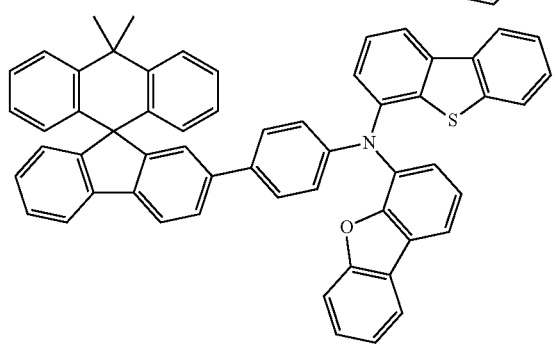
108
-continued
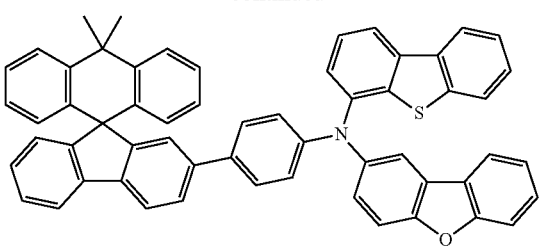
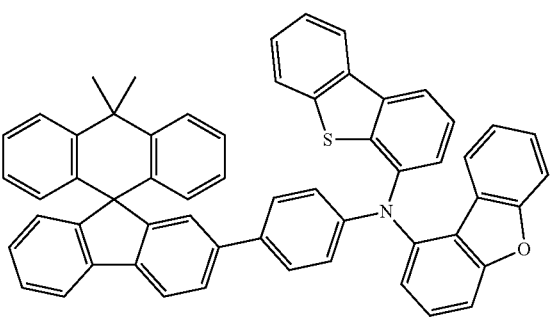
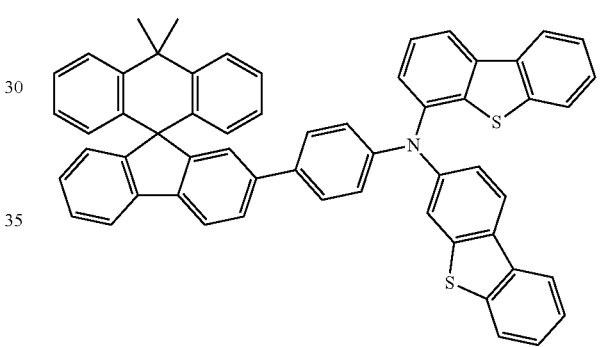
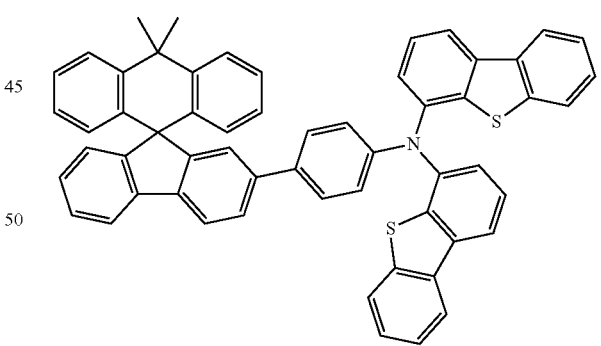
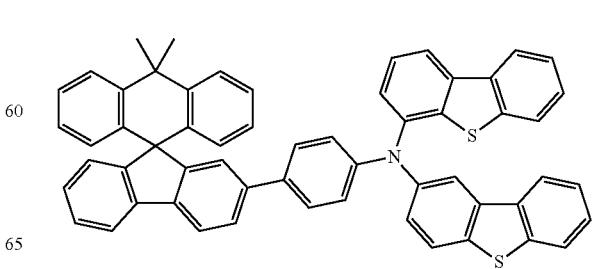

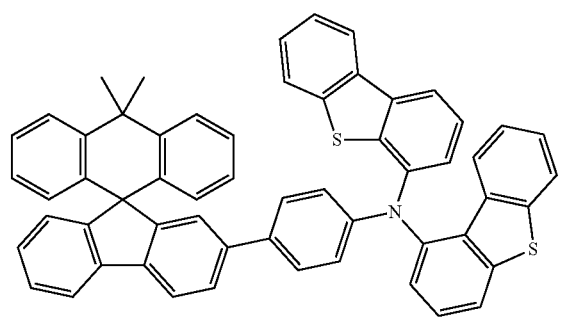
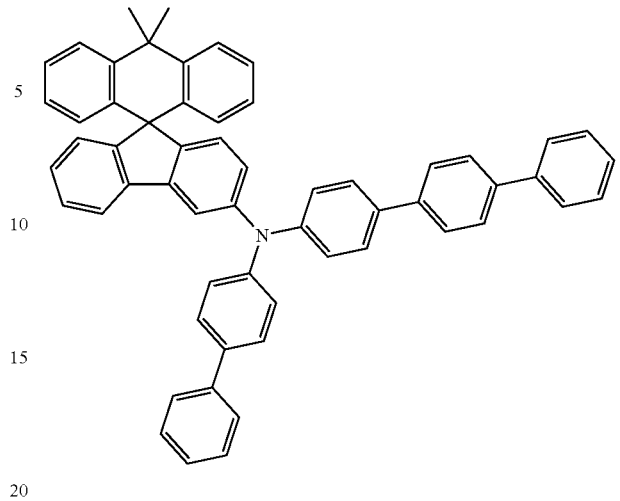
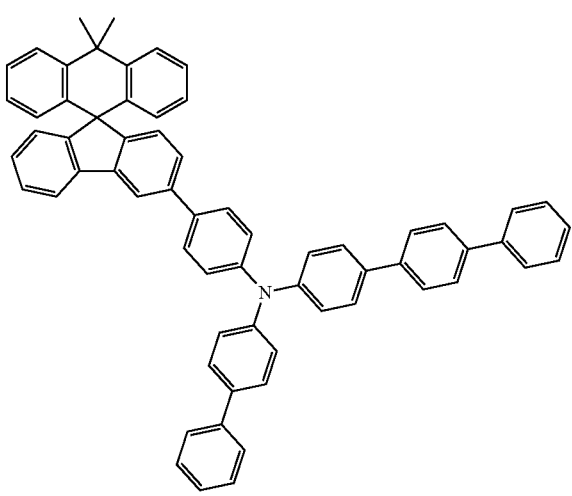
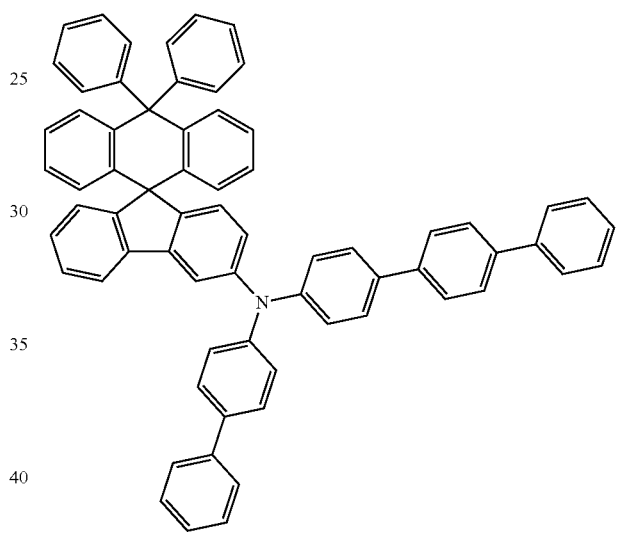
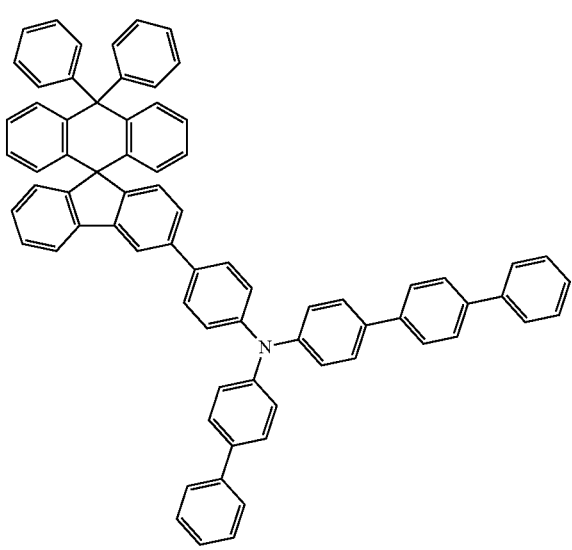
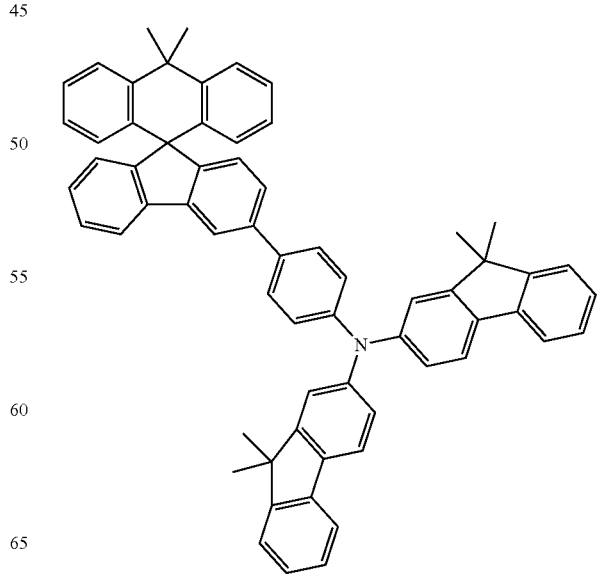

111
-continued
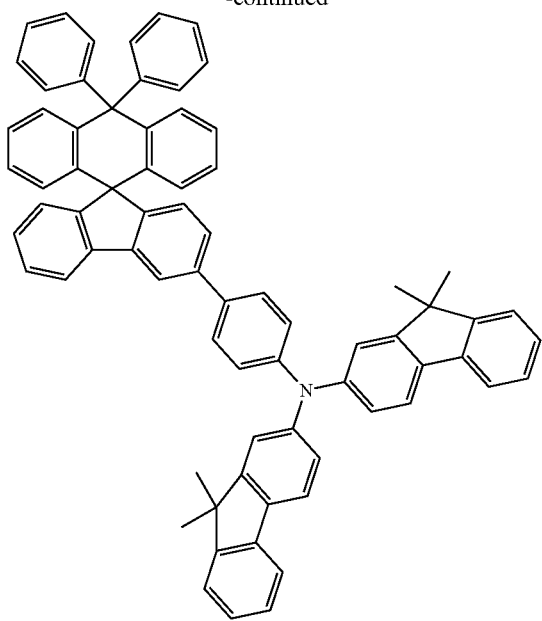
112
-continued
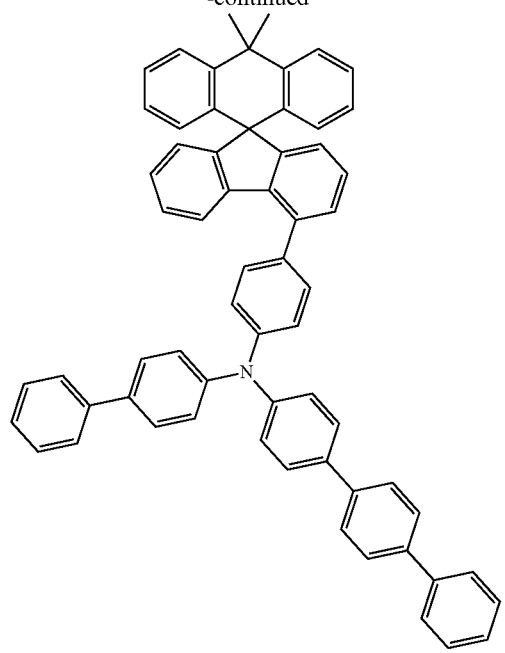
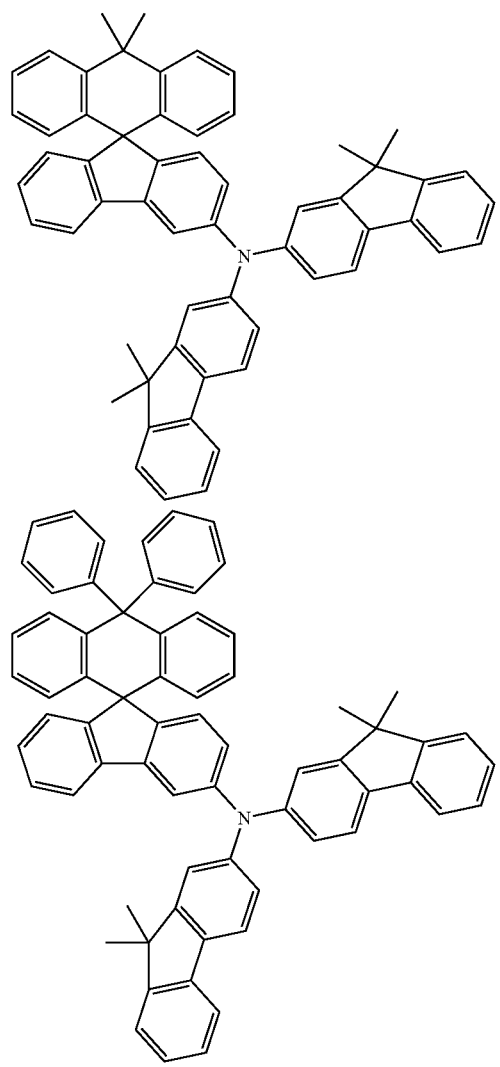
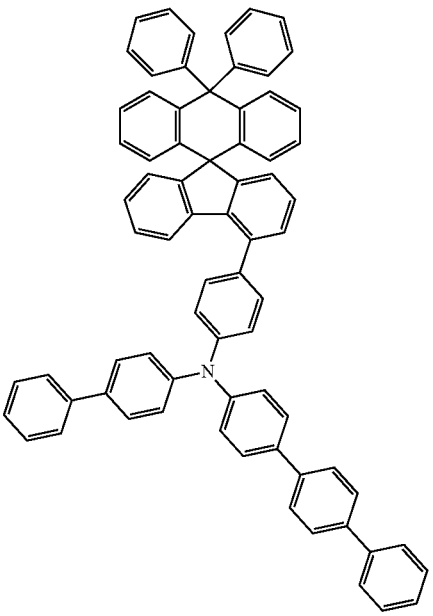

113
-continued
114
-continued
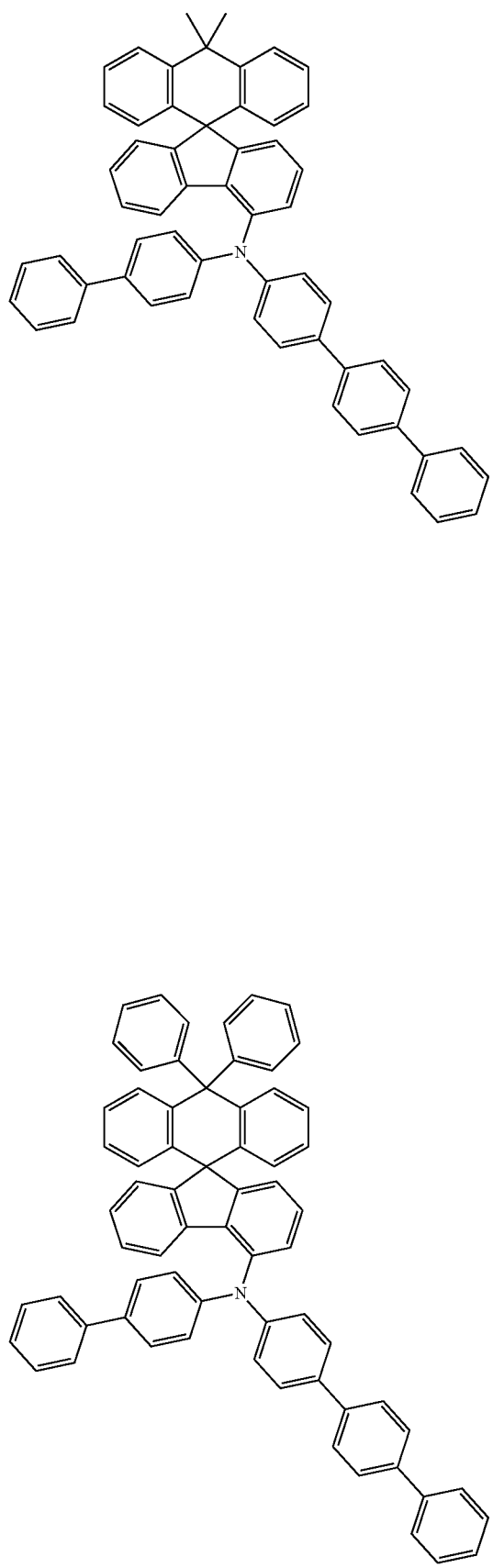
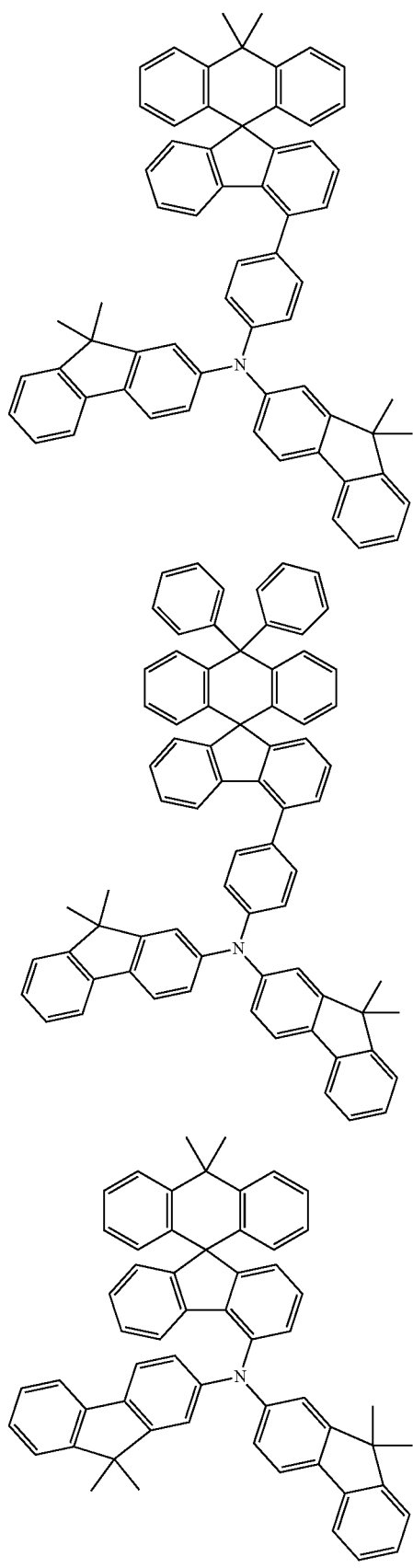

115
-continued
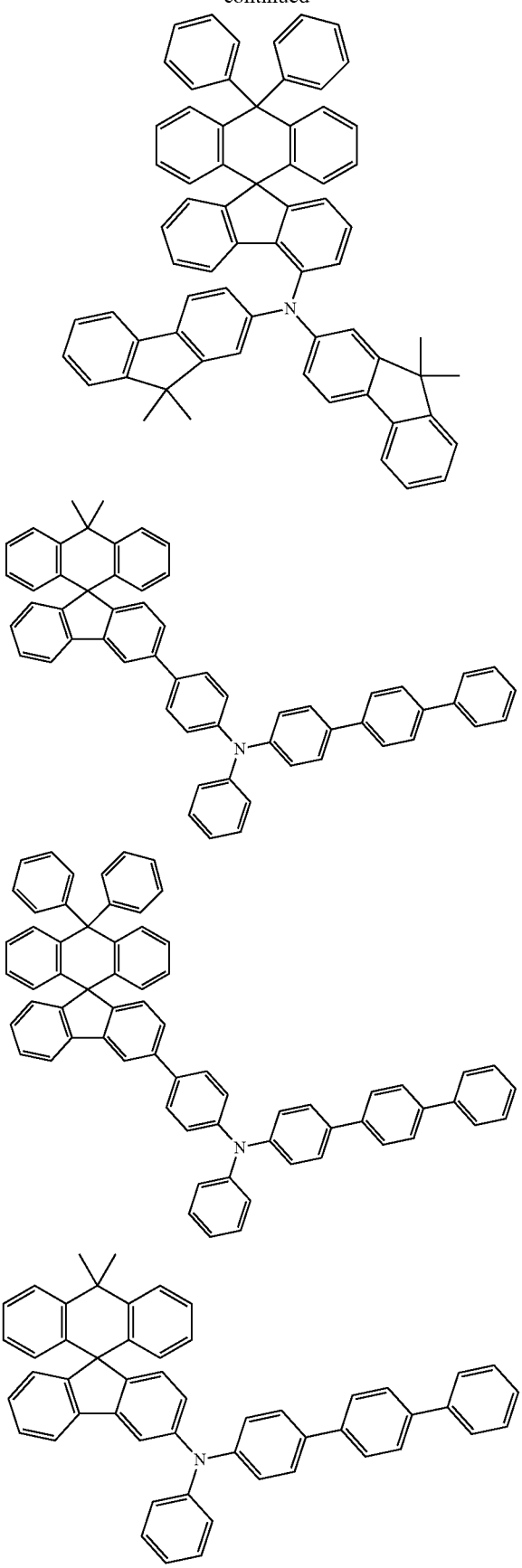
116
-continued
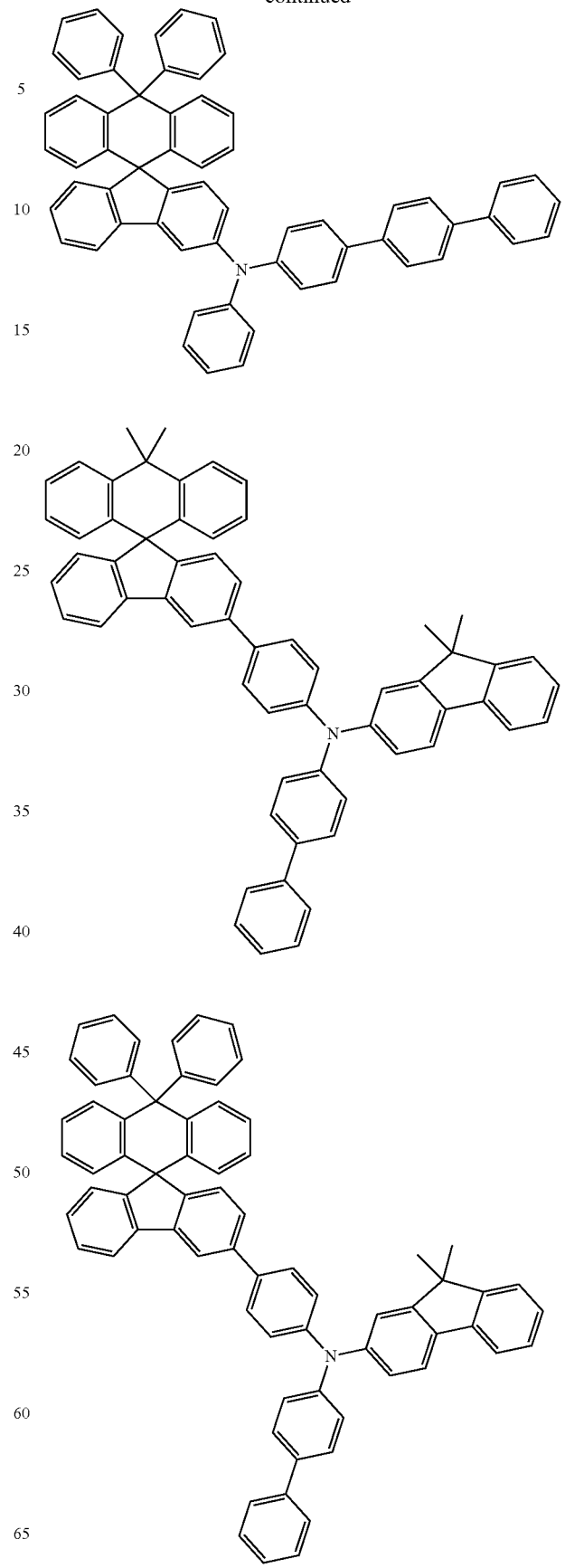

117
-continued
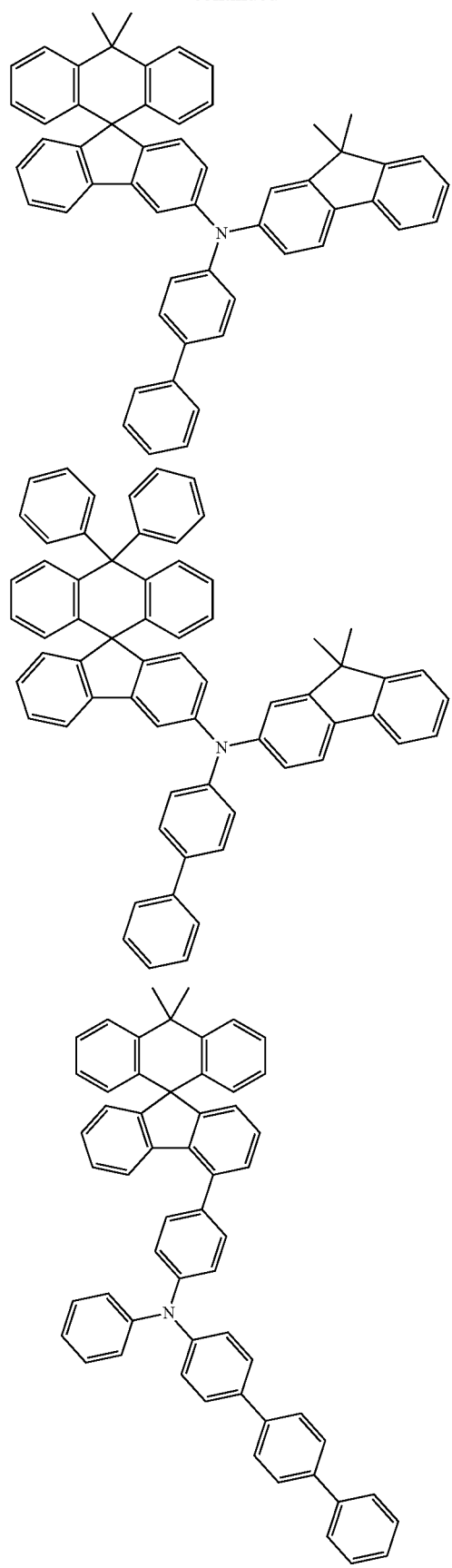
118
-continued
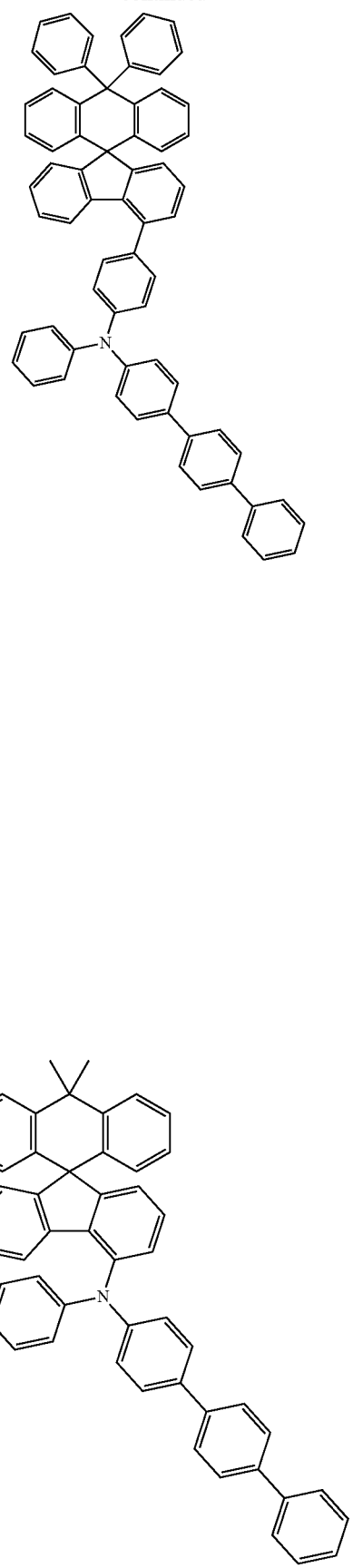

119
-continued
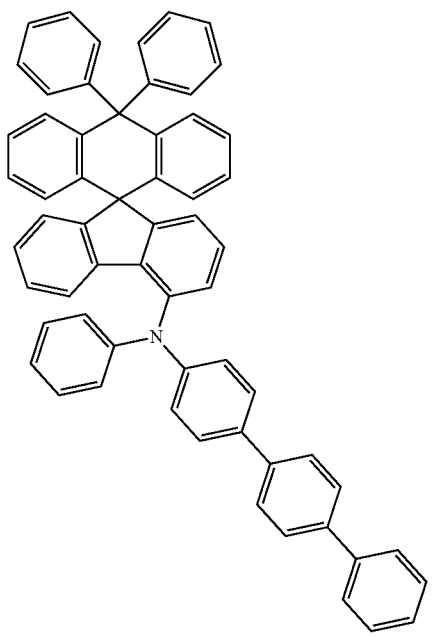
120
-continued
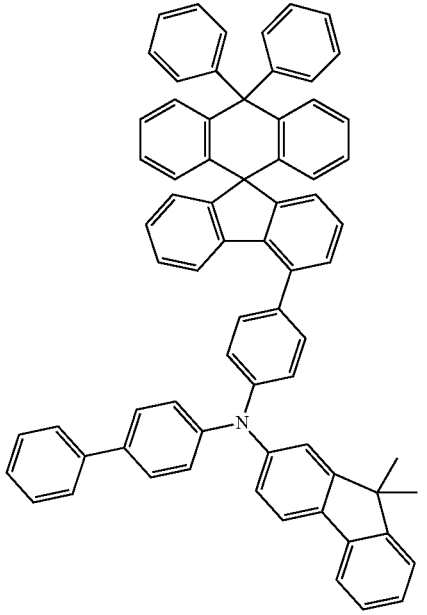
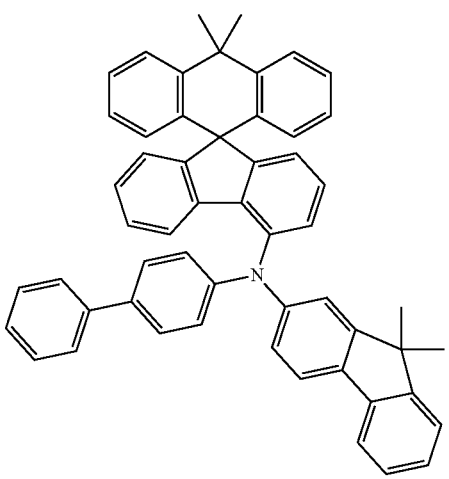
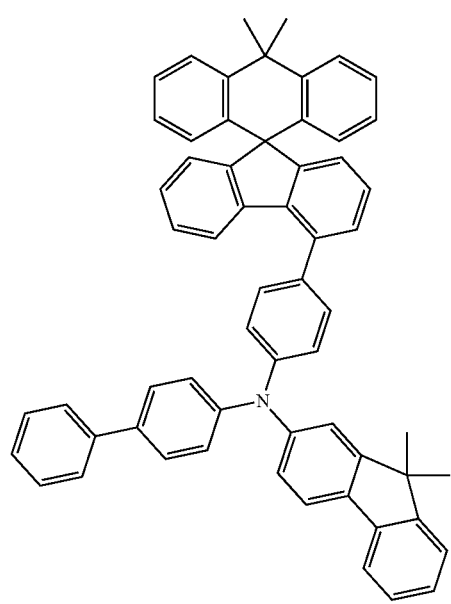
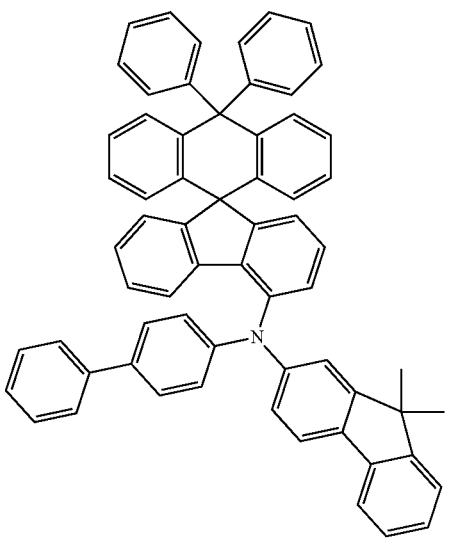

121
-continued
122
-continued
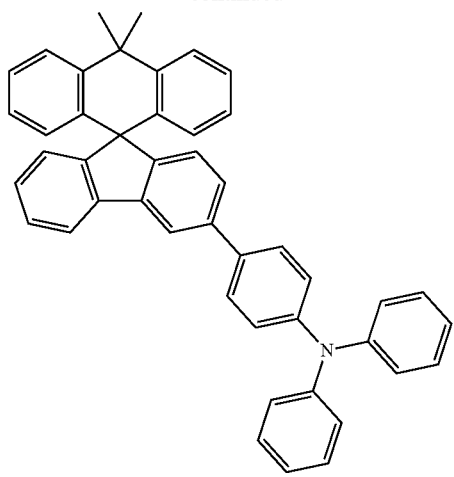
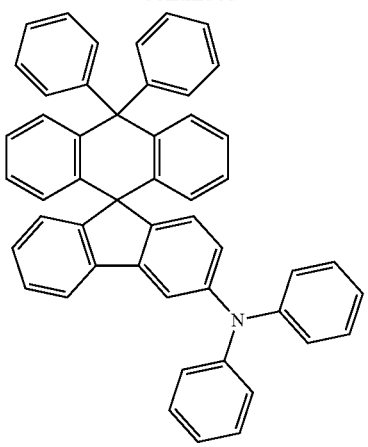
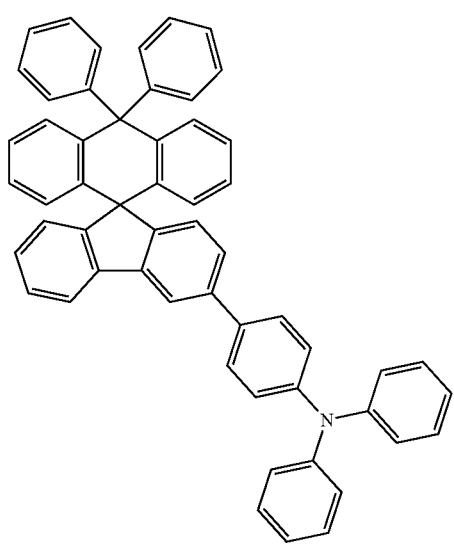
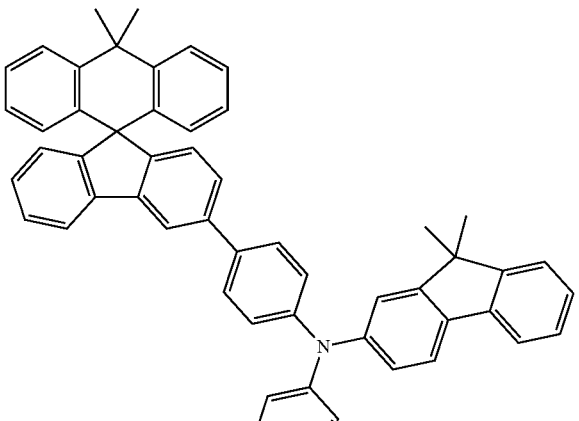
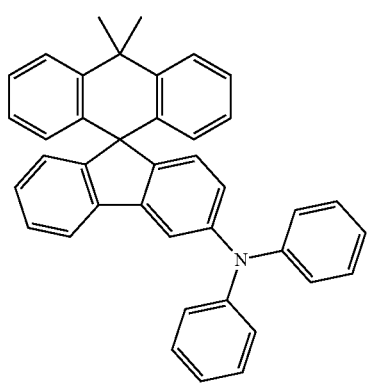
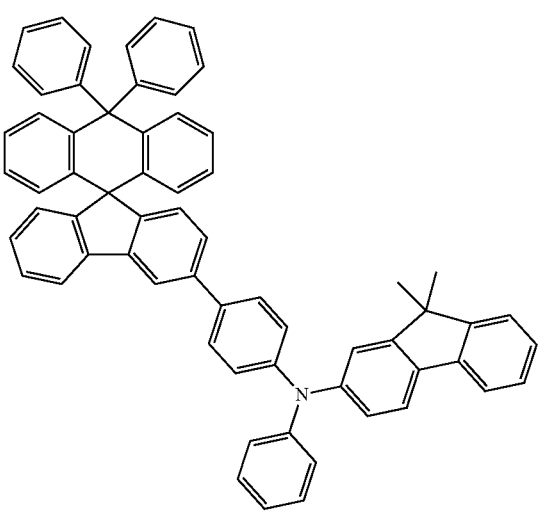

123
-continued
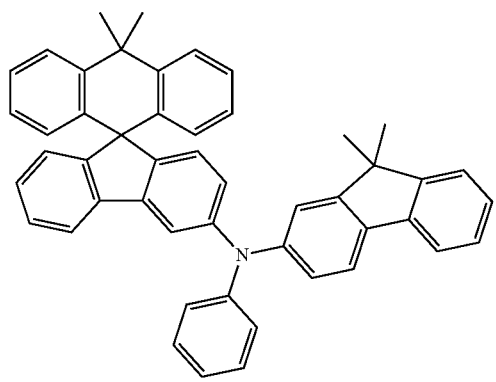
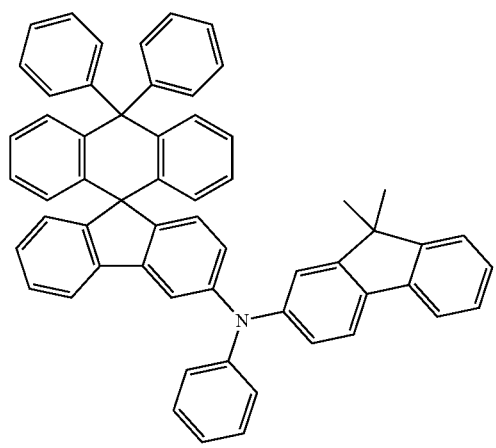
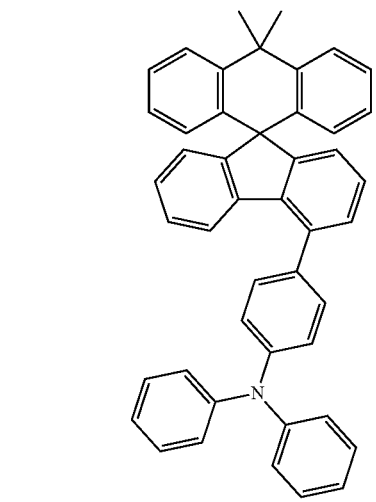
124
-continued
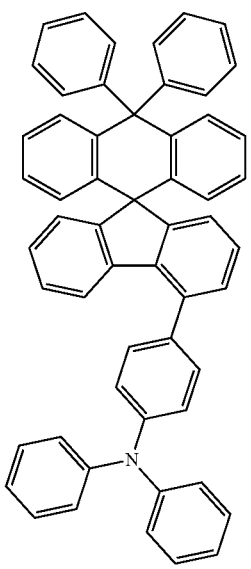
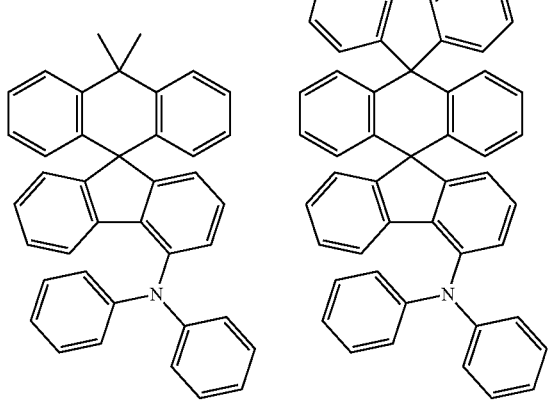
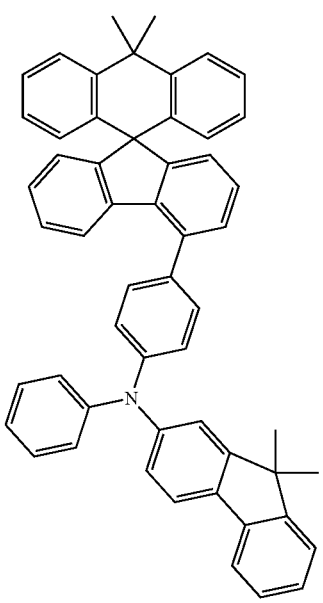

125
-continued
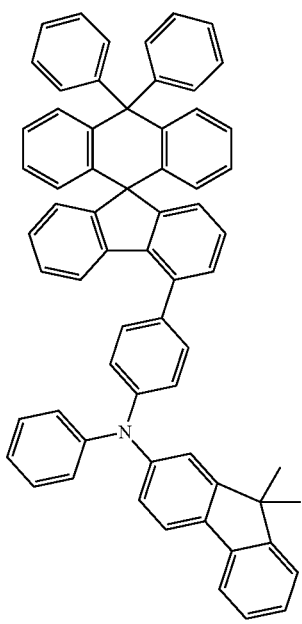
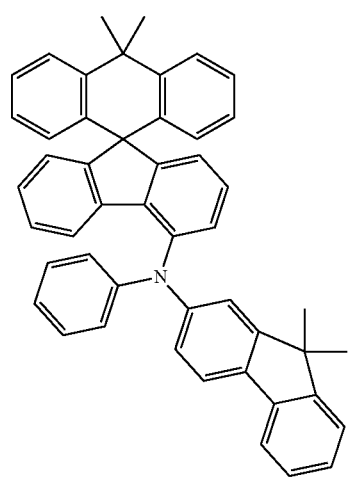 [SMILES: CC1(C)c2ccccc2-c2ccc(N(c3ccccc3)c3cccc4c3-c3ccccc3C43c4ccccc4C(C)(C)c4ccccc43)cc21]
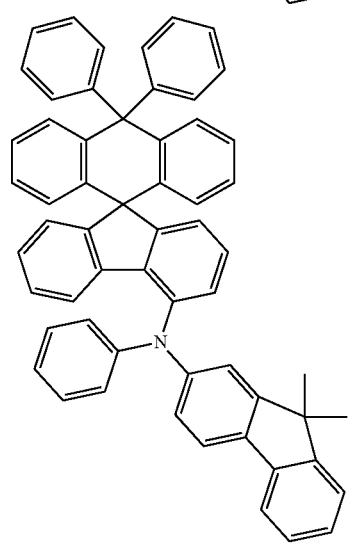
126
-continued
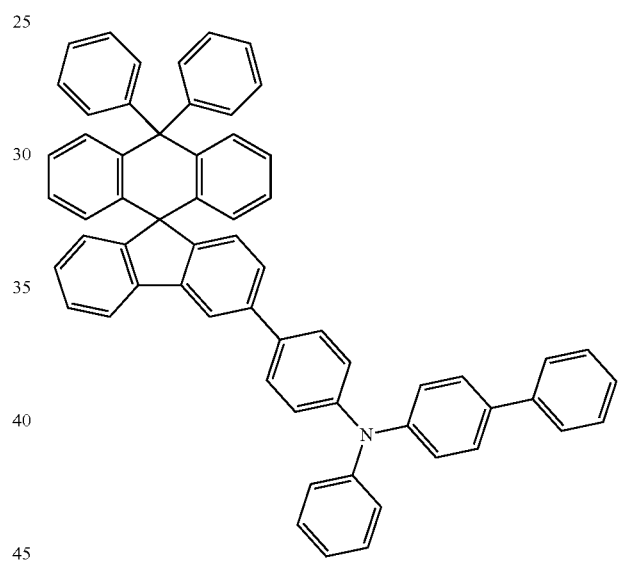
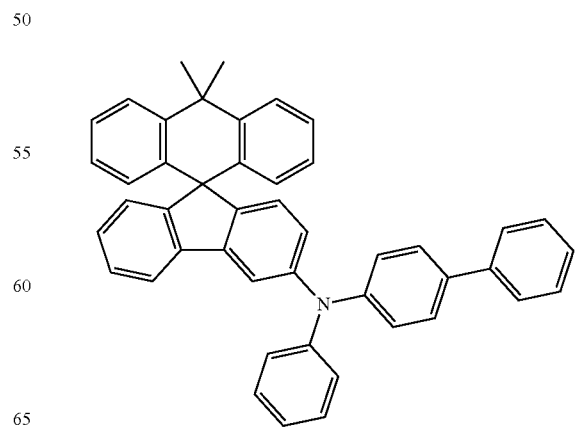

127
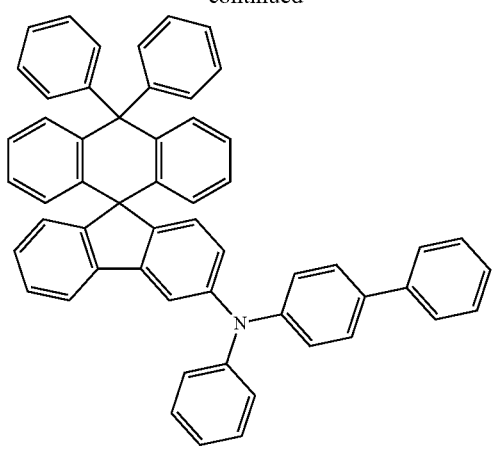
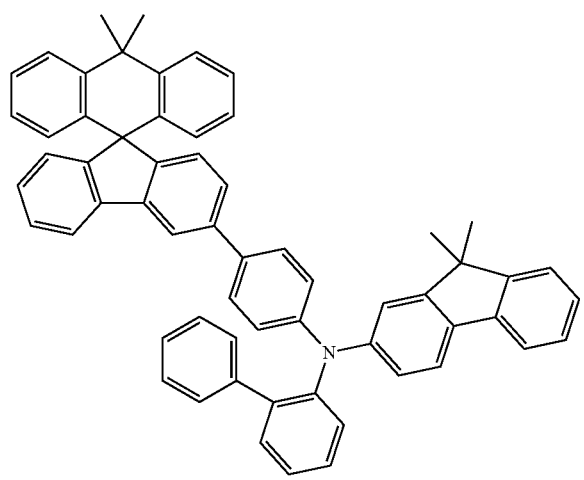
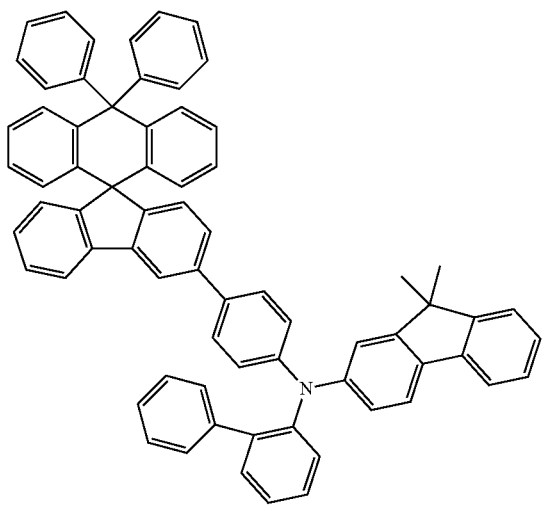
128
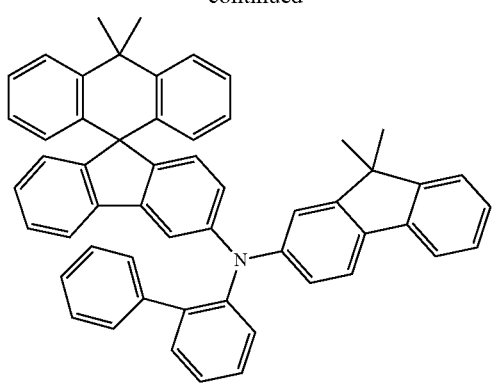
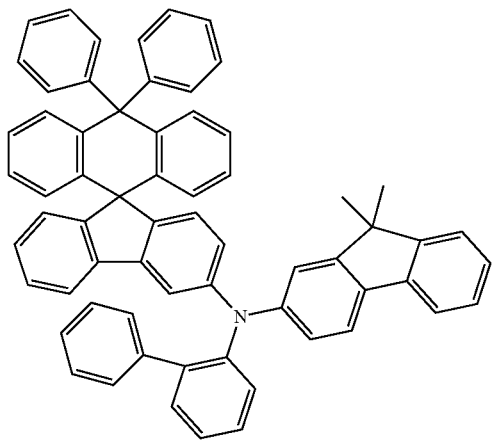
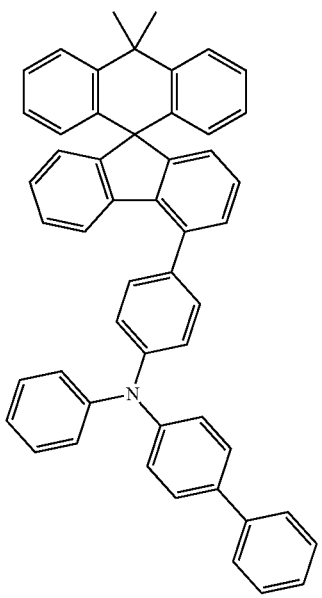

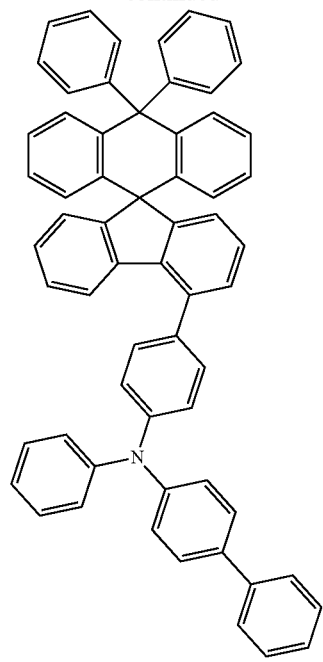
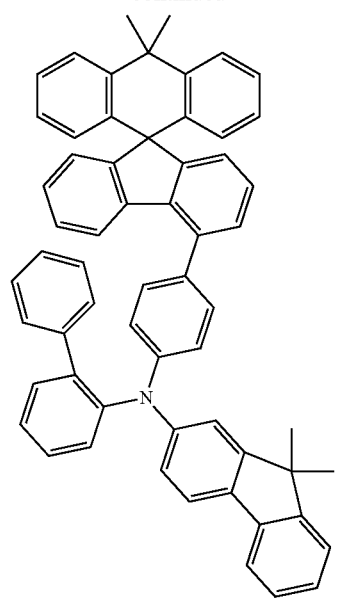
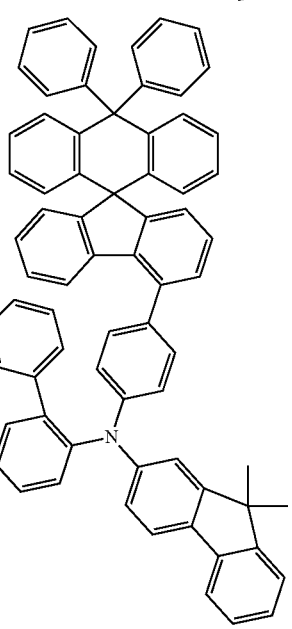
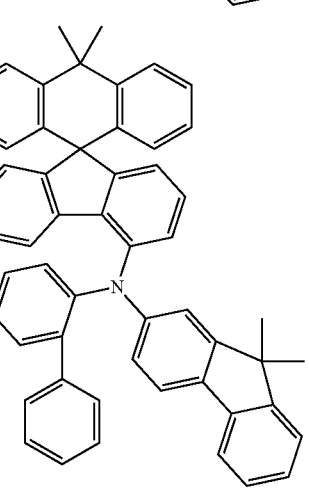

131
-continued
132
-continued
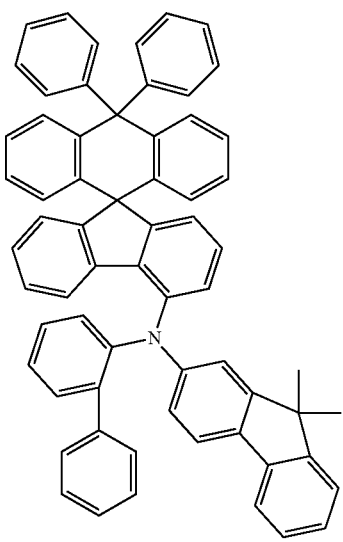
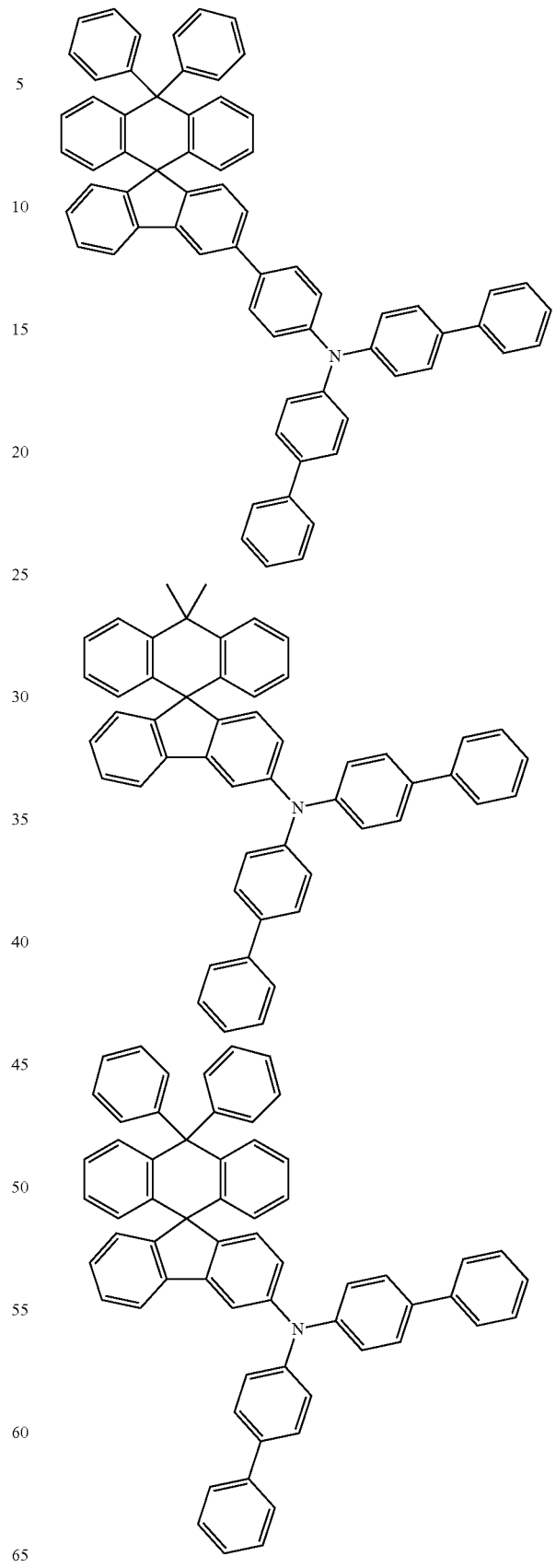
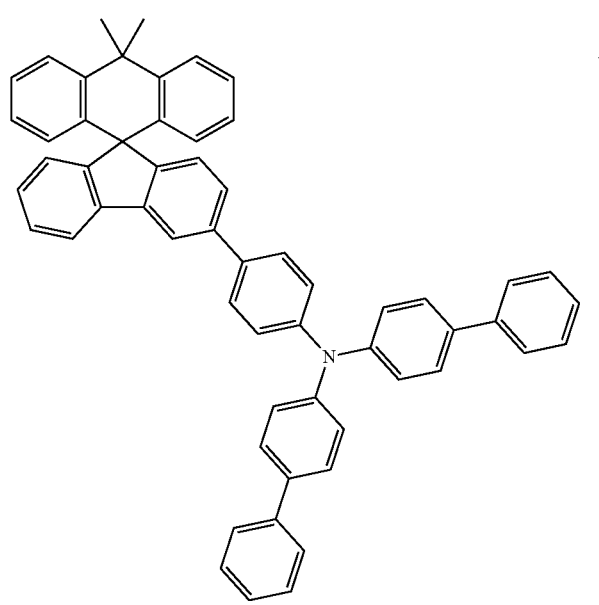

133
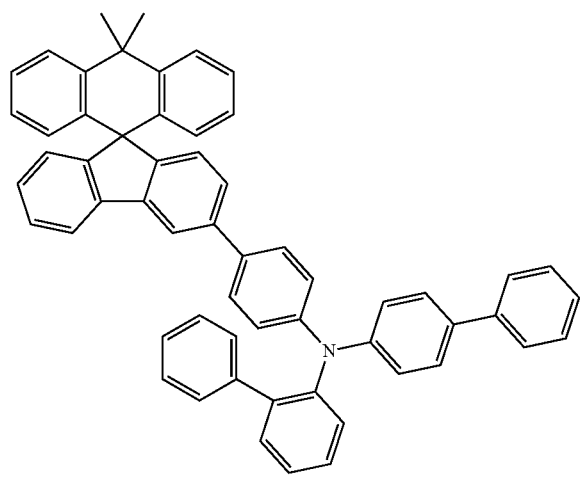
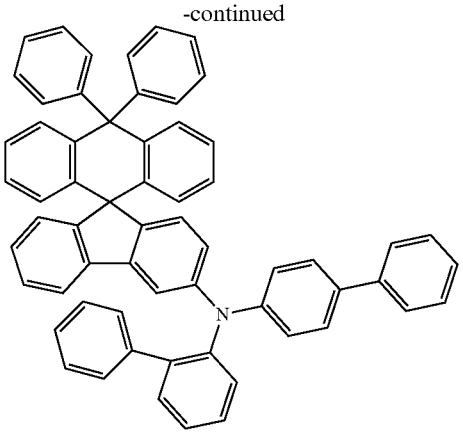
134

135
-continued
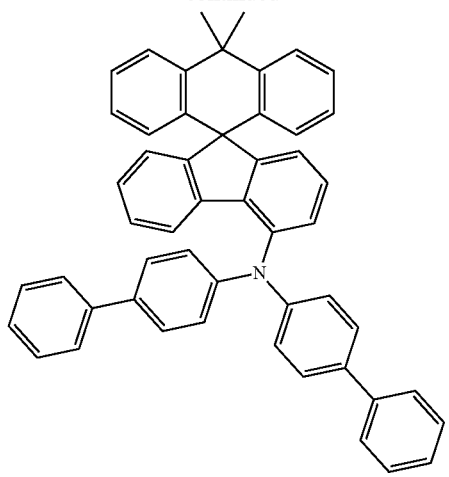
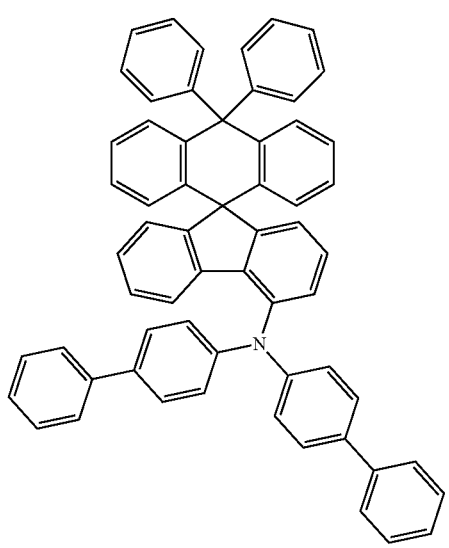

136
-continued
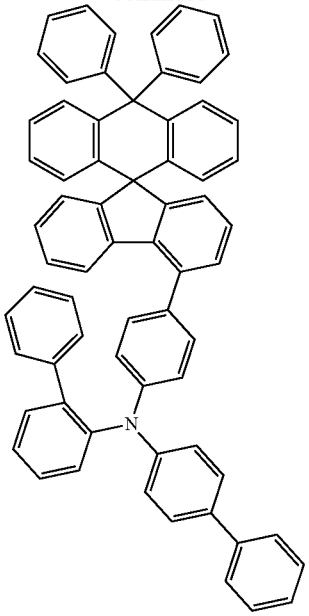
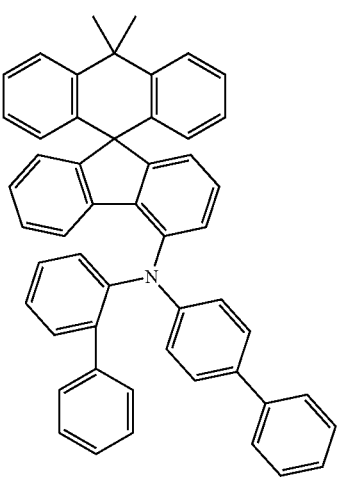 [SMILES: CC1(C)c2ccccc2-c2ccc(N(c3ccccc3-c3ccccc3)c3cccc4c3-c3ccccc3C43c4ccccc4C(C)(C)c4ccccc43)cc21]
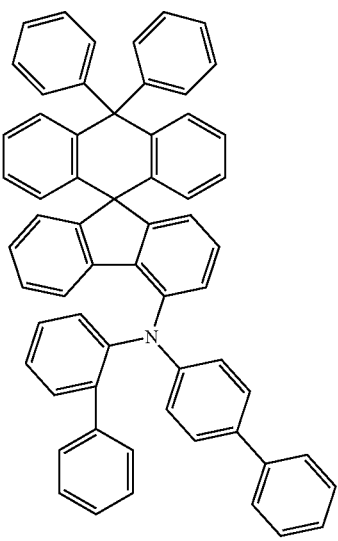

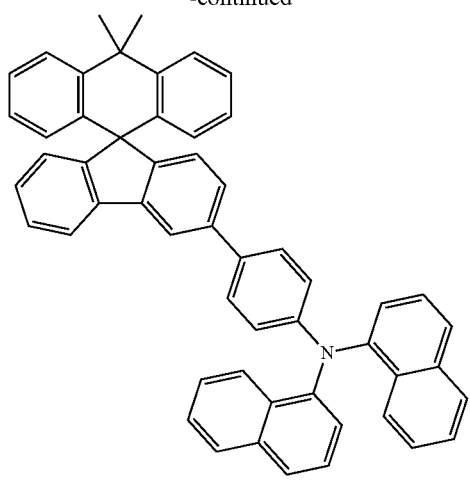
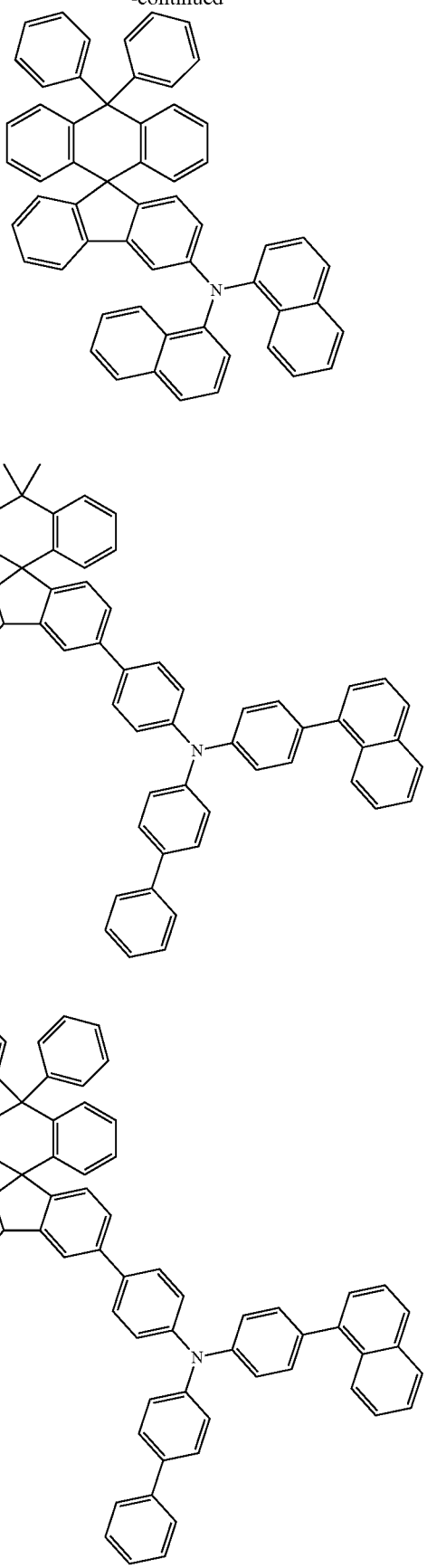

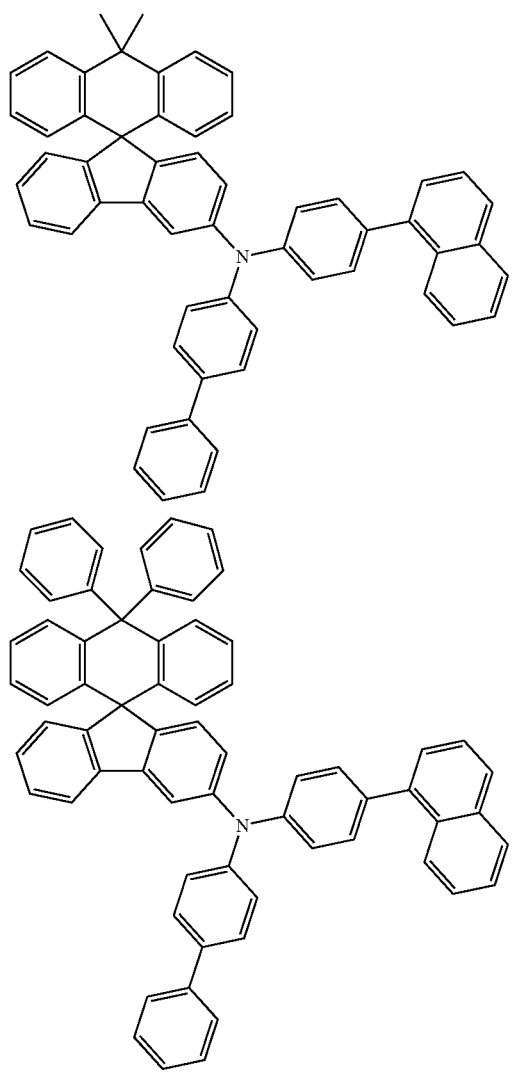
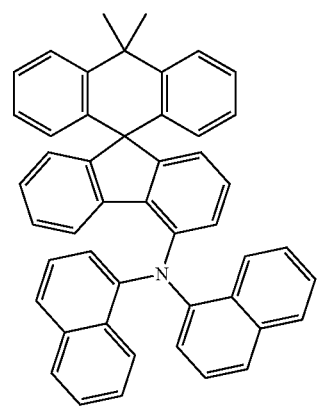
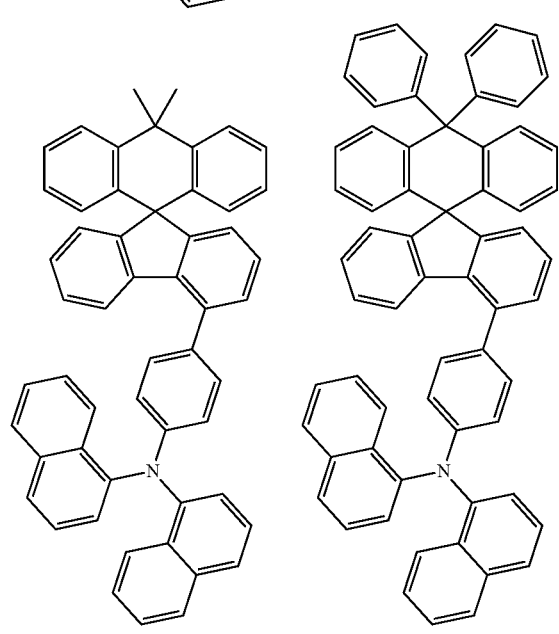
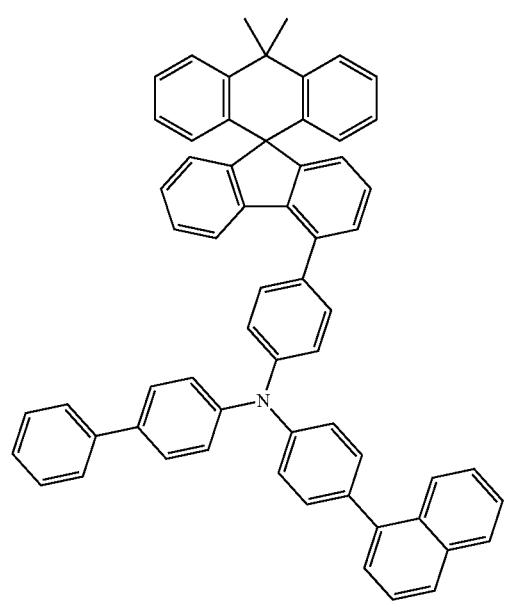

141
-continued
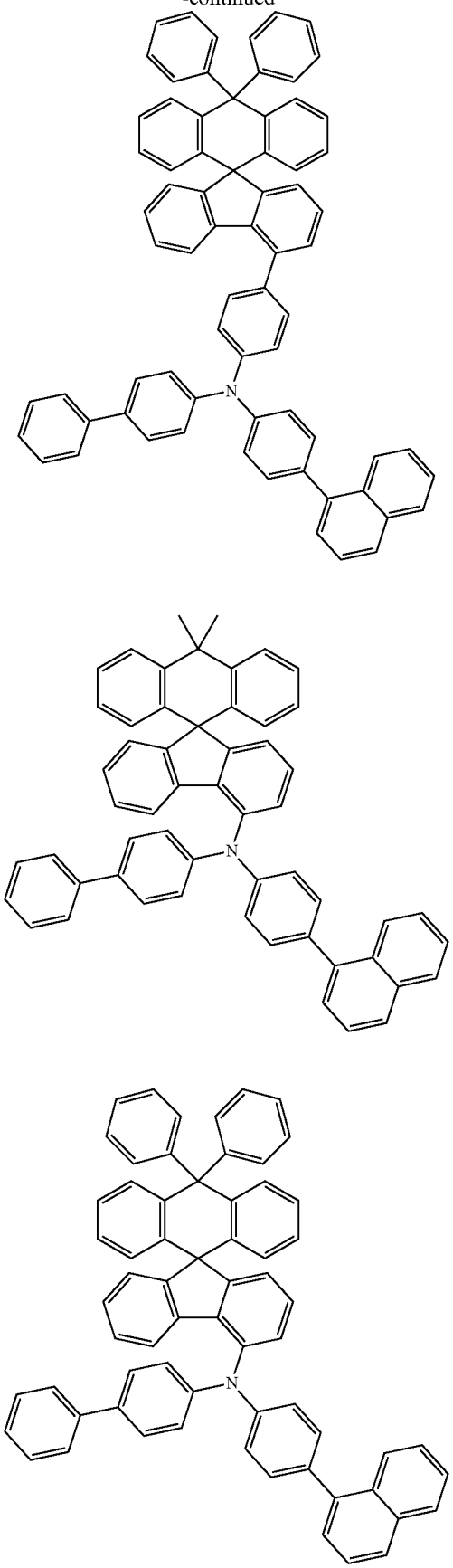
142
-continued
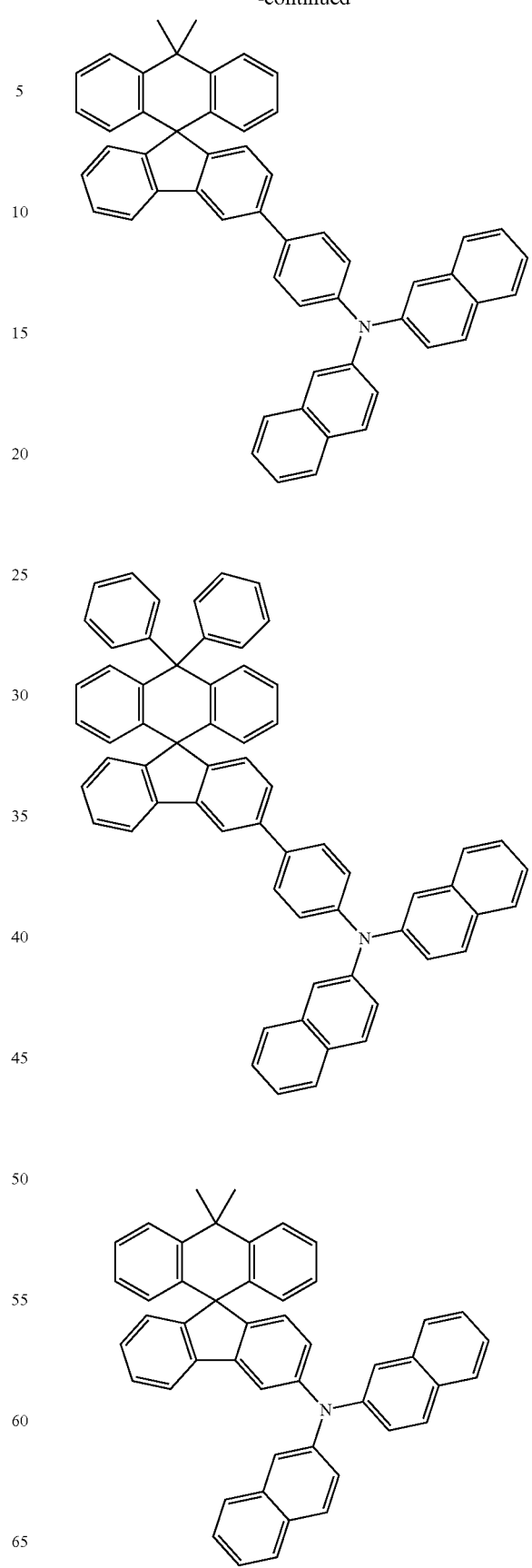

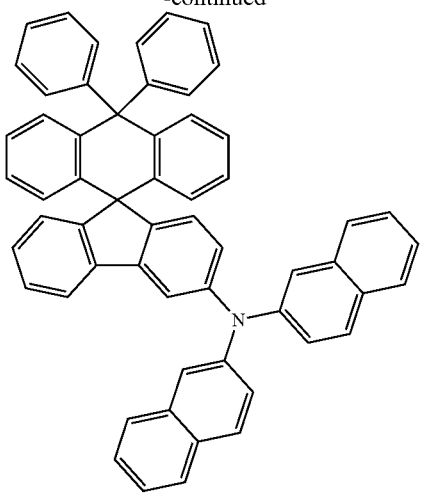
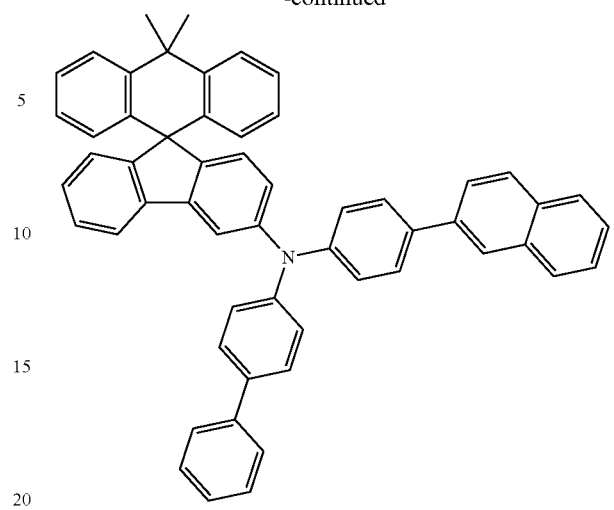
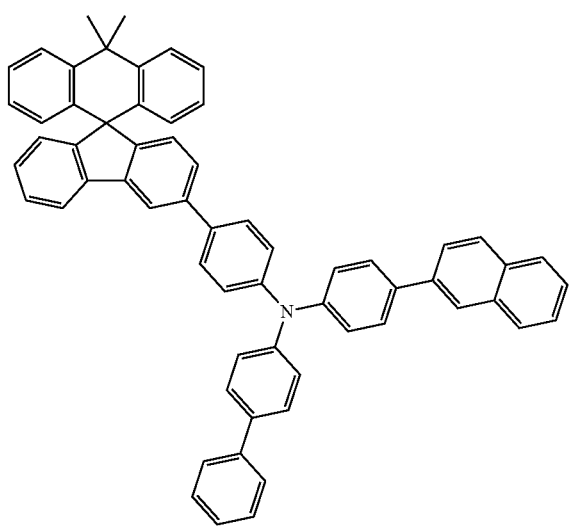
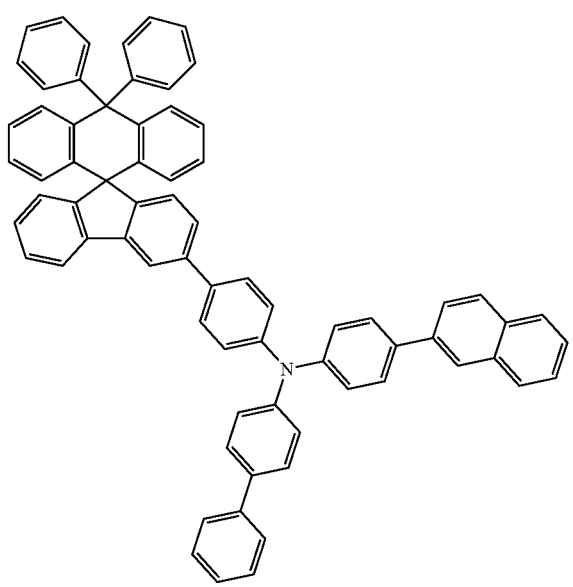
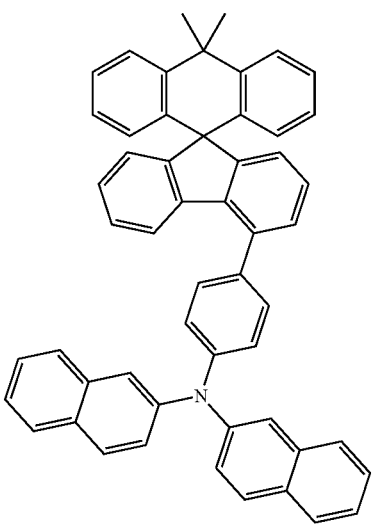

145
-continued
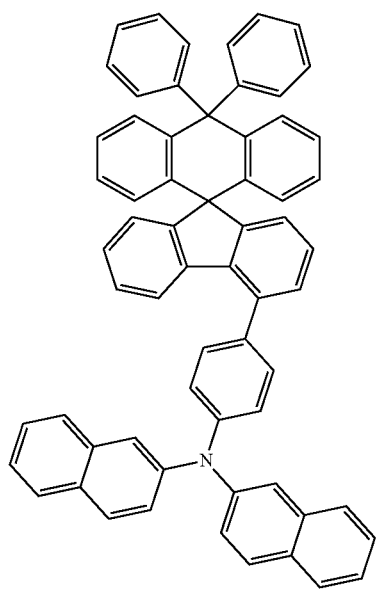
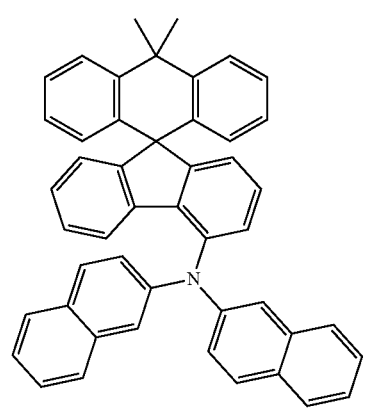
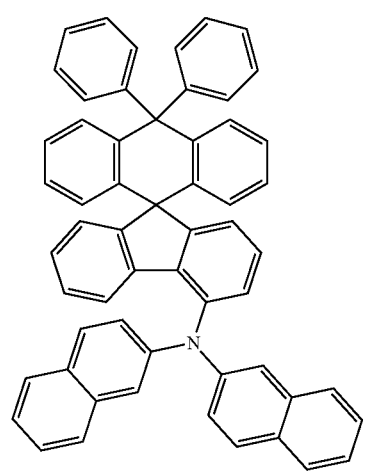
146
-continued
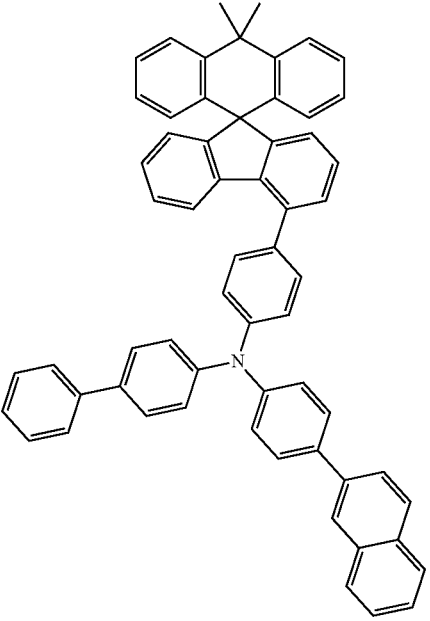
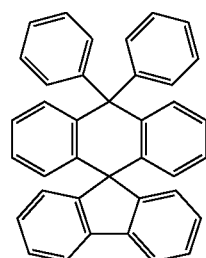
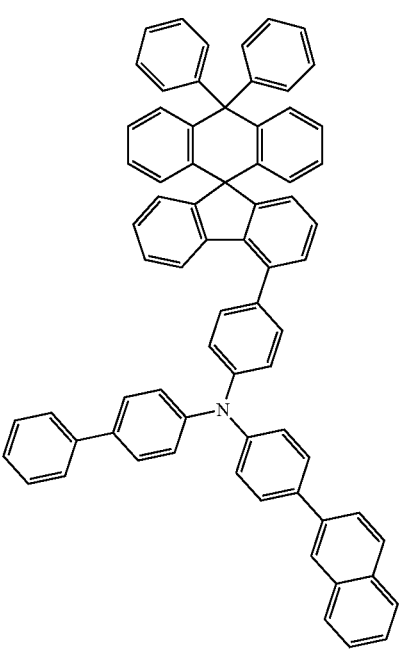

147
-continued
148
-continued
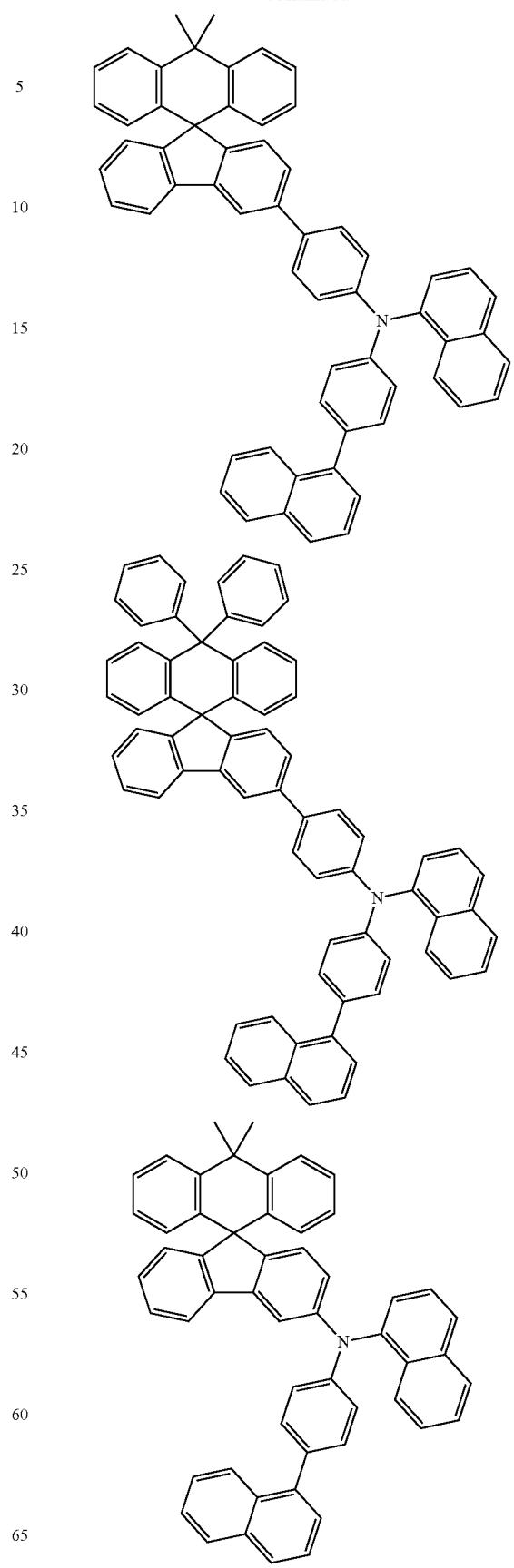

149
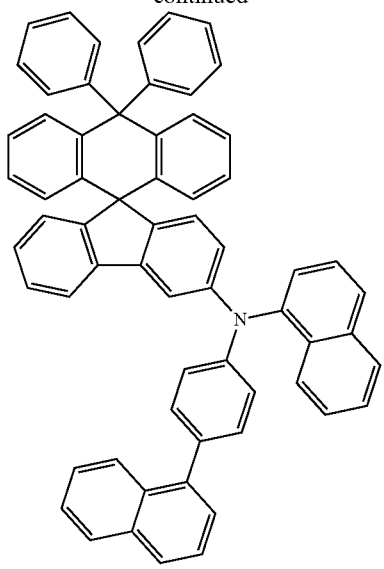
150
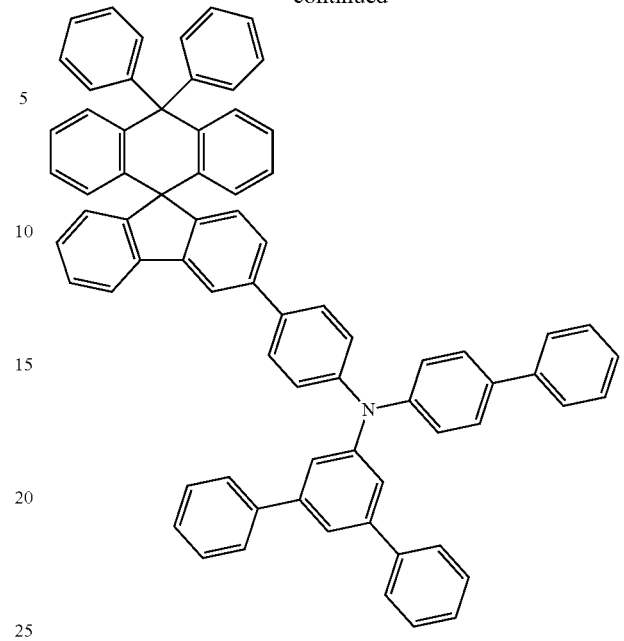
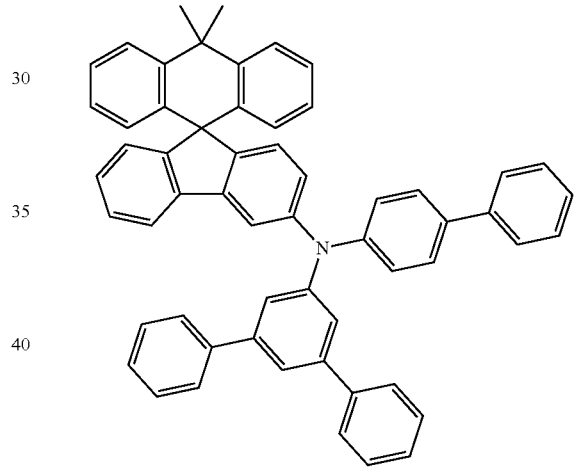
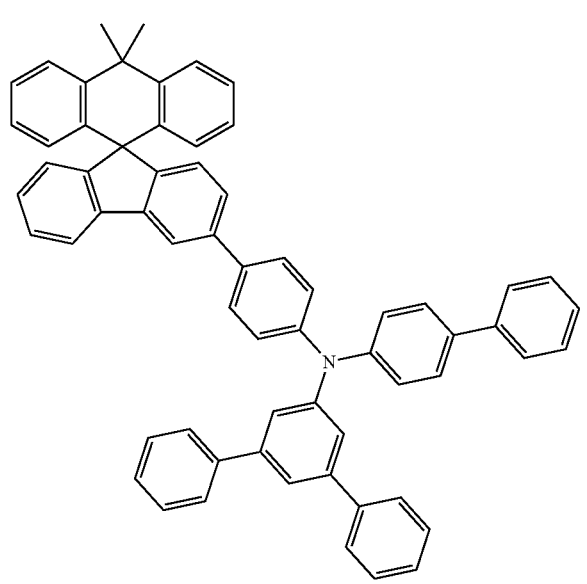
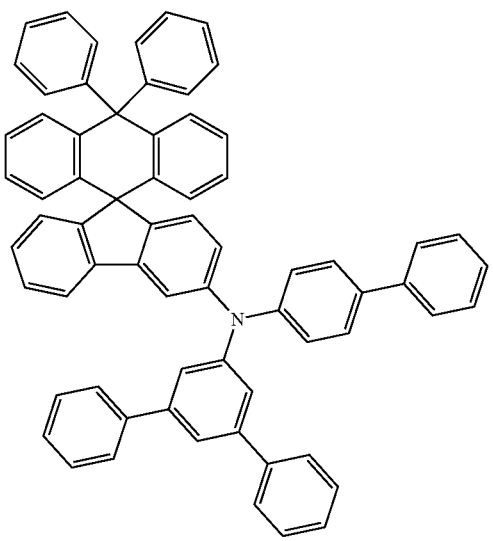

151
-continued
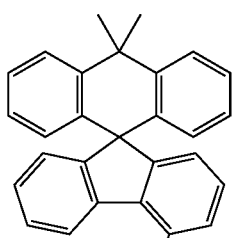
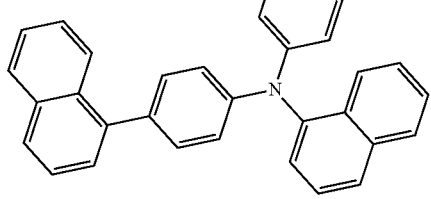
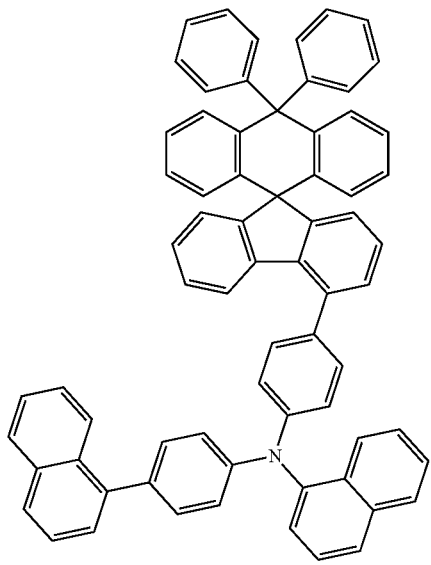
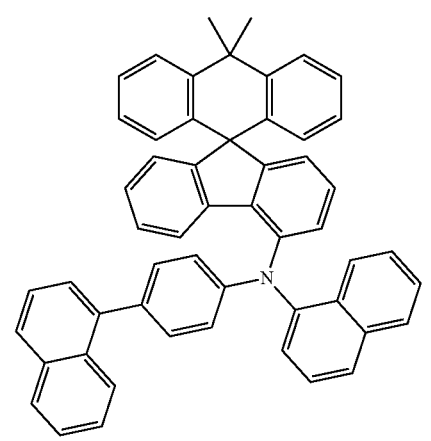
152
-continued
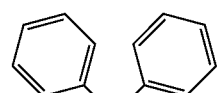
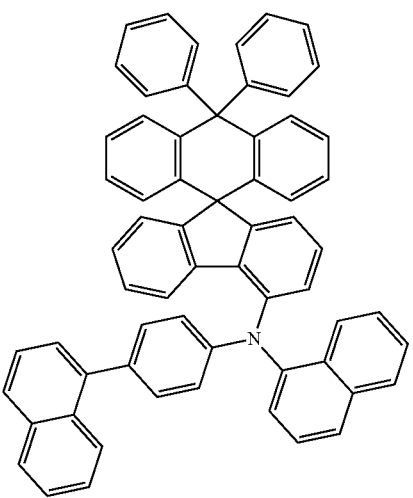
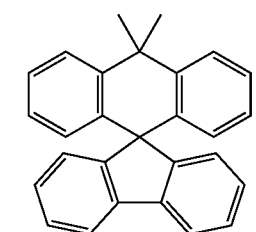
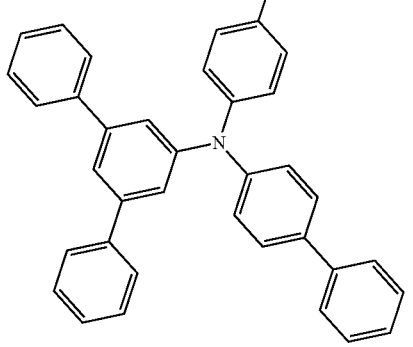
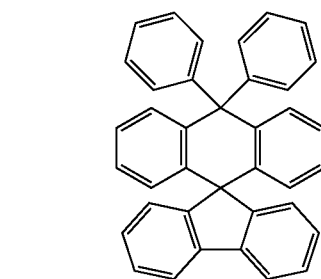
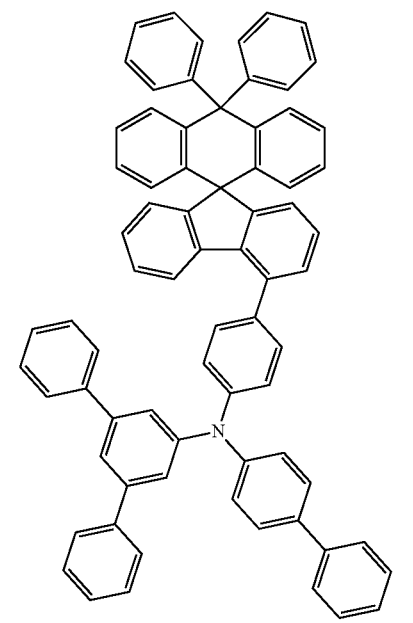

-continued
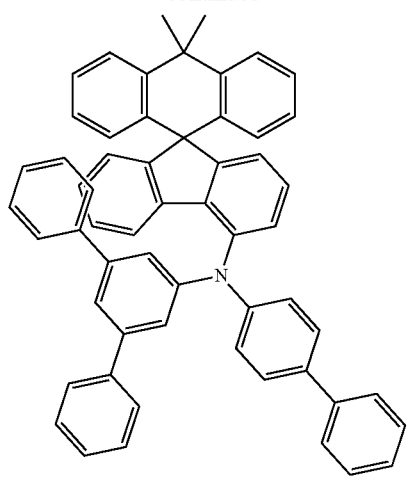
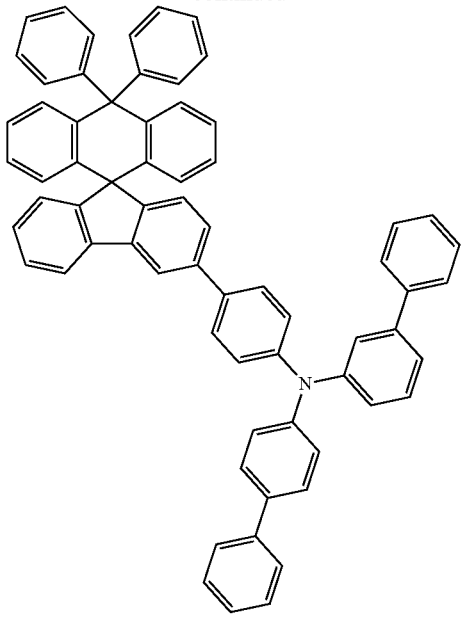
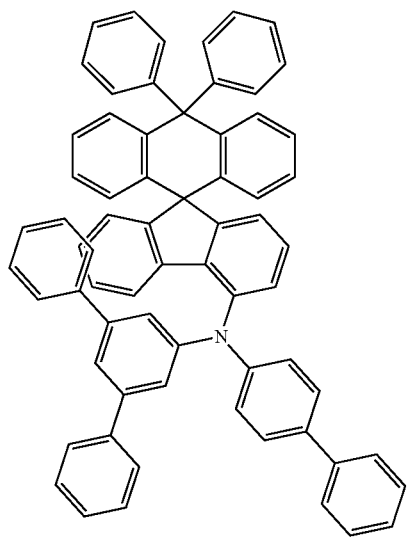
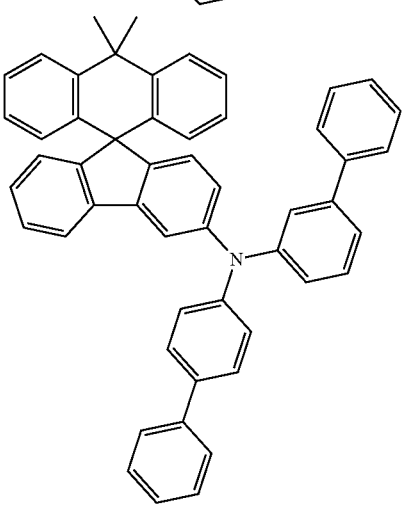
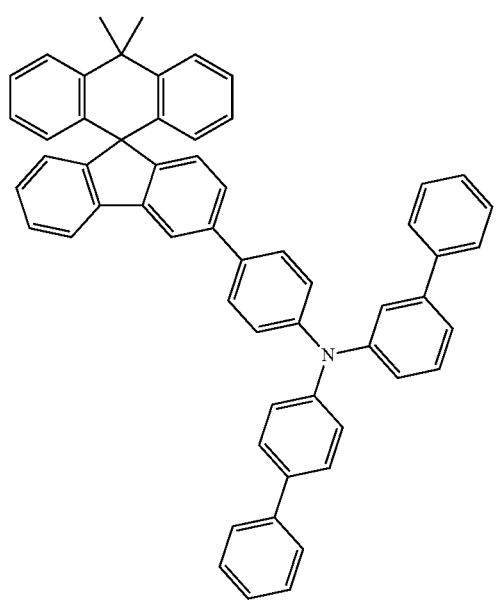
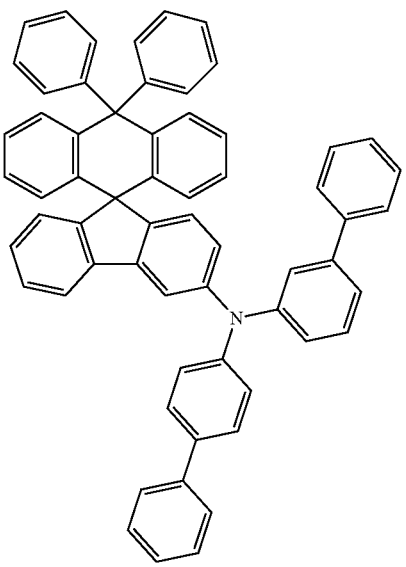

-continued
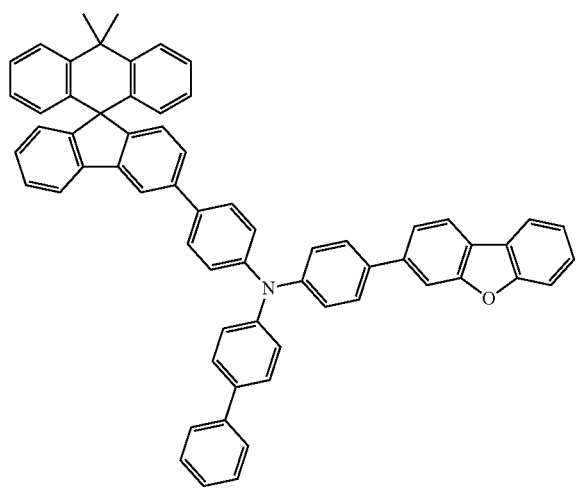
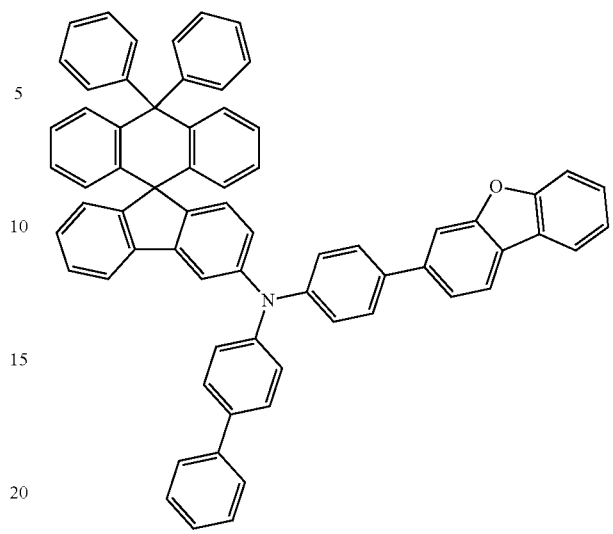
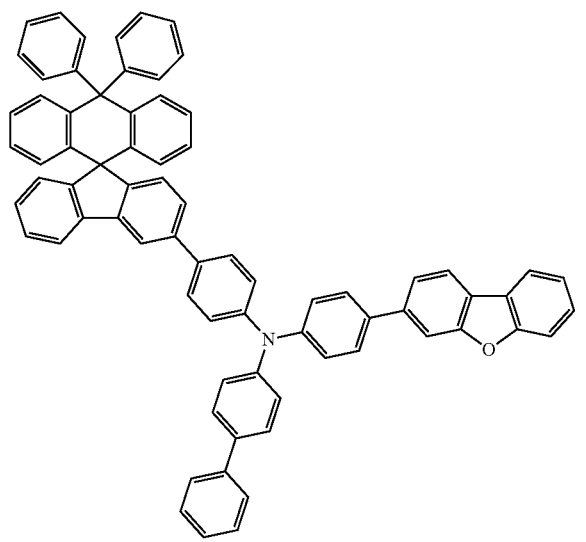
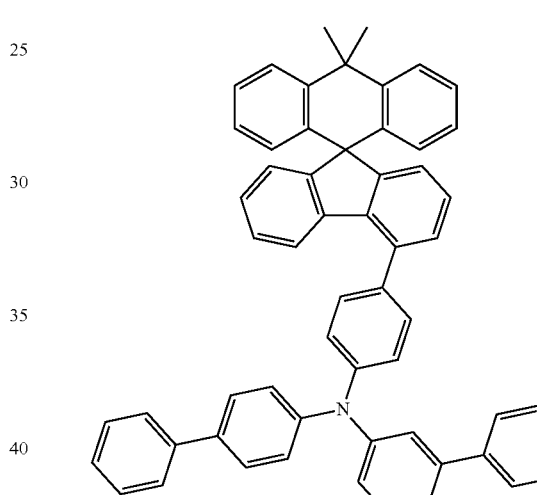
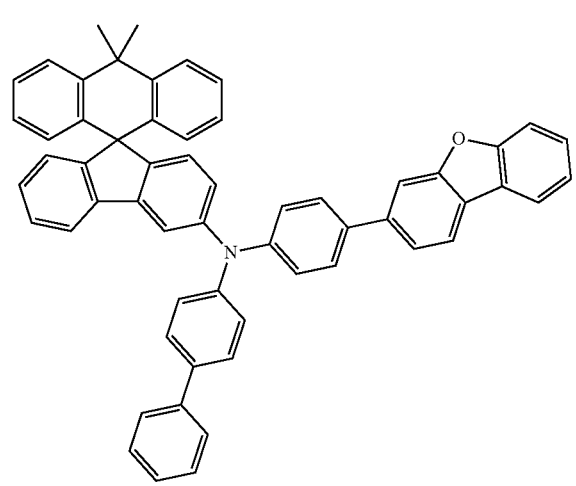
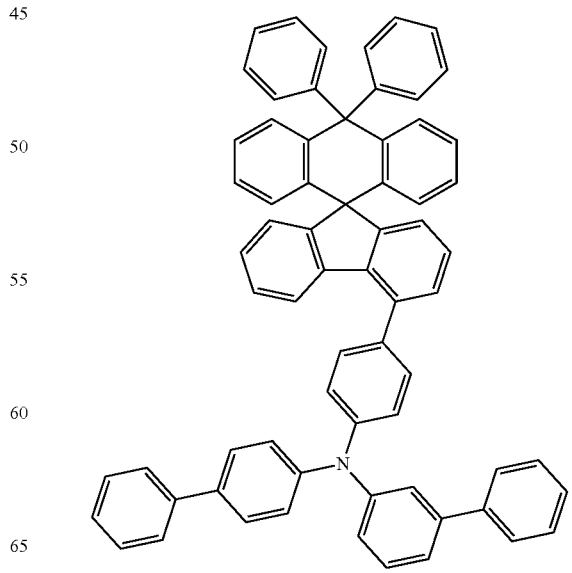

157
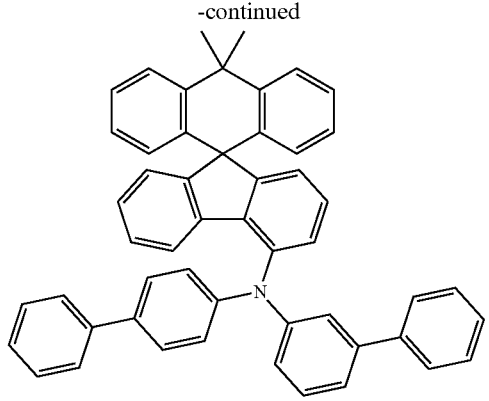
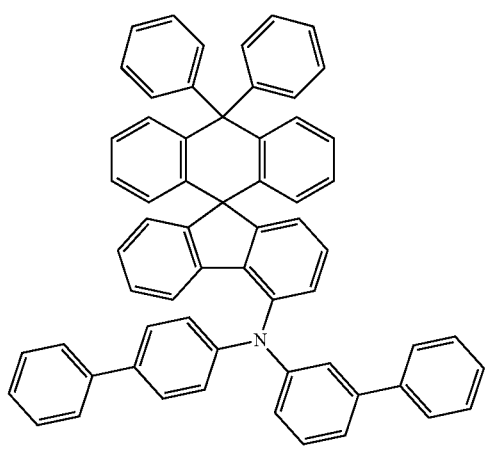
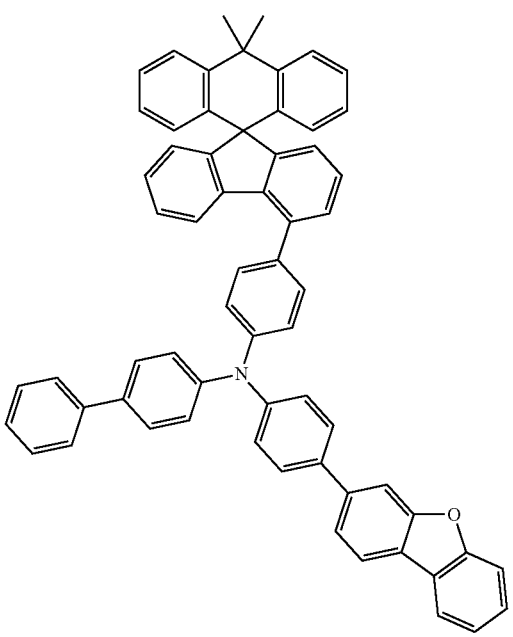
158
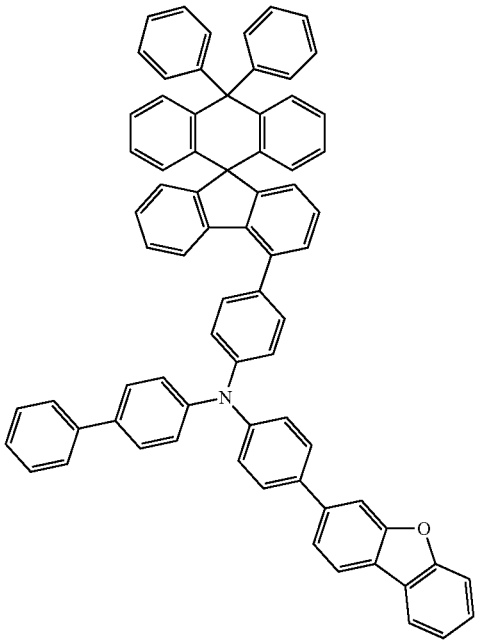
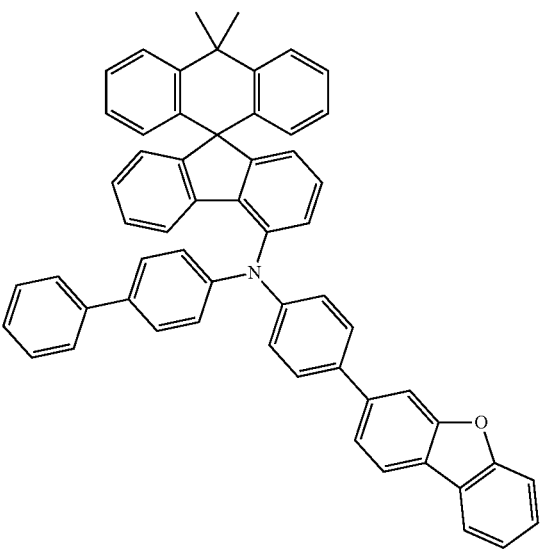

159
-continued
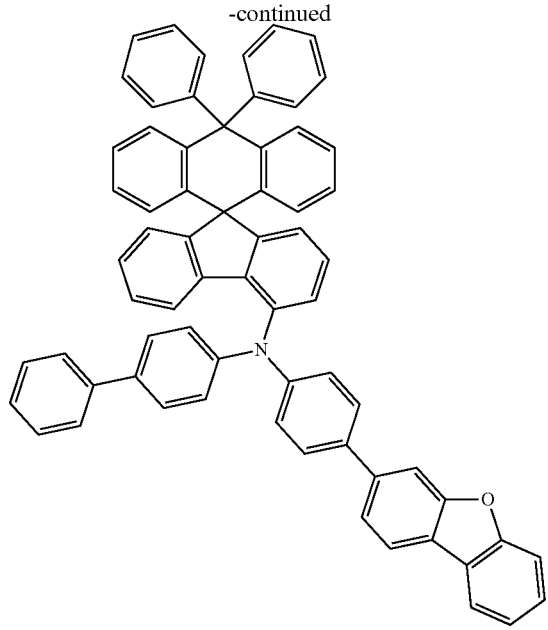
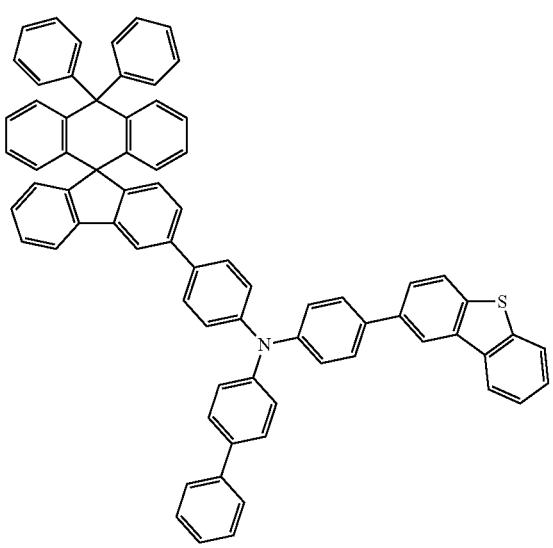
160
-continued
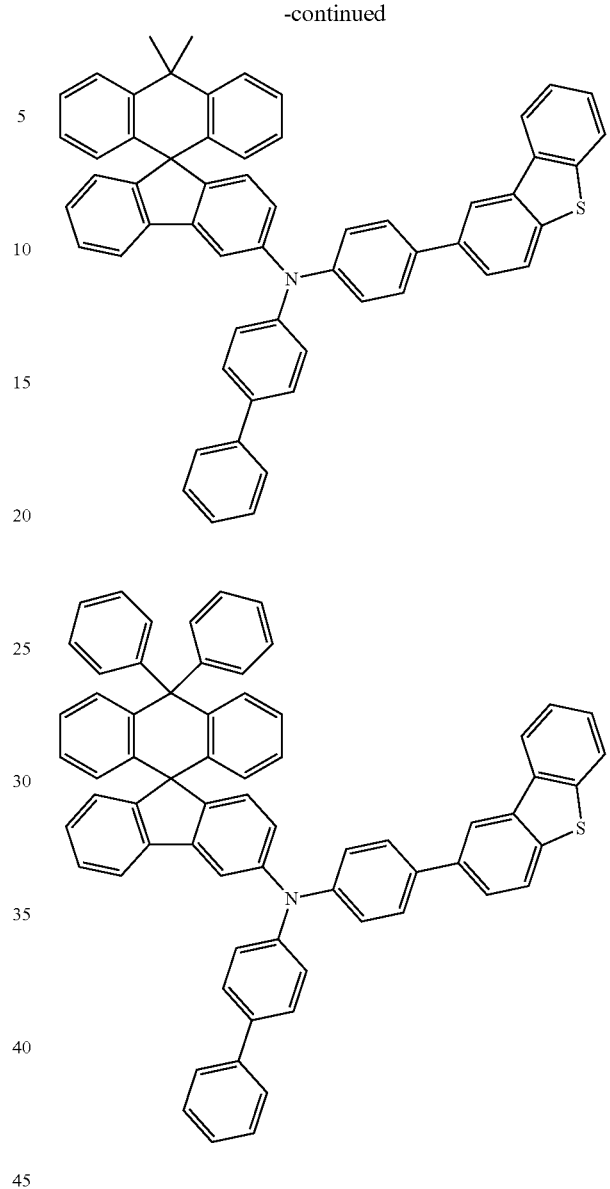
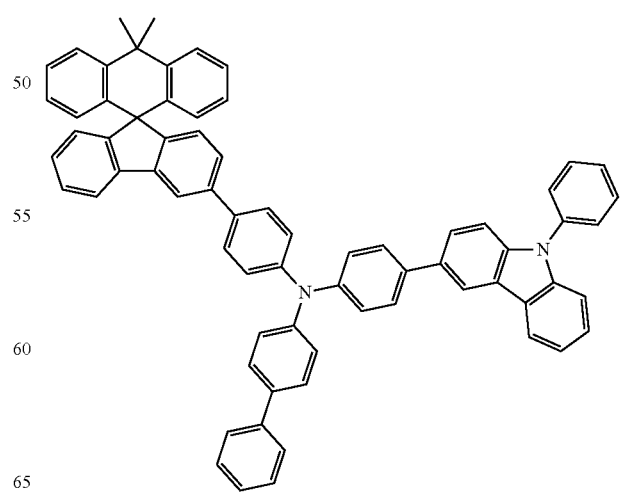

161
-continued
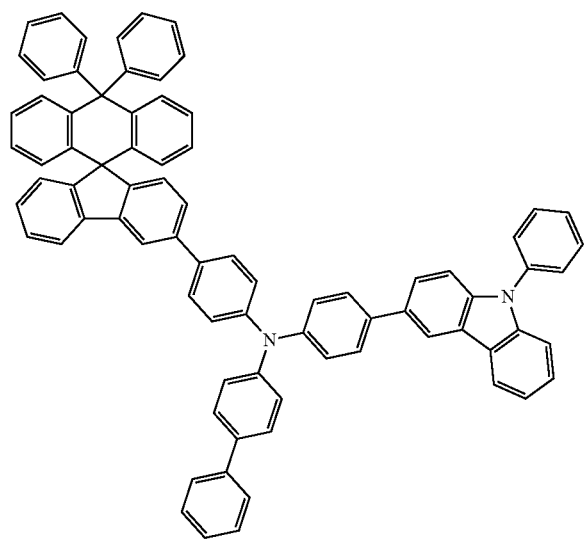
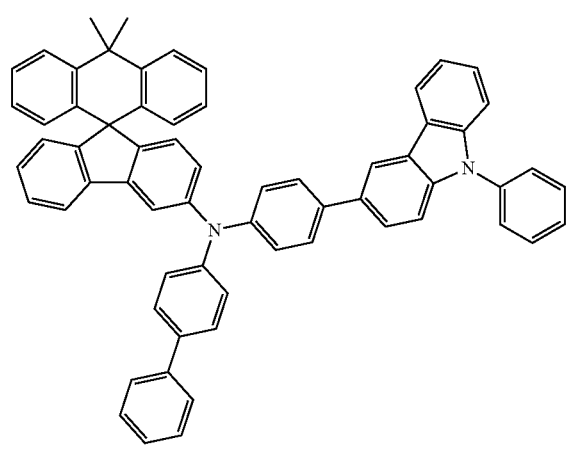
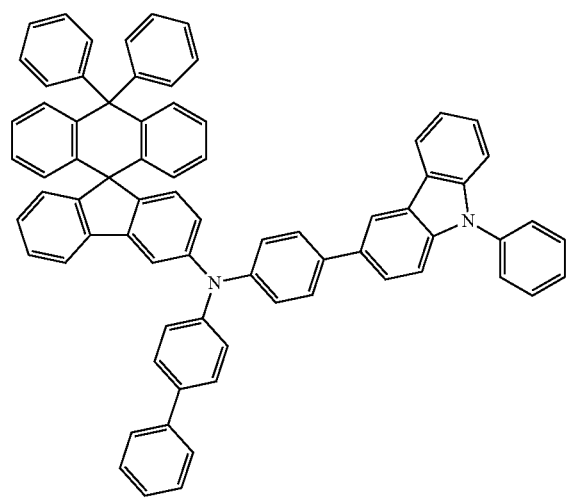
162
-continued
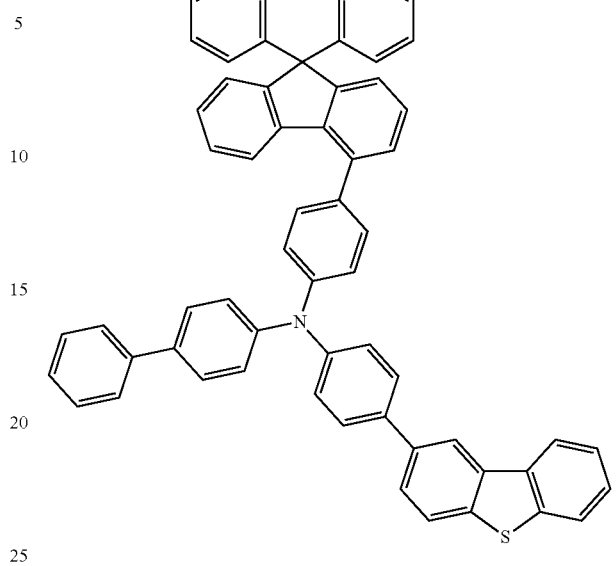
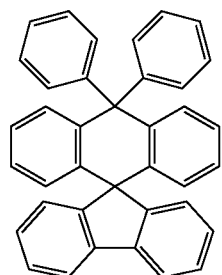

163
-continued
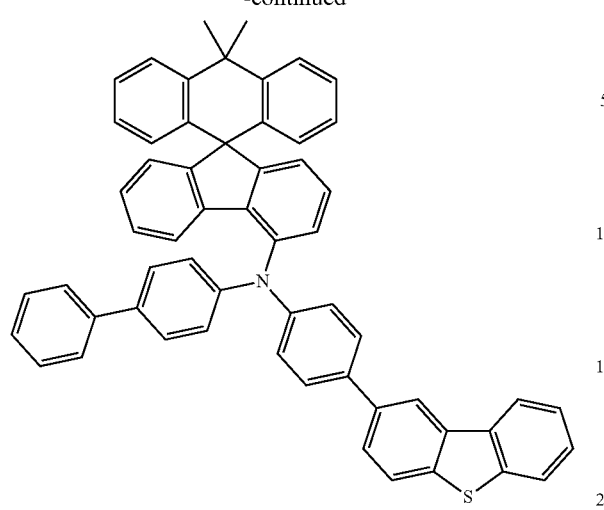
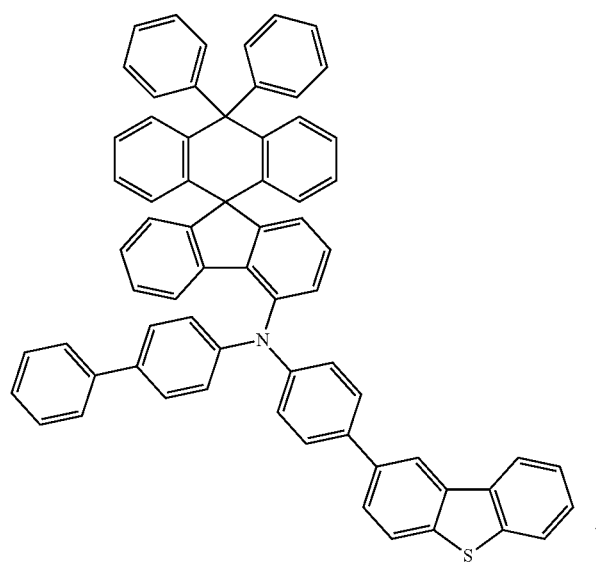
164
-continued
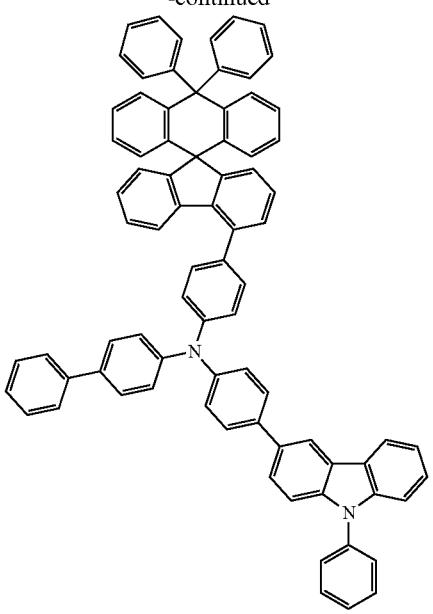
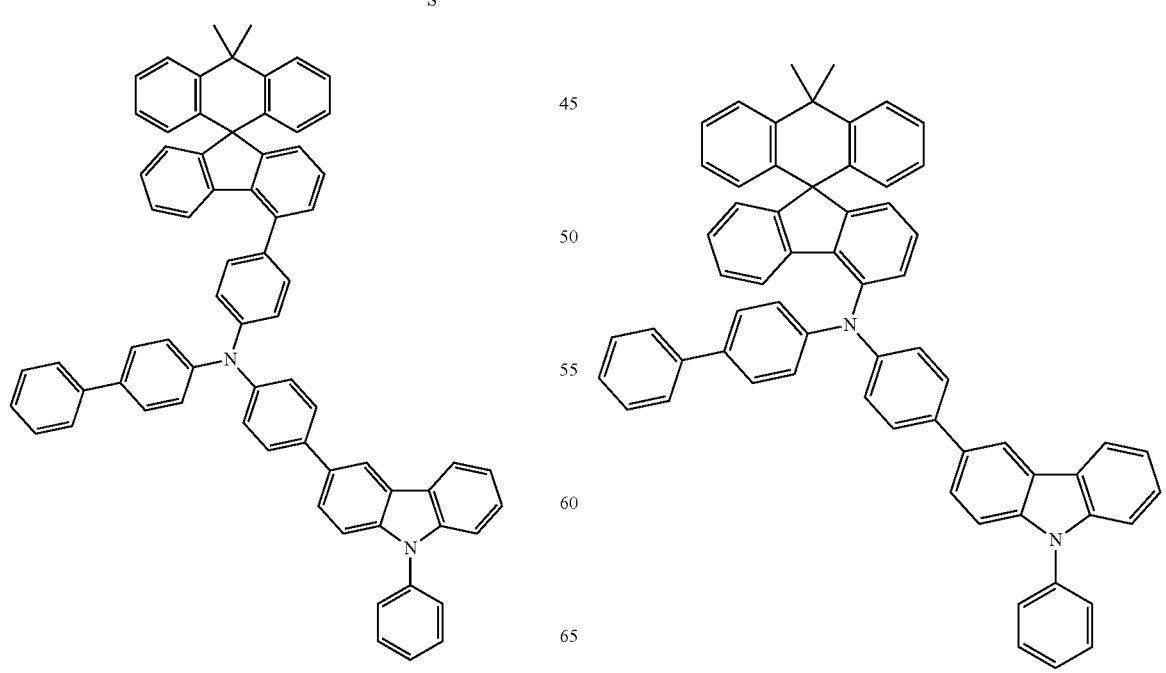

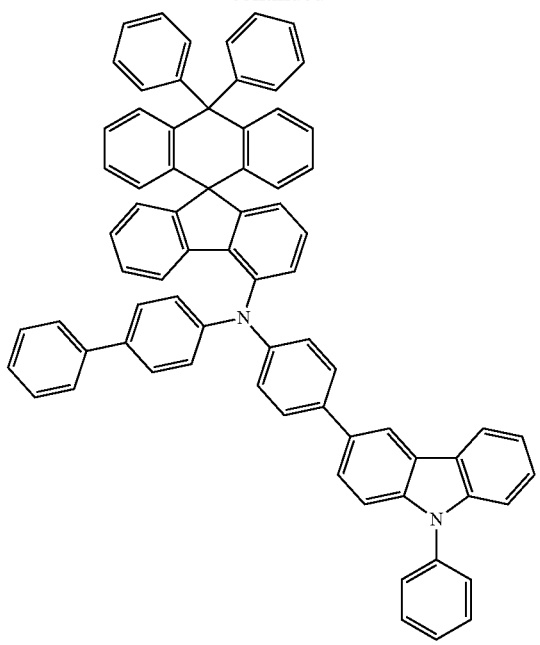
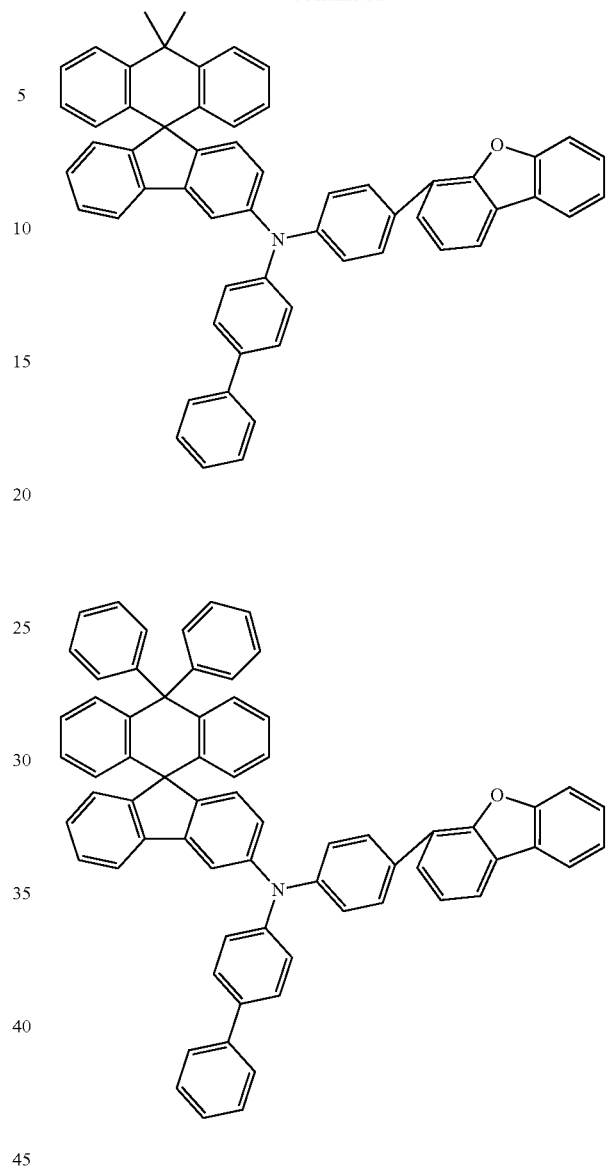
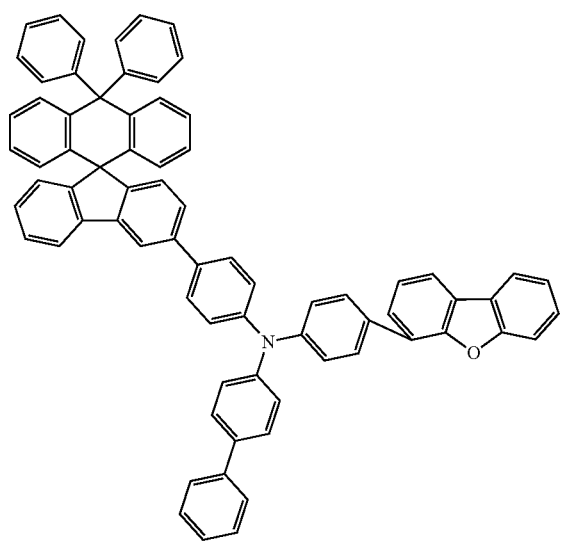
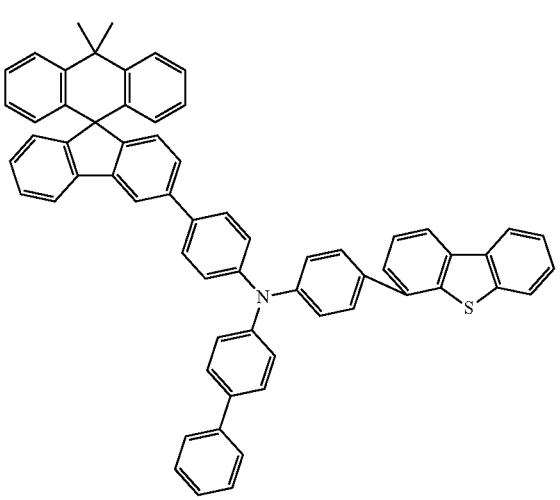

167
-continued
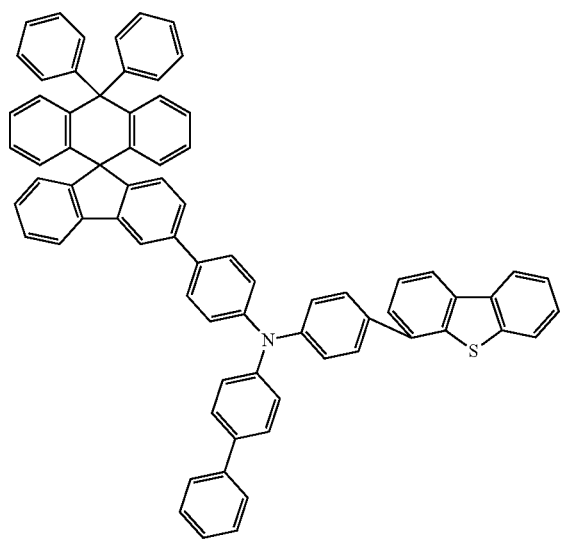
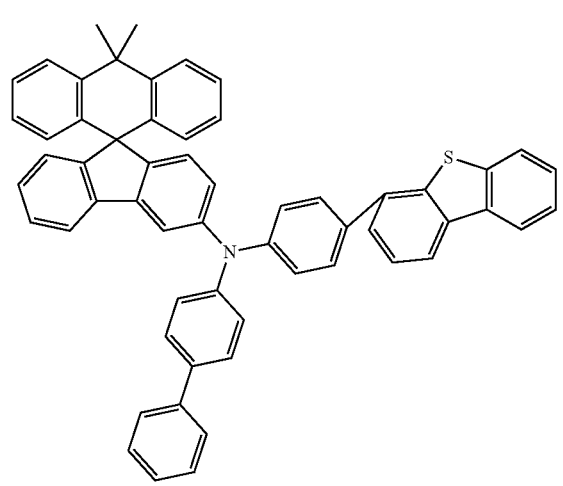
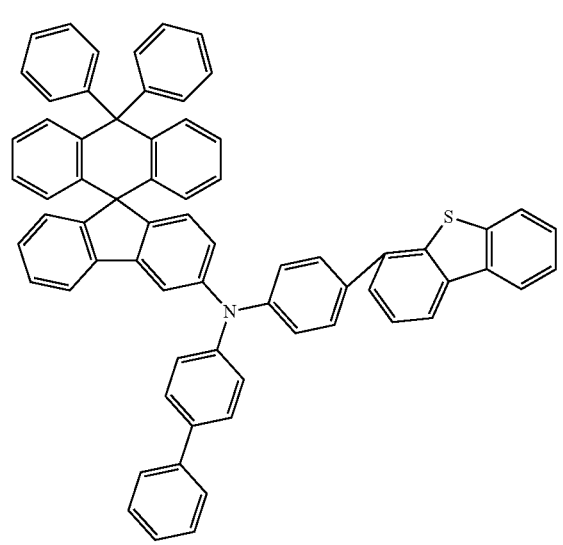
168
-continued
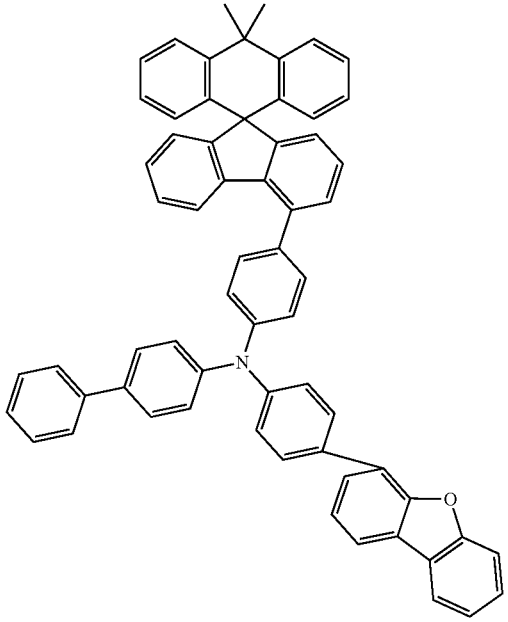
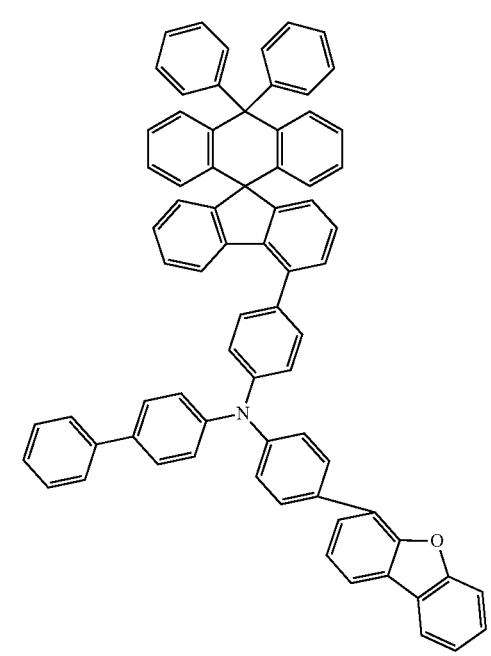

169
-continued
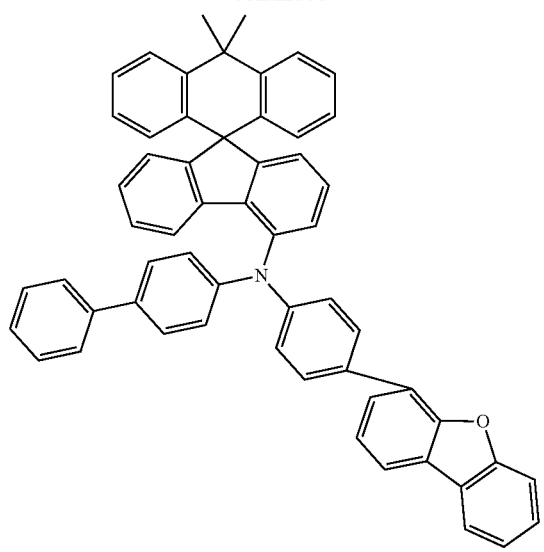
170
-continued
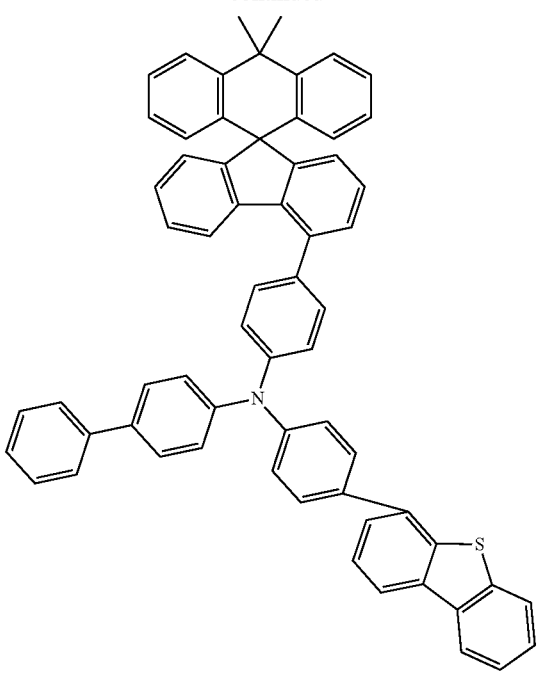
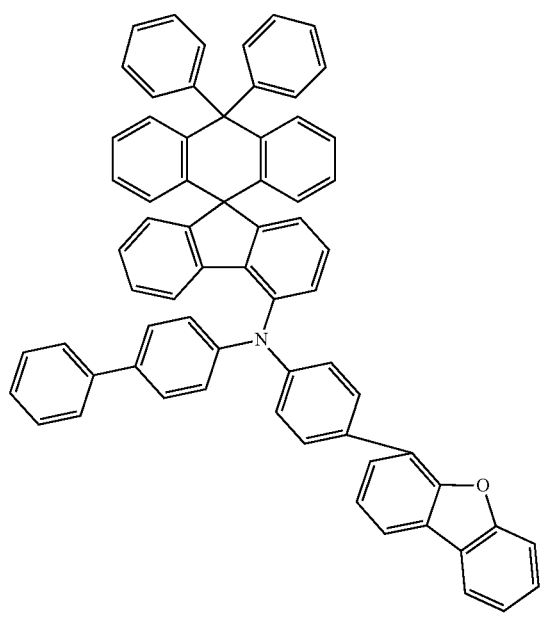
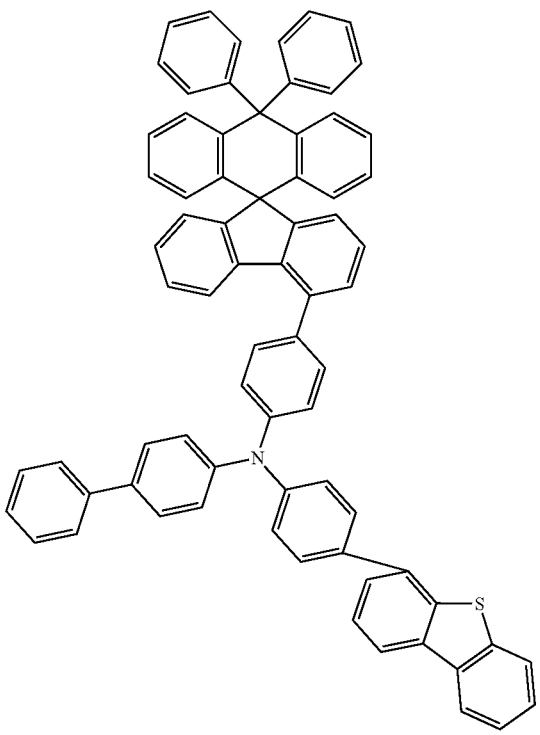

-continued

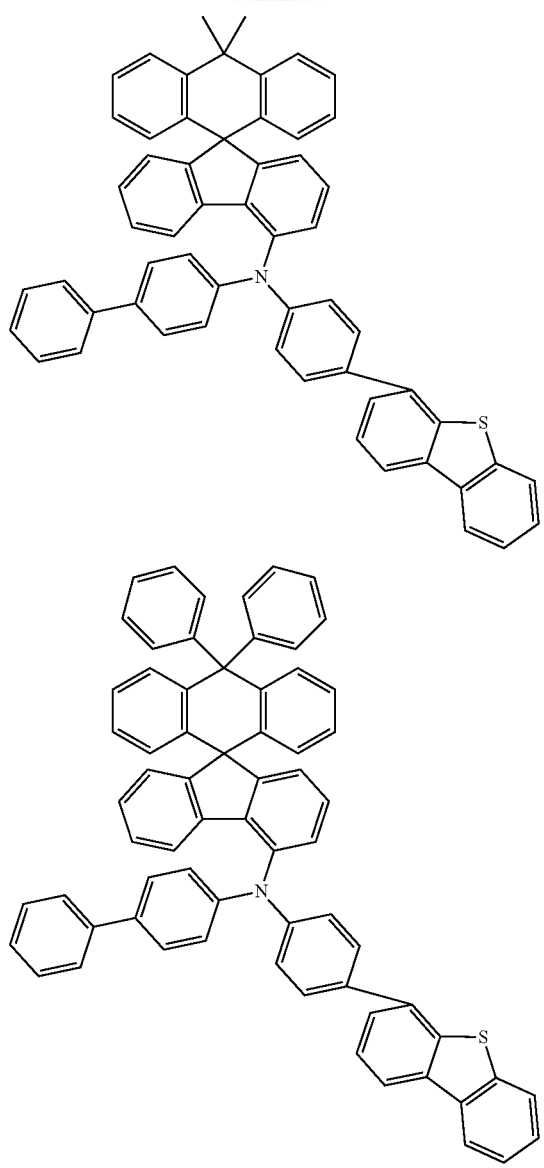 [SMILES: CC1(C)c2ccccc2C2(c3ccccc3-c3c(N(c4ccc(-c5ccccc5)cc4)c4ccc(-c5ccc6c(c5)oc5ccccc56)cc4)cccc32)c2ccccc21 ; c1ccc(-c2ccc(N(c3ccc(-c4ccc5c(c4)oc4ccccc45)cc3)c3cccc4c3-c3ccccc3C43c4ccccc4C(c4ccccc4)(c4ccccc4)c4ccccc43)cc2)cc1]

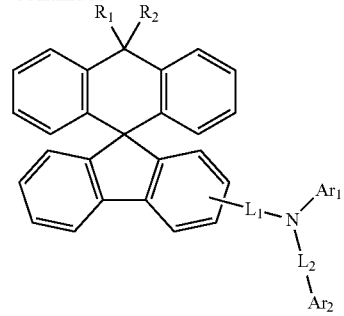

[Reaction Scheme 2]

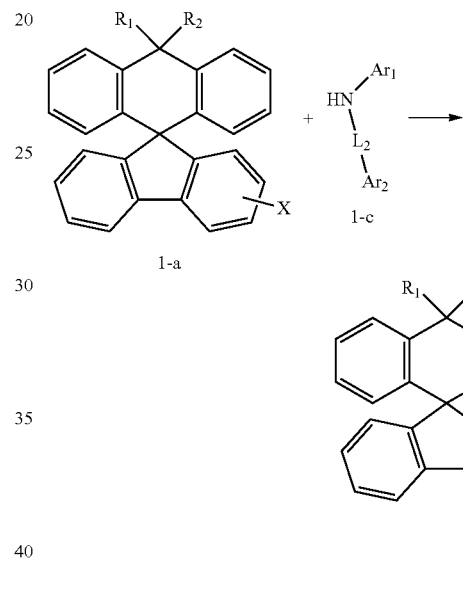

The compound represented by the Chemical Formula 1 may be prepared according to the preparation method as shown in the following Reaction Schemes 1 (when $L_1$ is $C_{6-60}$ arylene) or the following Reaction Scheme 2 (when $L_1$ is a bond).

[Reaction Scheme 1]

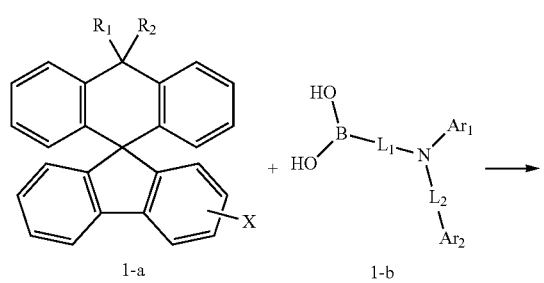

in the Reaction Schemes 1 and 2, $R_1$, $R_2$, $L_1$, $Ar_1$ and $Ar_2$ are as defined above, and X is halogen, preferably chloro.

The Reaction Scheme 1 is a Suzuki coupling reaction, which is a reaction of preparing a compound represented by the Chemical Formula 1 by reacting a compound represented by the Chemical Formula 1-a with a compound represented by the Chemical Formula 1-b. Reaction Scheme 2 is a reaction in which an amine group is substituted while a halogen is eliminated, which is a reaction of preparing a compound represented by the Chemical Formula 1 by reacting a compound represented by the Chemical Formula 1-a with a compound represented by the Chemical Formula 1-c. The preparation method can be further specified in the preparation examples to be described later.

In addition, the present disclosure provides an organic light emitting device comprising the compound represented by the Chemical Formula 1. In one example, the present disclosure provides an organic light emitting device comprising a first electrode; a second electrode provided at a side opposite to the first electrode; and at least one layer of organic material layers provided between the first electrode and the and the second electrode, wherein the at least one layer of the organic material layers comprises a compound represented by the Chemical Formula 1.

The organic material layer of the organic light emitting device of the present disclosure may have a single layer structure, but it may have a multilayered structure in which two or more organic material layers are stacked. For example, the organic light emitting device of the present disclosure may have a structure comprising a hole injection layer, a hole transport layer, an electron blocking layer, a light emitting layer, an electron transport layer, an electron injection layer and the like as the organic material layer. However, the structure of the organic light emitting device is not limited thereto, and it may include a smaller number of organic layers.

Further, the organic material layer may include a hole injection layer, a hole transport layer, or an electron blocking layer, wherein the hole injection layer, the hole transport layer, or the electron blocking layer comprises a compound represented by the Chemical Formula 1.

Further, the organic light emitting device according to the present disclosure may be a normal type organic light emitting device in which an anode, at least one organic material layer, and a cathode are sequentially stacked on a substrate. Further, the organic light emitting device according to the present disclosure may be an inverted type organic light emitting device in which a cathode, at least one organic material layer and an anode are sequentially stacked on a substrate. For example, the structure of an organic light emitting device according to an embodiment of the present disclosure is illustrated in FIG. 1.

FIG. 1 shows an example of an organic light emitting device comprising a substrate 1, an anode 2, an organic material layer 3, and a cathode 4.

FIG. 2 shows an example of an organic light emitting device comprising a substrate 1, an anode 2, a hole injection layer 5, a hole transport layer 6, an electron blocking layer 7, a light emitting layer 8, an electron transport layer 9, an electron injection layer 10, and a cathode 4. In such a structure, the compound represented by the Chemical Formula 1 may be included in at least one layer of the hole injection layer, the hole transport layer, and the electron blocking layer.

The organic light emitting device according to the present disclosure may be manufactured by materials and methods known in the art, except that at least one layer of the organic material layers comprises the compound represented by the Chemical Formula 1. In addition, when the organic light emitting device includes a plurality of organic material layers, the organic material layers may be formed of the same material or different materials.

For example, the organic light emitting device according to the present disclosure can be manufactured by sequentially stacking a first electrode, an organic material layer and a second electrode on a substrate. In this case, the organic light emitting device may be manufactured by depositing a metal, metal oxides having conductivity, or an alloy thereof on the substrate by using a PVD (physical vapor deposition) method such as a sputtering method or an e-beam evaporation method to form the anode, forming an organic material layer including the hole injection layer, the hole transport layer, the light emitting layer, and the electron transport layer thereon, and then depositing a material that can be used as the cathode thereon. In addition to such a method, the organic light emitting device may be manufactured by sequentially depositing a cathode material, an organic material layer and an anode material on a substrate.

In addition, the compound represented by the Chemical Formula 1 may be formed into an organic layer by a solution coating method as well as a vacuum deposition method at the time of manufacturing an organic light emitting device. Herein, the solution coating method means a spin coating, a dip coating, a doctor blading, an inkjet printing, a screen printing, a spray method, a roll coating, or the like, but is not limited thereto.

In addition to such a method, the organic light emitting device may be manufactured by sequentially depositing a cathode material, an organic material layer, and an anode material on a substrate (International Publication WO 2003/012890). However, the manufacturing method is not limited thereto.

For example, the first electrode is an anode and the second electrode is a cathode, or the first electrode is a cathode and the second electrode is an anode.

As the anode material, generally, a material having a large work function is preferably used so that holes can be smoothly injected into the organic material layer. Specific examples of the anode material include metals such as vanadium, chrome, copper, zinc, and gold, or an alloy thereof; metal oxides such as zinc oxides, indium oxides, indium tin oxides (ITO), and indium zinc oxides (IZO); a combination of metals and oxides, such as ZnO:Al or $SNO_2$:Sb; conductive polymers such as poly(3-methylthiophene), poly[3,4-(ethylene-1,2-dioxy)thiophene](PEDOT), polypyrrole, and polyaniline, and the like, but are not limited thereto.

As the cathode material, generally, a material having a small work function is preferably used so that electrons can be easily injected into the organic material layer. Specific examples of the cathode material include metals such as magnesium, calcium, sodium, potassium, titanium, indium, yttrium, lithium, gadolinium, aluminum, silver, tin, and lead, or an alloy thereof; a multilayered structure material such as LiF/Al or $LiO_2$/Al, and the like, but are not limited thereto.

The hole injection layer is a layer for injecting holes from the electrode, and the hole injection material is preferably a compound which has an ability of transporting the holes, a hole injecting effect in the anode and an excellent hole injecting effect to the light emitting layer or the light emitting material, prevents movement of an exciton generated in the light emitting layer to the electron injection layer or the electron injection material, and has an excellent thin film forming ability. It is preferable that a HOMO (highest occupied molecular orbital) of the hole injection material is between the work function of the anode material and a HOMO of a peripheral organic material layer. Specific examples of the hole injection material include a compound represented by the Chemical Formula 1 according to the present disclosure, or metal porphyrin, oligothiophene, an arylamine-based organic material, a hexanitrilehexaazatriphenylene-based organic material, a quinacridone-based organic material, a perylene-based organic material, anthraquinone, polyaniline and polythiophene-based conductive polymer, and the like, but are not limited thereto.

The hole transport layer is a layer that receives holes from a hole injection layer and transports the holes to the light emitting layer. The hole transport material is suitably a material having large mobility to the holes, which may receive holes from the anode or the hole injection layer and transfer the holes to the light emitting layer. Specific examples thereof include a compound represented by the Chemical Formula 1 according to the present disclosure, or an arylamine-based organic material, a conductive polymer, a block copolymer in which a conjugate portion and a non-conjugate portion are present together, and the like, but are not limited thereto.

The electron blocking layer serves to suppress the electrons injected from the cathode from being transmitted toward the anode without being recombined in the light emitting layer, thereby improving the efficiency of the organic light emitting device. In the present disclosure, the compound represented by the Chemical Formula 1 according to the present disclosure can be used as the substance constituting the electron blocking layer.

The light emitting material is a material capable of emitting light in the visible light region by combining holes and electrons respectively transported from the hole transport layer and the electron transport layer, and having good quantum efficiency for fluorescence or phosphorescence. Specific examples include 8-hydroxy-quinoline aluminum complex ($Alq_3$); carbazole-based compounds; dimerized styryl compounds; BAlq; 10-hydroxybenzoquinoline-metal compounds; benzoxazole, benzothiazole and benzimidazole-based compounds; poly(p-phenylenevinylene)(PPV)-based polymers; spiro compounds; polyfluorene, rubrene, and the like, but are not limited thereto.

The light emitting layer may include a host material and a dopant material. The host material may be a fused aromatic ring derivative, a heterocycle-containing compound or the like. Specific examples of the fused aromatic ring derivatives include anthracene derivatives, pyrene derivatives, naphthalene derivatives, pentacene derivatives, phenanthrene compounds, and fluoranthene compounds. Examples of heterocyclic compounds include carbazole derivatives, dibenzofuran derivatives, ladder-type furan compounds, pyrimidine derivatives, and the like, but are not limited thereto.

Examples of the dopant material include an aromatic amine derivative, a styrylamine compound, a boron complex, a fluoranthene compound, a metal complex, and the like. Specific examples of the aromatic amine derivatives include substituted or unsubstituted fused aromatic ring derivatives having an arylamino group, examples thereof include pyrene, anthracene, chrysene, and periflanthene having the arylamino group, and the like, the styrylamine compound is a compound where at least one arylvinyl group is substituted in substituted or unsubstituted arylamine, in which one or more substituent groups selected from the group consisting of an aryl group, a silyl group, an alkyl group, a cycloalkyl group, and an arylamino group are substituted or unsubstituted. Specific examples thereof include styrylamine, styryldiamine, styryltriamine, styryltetramine, and the like, but are not limited thereto. Further, examples of the metal complex include an iridium complex, a platinum complex, and the like, but are not limited thereto.

The electron transport layer is a layer receiving the electrons from the electron injection layer and transporting the electrons to the light emitting layer, the electron transport material is a material that can receive the electrons well from the cathode and transport the electrons to the light emitting layer, and a material having large mobility to the electrons is suitable. Specific examples thereof include an 8-hydroxyquinoline Al complex; a complex including $Alq_3$; an organic radical compound; a hydroxyflavone-metal complex, and the like, but are not limited thereto. The electron transport layer may be used together with a predetermined desired cathode material as used according to the prior art. Particularly, an example of an appropriate cathode material is a general material having the low work function and followed by an aluminum layer or a silver layer. Specific examples thereof include cesium, barium, calcium, ytterbium, and samarium, and each case is followed by the aluminum layer or the silver layer.

The electron injection layer is a layer injecting the electrons from the electrode, and a compound which has an ability of transporting the electrons, an electron injecting effect from the cathode, and an excellent electron injecting effect to the light emitting layer or the light emitting material, prevents movement of an exciton generated in the light emitting layer to the hole injection layer, and has an excellent thin film forming ability is preferable. Specific examples thereof include fluorenone, anthraquinodimethane, diphenoquinone, thiopyran dioxide, oxazole, oxadiazole, triazole, imidazole, perylene tetracarboxylic acid, fluorenylidene methane, anthrone, and the like, and its derivative, a metal complex compound, a nitrogen-containing 5-membered cycle derivative, and the like, but are not limited thereto.

Examples of the metal complex compound include 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato)gallium, bis(10-hydroxybenzo[h]quinolinato)beryllium, bis(10-hydroxybenzo[h]quinolinato)zinc, bis(2-methyl-8-quinolinato)chlorogallium, bis(2-methyl-8-quinolinato)(o-cresolato)gallium, bis(2-methyl-8-quinolinato)(1-naphtholato)aluminum, bis(2-methyl-8-quinolinato)(2-naphtholato)gallium, and the like, but are not limited thereto.

The organic light emitting device according to the present disclosure may be a front side emission type, a back side emission type, or a double side emission type according to the used material.

In addition, the compound represented by the Chemical Formula 1 may be included in an organic solar cell or an organic transistor in addition to an organic light emitting device.

The preparation of the compound represented by the Chemical Formula 1 and the organic light emitting device comprising the same will be described in detail in the following examples. However, these examples are presented for illustrative purposes only, and the scope of the present disclosure is not limited thereto.

Preparation Example 1

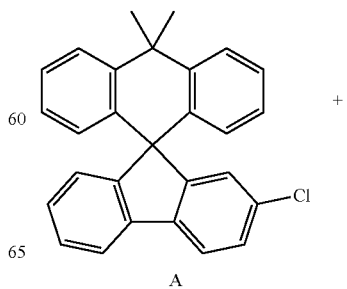

A

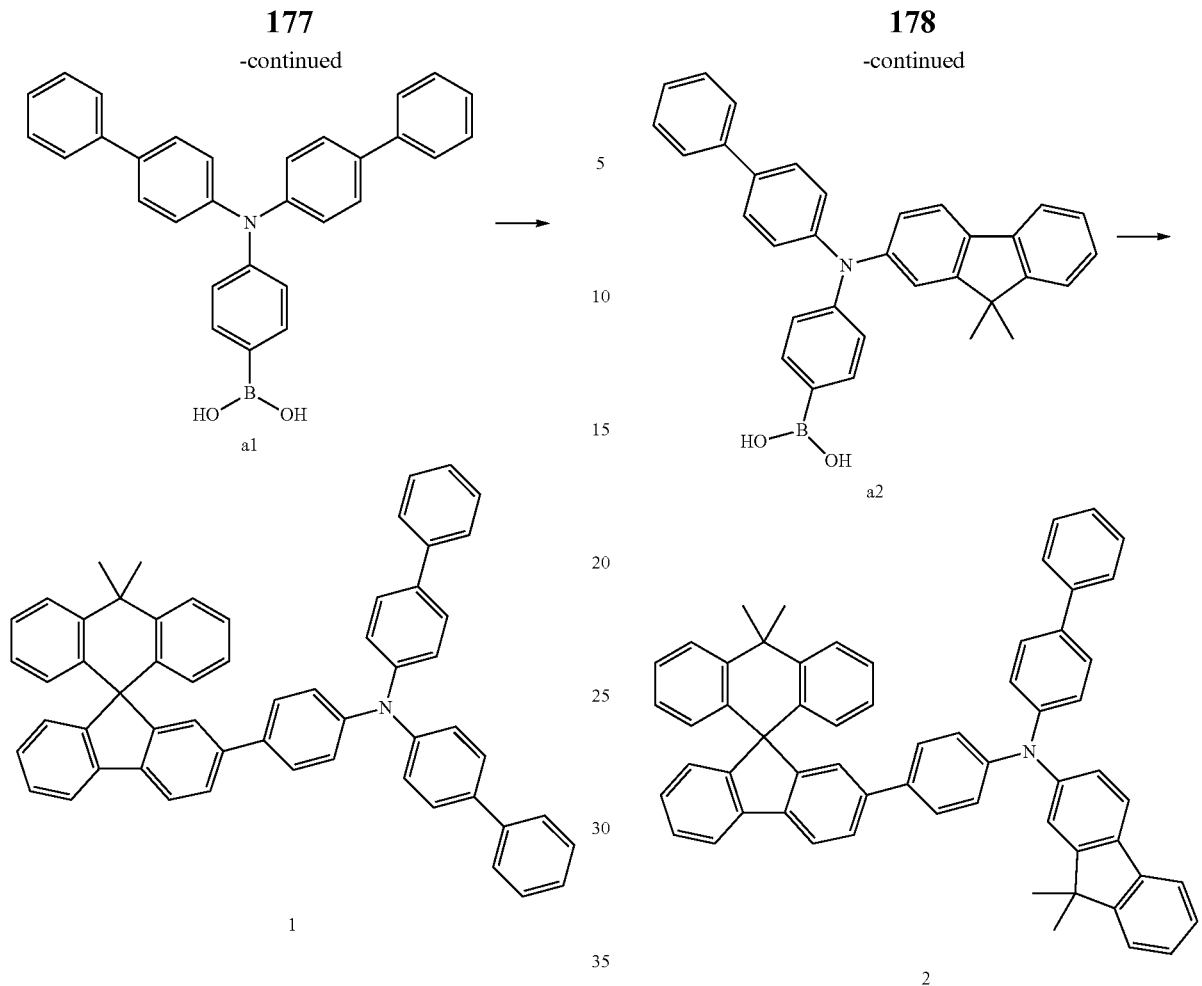

Compound A (7.45 g, 19.01 mmol) and Compound a1 (8.80 g, 19.96 mmol) were completely dissolved in 280 mL of tetrahydrofuran in a 500 mL round bottom flask under nitrogen atmosphere. Then, 2M potassium carbonate aqueous solution (140 mL) was added and tetrakis(triphenylphosphine)palladium (0.66 g, 0.57 mmol) were added thereto, and the resultant mixture was heated and stirred for 4 hours. The temperature was lowered to room temperature, the aqueous layer was removed, and the organic layer was dried over anhydrous magnesium sulfate, concentrated under reduced pressure, and recrystallized with 320 mL of ethyl acetate to give Preparation Example 1 (12.68 g, yield: 88%).

MS[M+H]$^+$=754

Compound A (6.28 g, 16.02 mmol) and Compound a2 (8.09 g, 16.82 mmol) were completely dissolved in 260 mL of tetrahydrofuran in a 500 mL round bottom flask under nitrogen atmosphere. Then, 2 M potassium carbonate aqueous solution (130 mL) was added and tetrakis(triphenylphosphine)palladium (0.56 g, 0.48 mmol) was added thereto, and the resultant mixture was heated and stirred for 3 hours. The temperature was lowered to room temperature, the aqueous layer was removed, and the organic layer was dried over anhydrous magnesium sulfate, concentrated under reduced pressure, and recrystallized with 260 mL of ethyl acetate to give Preparation Example 2 (8.76 g, yield: 73%).

MS[M+H]$^+$=794

Preparation Example 2

Preparation Example 3

-continued

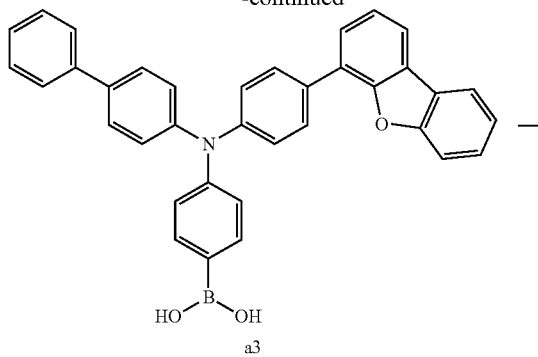

a3

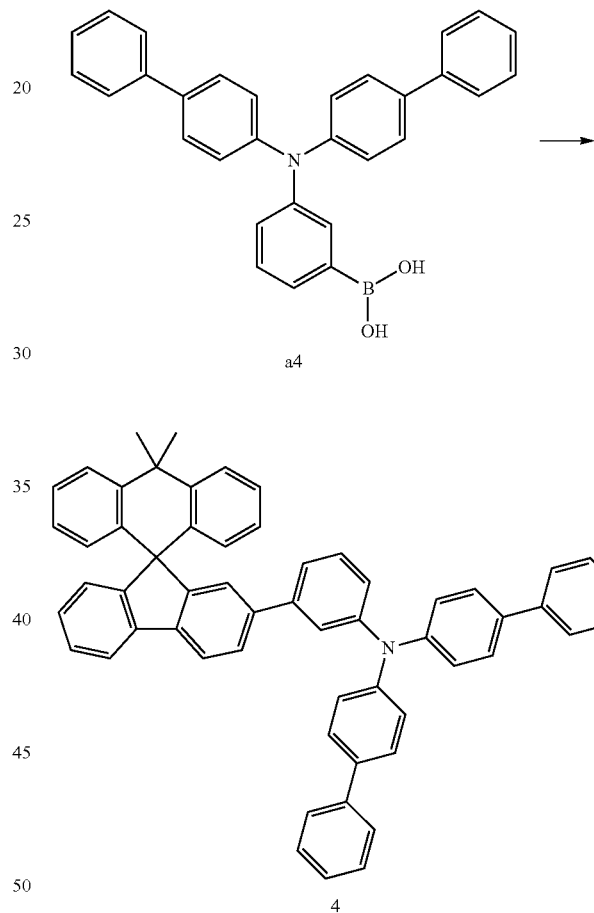

3

Preparation Example 4

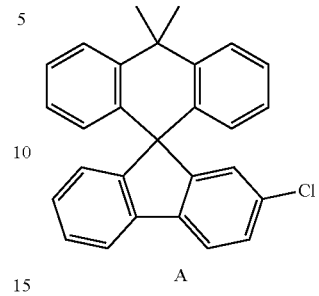

A

[structure]

a4

[structure]

4

Compound A (5.97 g, 15.23 mmol) and Compound a3 (8.49 g, 15.99 mmol) were completely dissolved in 320 mL of tetrahydrofuran in a 500 mL round bottom flask under nitrogen atmosphere. Then, 2 M potassium carbonate aqueous solution (160 mL) was added and tetrakis(triphenylphosphine)palladium (0.53 g, 0.46 mmol) was added thereto, and the resultant mixture was heated and stirred for 4 hours. The temperature was lowered to room temperature, the aqueous layer was removed, and the organic layer was dried over anhydrous magnesium sulfate, concentrated under reduced pressure, and recrystallized with 250 mL of tetrahydrofuran to give Preparation Example 3 (12.68 g, yield: 88%).

MS[M+H]$^+$=844

Compound A (4.69 g, 11.96 mmol) and Compound a4 (5.54 g, 12.56 mmol) were completely dissolved in 220 mL of tetrahydrofuran in a 500 mL round bottom flask under nitrogen atmosphere. Then, 2 M potassium carbonate aqueous solution (110 mL) was added and tetrakis(triphenylphosphine)palladium (0.41 g, 0.36 mmol) was added thereto, and the resultant mixture was heated and stirred for 2 hours. The temperature was lowered to room temperature, the aqueous layer was removed, and the organic layer was dried over anhydrous magnesium sulfate, concentrated under reduced pressure, and recrystallized with 250 mL of ethyl acetate to give Preparation Example 4 (7.77 g, yield: 86%).

MS[M+H]$^+$=754

Preparation Example 5

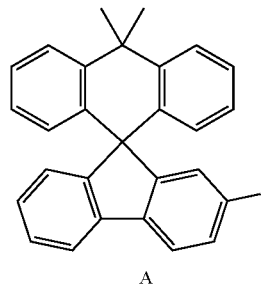

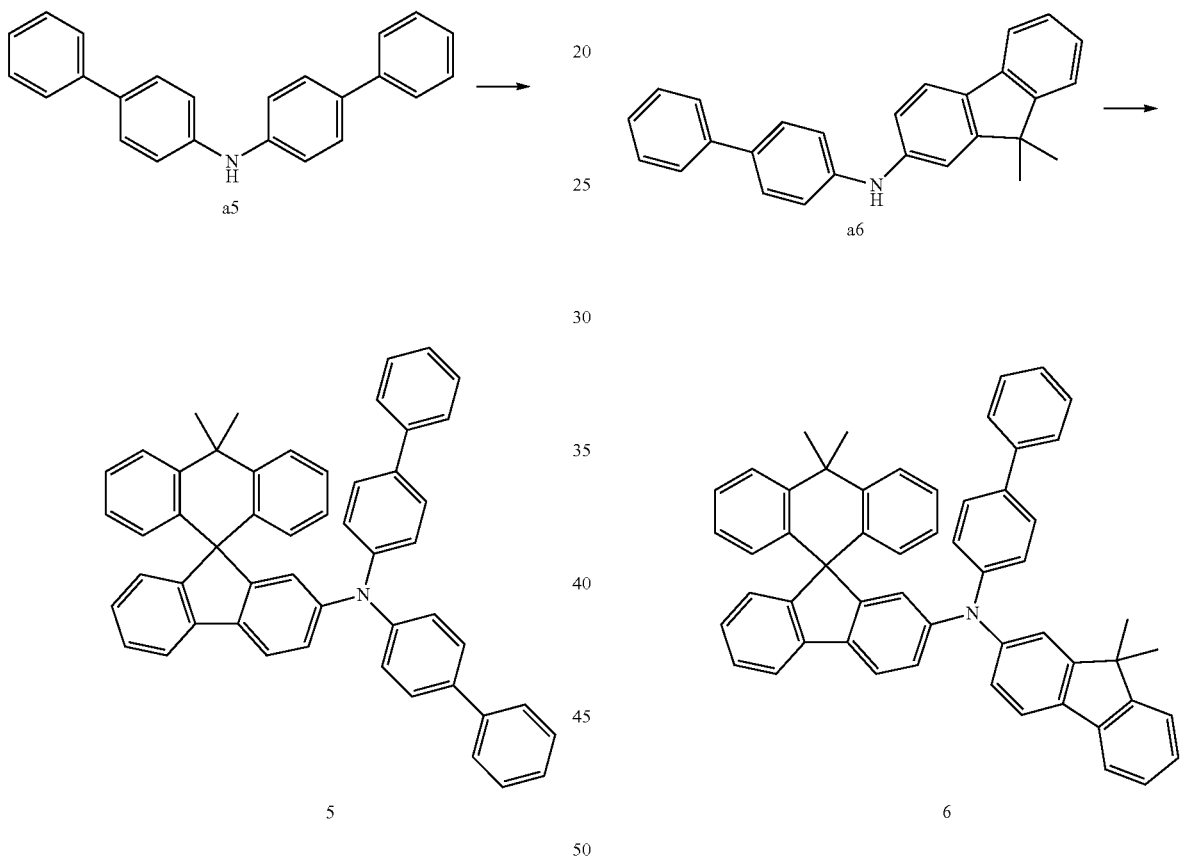

Compound A (7.56 g, 19.29 mmol) and Compound a5 (6.50 g, 20.25 mmol) were completely dissolved in 180 mL of xylene in a 500 mL round bottom flask under nitrogen atmosphere. Then, NaOtBu (2.22 g, 23.14 mmol) was added and bis(tri-tert-butylphosphine)palladium(0) (0.10 g, 0.19 mmol) was added thereto, and the resultant mixture was heated and stirred for 4 hours. The temperature was lowered to room temperature, and filtering was carried out to remove a base. Then, xylene was concentrated under reduced pressure and recrystallized with 180 mL of ethyl acetate to give Preparation Example 5 (10.12 g, yield: 78%).

MS[M+H]$^+$=678

Preparation Example 6

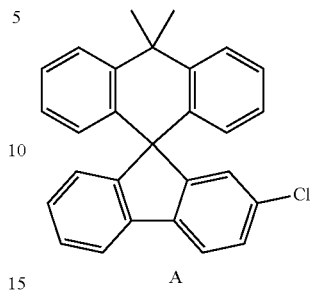

Compound A (7.56 g, 19.29 mmol) and Compound a6 were completely dissolved in 220 mL of xylene in a 500 mL round bottom flask under nitrogen atmosphere. Then, NaOtBu (2.22 g, 23.14 mmol) was added and bis(tri-tert-butylphosphine)palladium(0)(0.10 g, 0.19 mmol) was added thereto, and the resultant mixture was heated and stirred for 4 hours. The temperature was lowered to room temperature, and filtering was carried out to remove a base. Then, xylene was concentrated under reduced pressure and recrystallized with 180 mL of ethyl acetate to give Preparation Example 6 (10.12 g, yield: 78%).

MS[M+H]$^+$=718

183
Preparation Example 7

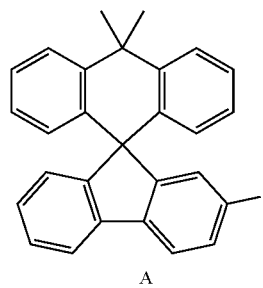

A

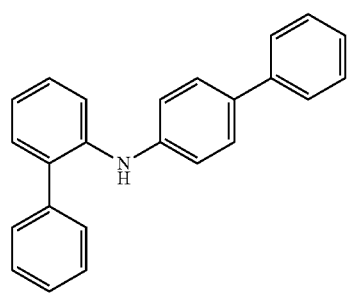

a7

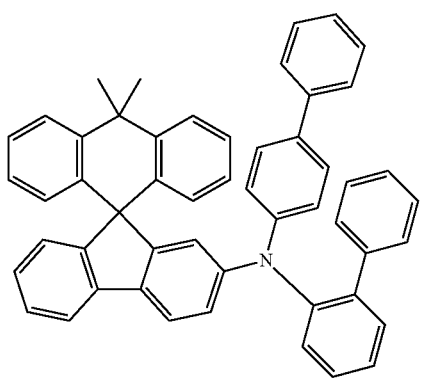

7

Compound A (5.98 g, 15.26 mmol) and Compound a7 (5.14 g, 16.02 mmol) were completely dissolved in 160 mL of xylene in a 500 mL round bottom flask under nitrogen atmosphere. Then, NaOtBu (1.76 g, 18.31 mmol) was added and bis(tri-tert-butylphosphine)palladium(0) (0.08 g, 0.15 mmol) was added thereto, and the resultant mixture was heated and stirred for 7 hours. The temperature was lowered to room temperature, and filtering was carried out to remove a base. Then, xylene was concentrated under reduced pressure and recrystallized with 240 mL of ethyl acetate to give Preparation Example 7 (6.15 g, yield: 59%).

MS[M+H]$^+$=678

184
Preparation Example 8

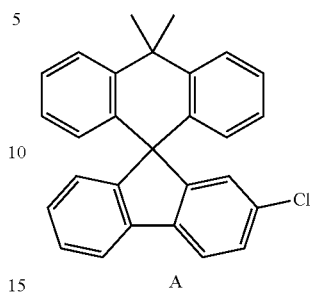

A

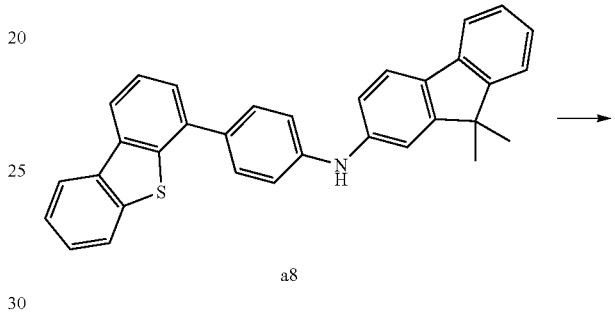

a8

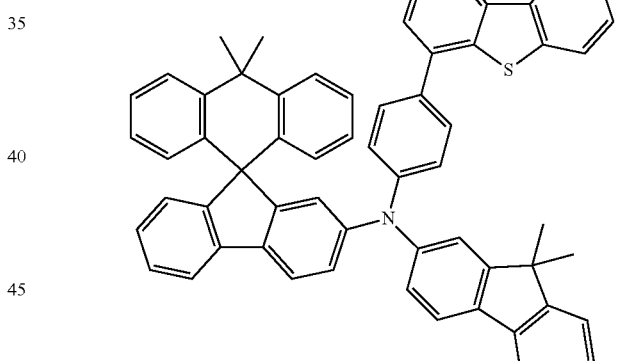

8

Compound A (4.65 g, 11.86 mmol) and Compound a8 (5.82 g, 12.46 mmol) were completely dissolved in 260 mL of xylene in a 500 mL round bottom flask under nitrogen atmosphere. Then, NaOtBu (1.37 g, 14.23 mmol) was added and bis(tri-tert-butylphosphine)palladium(0) (0.06 g, 0.12 mmol) was added thereto, and the resultant mixture was heated and stirred for 6 hours. The temperature was lowered to room temperature, and filtering was carried out to remove a base. Then, xylene was concentrated under reduced pressure and recrystallized with 220 mL of ethyl acetate to give Preparation Example 8 (7.23 g, yield: 74%).

MS[M+H]$^+$=824

Preparation Example 9

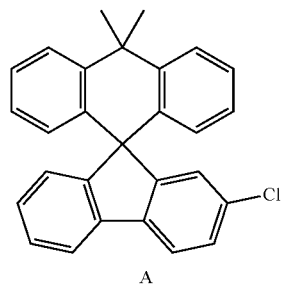

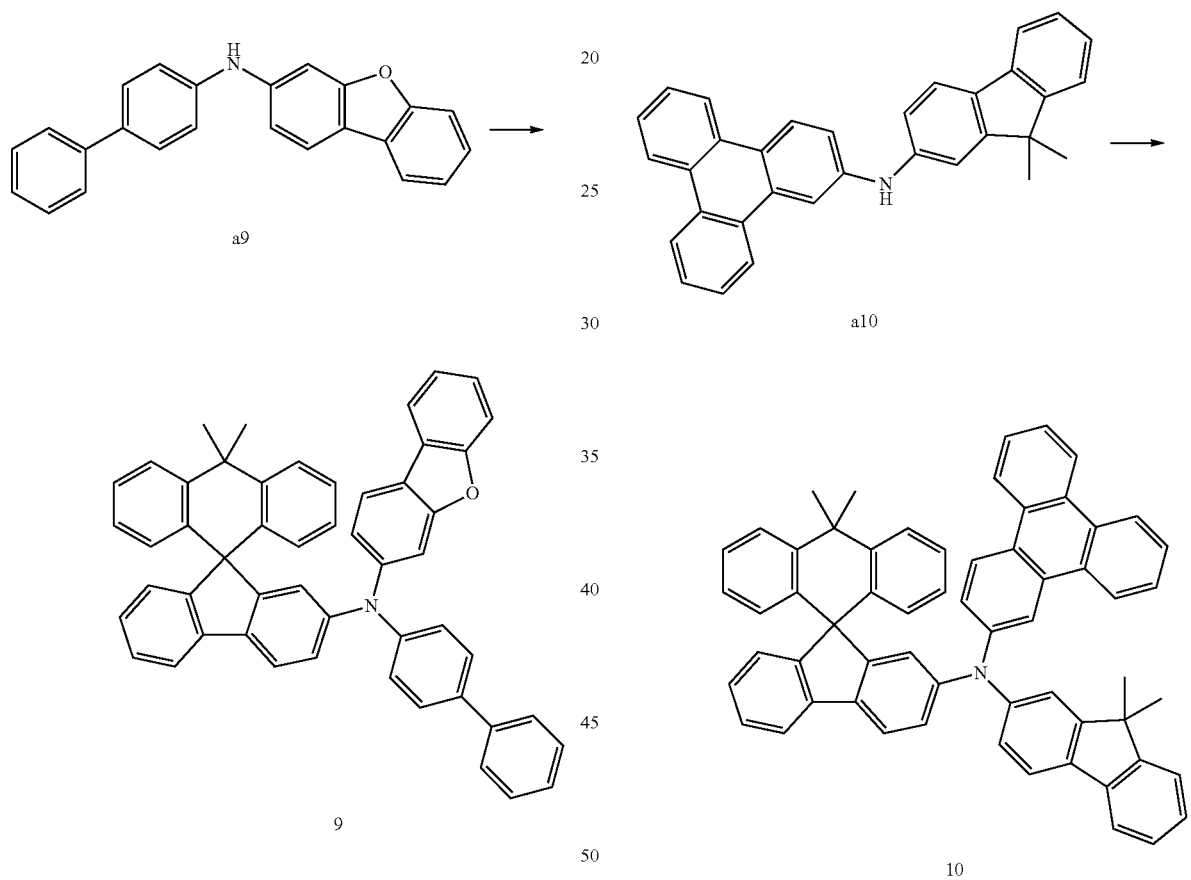

Compound A (5.25 g, 13.39 mmol) and Compound a9 (4.71 g, 14.06 mmol) were completely dissolved in 220 mL of xylene in a 500 mL round bottom flask under nitrogen atmosphere. Then, NaOtBu (1.54 g, 16.07 mmol) was added and bis(tri-tert-butylphosphine)palladium(0) (0.07 g, 0.13 mmol) was added thereto, and the resultant mixture was heated and stirred for 6 hours. The temperature was lowered to room temperature, and filtering was carried out to remove a base. Then, xylene was concentrated under reduced pressure and recrystallized with 220 mL of ethyl acetate to give Preparation Example 9 (6.44 g, yield: 69%).

MS[M+H]$^+$=692

Preparation Example 10

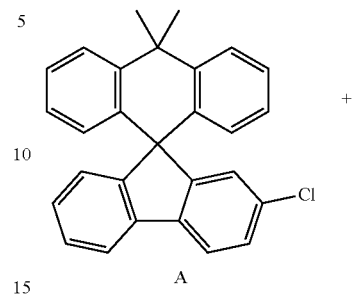

Compound A (6.33 g, 16.15 mmol) and Compound a10 (7.38 g, 16.96 mmol) were completely dissolved in 230 mL of xylene in a 500 mL round bottom flask under nitrogen atmosphere. Then, NaOtBu (1.86 g, 19.38 mmol) was added and bis(tri-tert-butylphosphine)palladium(0) (0.08 g, 0.16 mmol) was added thereto, and the resultant mixture was heated and stirred for 4 hours. The temperature was lowered to room temperature, and filtering was carried out to remove a base. Then, xylene was concentrated under reduced pressure and recrystallized with 240 mL of ethyl acetate to give Preparation Example 10 (10.88 g, yield: 85%).

MS[M+H]$^+$=792

Preparation Example 11

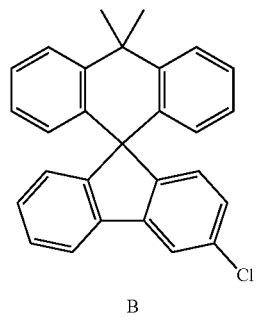

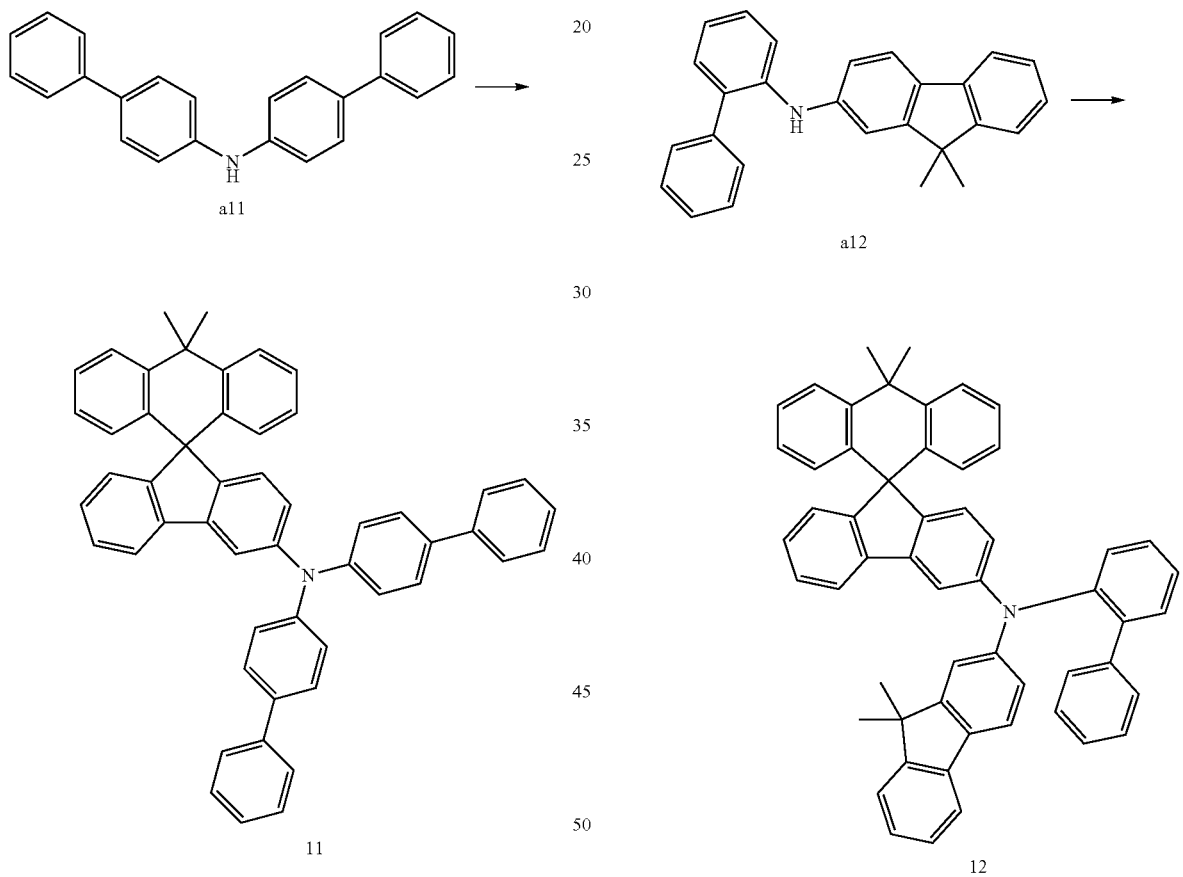

Compound B (7.56 g, 19.29 mmol) and Compound a11 (6.50 g, 20.25 mmol) were completely dissolved in 180 mL of xylene in a 500 mL round bottom flask under nitrogen atmosphere. Then, NaOtBu (2.22 g, 23.14 mmol) was added and bis(tri-tert-butylphosphine)palladium(0) (0.10 g, 0.19 mmol) was added thereto, and the resultant mixture was heated and stirred for 4 hours. The temperature was lowered to room temperature, and filtering was carried out to remove a base. Then, xylene was concentrated under reduced pressure and recrystallized with 180 mL of ethyl acetate to give Preparation Example 11 (10.12 g, yield: 78%).

MS[M+H]$^+$=678

Preparation Example 12

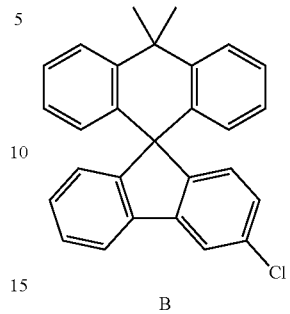

Compound B (4.89 g, 12.47 mmol) and Compound a12 (4.73 g, 13.10 mmol) were completely dissolved in 250 mL of xylene in a 500 mL round bottom flask under nitrogen atmosphere. Then, NaOtBu (1.44 g, 14.97 mmol) was added and bis(tri-tert-butylphosphine)palladium(0) (0.06 g, 0.12 mmol) was added thereto, and the resultant mixture was heated and stirred for 3 hours. The temperature was lowered to room temperature, and filtering was carried out to remove a base. Then, xylene was concentrated under reduced pressure and recrystallized with 210 mL of ethyl acetate to give Preparation Example 12 (5.27 g, yield: 59%).

MS[M+H]$^+$=718

Preparation Example 13

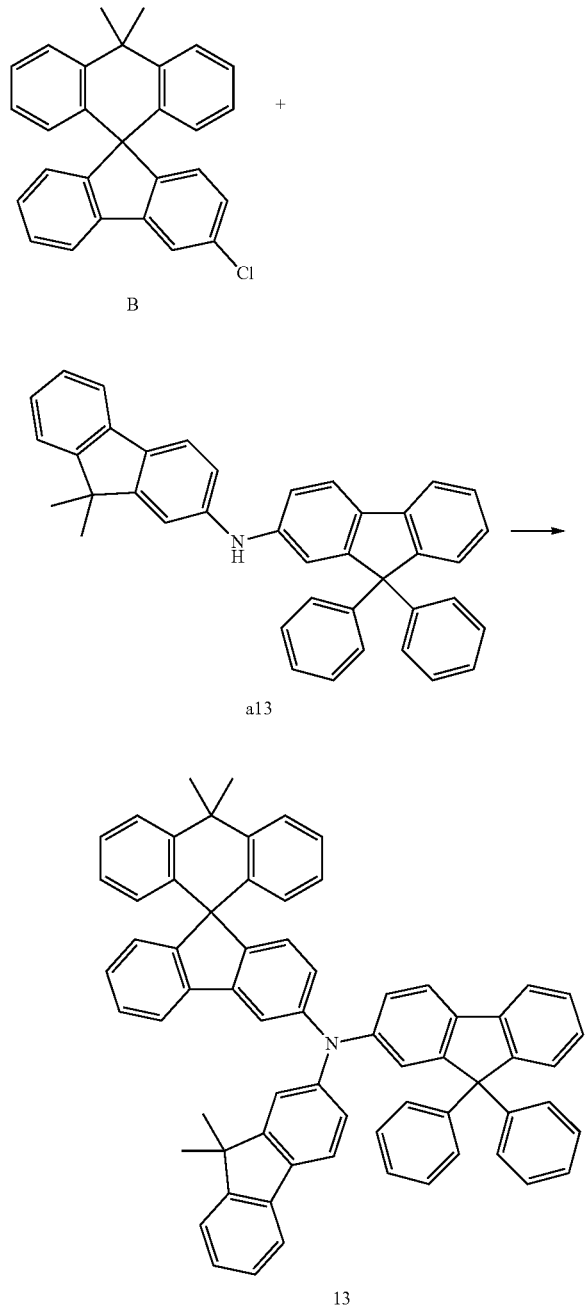

Compound B (4.25 g, 10.84 mmol) and Compound a13 (5.98 g, 11.38 mmol) were completely dissolved in 270 mL of xylene in a 500 mL round bottom flask under nitrogen atmosphere. Then, NaOtBu (1.25 g, 13.01 mmol) was added and bis(tri-tert-butylphosphine)palladium(0) (0.06 g, 0.12 mmol) was added thereto, and the resultant mixture was heated and stirred for 3 hours. The temperature was lowered to room temperature, and filtering was carried out to remove a base. Then, xylene was concentrated under reduced pressure and recrystallized with 240 mL of tetrahydrofuran to give Preparation Example 13 (7.63 g, yield: 80%).

MS[M+H]$^+$=882

Preparation Example 14

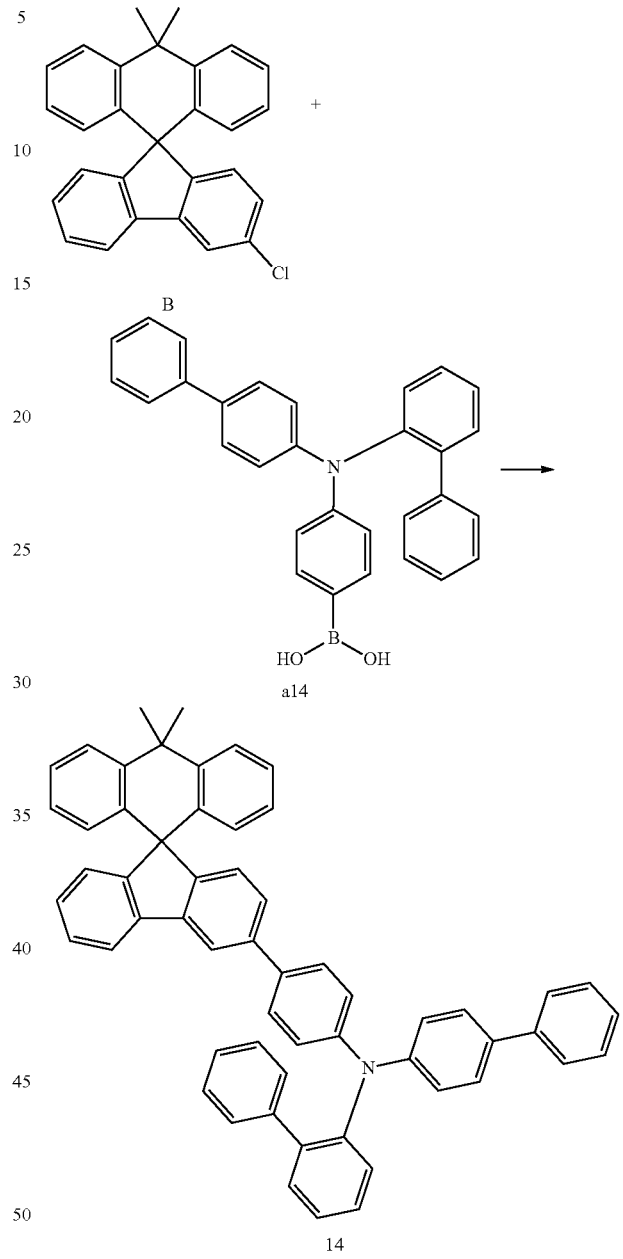

Compound B (7.45 g, 19.01 mmol) and Compound a14 (8.80 g, 19.96 mmol) were completely dissolved in 280 mL of tetrahydrofuran in a 500 mL round bottom flask under nitrogen atmosphere. Then, 2 M potassium carbonate aqueous solution (140 mL) was added and tetrakis(triphenylphosphine)palladium (0.66 g, 0.57 mmol) was added thereto, and the resultant mixture was heated and stirred for 4 hours. The temperature was lowered to room temperature, and the aqueous layer was removed, and the organic layer was dried over anhydrous magnesium sulfate, concentrated under reduced pressure, and recrystallized with 320 mL of ethyl acetate to give Preparation Example 14 (12.68 g, yield: 88%).

MS[M+H]$^+$=754

Preparation Example 15

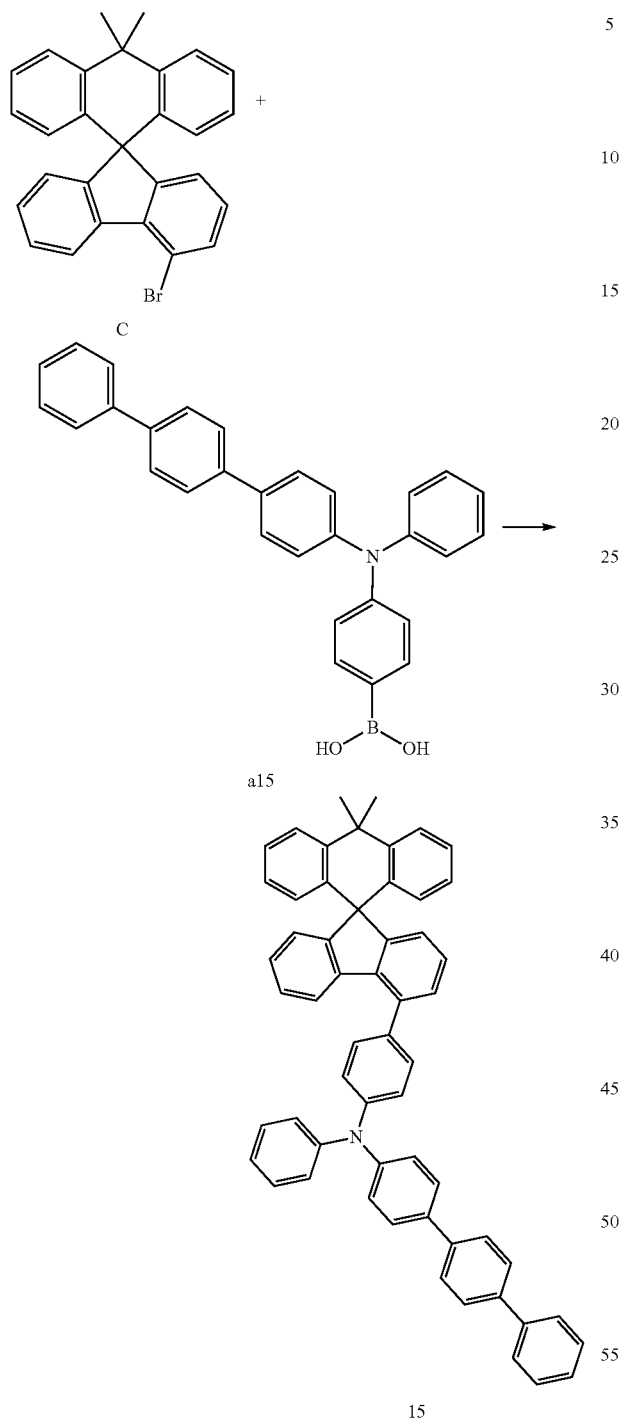

15

Compound C (5.61 g, 14.31 mmol) and Compound a15 (6.63 g, 15.03 mmol) were completely dissolved in 260 mL of tetrahydrofuran in a 500 mL round bottom flask under nitrogen atmosphere. Then, 2 M potassium carbonate aqueous solution (130 mL) was added and tetrakis(triphenylphosphine)palladium (0.50 g, 0.43 mmol) was added thereto, and the resultant mixture was heated and stirred for 6 hours. The temperature was lowered to room temperature, and the aqueous layer was removed, and the organic layer was dried over anhydrous magnesium sulfate, concentrated under reduced pressure, and recrystallized with 310 mL of ethyl acetate to give Preparation Example 15 (8.24 g, yield: 76%).

MS[M+H]$^+$=754

Preparation Example 16

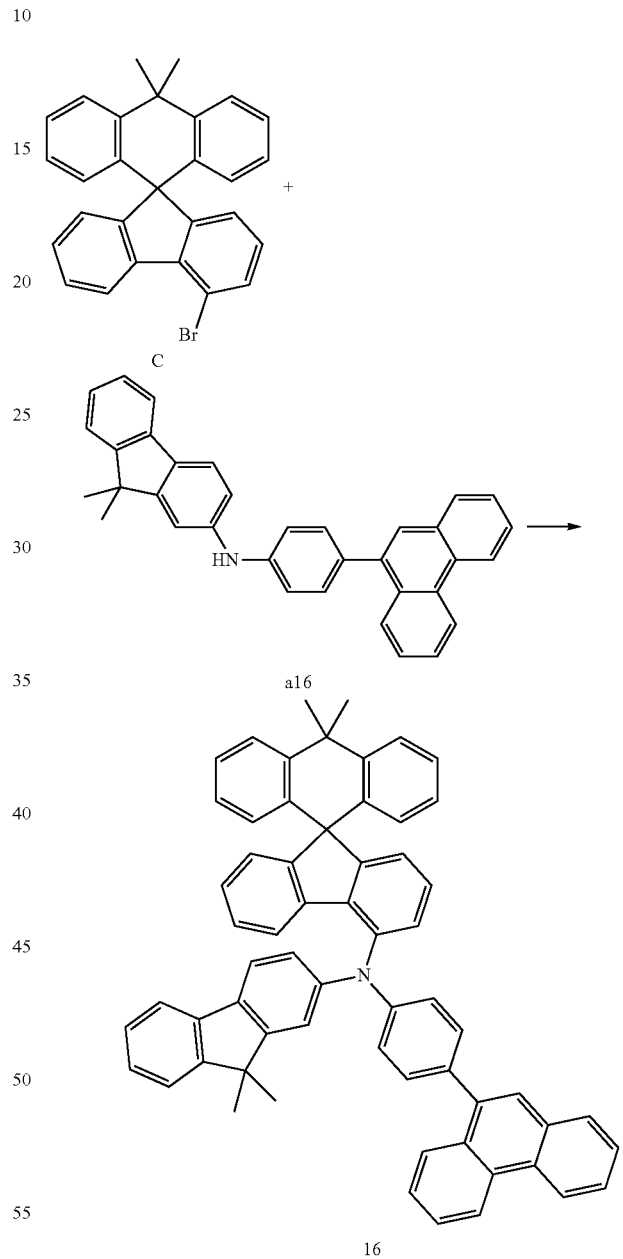

16

Compound C (4.25 g, 10.84 mmol) and Compound a16 (5.98 g, 11.38 mmol) were completely dissolved in 270 mL of xylene in a 500 mL round bottom flask under nitrogen atmosphere. Then, NaOtBu (1.25 g, 13.01 mmol) was added and bis(tri-tert-butylphosphine)palladium(0) (0.06 g, 0.12 mmol) was added thereto, and the resultant mixture was heated and stirred for 3 hours. The temperature was lowered to room temperature, and filtering was carried out to remove a base. Then, xylene was concentrated under reduced pressure and recrystallized with 240 mL of tetrahydrofuran to give Preparation Example 16 (7.63 g, yield: 80%).
MS[M+H]$^+$=818

Preparation Example 17

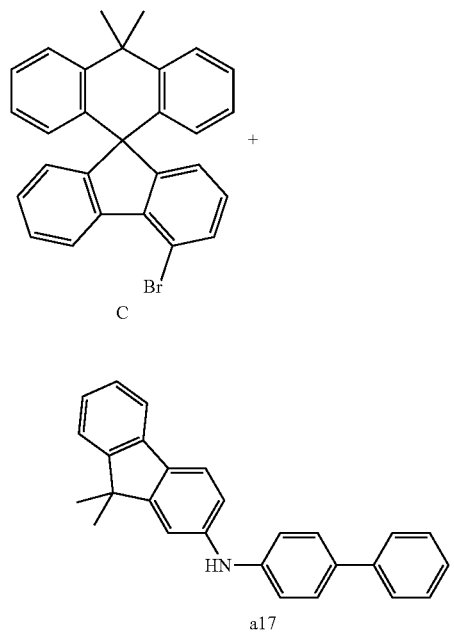

a17

17

Preparation Example 18

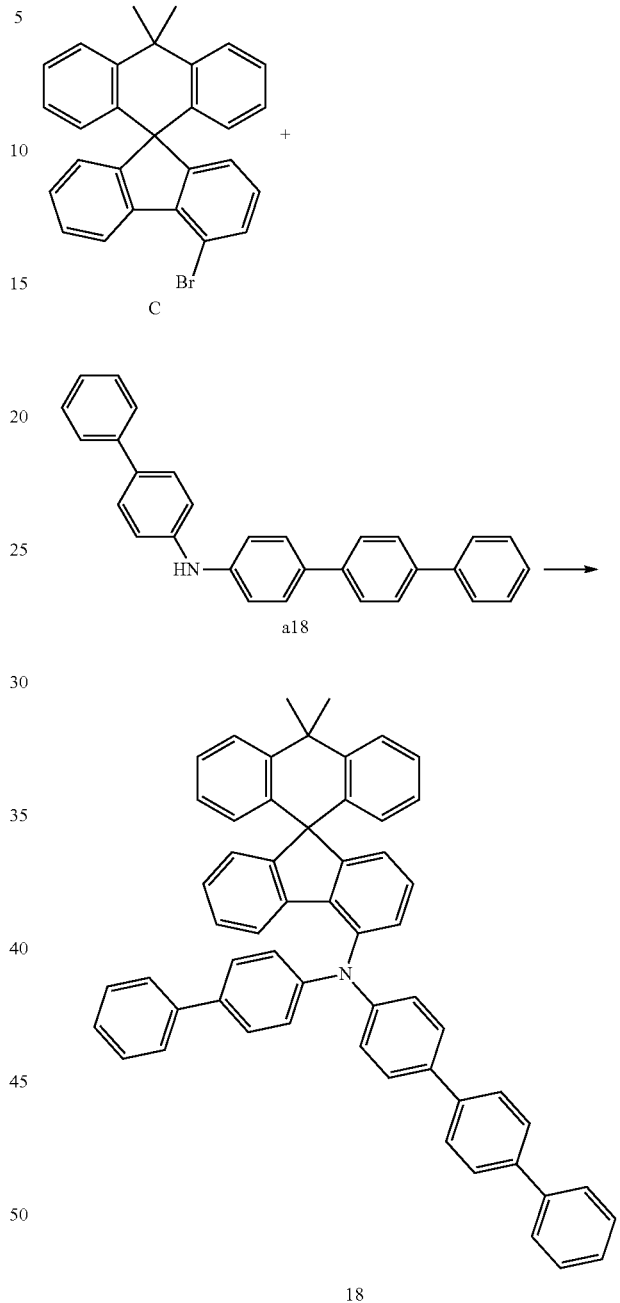

a18

18

Compound C (3.98 g, 10.15 mmol) and Compound a17 (4.91 g, 10.66 mmol) were completely dissolved in 230 mL of xylene in a 500 mL round bottom flask under nitrogen atmosphere. Then, NaOtBu (1.17 g, 12.18 mmol) was added and bis(tri-tert-butylphosphine)palladium(0) (0.05 g, 0.10 mmol) was added thereto, and the resultant mixture was heated and stirred for 2 hours. The temperature was lowered to room temperature, and filtering was carried out to remove a base. Then, xylene was concentrated under reduced pressure and recrystallized with 270 mL of tetrahydrofuran to give Preparation Example 17 (7.63 g, yield: 80%).
MS[M+H]$^+$=718

Compound C (4.49 g, 11.45 mmol) and Compound a18 (4.77 g, 12.03 mmol) were completely dissolved in 250 mL of xylene in a 500 mL round bottom flask under nitrogen atmosphere. Then, NaOtBu (1.32 g, 13.74 mmol) was added and bis(tri-tert-butylphosphine)palladium(0) (0.06 g, 0.11 mmol) was added thereto, and the resultant mixture was heated and stirred for 3 hours. The temperature was lowered to room temperature, and filtering was carried out to remove a base. Then, xylene was concentrated under reduced pressure and recrystallized with 240 mL of tetrahydrofuran to give Preparation Example 18 (7.79 g, yield: 90%).
MS[M+H]$^+$=754

Preparation Example 19

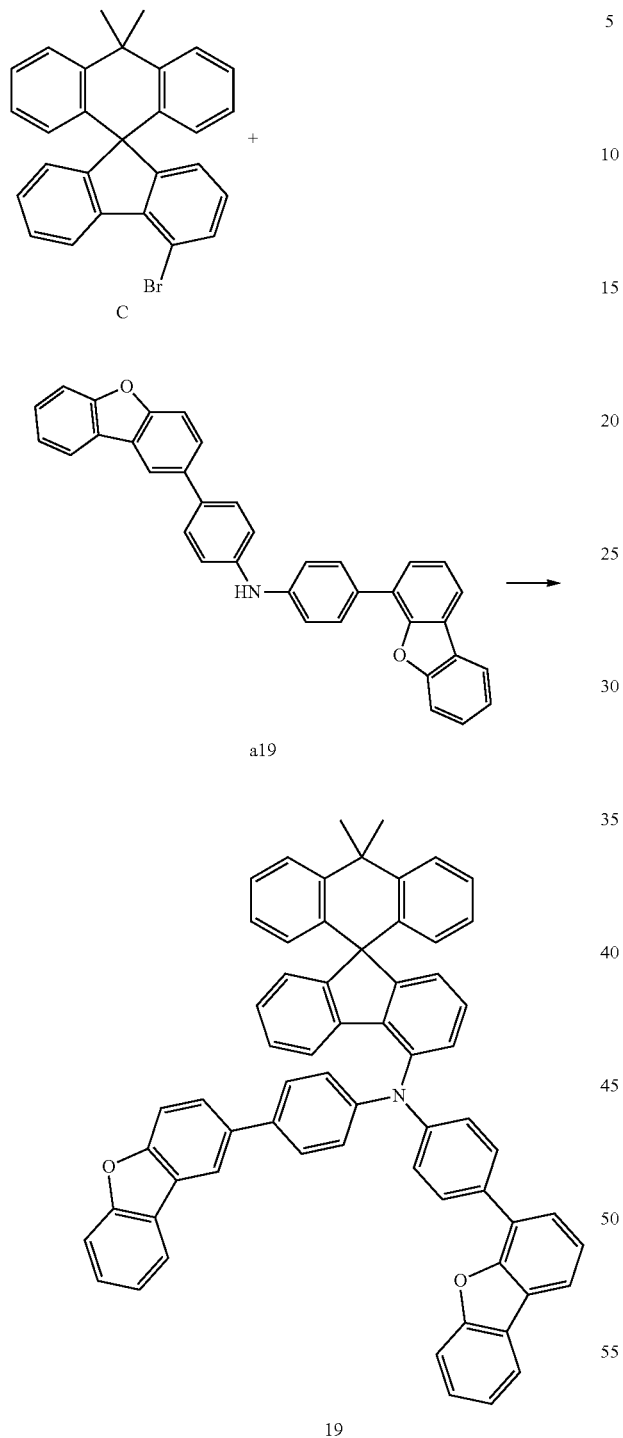

a19

19

Compound C (5.55 g, 14.16 mmol) and Compound a19 (7.45 g, 14.87 mmol) were completely dissolved in 270 mL of xylene in a 500 mL round bottom flask under nitrogen atmosphere. Then, NaOtBu (1.63 g, 16.99 mmol) was added and bis(tri-tert-butylphosphine)palladium(0) (0.07 g, 0.14 mmol) was added thereto, and the resultant mixture was heated and stirred for 4 hours. The temperature was lowered to room temperature, and filtering was carried out to remove a base. Then, xylene was concentrated under reduced pressure and recrystallized with 240 mL of tetrahydrofuran to give Preparation Example 19 (8.52 g, yield: 80%).

MS[M+H]$^+$=858

Preparation Example 20

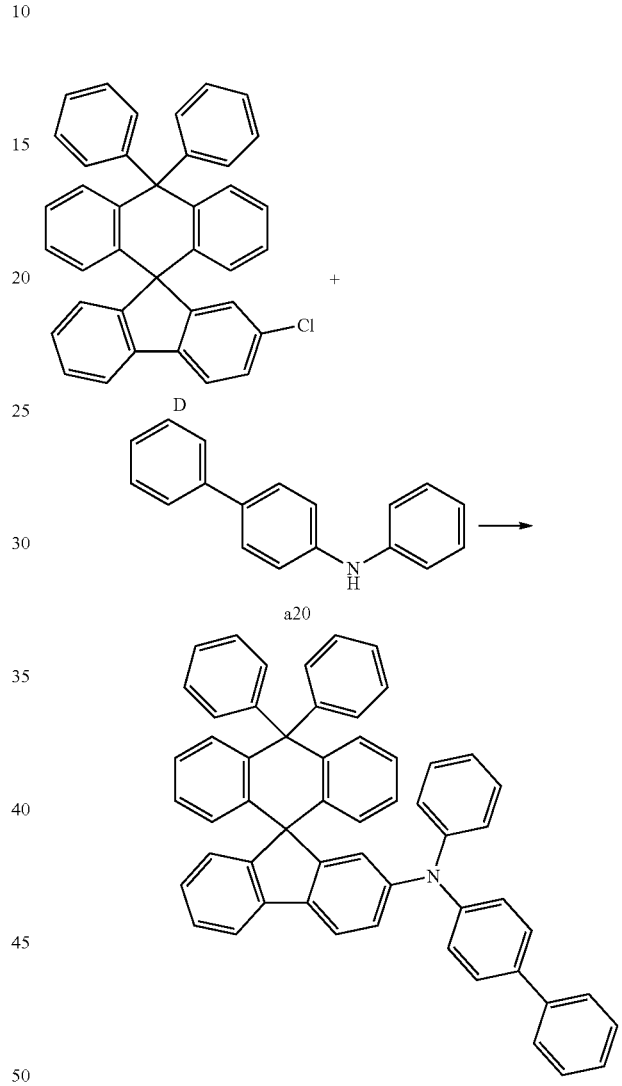

a20

20

Compound D (6.28 g, 12.17 mmol) and Compound a20 (3.13 g, 12.78 mmol) were completely dissolved in 220 mL of xylene in a 500 mL round bottom flask under nitrogen atmosphere. Then, NaOtBu (1.40 g, 14.60 mmol) was added and bis(tri-tert-butylphosphine)palladium(0) (0.06 g, 0.12 mmol) was added thereto, and the resultant mixture was heated and stirred for 3 hours. The temperature was lowered to room temperature, and filtering was carried out to remove a base. Then, xylene was concentrated under reduced pressure and recrystallized with 220 mL of ethyl acetate to give Preparation Example 20 (6.76 g, yield: 77%).

MS[M+H]$^+$=726

Preparation Example 21

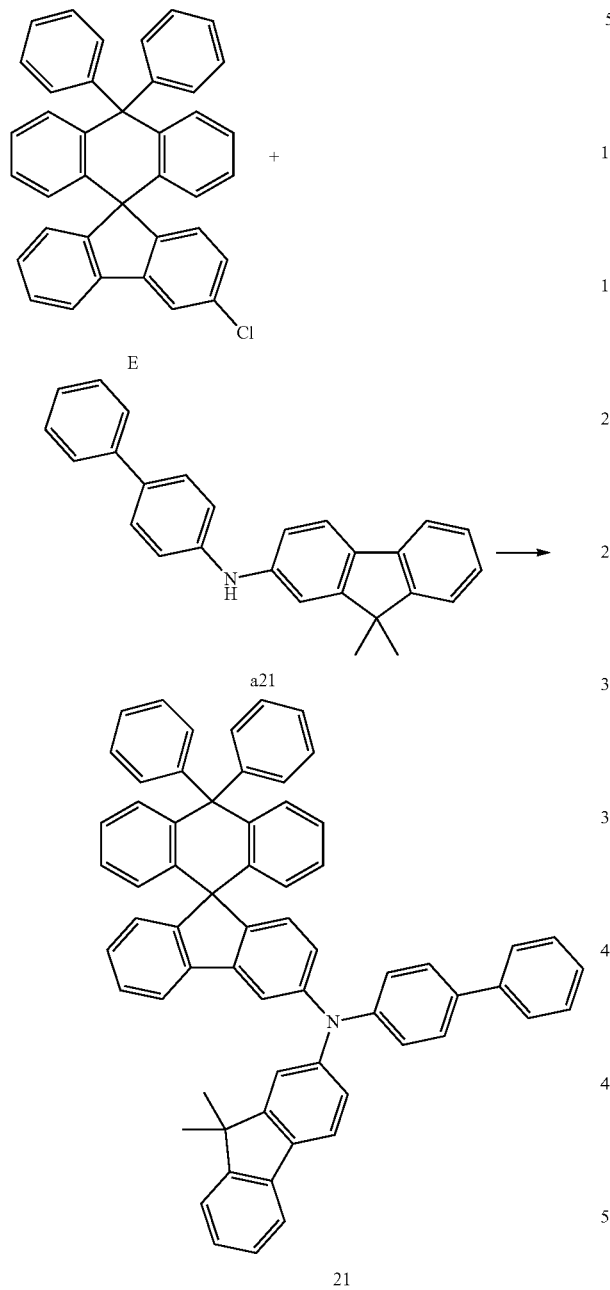

Compound E (5.05 g, 9.79 mmol) and Compound a21 (3.71 g, 10.28 mmol) were completely dissolved in 280 mL of xylene in a 500 mL round bottom flask under nitrogen atmosphere. Then, NaOtBu (1.13 g, 11.74 mmol) was added and bis(tri-tert-butylphosphine)palladium(0) (0.05 g, 0.12 mmol) was added thereto, and the resultant mixture was heated and stirred for 3 hours. The temperature was lowered to room temperature, and filtering was carried out to remove a base. Then, xylene was concentrated under reduced pressure and recrystallized with 210 mL of ethyl acetate to give Preparation Example 21 (6.68 g, yield: 81%).

MS[M+H]$^+$=842

Preparation Example 22

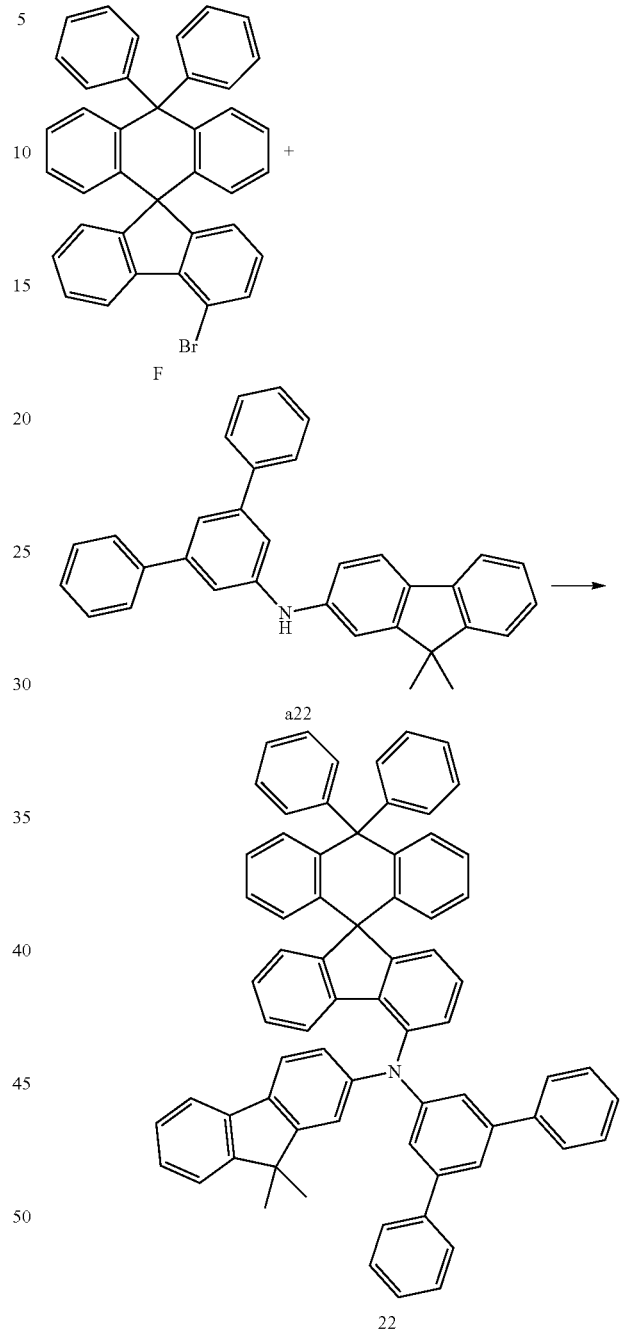

Compound F (7.18 g, 12.82 mmol) and Compound a22 (5.88 g, 13.46 mmol) were completely dissolved in 320 mL of xylene in a 500 mL round bottom flask under nitrogen atmosphere. Then, NaOtBu (1.48 g, 15.39 mmol) was added and bis(tri-tert-butylphosphine)palladium(0) (0.07 g, 0.13 mmol) was added thereto, and the resultant mixture was heated and stirred for 3 hours. The temperature was lowered to room temperature, and filtering was carried out to remove a base. Then, xylene was concentrated under reduced pressure and recrystallized with 210 mL of ethyl acetate to give Preparation Example 22 (6.68 g, yield: 81%).

MS[M+H]$^+$=918

Example 1-1

A glass substrate on which a thin film of ITO (indium tin oxide) was applied to a thickness of 1,000 Å was immersed into distilled water having detergent dissolved therein and washed by ultrasonic wave. The used detergent was the product commercially available from Fisher Co. and the distilled water was one which had been twice filtered by using a filter commercially available from Millipore Co. The ITO was washed for 30 minutes, and ultrasonic washing was then repeated twice for 10 minutes by using distilled water. After the completion of washing with distilled water, washing with ultrasonic waves was performed using solvent such as isopropyl alcohol, acetone and methanol, and the resulting product was dried and transported to the plasma washing machine. Further, the substrate was washed using oxygen plasma for 5 minutes, and then transferred to a vacuum deposition machine.

A compound represented by Chemical Formula HAT below was thermally vacuum-deposited in a thickness of 100 Å on the prepared ITO transparent electrode to form a hole injection layer. A compound represented by Chemical Formula HT1 below (1250 Å) was vacuum-deposited on the hole injection layer to form a hole transport layer. Then, the previously prepared compound of Preparation Example 1 was vacuum-deposited in a thickness of 150 Å on the hole transport layer to form an electron blocking layer. Then, a compound represented by Chemical Formula BH below and a compound represented by Chemical Formula BD below were vacuum-deposited at a weight ratio of 25:1 in a thickness of 200 Å on the electron blocking layer to form a light emitting layer. A compound represented by Chemical Formula HB1 below was vacuum-deposited on the light emitting layer in a thickness of 50 Å to form a hole blocking layer. Then, a compound represented by Chemical Formula ET1 below and a compound represented by Chemical Formula LIQ below were vacuum-deposited at a weight ratio of 1:1 on the hole blocking layer to form an electron injection and transport layer in a thickness of 310 Å. Lithium fluoride (LiF) in a thickness of 10 Å and aluminum in a thickness of 1,000 Å were sequentially deposited on the electron injection and transport layer to form a cathode.

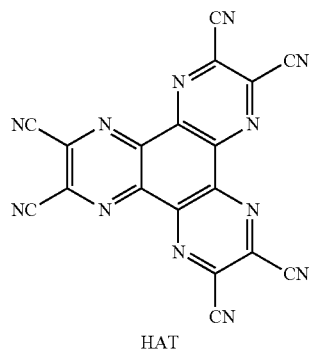

HAT

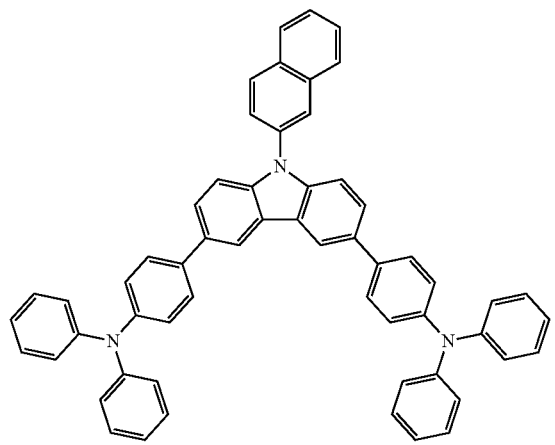

HT1

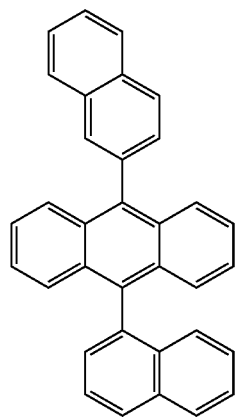

BH

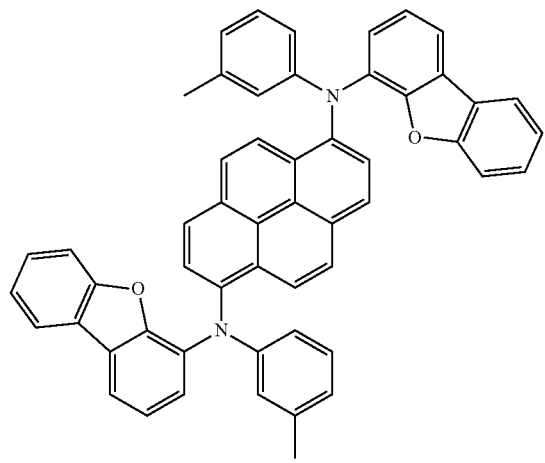

BD

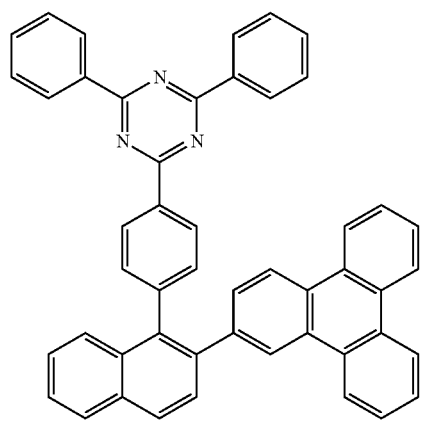

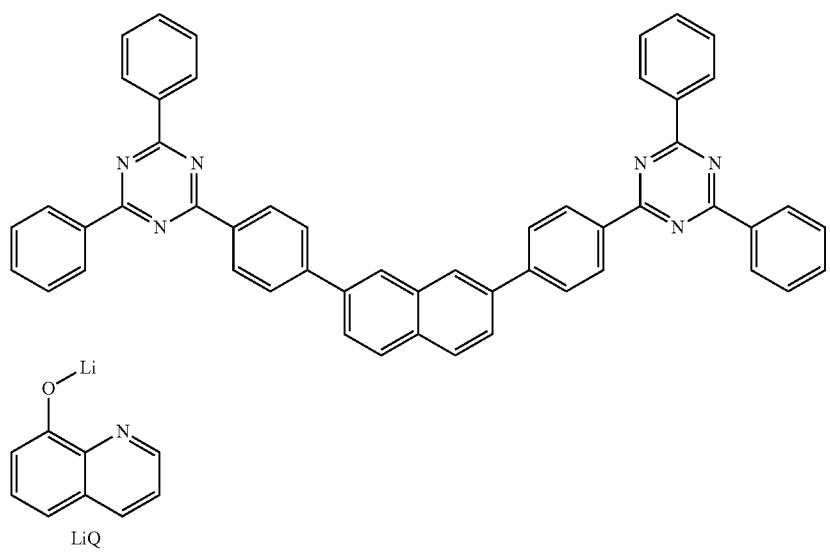

HB1

ET1

LiQ

In the above process, the vapor deposition rate of the organic material was maintained at 0.4 to 0.7 Å/sec, the vapor deposition rate of lithium fluoride of the cathode was maintained at 0.3 Å/sec, and the vapor deposition rate of aluminum was maintained at 2 Å/sec. The degree of vacuum during vapor deposition was maintained at $2\times10^{-7}$ $5\times10^{-6}$ torr. Thereby, an organic light emitting device was manufactured.

Examples 1-2 to 1-16

The organic light emitting device was manufactured in the same manner as in Example 1-1, except that the compounds shown in Table 1 below were used instead of the compound of Preparation Example 1.

Comparative Examples 1-1 to 1-3

The organic light emitting devices were manufactured in the same manner as in Example 1-1, except that the compounds shown in Table 1 below were used instead of the compound of Preparation Example 1. The compounds of EB1, EB2 and EB3 used in Table 1 below are as follows.

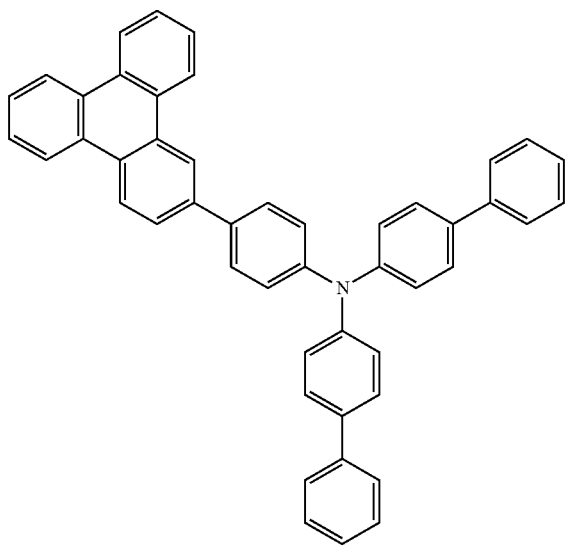

EB1

-continued

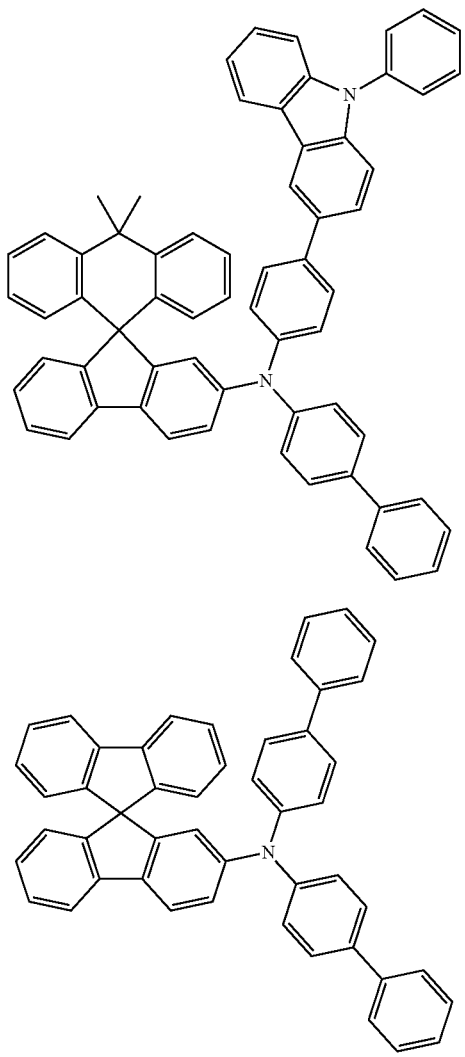

Experimental Example 1

The voltage, efficiency, color coordinate and lifetime were measured when an electric current was applied to the organic light emitting devices manufactured in the Examples and Comparative Examples, and the results are shown in Table 1 below. T95 means a time taken until luminance was reduced to 95% of the initial luminance (6000 nit).

TABLE 1

| | Compound (Electron blocking layer) | Voltage (V@10 mA/cm$^2$) | Efficiency (cd/A@10 mA/cm$^2$) | Color coordinate (x, y) | T95 (hr) |
|---|---|---|---|---|---|
| Example 1-1 | Preparation Example 1 | 4.50 | 6.31 | (0.140, 0.046) | 280 |
| Example 1-2 | Preparation Example 3 | 4.33 | 6.53 | (0.141, 0.046) | 285 |
| Example 1-3 | Preparation Example 4 | 4.56 | 6.34 | (0.143, 0.047) | 295 |
| Example 1-4 | Preparation Example 5 | 4.40 | 6.45 | (0.142, 0.048) | 280 |
| Example 1-5 | Preparation Example 6 | 4.53 | 6.36 | (0.140, 0.044) | 275 |
| Example 1-6 | Preparation Example 7 | 4.56 | 6.37 | (0.141, 0.046) | 285 |
| Example 1-7 | Preparation Example 9 | 4.64 | 6.29 | (0.140, 0.044) | 290 |
| Example 1-8 | Preparation Example 10 | 4.46 | 6.44 | (0.141, 0.046) | 260 |
| Example 1-9 | Preparation Example 11 | 4.41 | 6.42 | (0.138, 0.044) | 280 |
| Example 1-10 | Preparation Example 14 | 4.50 | 6.33 | (0.139, 0.043) | 295 |
| Example 1-11 | Preparation Example 15 | 4.53 | 6.35 | (0.140, 0.047) | 285 |
| Example 1-12 | Preparation Example 17 | 4.56 | 6.31 | (0.141, 0.046) | 270 |
| Example 1-13 | Preparation Example 18 | 4.68 | 6.26 | (0.138, 0.044) | 265 |
| Example 1-14 | Preparation Example 19 | 4.63 | 6.28 | (0.139, 0.043) | 285 |
| Example 1-15 | Preparation Example 20 | 4.62 | 6.23 | (0.142, 0.045) | 275 |
| Example 1-16 | Preparation Example 21 | 4.61 | 6.27 | (0.141, 0.044) | 290 |
| Comparative Example 1-1 | EB1 | 5.12 | 5.84 | (0.141, 0.045) | 240 |
| Comparative Example 1-2 | EB2 | 4.97 | 5.86 | (0.143, 0.048) | 235 |
| Comparative Example 1-3 | EB3 | 4.72 | 5.43 | (0.143, 0.048) | 220 |

As shown in Table 1, the organic light emitting devices manufactured using the compound of the present disclosure as an electron blocking layer exhibited excellent characteristics in terms of efficiency, driving voltage and stability of the organic light emitting device. In particular, they exhibited lower voltage, higher efficiency, and longer lifetime characteristics than those of the organic light emitting device manufactured using the compound of Comparative Example 1-2 to which an amine containing carbazole was connected as an electron blocking layer. In addition, the organic light emitting device manufactured using the compound of Comparative Example 1-3 having a structure similar to the core of the present disclosure but containing no methyl group as the electron blocking layer showed that the efficiency was decreased by 10% or more and the lifetime by 30% or more.

From the results in Table 1, it could be confirmed that the compound according to the present disclosure had excellent electron blocking capability and thus could be applied to an organic light emitting device.

Examples 2-1 to 2-22

The organic light emitting device was manufactured in the same manner as in Comparative Example 1-1, except that the compounds shown in Table 2 below were used instead of the compound represented by Chemical Formula HT1 in Comparative Example 1-1.

Comparative Examples 2-1 and 2-2

The organic light emitting device was manufactured in the same manner as in Comparative Example 1-1, except that the compounds shown in Table 2 below were used instead of the compound represented by Chemical Formula HT1 in Comparative Example 1-1. The compounds of HT2 and HT3 used in Table 2 below are as follows.

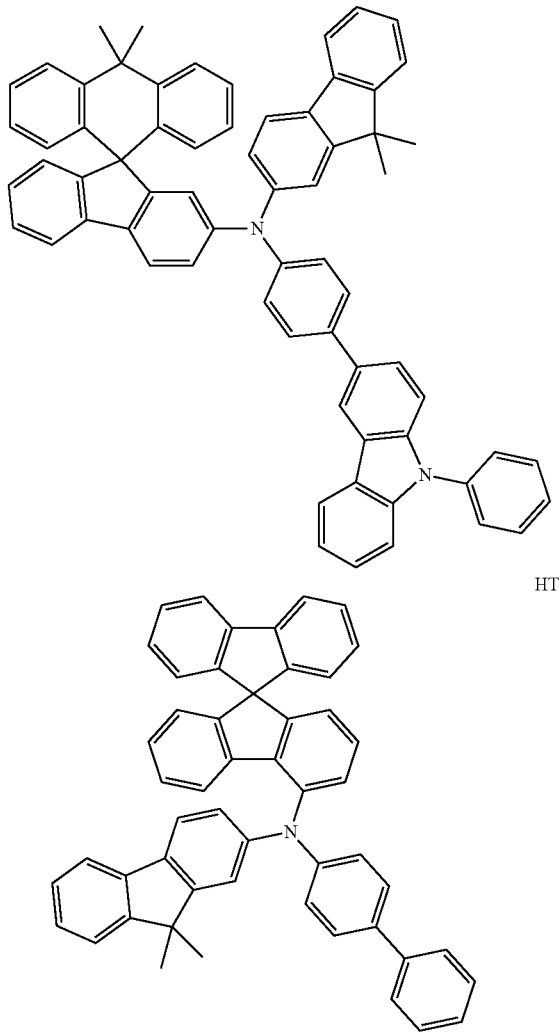

Experimental Example 2

The voltage, efficiency, color coordinate and lifetime were measured when an electric current was applied to the organic light emitting devices manufactured in the Examples and Comparative Examples, and the results are shown in Table 2 below. T95 means a time taken until luminance was reduced to 95% of the initial luminance (6000 nit).

TABLE 2

| | Compound (Hole transport layer) | Voltage (V@10 mA/cm$^2$) | Efficiency (cd/A@10 mA/cm$^2$) | Color coordinate (x, y) | T95 (hr) |
|---|---|---|---|---|---|
| Comparative Example 1-1 | HT1 | 5.12 | 5.84 | (0.141, 0.045) | 240 |
| Example 2-1 | Preparation Example 1 | 4.50 | 6.31 | (0.140, 0.046) | 280 |
| Example 2-2 | Preparation Example 2 | 4.38 | 6.53 | (0.139, 0.045) | 270 |
| Example 2-3 | Preparation Example 3 | 4.33 | 6.58 | (0.141, 0.046) | 285 |
| Example 2-4 | Preparation Example 4 | 4.56 | 6.34 | (0.143, 0.047) | 295 |
| Example 2-5 | Preparation Example 5 | 4.40 | 6.45 | (0.142, 0.048) | 280 |
| Example 2-6 | Preparation Example 6 | 4.53 | 6.36 | (0.140, 0.044) | 275 |
| Example 2-7 | Preparation Example 7 | 4.56 | 6.37 | (0.141, 0.046) | 285 |
| Example 2-8 | Preparation Example 8 | 4.40 | 6.45 | (0.142, 0.048) | 280 |
| Example 2-9 | Preparation Example 9 | 4.64 | 6.29 | (0.140, 0.044) | 290 |
| Example 2-10 | Preparation Example 10 | 4.46 | 6.44 | (0.141, 0.046) | 260 |
| Example 2-11 | Preparation Example 11 | 4.41 | 6.42 | (0.138, 0.044) | 280 |
| Example 2-12 | Preparation Example 12 | 4.43 | 6.38 | (0.141, 0.046) | 260 |
| Example 2-13 | Preparation Example 13 | 4.51 | 6.35 | (0.140, 0.047) | 285 |
| Example 2-14 | Preparation Example 14 | 4.50 | 6.33 | (0.139, 0.043) | 295 |
| Example 2-15 | Preparation Example 15 | 4.53 | 6.35 | (0.140, 0.047) | 285 |
| Example 2-16 | Preparation Example 16 | 4.61 | 6.29 | (0.140, 0.046) | 265 |
| Example 2-17 | Preparation Example 17 | 4.56 | 6.31 | (0.141, 0.046) | 270 |
| Example 2-18 | Preparation Example 18 | 4.68 | 6.26 | (0.138, 0.044) | 265 |
| Example 2-19 | Preparation Example 19 | 4.63 | 6.28 | (0.139, 0.043) | 285 |
| Example 2-20 | Preparation Example 20 | 4.62 | 6.23 | (0.142, 0.045) | 275 |
| Example 2-21 | Preparation Example 21 | 4.61 | 6.27 | (0.141, 0.044) | 290 |
| Example 2-22 | Preparation Example 22 | 4.58 | 6.31 | (0.139, 0.047) | 270 |
| Comparative Example 2-1 | HT2 | 5.07 | 5.86 | (0.143, 0.048) | 235 |
| Comparative Example 2-2 | HT3 | 4.92 | 5.43 | (0.143, 0.048) | 220 |

As shown in Table 2, the organic light emitting devices manufactured using the compound of the present disclosure as a hole transport layer exhibited excellent characteristics in terms of efficiency, driving voltage and/or stability of the organic light emitting device. In particular, the organic light emitting devices of Examples exhibited lower voltage, higher efficiency, and longer lifetime characteristics than those of the organic light emitting device manufactured using the compound represented by Chemical Formula HT2 to which an amine containing carbazole was connected as a hole transport layer. In addition, the organic light emitting device manufactured using the compound represented by Chemical Formula HT3 having a structure similar to that of the core of the present disclosure but containing no methyl group showed that the efficiency was decreased by 5% or more and the lifetime by 20% or more.

Example 3-1

A glass substrate on which a thin film of ITO (indium tin oxide) was applied to a thickness of 1,000 Å was immersed into distilled water having detergent dissolved therein and washed by ultrasonic wave. At that time, the used detergent was the product commercially available from Fisher Co. and the distilled water was one which had been twice filtered by using a filter commercially available from Millipore Co. The ITO was washed for 30 minutes, and ultrasonic washing was then repeated twice for 10 minutes by using distilled water. After the completion of washing with distilled water, washing with ultrasonic waves was performed using solvent such as isopropyl alcohol, acetone and methanol, and the resulting product was dried and transported to the plasma washing machine. Further, the substrate was washed using oxygen plasma for 5 minutes, and then transferred to a vacuum deposition machine.

On the ITO transparent electrode thus prepared, a compound represented by Chemical Formula HI1 below was formed in a thickness of 1100 Å as a hole injection layer, wherein a compound of Chemical Formula A-1 below was p-doped at a concentration of 2%. The compound of Preparation Example 1 previously prepared was vacuum-deposited on the hole injection layer to form a hole transport layer in a thickness of 350 Å. Then, a compound of Chemical Formula EB1 below was vacuum-deposited in a film thickness of 150 Å on the hole transport layer to form an electron blocking layer. Then, a host composition in which a compound of Chemical Formula YGH-1 below and a compound of Chemical Formula YGH-2 below were mixed at a weight ratio of 6:4, and a compound of Chemical Formula YGD-1 which is a phosphorescent dopant in an amount of 6% by weight relative to the host composition, were vacuum-deposited together on the EB1 vapor-deposited film to form a green light emitting layer in a thickness of 350 Å. A compound of Chemical Formula HB1 below was vacuum-deposited in a thickness of 50 Å on the light emitting layer to form a hole blocking layer. Then, a compound of Chemical Formula ET1 below and a compound of Chemical Formula LIQ below were vacuum-deposited at a weight ratio of 2:1 on the hole blocking layer to form an electron injection and transport layer in a thickness of 300 Å. Lithium fluoride (LiF) in a thickness of 12 Å and aluminum in a thickness of 1,000 Å were sequentially deposited on the electron injection and transport layer to form a cathode.

HI1

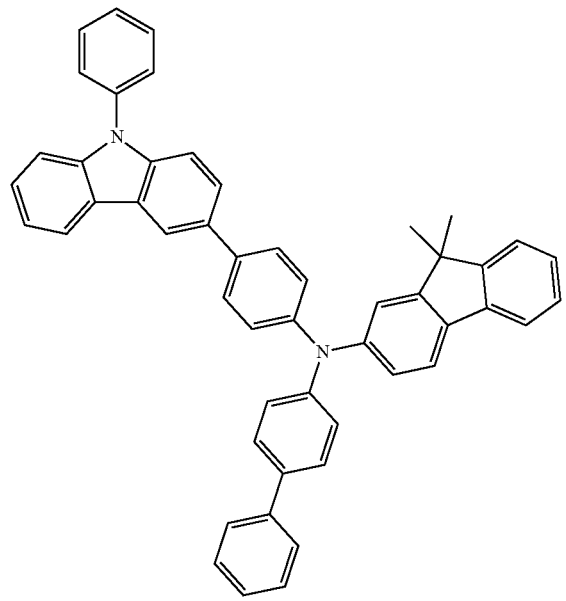

A-1

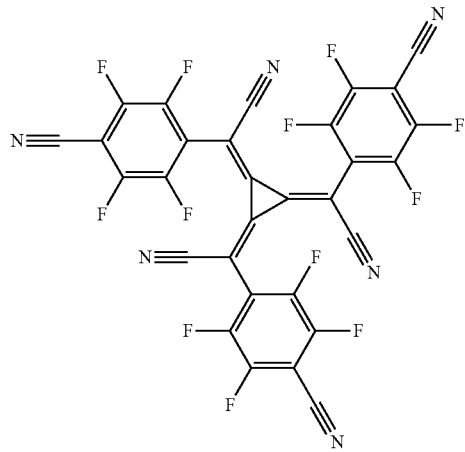

EB1

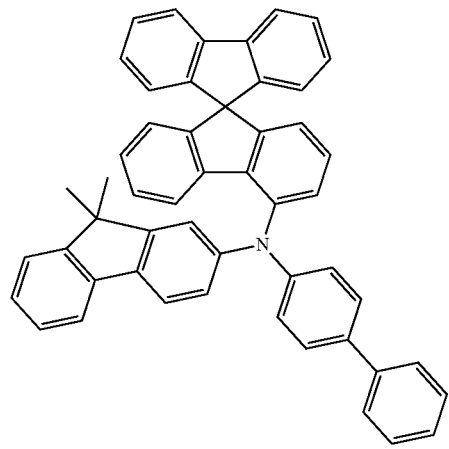

YGH-1

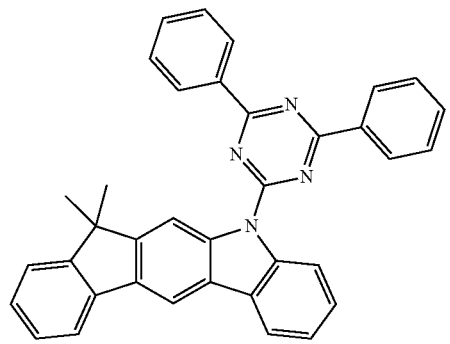

-continued

YGH-2

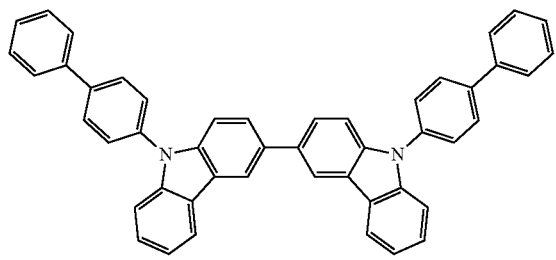

YGD-1

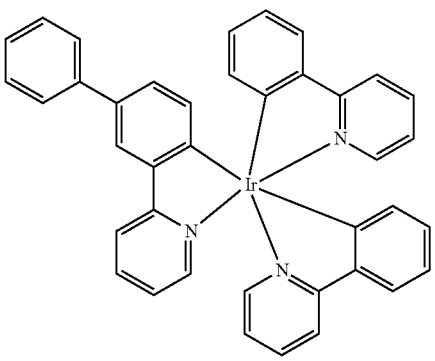

HB1

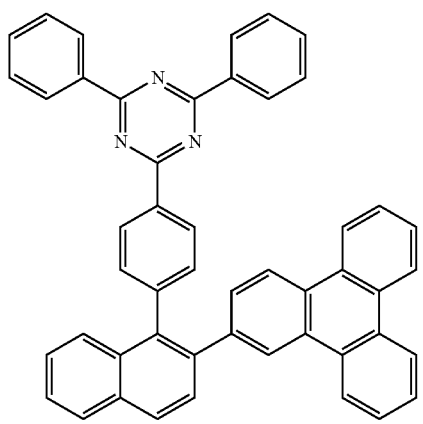

ET1

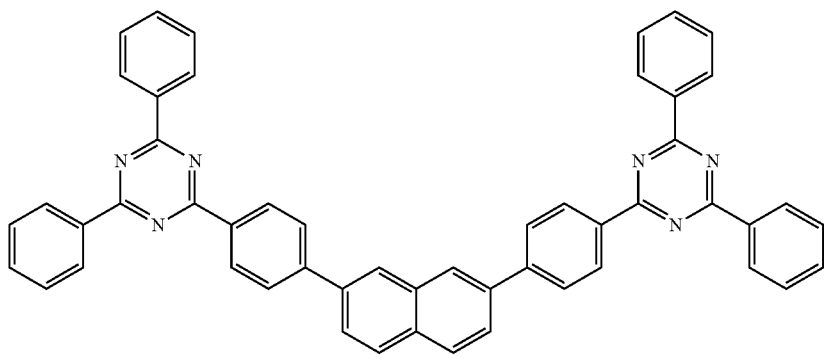

LiQ

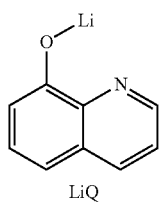

In the above process, the vapor deposition rate of the organic material was maintained at 0.4 to 0.7 Å/sec, the vapor deposition rate of lithium fluoride of the cathode was maintained at 0.3 Å/sec, and the vapor deposition rate of aluminum was maintained at 2 Å/sec. The degree of vacuum during vapor deposition was maintained at $2\times10^{-7}$~$5\times10^{-6}$ torr. Thereby, an organic light emitting device was manufactured.

Examples 3-2 to 3-16

The organic light emitting device was manufactured in the same manner as in Example 3-1, except that the compounds shown in Table 3 below were used instead of the compound of Preparation Example 1.

Comparative Examples 3-1 to 3-3

The organic light emitting devices were manufactured in the same manner as in Example 3-1, except that the compounds shown in Table 3 below were used instead of the compound of Preparation Example 1. The compounds of EB4, EB5 and EB6 used in Table 3 below are as follows.

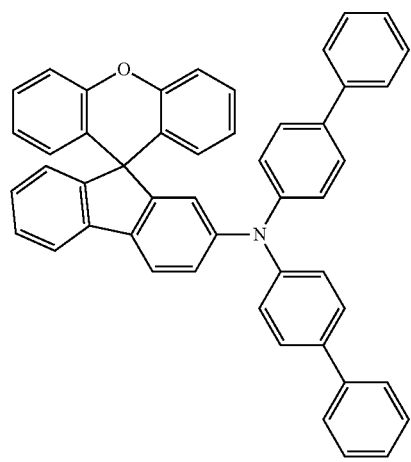

EB4

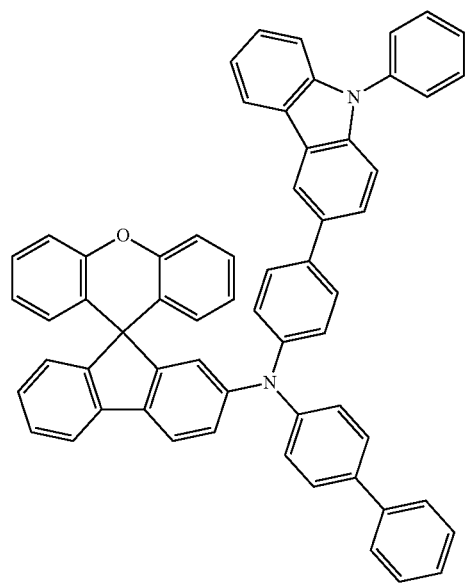

EB5

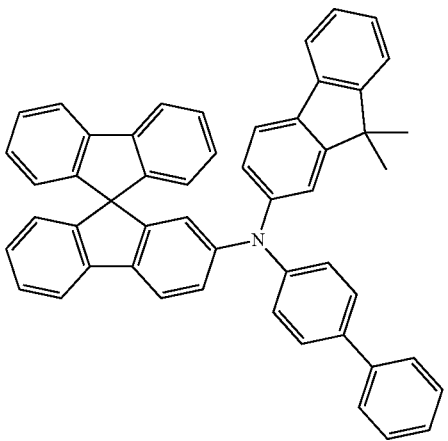

EB6

Experimental Example 3

The voltage, efficiency, color coordinate and lifetime were measured when an electric current was applied to the organic light emitting devices manufactured in the Examples and Comparative Examples, and the results are shown in Table 3 below. T98 means a time taken until luminance was reduced to 98% of the initial luminance (6000 nit).

TABLE 3

| | Compound (Hole transport layer) | Voltage (V@10 mA/cm$^2$) | Efficiency (cd/A@10 mA/cm$^2$) | Color coordinate (x,y) | T98 (hr) |
|---|---|---|---|---|---|
| Example 3-1 | Preparation Example 1 | 3.58 | 145.92 | (0.254, 0.711) | 240 |
| Example 3-2 | Preparation Example 2 | 3.56 | 146.11 | (0.255, 0.712) | 235 |
| Example 3-3 | Preparation Example 3 | 3.62 | 145.25 | (0.256, 0.711) | 235 |
| Example 3-4 | Preparation Example 4 | 3.63 | 145.34 | (0.256, 0.713) | 230 |
| Example 3-5 | Preparation Example 5 | 4.35 | 136.13 | (0.262, 0.705) | 170 |
| Example 3-6 | Preparation Example 6 | 4.36 | 136.39 | (0.264, 0.706) | 165 |
| Example 3-7 | Preparation Example 7 | 4.38 | 135.91 | (0.262, 0.707) | 160 |
| Example 3-8 | Preparation Example 8 | 4.37 | 135.73 | (0.263, 0.705) | 175 |
| Example 3-9 | Preparation Example 11 | 4.12 | 137.97 | (0.261, 0.706) | 170 |
| Example 3-10 | Preparation Example 12 | 4.10 | 138.62 | (0.265, 0.702) | 175 |
| Example 3-11 | Preparation Example 14 | 3.82 | 143.50 | (0.254, 0.711) | 220 |
| Example 3-12 | Preparation Example 15 | 3.86 | 142.44 | (0.255, 0.710) | 215 |
| Example 3-13 | Preparation Example 17 | 4.18 | 138.97 | (0.261, 0.705) | 150 |
| Example 3-14 | Preparation Example 18 | 4.17 | 139.62 | (0.263, 0.708) | 145 |
| Example 3-15 | Preparation Example 20 | 4.35 | 136.13 | (0.266, 0.709) | 180 |
| Example 3-16 | Preparation Example 21 | 4.36 | 136.39 | (0.267, 0.708) | 195 |
| Comparative Example 3-1 | EB4 | 4.61 | 126.94 | (0.263, 0.704) | 60 |

TABLE 3-continued

|  | Compound (Hole transport layer) | Voltage (V@10 mA/cm$^2$) | Efficiency (cd/A@10 mA/cm$^2$) | Color coordinate (x,y) | T98 (hr) |
| --- | --- | --- | --- | --- | --- |
| Comparative Example 3-2 | EB5 | 4.77 | 125.66 | (0.262, 0.707) | 115 |
| Comparative Example 3-3 | EB6 | 4.52 | 127.43 | (0.261, 0.706) | 85 |

As shown in Table 3, the organic light emitting devices manufactured using the compound of the present disclosure as a hole transport layer of a green light emitting device (phosphorescence) exhibited excellent characteristics in terms of efficiency, driving voltage and stability of the organic light emitting device. They exhibited lower voltage, higher efficiency, and longer lifetime than those of the organic light emitting devices manufactured using the compound of Comparative Example 1-2 in which amines containing carbazole are directly connected as a hole transport layer. In addition, the organic light emitting device manufactured using the compound of Comparative Examples 3-1 and 3-3 having a structure similar to the core of the present disclosure but containing no methyl group showed that lifetime was decreased by 50-60% or more. When comparing Examples 3-1 to 3-4 with Examples 3-5 to 3-8, substances in which a phenyl group was connected as a linker rather than a direct bond showed the best characteristic (especially, lifetime). When comparing Examples 3-9 to 3-12, substances containing a phenyl linker in the direction 3 of the present disclosure showed a similar tendency. In Examples 3-13 to 3-16, it was found that a substance in which the core of the present disclosure is composed of a phenyl group instead of a methyl group is a direct bond, but lifetime characteristic is relatively better.

From the results in Table 3, it was confirmed that the compound according to the present disclosure had excellent hole transporting capability in a device using a phosphorescent green light emitting layer and thus could be applied to an organic light emitting device.

Example 4-1

A glass substrate on which a thin film of ITO (indium tin oxide) was applied to a thickness of 1,000 Å was immersed into distilled water having detergent dissolved therein and washed by ultrasonic wave. At that time, the used detergent was the product commercially available from Fisher Co. and the distilled water was one which had been twice filtered by using a filter commercially available from Millipore Co. The ITO was washed for 30 minutes, and ultrasonic washing was then repeated twice for 10 minutes by using distilled water. After the completion of washing with distilled water, washing with ultrasonic waves was performed using solvent such as isopropyl alcohol, acetone and methanol, and the resulting product was dried and transported to the plasma washing machine. Further, the substrate was washed using oxygen plasma for 5 minutes, and then transferred to a vacuum deposition machine.

On the ITO transparent electrode thus prepared, a compound of Chemical Formula HI1 below was formed in a thickness of 1150 Å as a hole injection layer, wherein a compound of Chemical Formula A-1 below was p-doped at a concentration of 1.5%. The compound of Preparation Example 1 previously prepared was vacuum-deposited on the hole injection layer to form a hole transport layer in a thickness of 800 Å. Then, a compound of Chemical Formula EB1 below was vacuum-deposited in a film thickness of 150 Å on the hole transport layer to form an electron blocking layer. Then, a compound of Chemical Formula RH-1 below and a compound of Chemical Formula RD-1 below were vacuum-deposited at a weight ratio of 98:2 on the EB1 vapor-deposited film to form a red light emitting layer in a thickness of 360 Å. A compound of Chemical Formula HB1 below was vacuum-deposed in a thickness of 30 Å on the light emitting layer to form a hole blocking layer. Then, a compound of Chemical Formula ET1 below and a compound of Chemical Formula LIQ below were vacuum-deposited at a weight ratio of 2:1 on the hole blocking layer to form an electron injection and transport layer in a thickness of 300 Å. Lithium fluoride (LiF) in a thickness of 12 Å and aluminum in a thickness of 1,000 Å were sequentially deposited on the electron injection and transport layer to form a cathode.

HI1

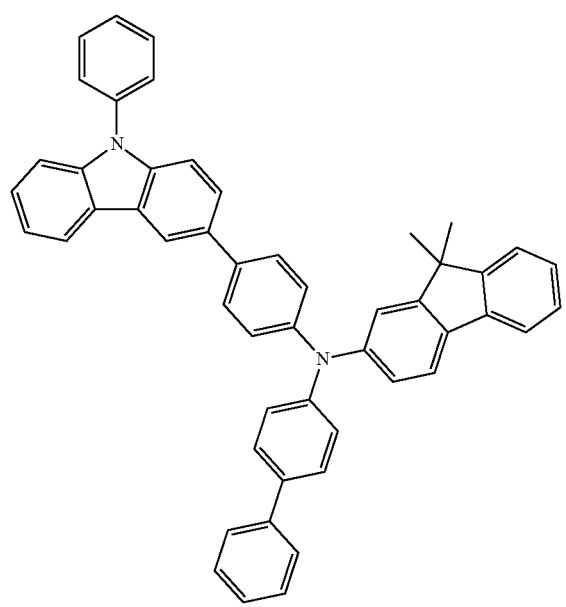

A-1

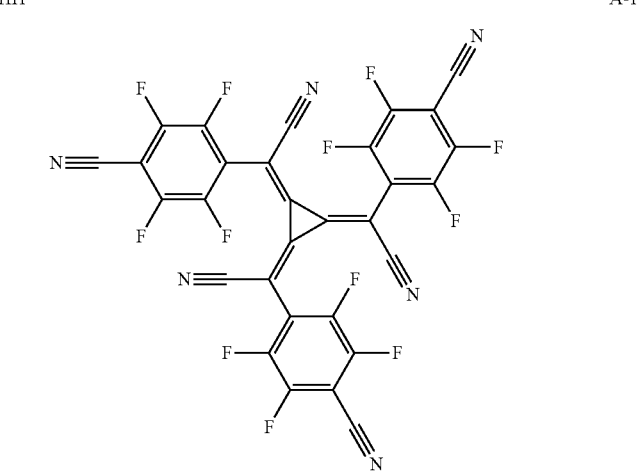

-continued
EB1
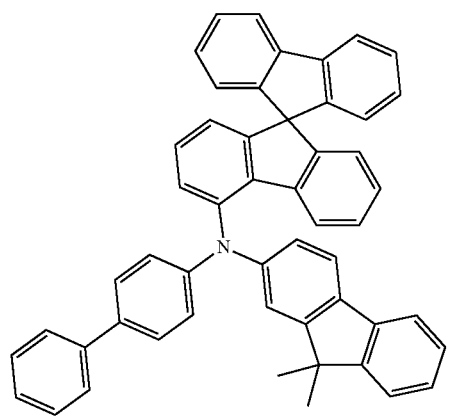
RH-1
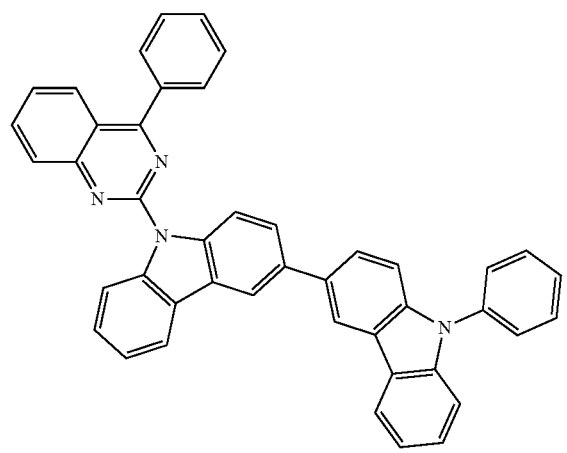
RD-1
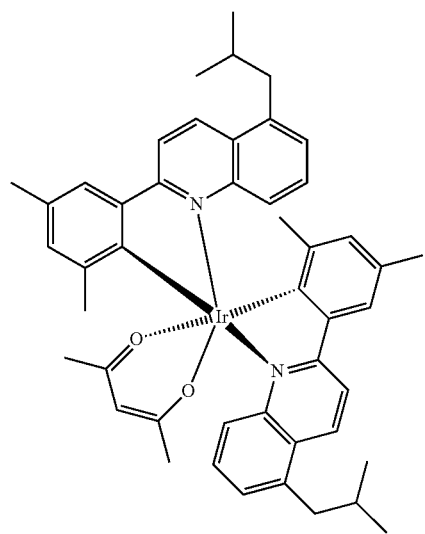
HB1
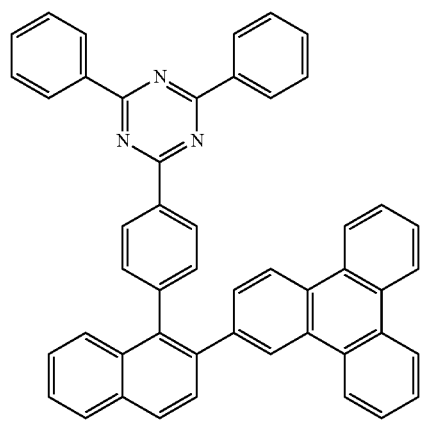
ET1
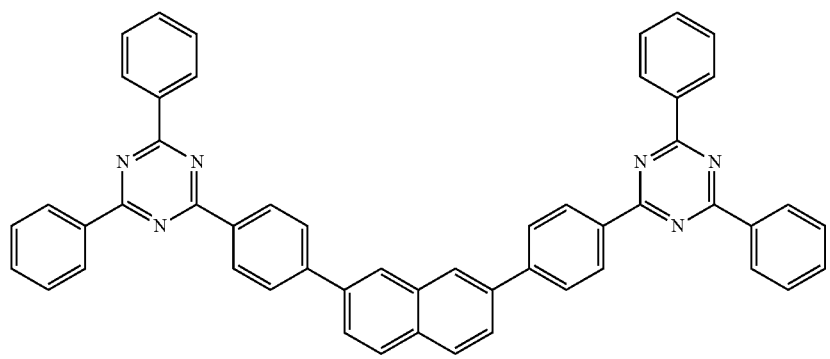
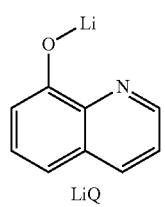
LiQ In the above process, the vapor deposition rate of the organic material was maintained at 0.4 to 0.7 Å/sec, the vapor deposition rate of lithium fluoride of the cathode was maintained at 0.3 Å/sec, and the vapor deposition rate of aluminum was maintained at 2 Å/sec. The degree of vacuum during vapor deposition was maintained at $2\times10^{-7}$~$5\times10^{-6}$ torr. Thereby, an organic light emitting device was manufactured.

Examples 4-2 to 4-16

The organic light emitting device was manufactured in the same manner as in Example 4-1, except that the compounds shown in Table 4 below were used instead of the compound of Preparation Example 1.

Comparative Examples 4-1 to 4-3

The organic light emitting devices were manufactured in the same manner as in Example 4-1, except that the compounds shown in Table 4 below were used instead of the compound of Preparation Example 1. The compounds of HT5, HT6 and HT7 used in Table 4 below are as follows.

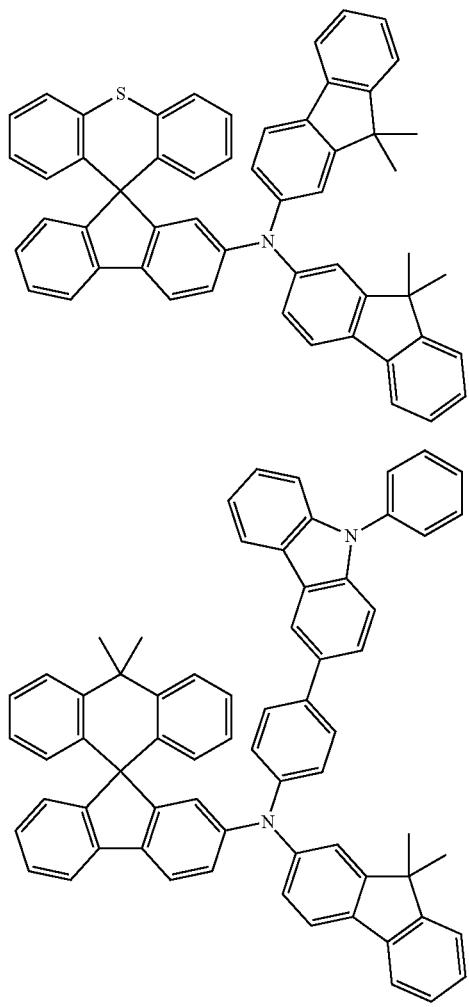

HT5

HT6

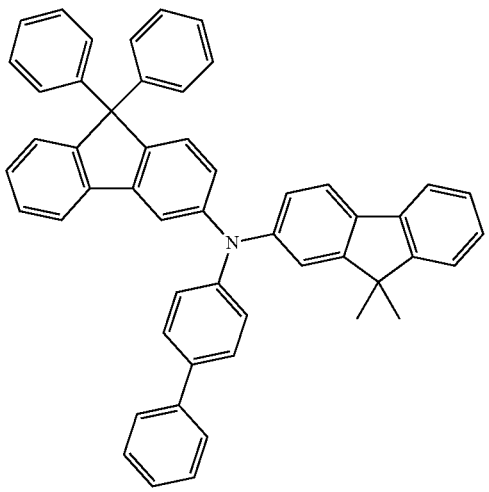

HT7

Experimental Example 4

The voltage, efficiency, color coordinate and lifetime were measured when an electric current was applied to the organic light emitting devices manufactured in the Examples and Comparative Examples, and the results are shown in Table 4 below. T98 means a time taken until luminance was reduced to 98% of the initial luminance (4500 nit).

TABLE 4

| | Compound (Hole transport layer) | Voltage (V@10 mA/cm$^2$) | Efficiency (cd/A@10 mA/cm$^2$) | Color coordinate (x,y) | T98 (hr) |
|---|---|---|---|---|---|
| Example 4-1 | Preparation Example 1 | 4.08 | 47.21 | (0.685, 0.315) | 340 |
| Example 4-2 | Preparation Example 2 | 4.09 | 47.10 | (0.686, 0.314) | 335 |
| Example 4-3 | Preparation Example 3 | 4.04 | 46.55 | (0.685, 0.315) | 335 |
| Example 4-4 | Preparation Example 4 | 4.07 | 45.96 | (0.686, 0.316) | 330 |
| Example 4-5 | Preparation Example 5 | 4.45 | 42.17 | (0.688, 0.318) | 270 |
| Example 4-6 | Preparation Example 6 | 4.49 | 42.39 | (0.689, 0.319) | 265 |
| Example 4-7 | Preparation Example 7 | 4.41 | 42.71 | (0.687, 0.317) | 260 |
| Example 4-8 | Preparation Example 8 | 4.43 | 42.62 | (0.688, 0.321) | 275 |
| Example 4-9 | Preparation Example 11 | 4.32 | 43.83 | (0.687, 0.323) | 270 |
| Example 4-10 | Preparation Example 12 | 4.37 | 43.94 | (0.688, 0.320) | 275 |
| Example 4-11 | Preparation Example 14 | 4.15 | 44.45 | (0.686, 0.316) | 320 |
| Example 4-12 | Preparation Example 15 | 4.13 | 44.70 | (0.686, 0.317) | 315 |
| Example 4-13 | Preparation Example 17 | 4.36 | 43.72 | (0.690, 0.318) | 250 |
| Example 4-14 | Preparation Example 18 | 4.37 | 43.56 | (0.689, 0.319) | 245 |
| Example 4-15 | Preparation Example 20 | 4.01 | 45.64 | (0.690, 0.320) | 280 |
| Example 4-16 | Preparation Example 21 | 4.05 | 45.61 | (0.685, 0.315) | 295 |
| Comparative Example 4-1 | HT5 | 5.32 | 38.69 | (0.692, 0.324) | 145 |

TABLE 4-continued

| Compound (Hole transport layer) | Voltage (V@10 mA/cm²) | Efficiency (cd/A@10 mA/cm²) | Color coordinate (x,y) | T98 (hr) |
|---|---|---|---|---|
| Comparative Example 4-2 | HT6 | 4.87 | 45.63 | (0.687, 0.319) | 190 |
| Comparative Example 4-3 | HT7 | 5.13 | 41.05 | (0.693, 0.323) | 160 |

As shown in Table 4, the organic light emitting devices manufactured using the compound of the present disclosure as a hole transport layer of a green light emitting device (phosphorescence) exhibited excellent characteristics in terms of efficiency, driving voltage and stability of the organic light emitting device. They exhibited lower voltage, higher efficiency, and longer lifetime than those of the organic light emitting devices manufactured using the compound of Comparative Example 4-2 in which amines containing carbazole are directly connected as a hole transport layer. In addition, the organic light emitting device manufactured using the compound of Comparative Examples 4-1 and 4-3 having a structure similar to the core of the present disclosure but containing no methyl group showed that voltage was increased by 20% or more, efficiency was decreased by 5-10% or more and lifetime was decreased by 60-70% or more. This is because 800 Å is used as a hole transport layer of the red light emitting layer, compared with the device deposited in a thickness of 300 Å as the hole transport layer of the green light emitting layer in Experimental Example 3 described above. Therefore, it can be concluded that the core of the present disclosure has relatively higher hole mobility capability than the materials of Comparative Examples 4-1 and 4-3. When compared with Examples 4-1 to 4-4 with Examples 4-5 to 4-8, the substances in which the phenyl group was connected as a linker rather than a direct bond showed the best characteristics (especially, lifetime). Comparing Examples 4-9 to 4-12, the compounds containing a phenyl linker in the direction 3 of the present disclosure also showed the same tendency. In Examples 4-13 to 4-16, it was found that the substances in which the core of the present disclosure was composed of a phenyl group instead of a methyl group was a direct bond, but lifetime characteristics were relatively better.

From the results in Table 4, it was confirmed that the compound according to the present disclosure had excellent hole transporting capability in a device using a phosphorescent green light emitting layer and thus could be applied to an organic light emitting device.

Description of symbols

1: substrate
2: anode
3: organic material layer
4: cathode
5: hole injection layer
6: hole transport layer
7: electron blocking layer
8: light emitting layer
9: electron transport layer
10: electron injection layer

The invention claimed is:

1. A compound represented by the following Chemical Formula 1:

[Chemical Formula 1]

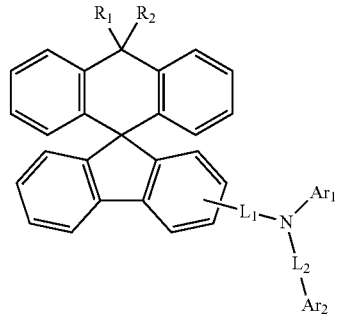

wherein in Chemical Formula 1, both $R_1$ and $R_2$ are methyl, or both $R_1$ and $R_2$ are phenyl, $L_1$ and $L_2$ are each independently a bond; or substituted or unsubstituted $C_{6-60}$ arylene, provided that when both $R_1$ and $R_2$ are methyl, $L_1$ is substituted or unsubstituted $C_{6-60}$ arylene, and $Ar_1$ and $Ar_2$ are each independently substituted or unsubstituted $C_{6-60}$ aryl; or $C_{2-60}$ heteroaryl containing O or S.

2. The compound of claim 1, wherein the compound represented by Chemical Formula 1 is represented by the following Chemical Formulas 1-1, 1-2, or 1-3:

[Chemical Formula 1-1]

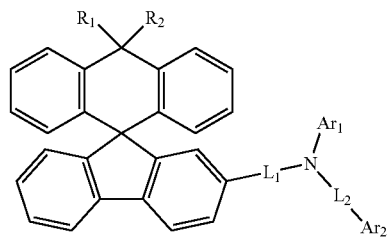

[Chemical Formula 1-2]

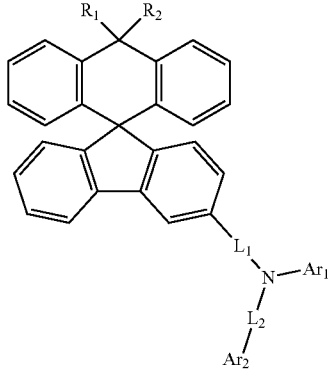

[Chemical Formula 1-3]

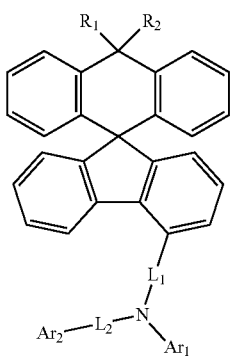

wherein, in Chemical Formula 1-1 to 1-3, $R_1$, $R_2$, $L_1$, $L_2$, $Ar_1$, and $Ar_2$ are as defined in claim 1.

3. The compound of claim 1, wherein $L_1$ and $L_2$ are each independently a bond, phenylene, biphenyldiyl, terphenyldiyl, quarterphenyldiyl, naphthalenediyl, anthracenediyl, dimethylfluorenediyl, phenanthrendiyl, pyrenediyl, or triphenylenediyl, provided that when both $R_1$ and $R_2$ are methyl, $L_1$ is phenylene, biphenyldiyl, terphenyldiyl, quarterphenyldiyl, naphthalenediyl, anthracenediyl, dimethylfluorenediyl, phenanthrendiyl, pyrenediyl, or triphenylenediyl.

4. The compound of claim 1, wherein both $R_1$ and $R_2$ are phenyl, $L_1$ is a bond, and $L_2$ is a bond, or phenylene.

5. The compound of claim 1, wherein $Ar_1$ and $Ar_2$ are each independently phenyl unsubstituted or substituted with any one substituent selected from the group consisting of $C_{1-4}$ alkyl, halogen, cyano, and tri($C_{1-4}$ alkyl)silyl; biphenylyl; terphenylyl; quaterphenylyl; naphthyl; anthracenyl; phenanthrenyl; triphenylenyl; dimethylfluorenyl; diphenylfluorenyl; dibenzofuranyl; or dibenzothiophenyl.

6. The compound of claim 1, wherein the compound represented by the Chemical Formula 1 is any one selected from the group consisting of:

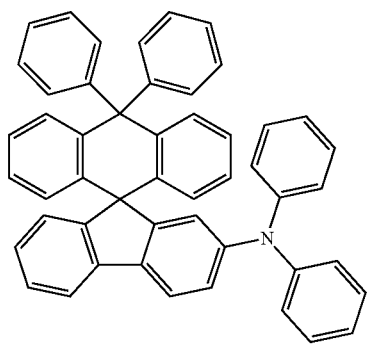

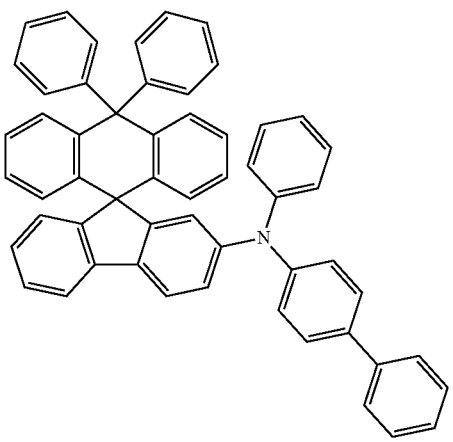

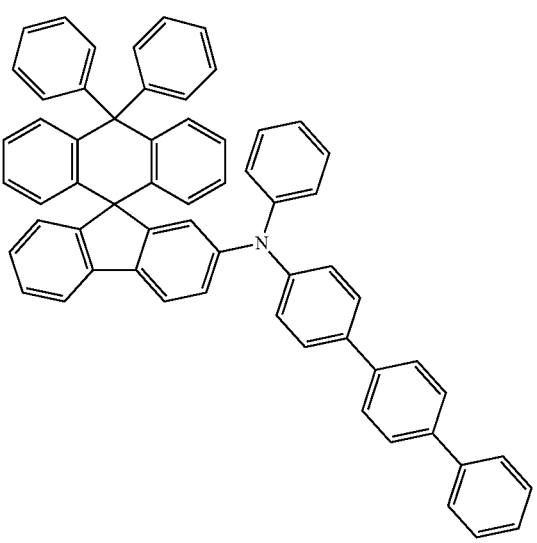 [SMILES: c1ccc(-c2ccc(-c3ccc(N(c4ccccc4)c4ccc5c(c4)C4(c6ccccc6-5)c5ccccc5C(c5ccccc5)(c5ccccc5)c5ccccc54)cc3)cc2)cc1]

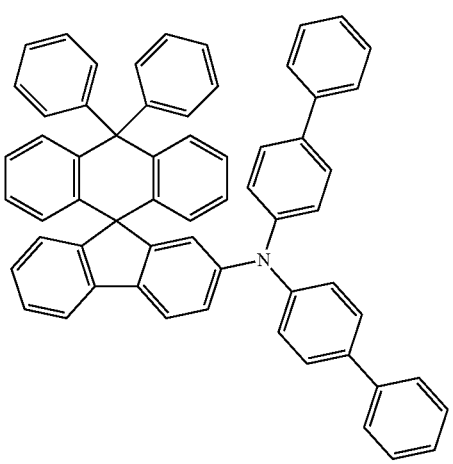

223
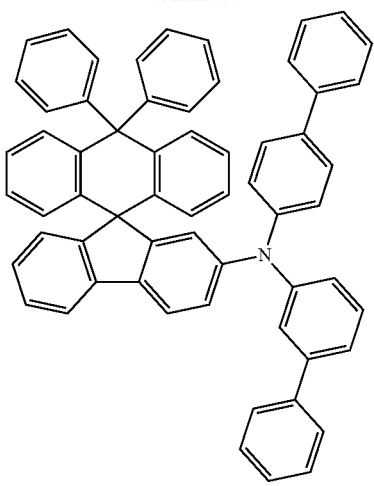
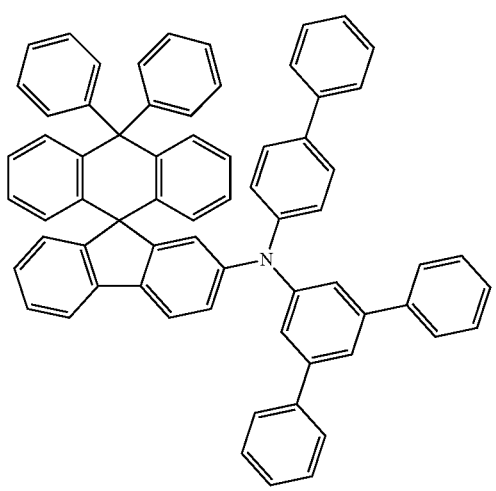
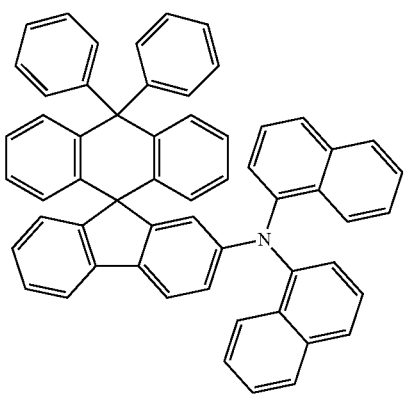
224
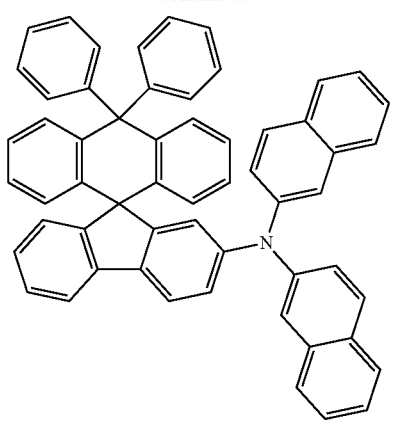
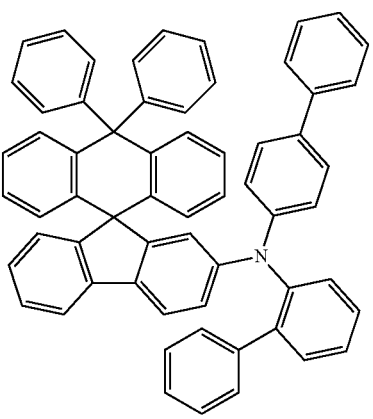
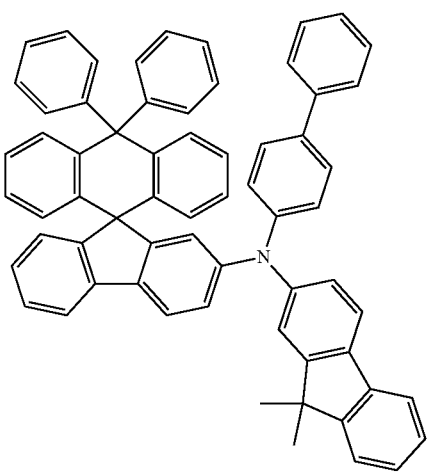

225
-continued
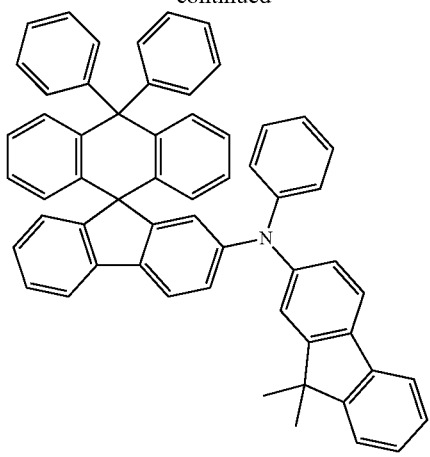
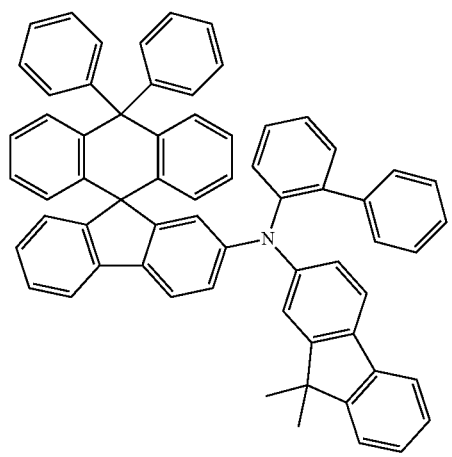
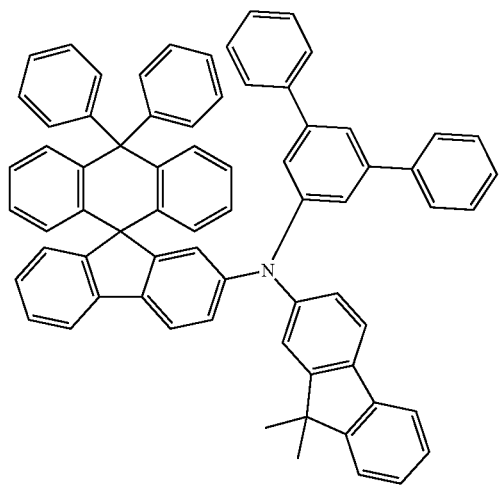
226
-continued
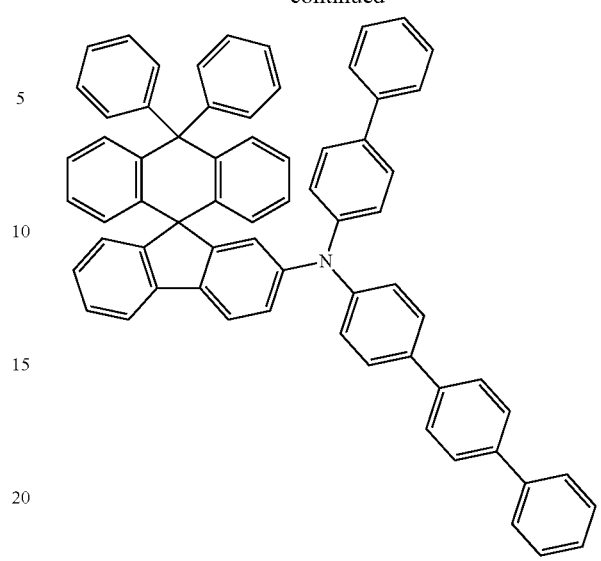
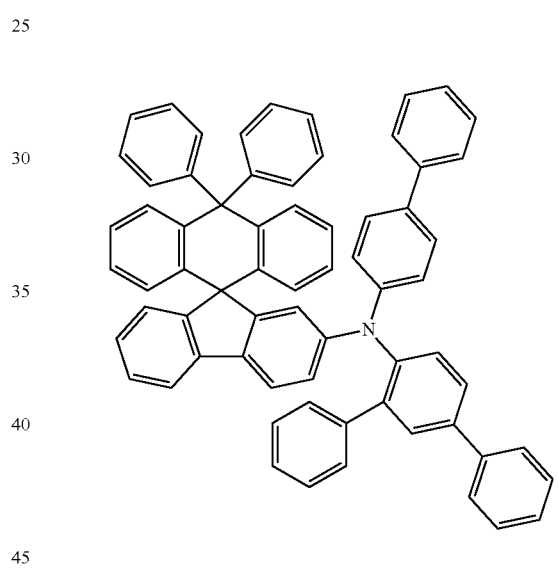
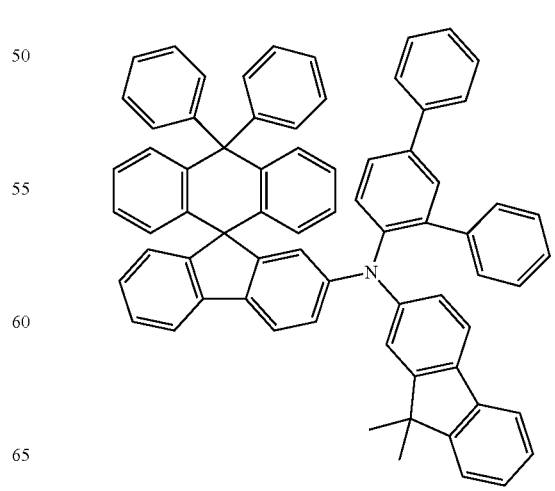

227
-continued
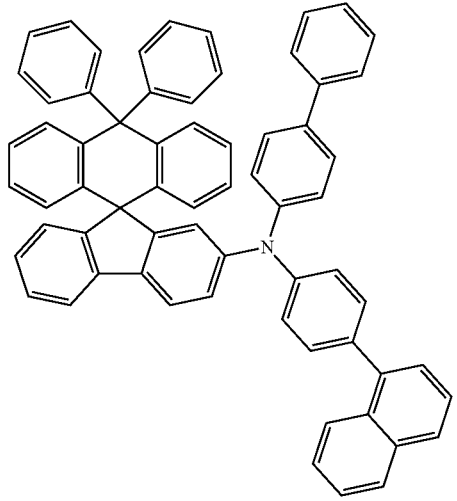 [SMILES: c1ccc(-c2ccc(N(c3ccc(-c4cccc5ccccc45)cc3)c3ccc4c(c3)C3(c5ccccc5-4)c4ccccc4C(c4ccccc4)(c4ccccc4)c4ccccc43)cc2)cc1]
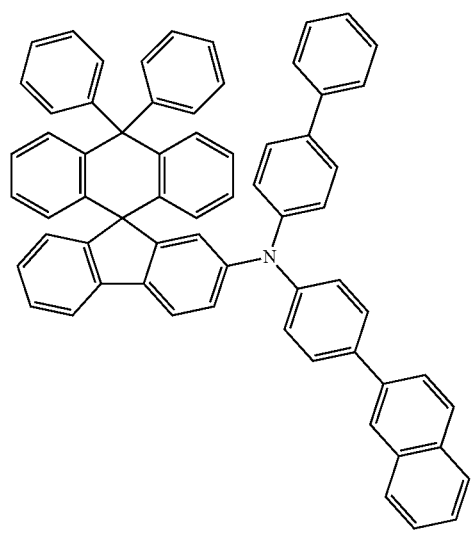
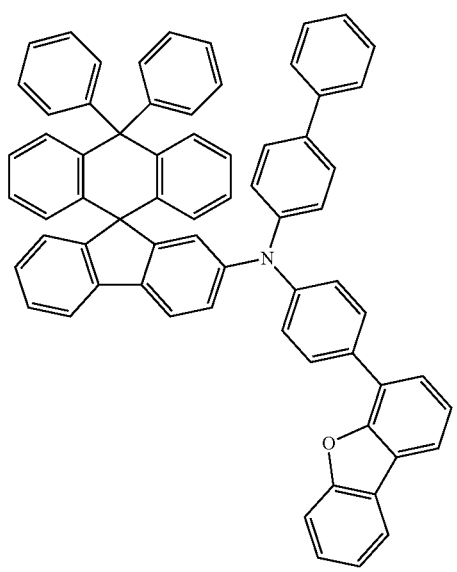
228
-continued
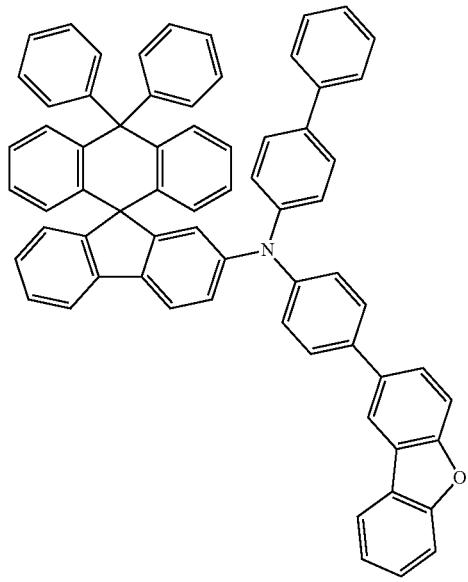 [SMILES: c1ccc(-c2ccc(N(c3ccc(-c4ccc5oc6ccccc6c5c4)cc3)c3ccc4c(c3)C3(c5ccccc5-4)c4ccccc4C(c4ccccc4)(c4ccccc4)c4ccccc43)cc2)cc1]
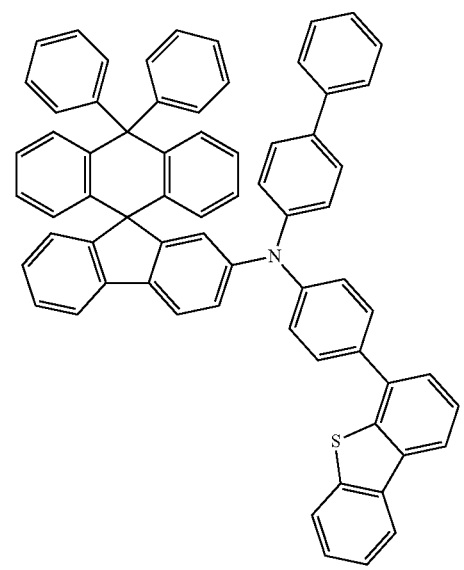
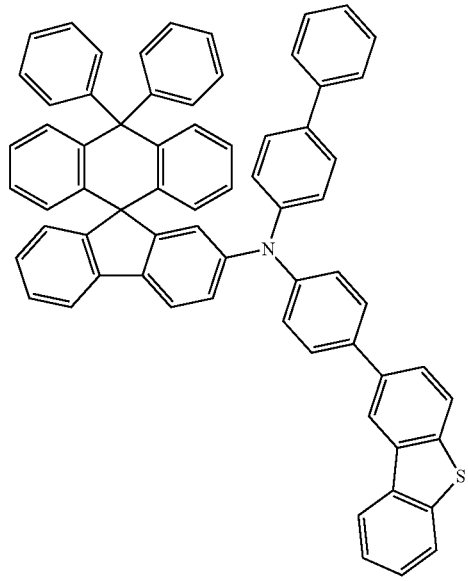

229
-continued
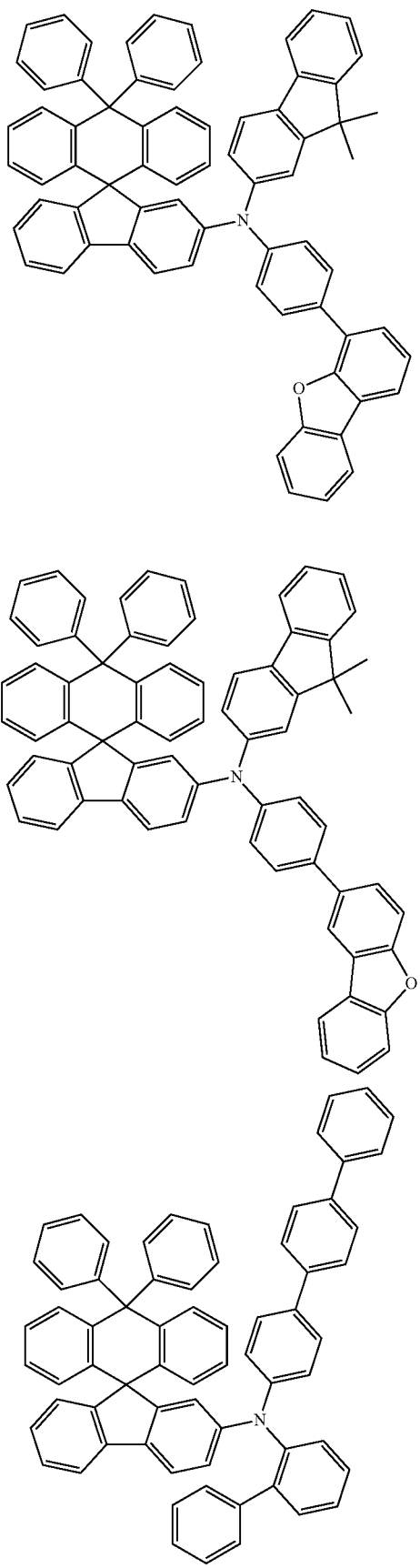
230
-continued
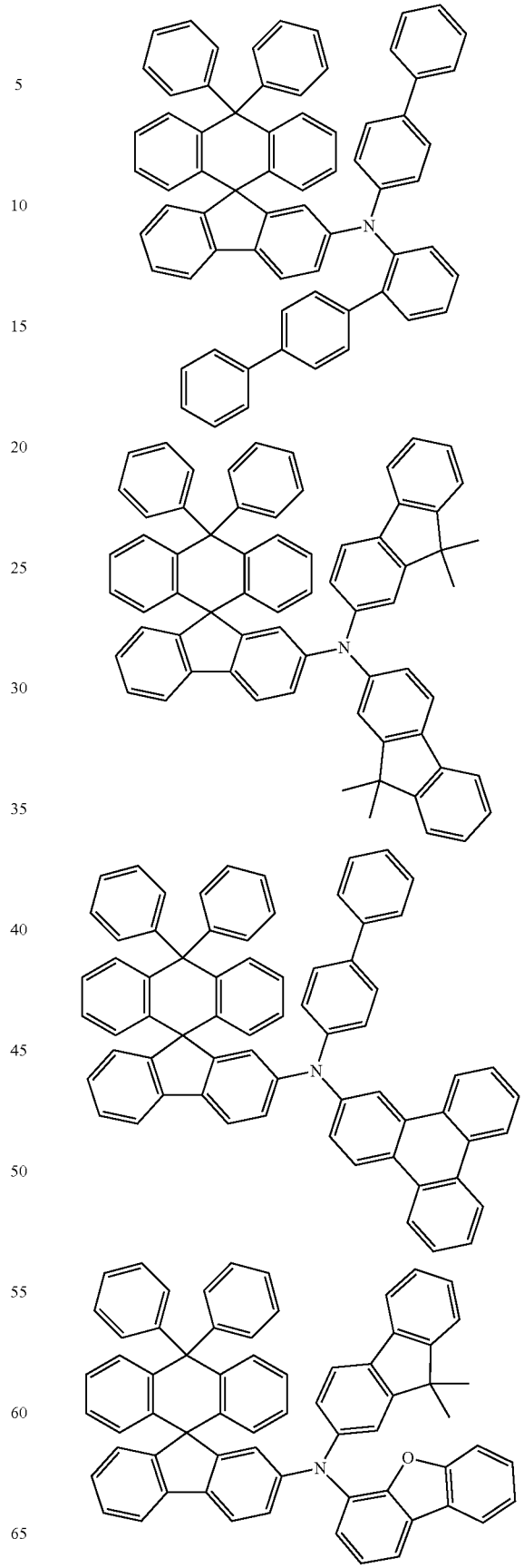

231
-continued
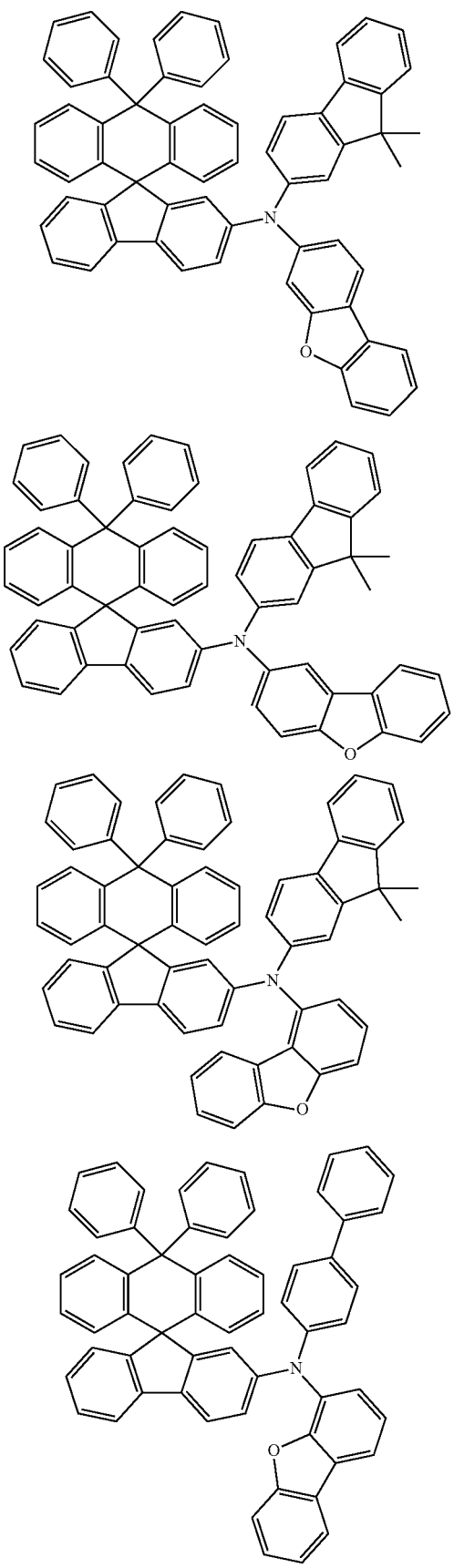
232
-continued
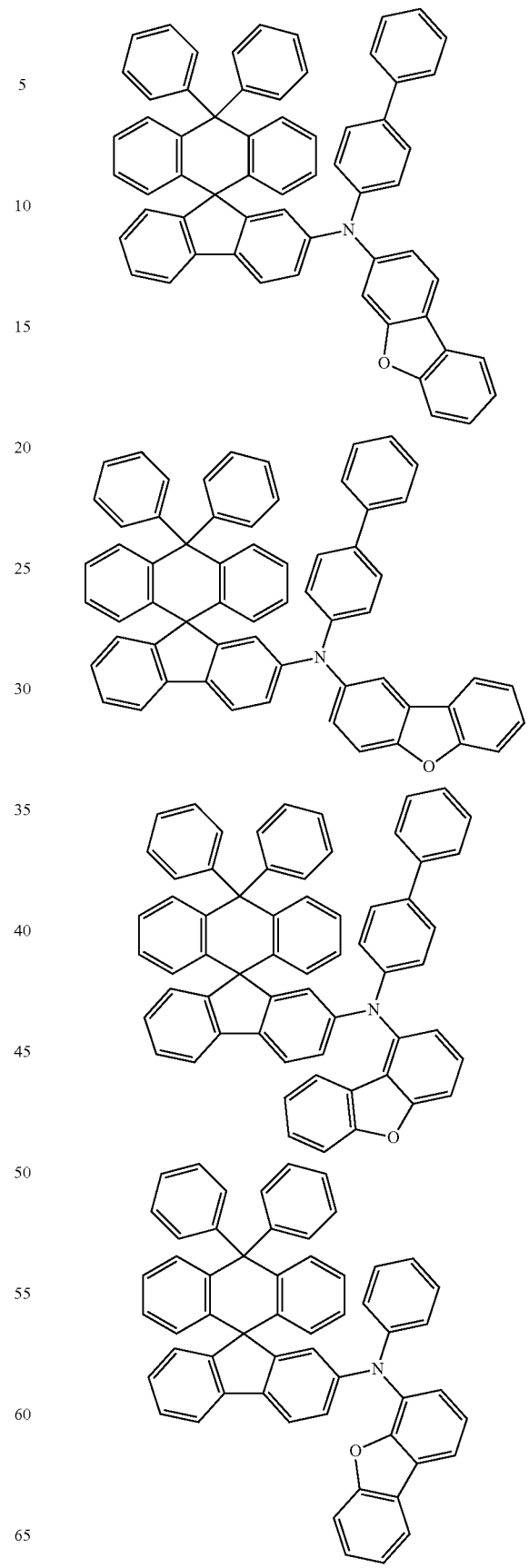

233
-continued
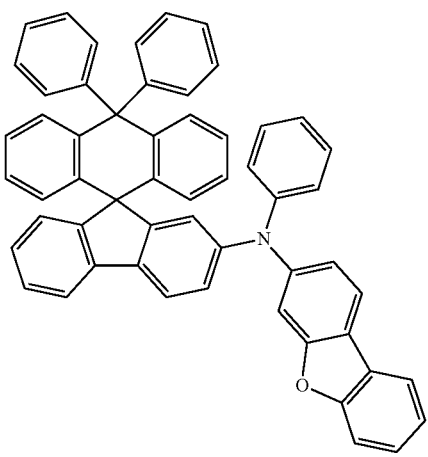
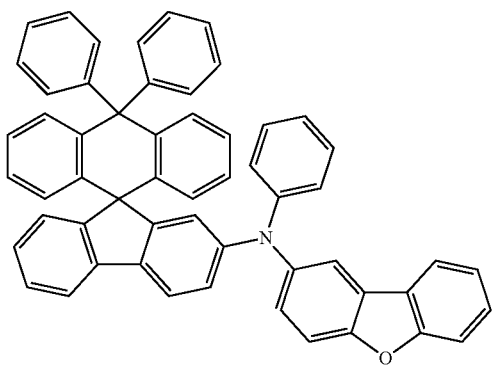
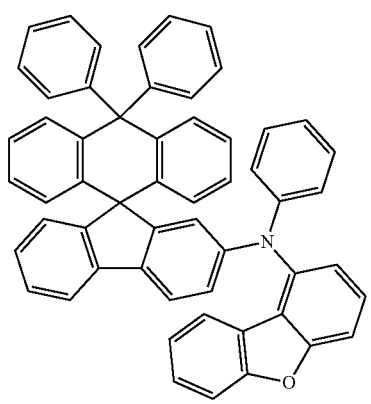
234
-continued
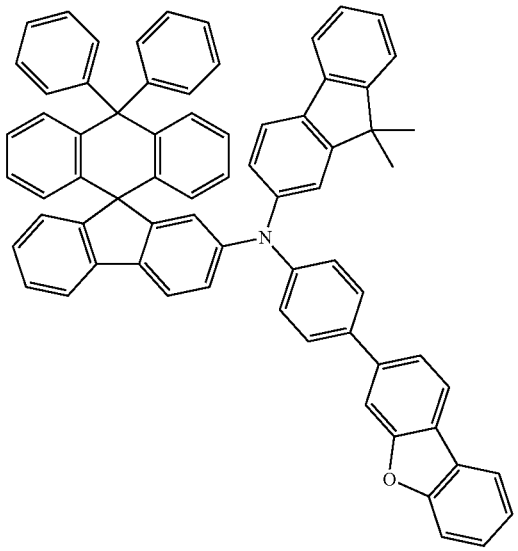
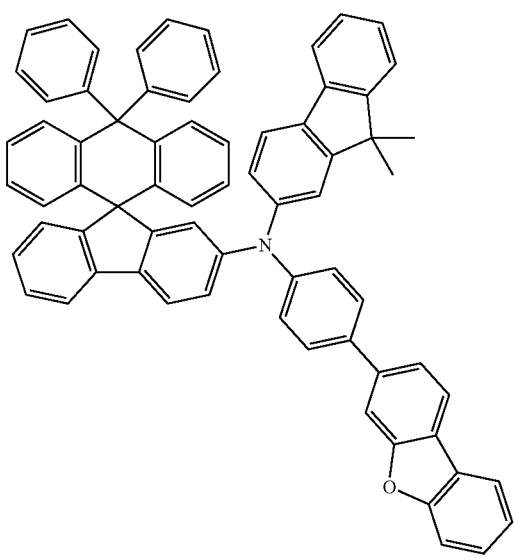 [SMILES: CC1(C)c2ccccc2-c2ccc(N(c3ccc(-c4ccc5c(c4)sc4ccccc45)cc3)c3ccc4c(c3)C3(c5ccccc5-4)c4ccccc4C(c4ccccc4)(c4ccccc4)c4ccccc43)cc21]
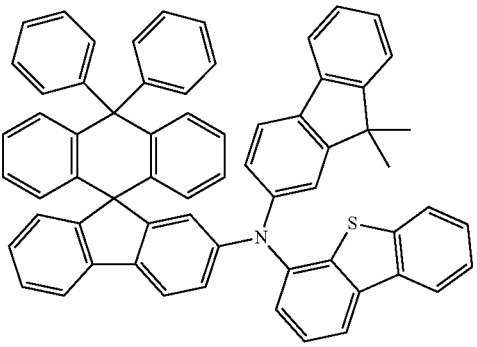

235
-continued
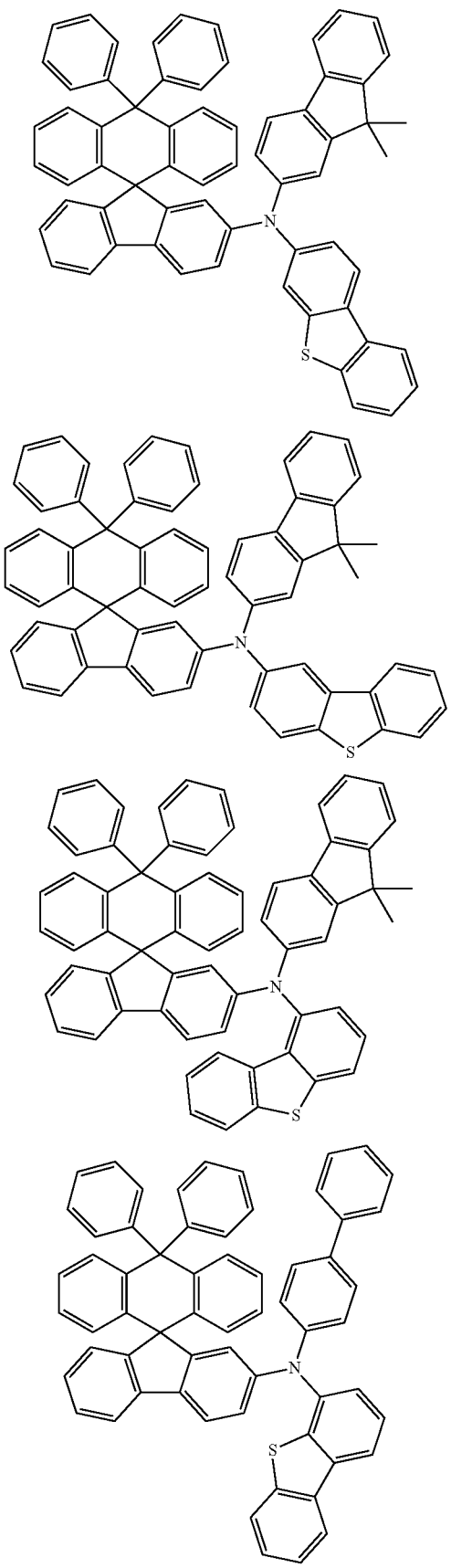
236
-continued
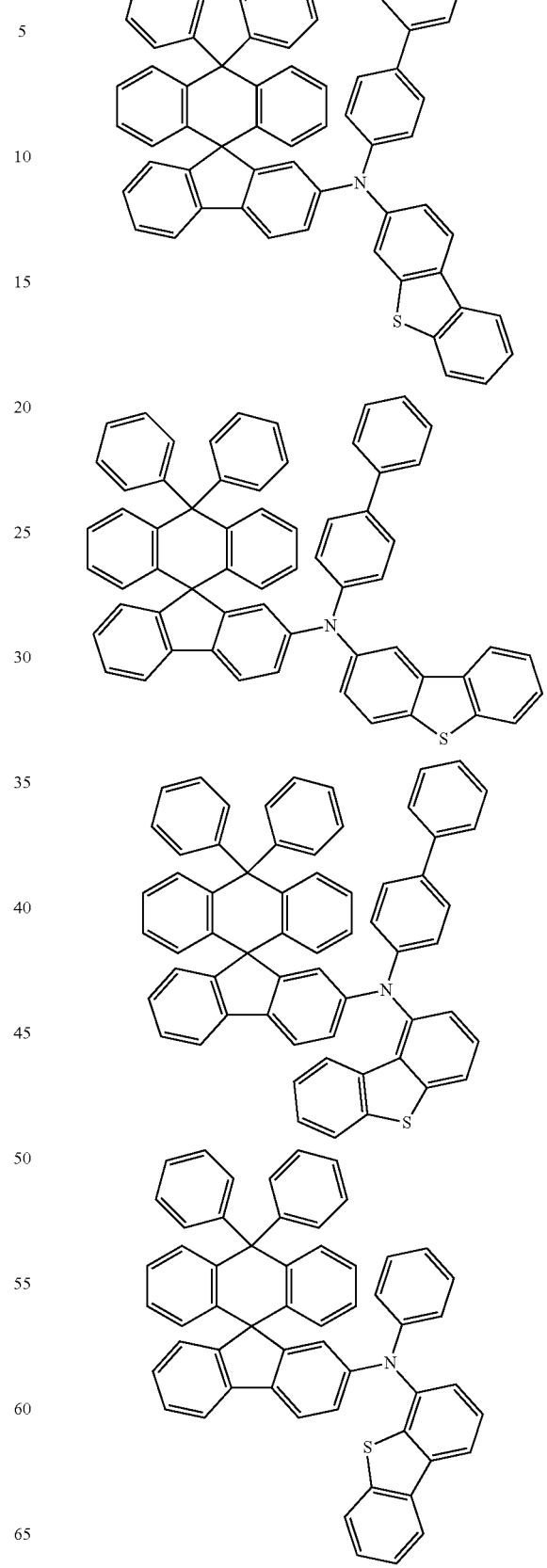

237
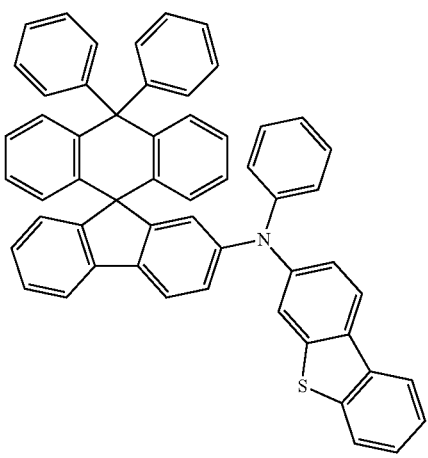
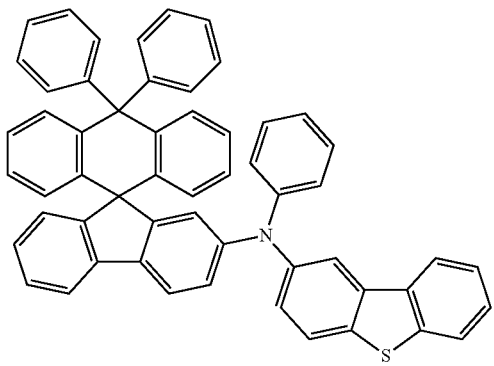
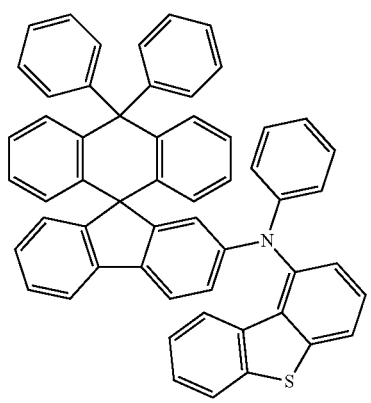
238
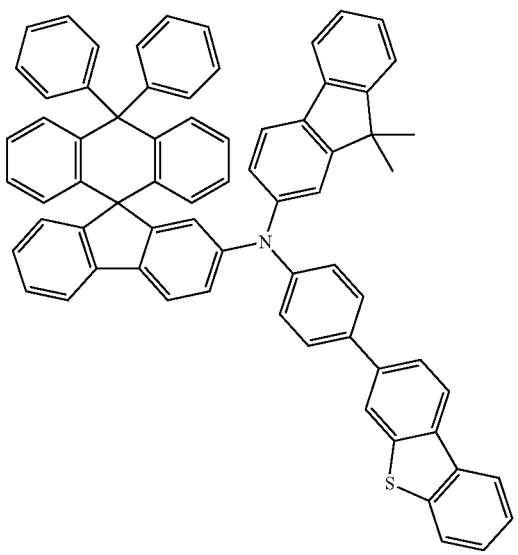
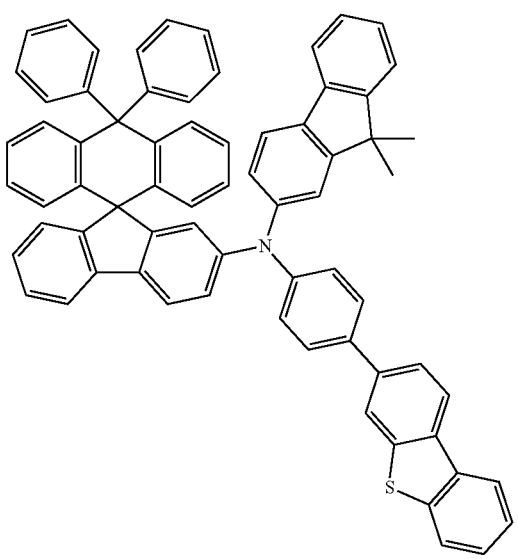
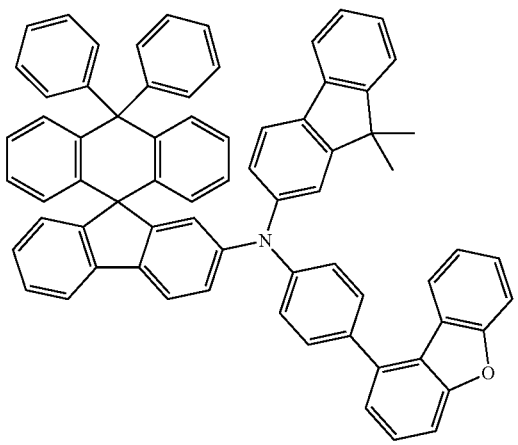

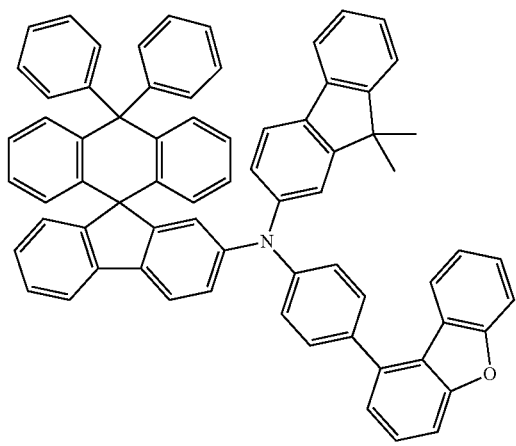
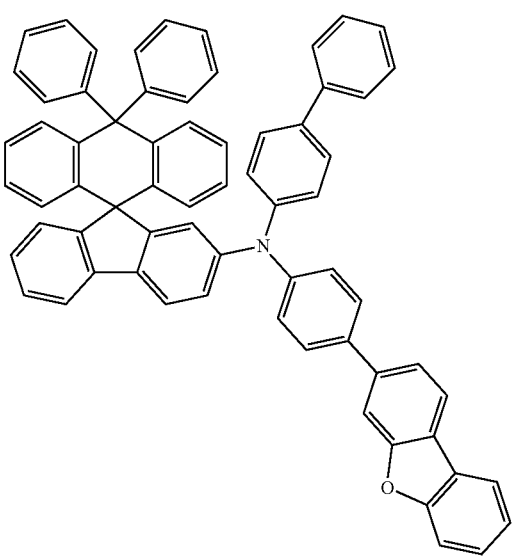 [SMILES: c1ccc(-c2ccc(N(c3ccc(-c4ccc5c(c4)oc4ccccc45)cc3)c3ccc4c(c3)C3(c5ccccc5-4)c4ccccc4C(c4ccccc4)(c4ccccc4)c4ccccc43)cc2)cc1]
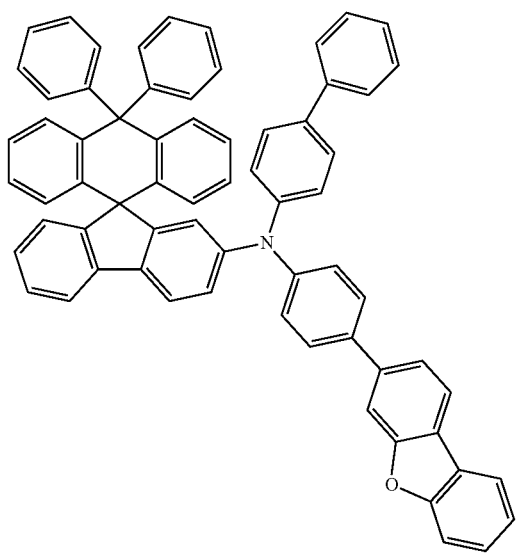
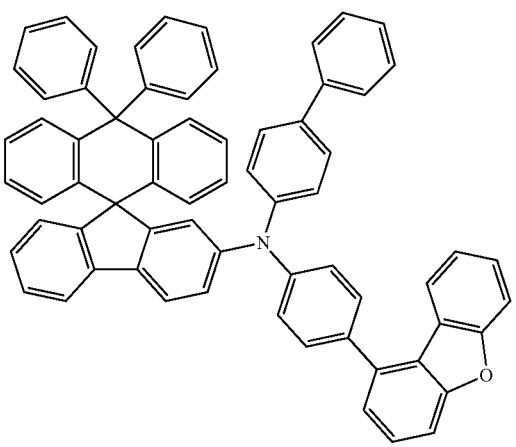
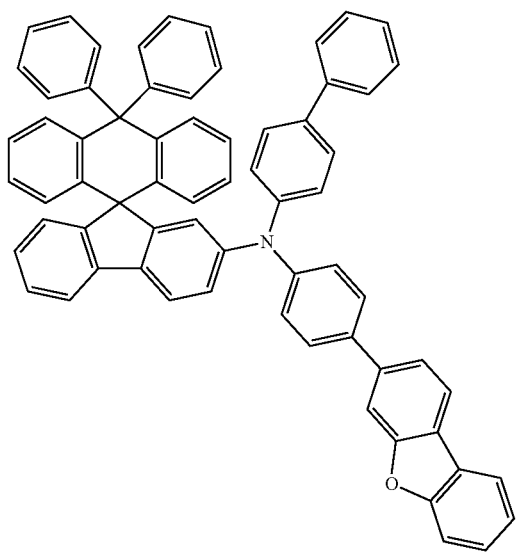
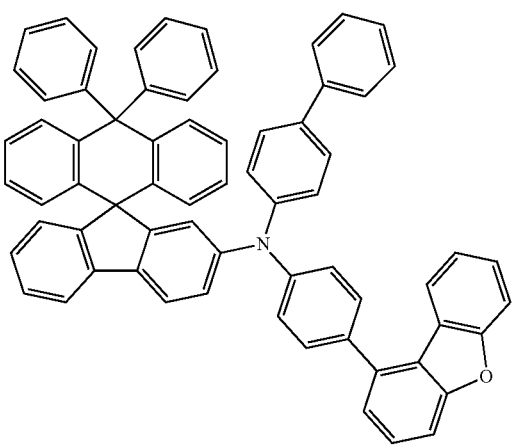

241
-continued
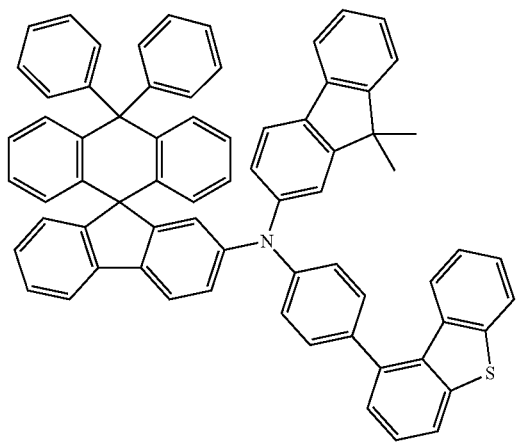
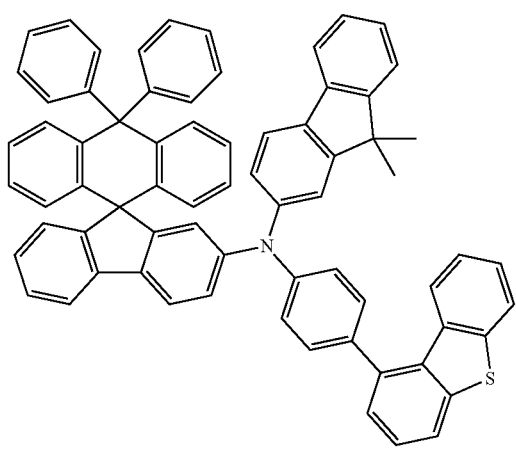 [SMILES: CC1(C)c2ccccc2-c2ccc(N(c3ccc(-c4cccc5sc6ccccc6c45)cc3)c3ccc4c(c3)C3(c5ccccc5-4)c4ccccc4C(c4ccccc4)(c4ccccc4)c4ccccc43)cc21]
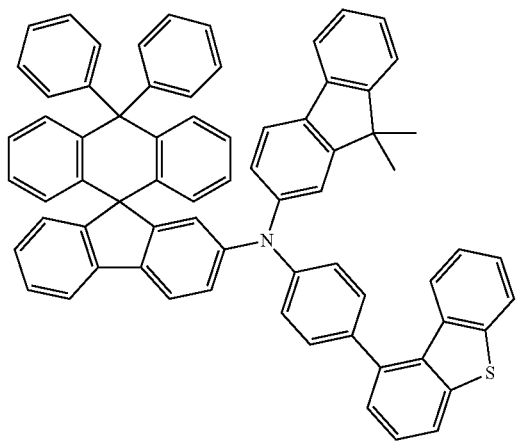
242
-continued
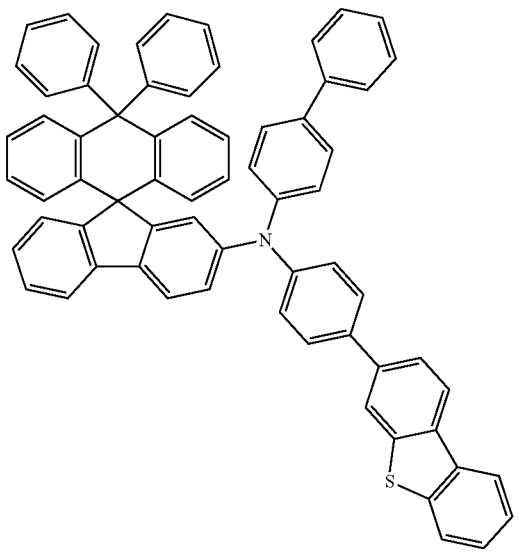
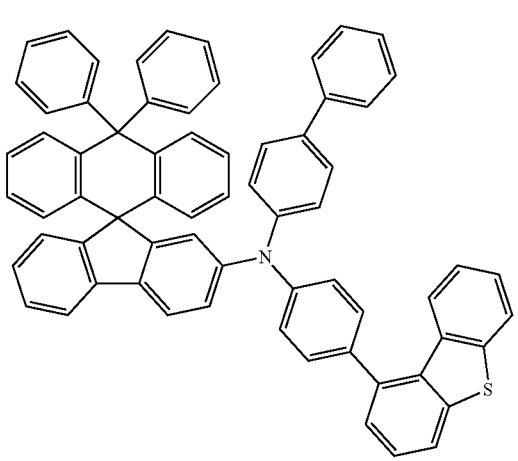

243
-continued
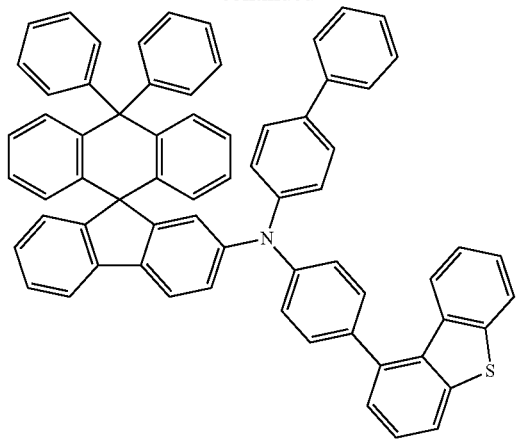
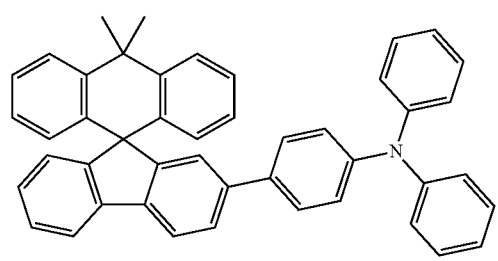
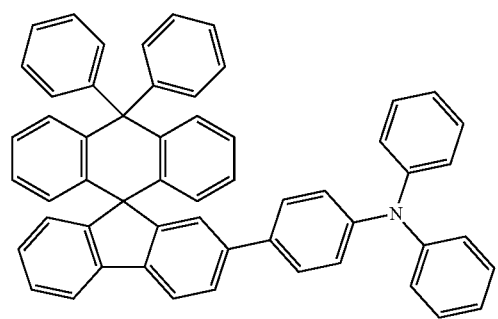
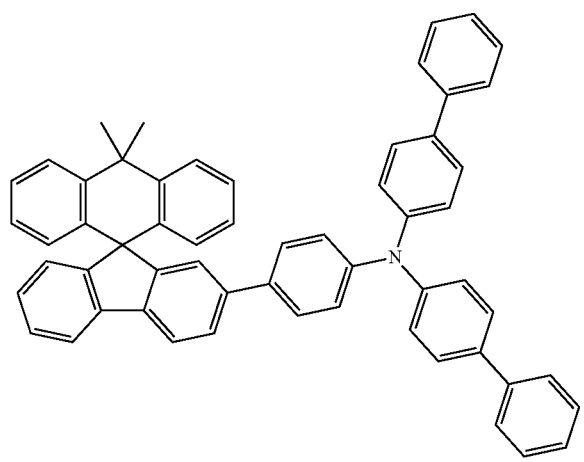
244
-continued
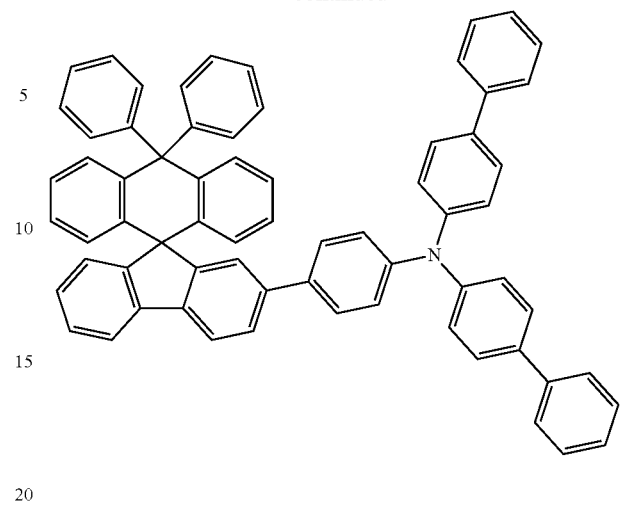
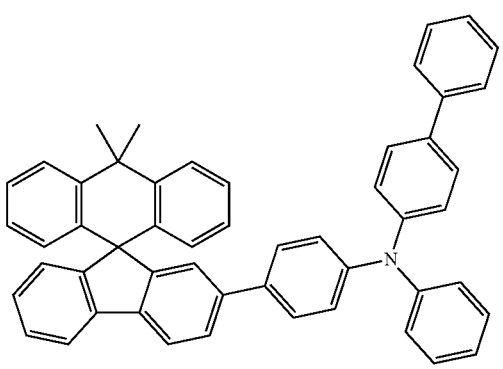
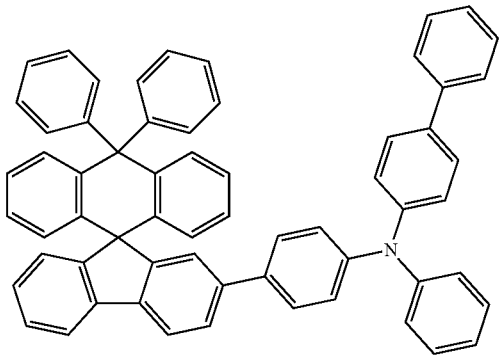
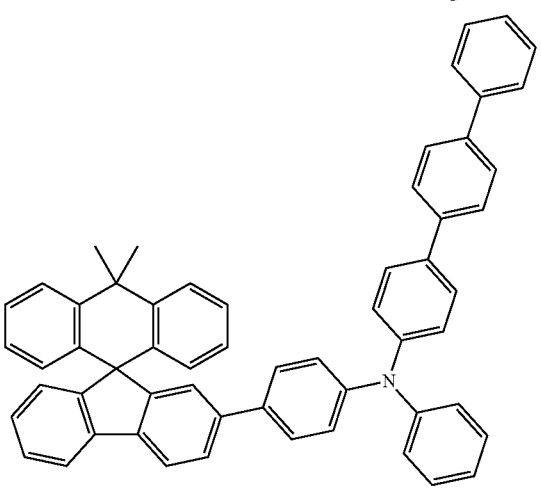

245
-continued
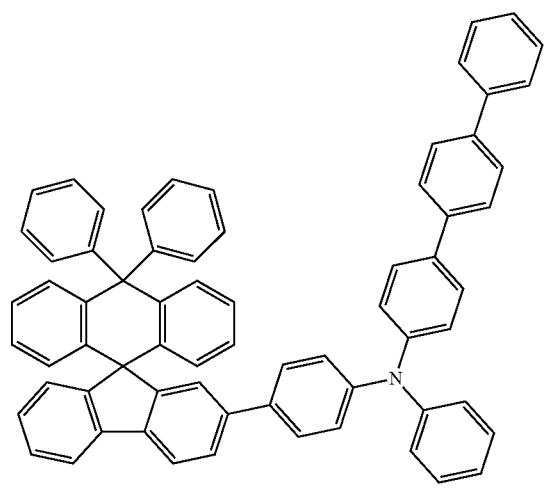
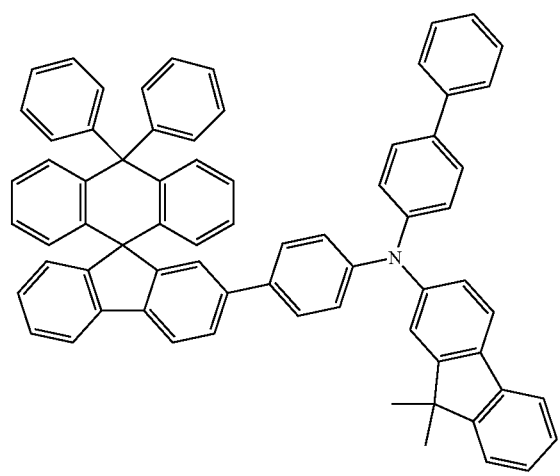
246
-continued
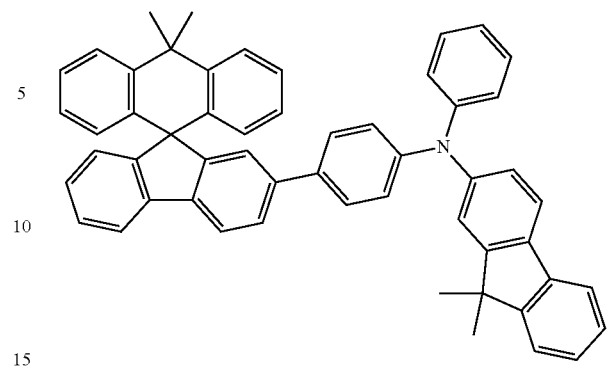
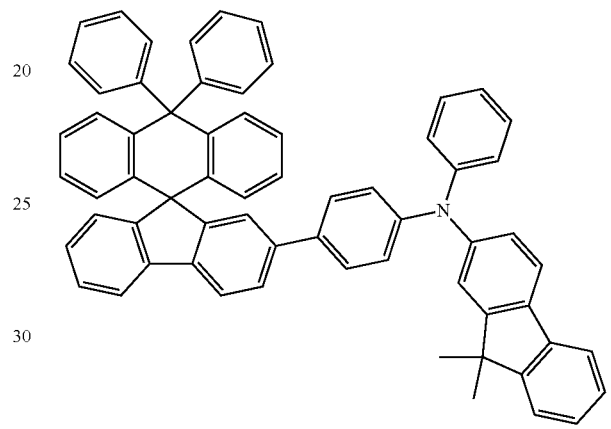
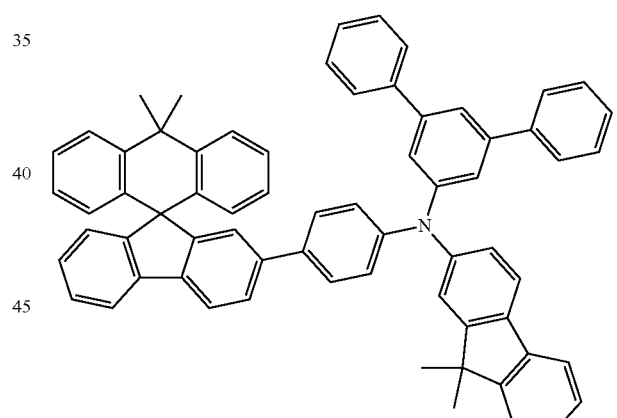
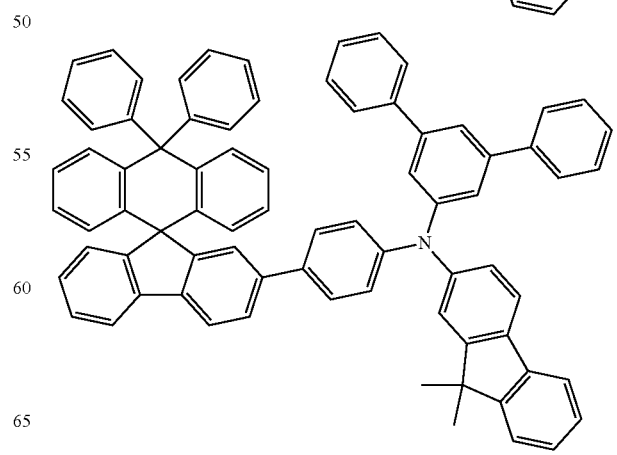

247
-continued
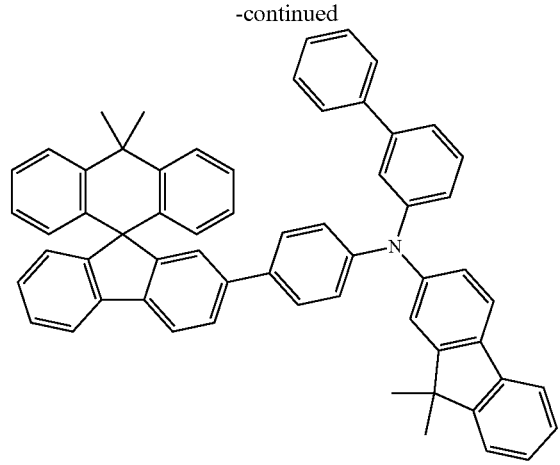
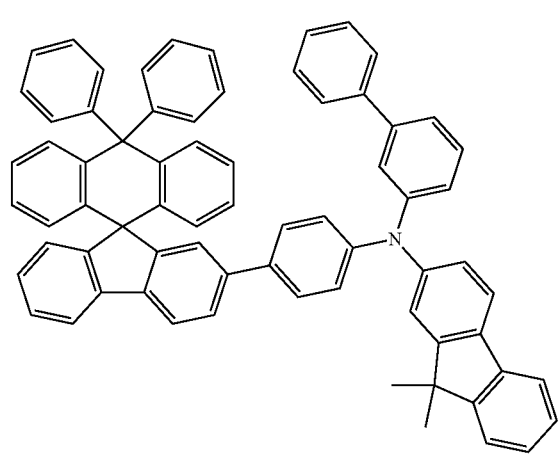
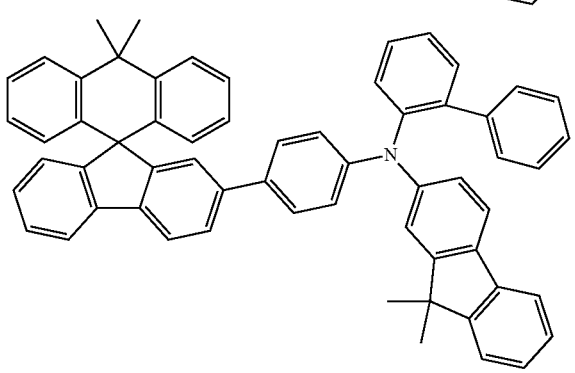
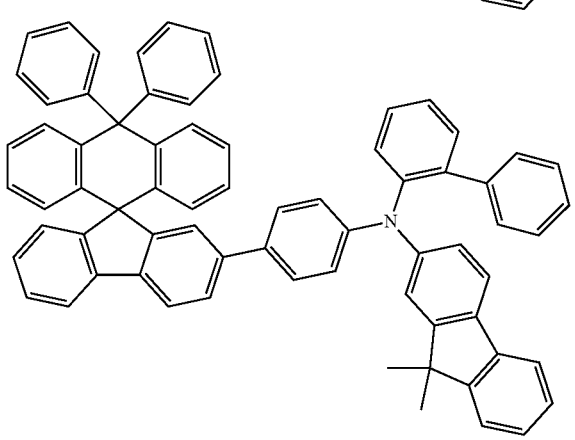
248
-continued
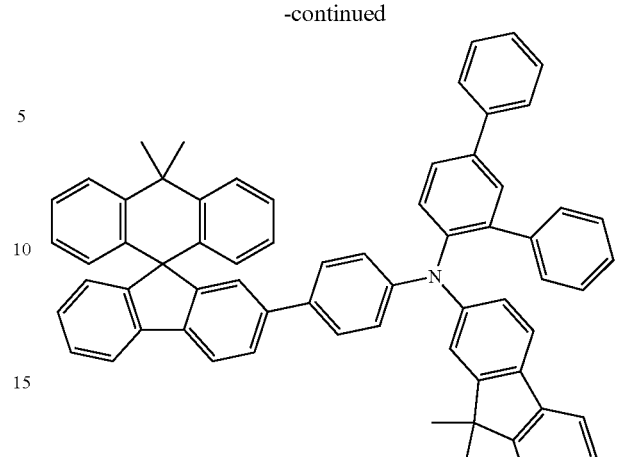
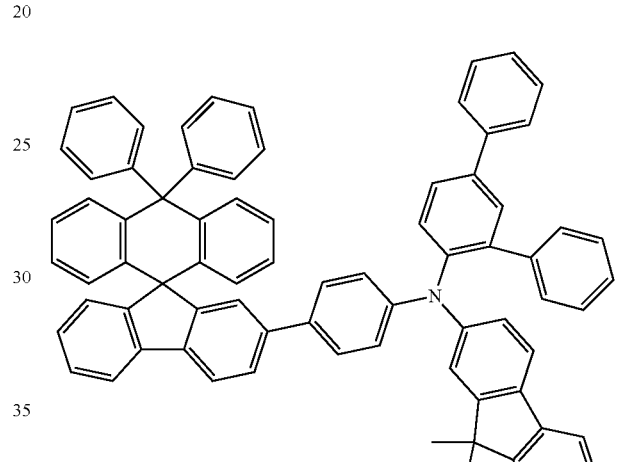
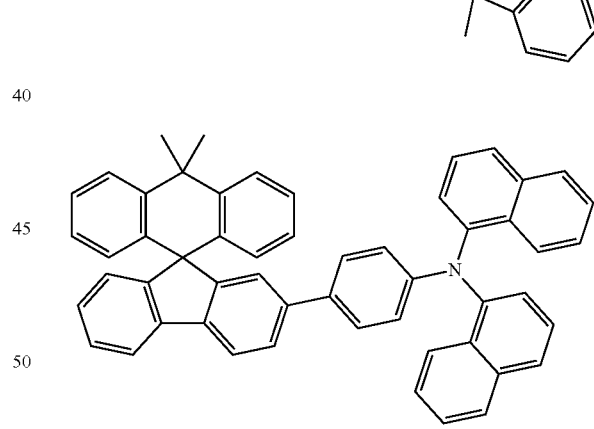
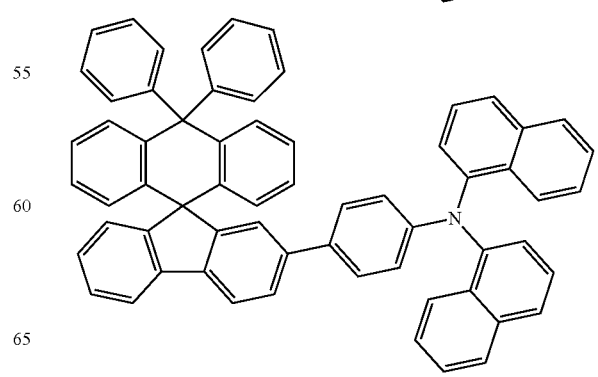

249
-continued
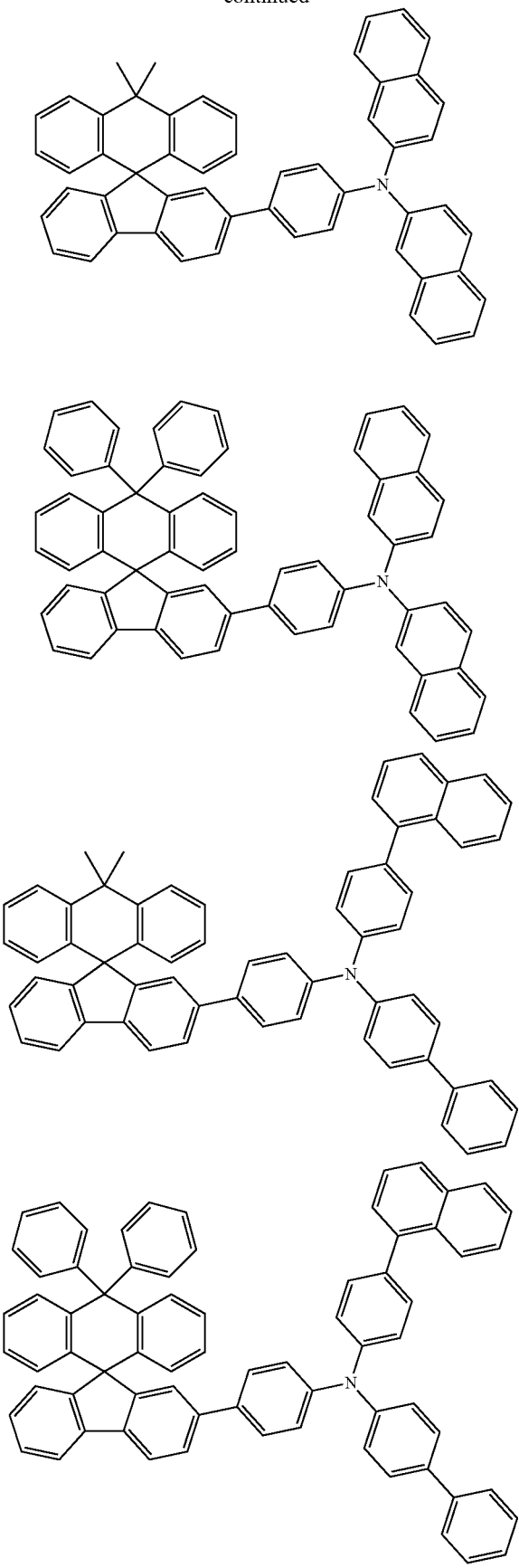
250
-continued
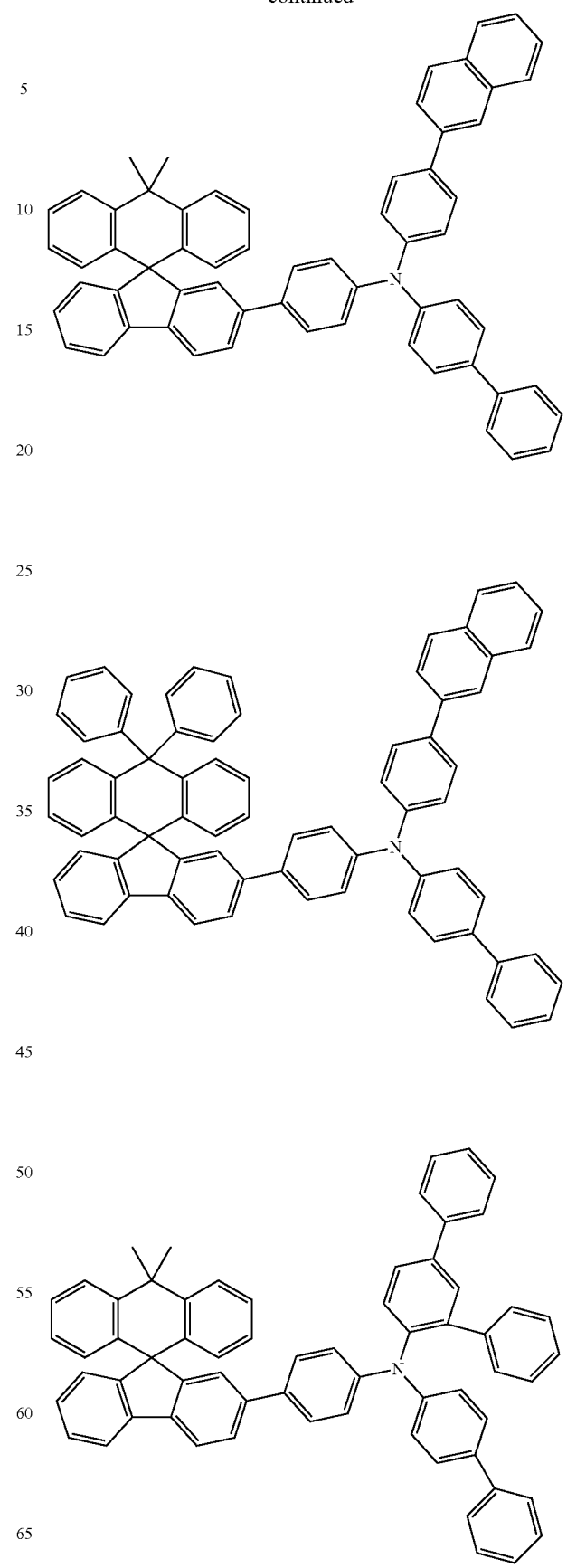

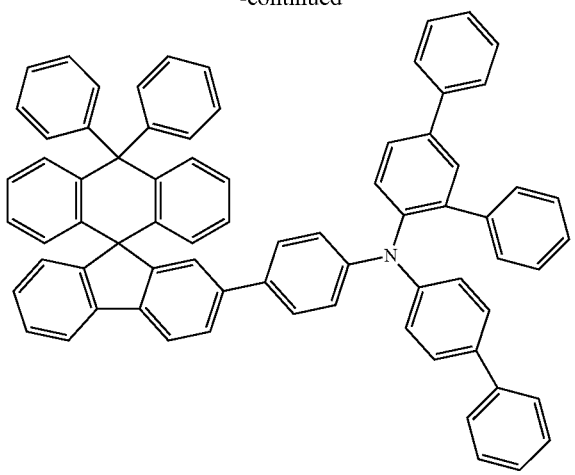
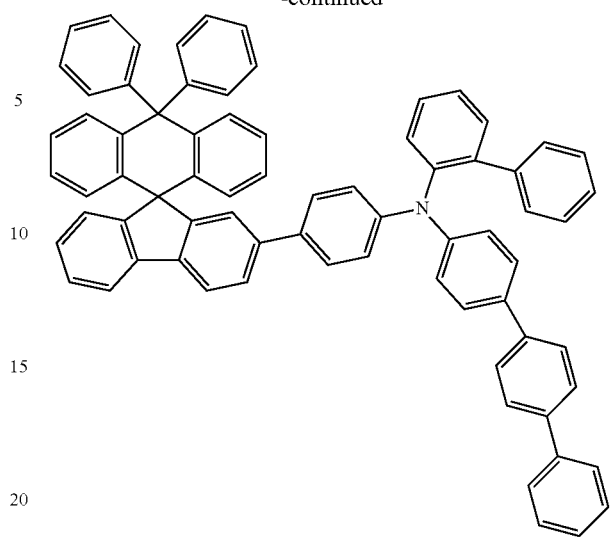

253
-continued
254
-continued
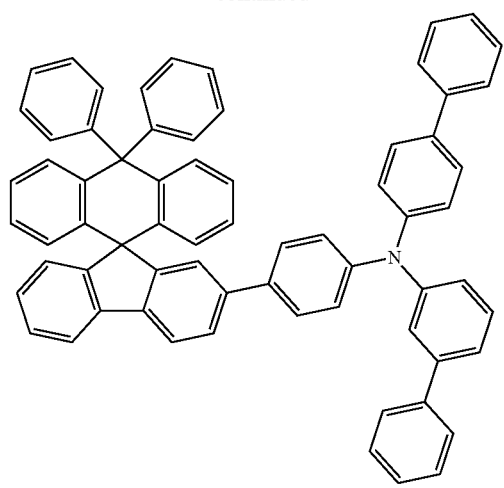
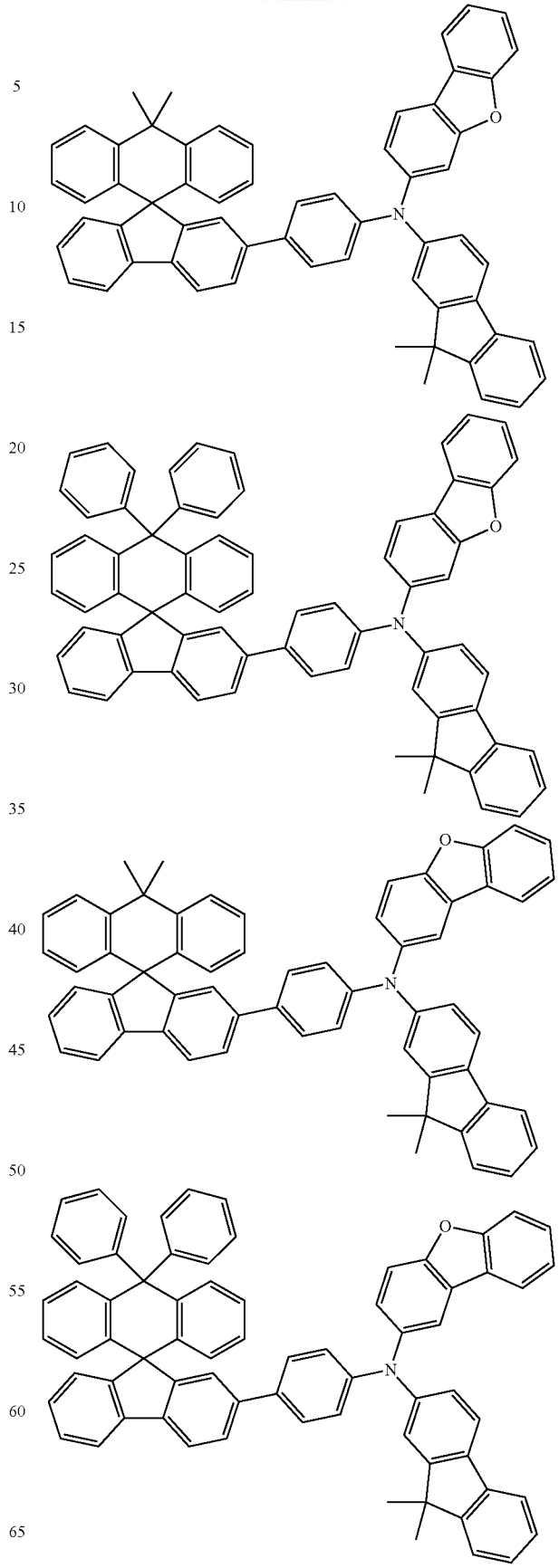

255
-continued
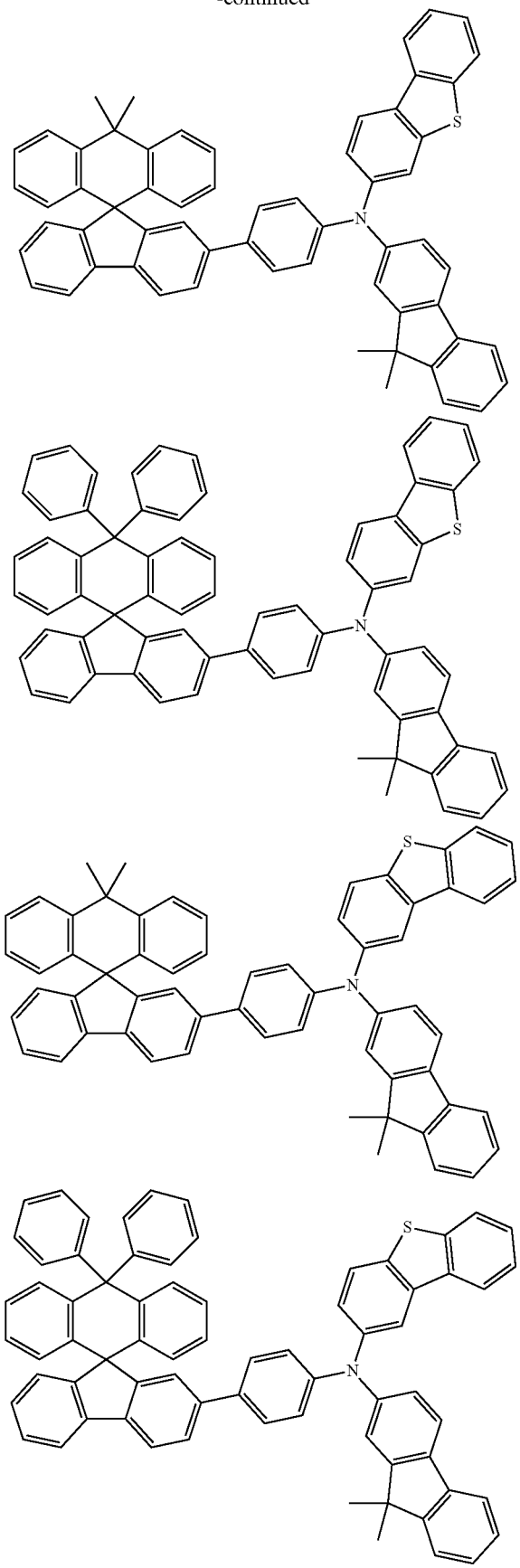
256
-continued
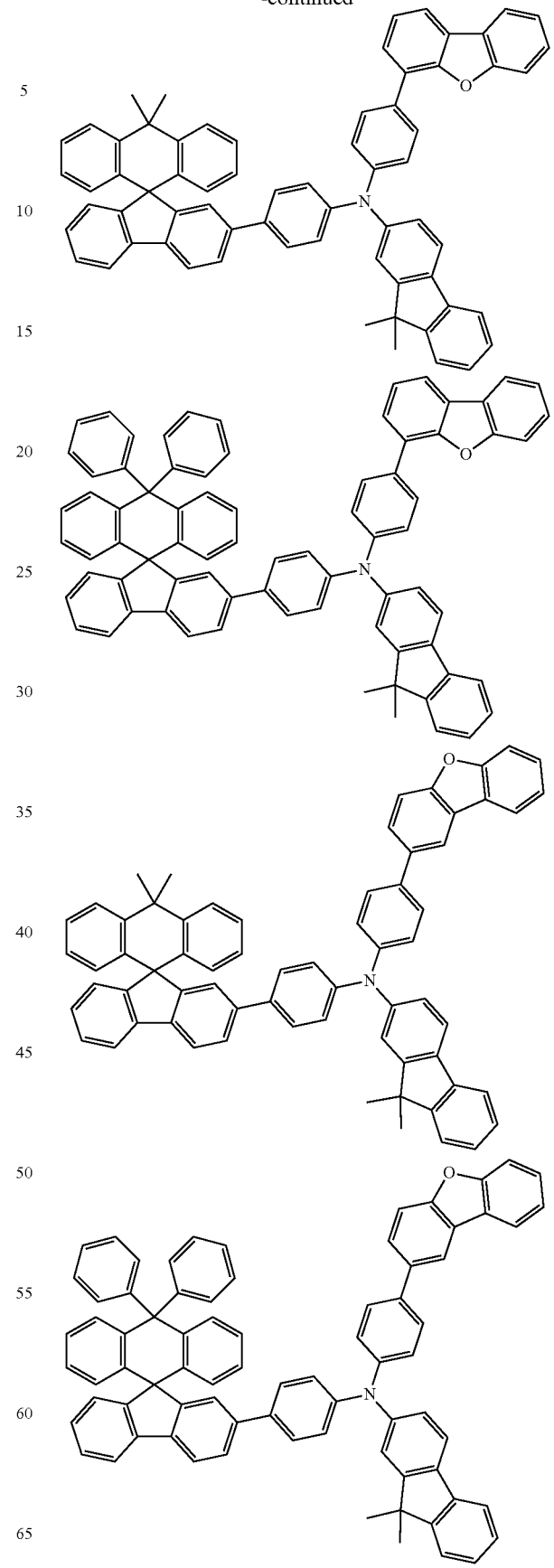

257
-continued
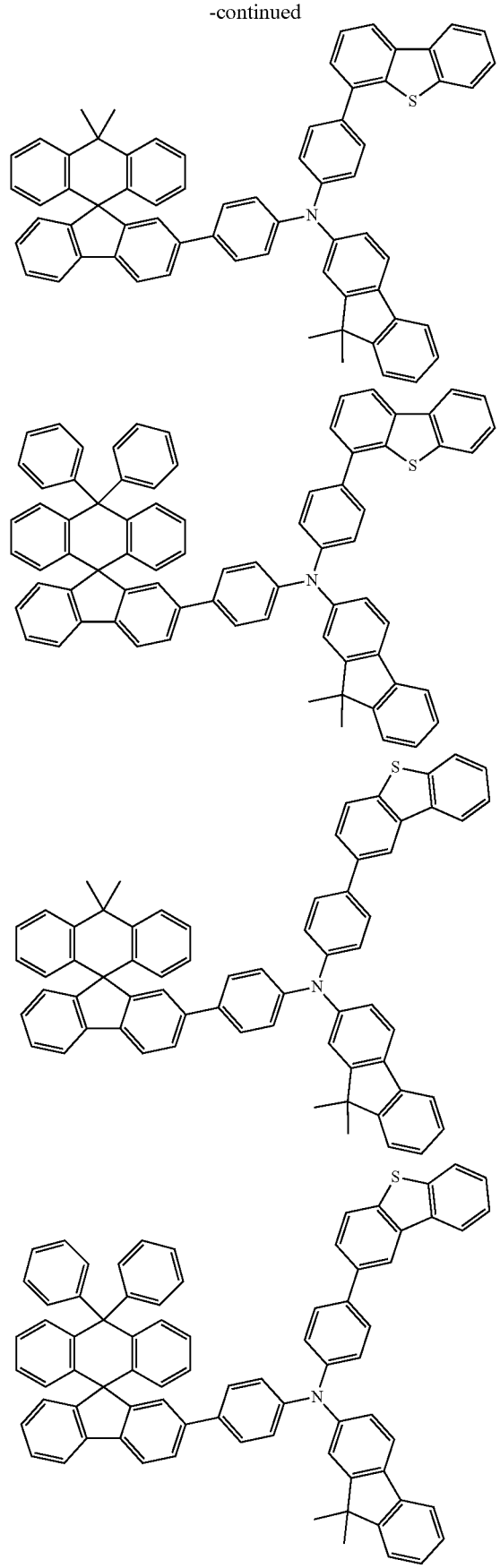
258
-continued
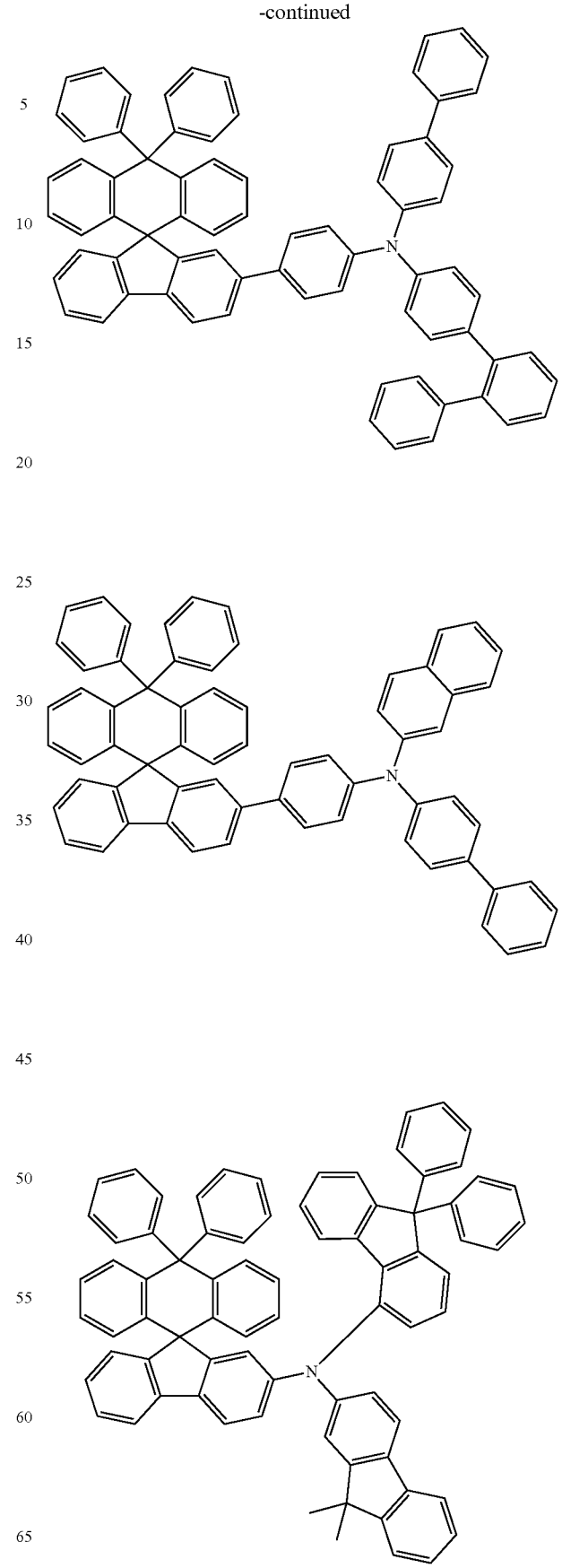

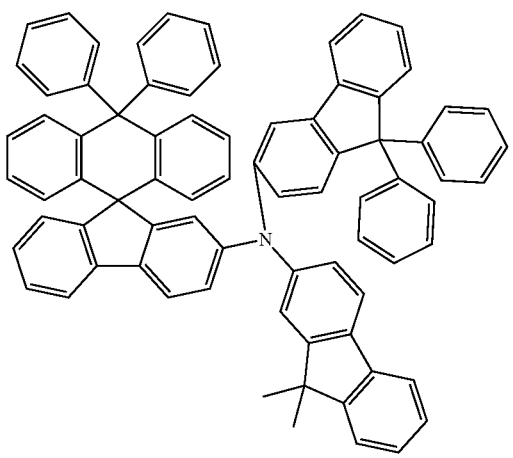
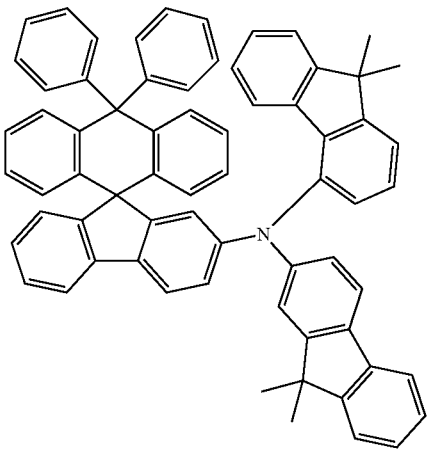
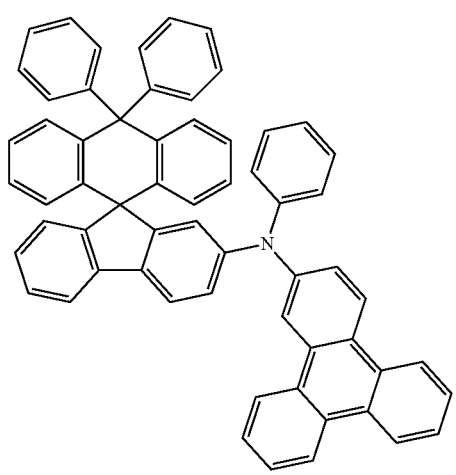
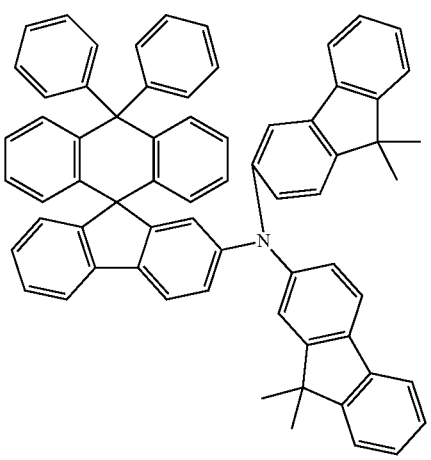
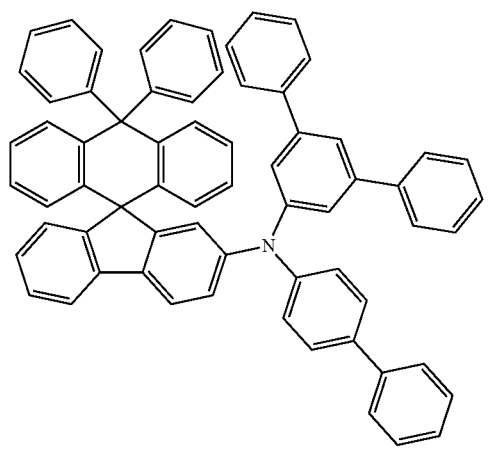
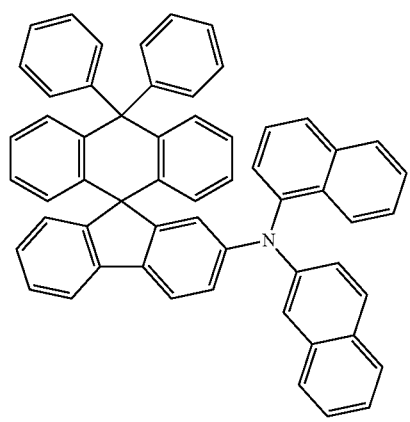

261
-continued
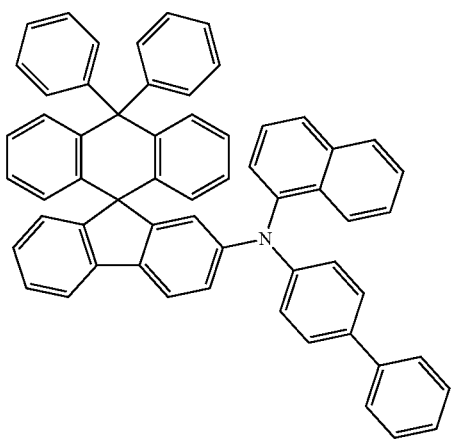
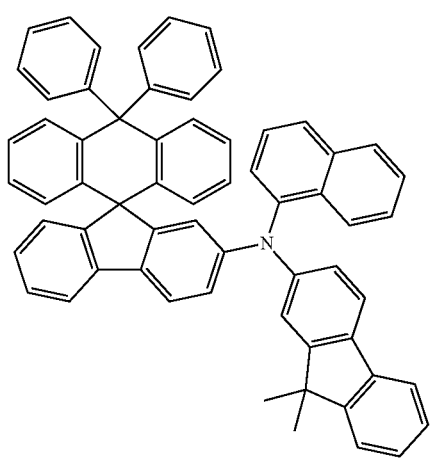 [SMILES: CC1(C)c2ccccc2-c2ccc(N(c3ccc4c(c3)C3(c5ccccc5-4)c4ccccc4C(c4ccccc4)(c4ccccc4)c4ccccc43)c3cc4ccccc4c4ccccc34)cc21]
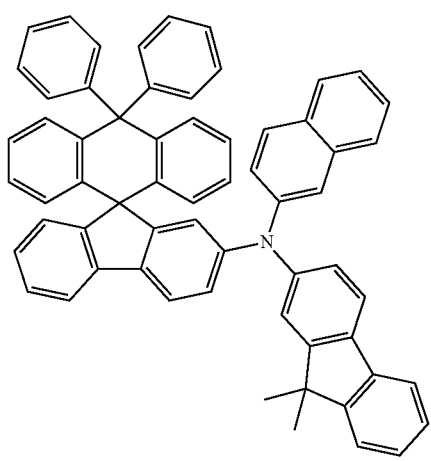
262
-continued
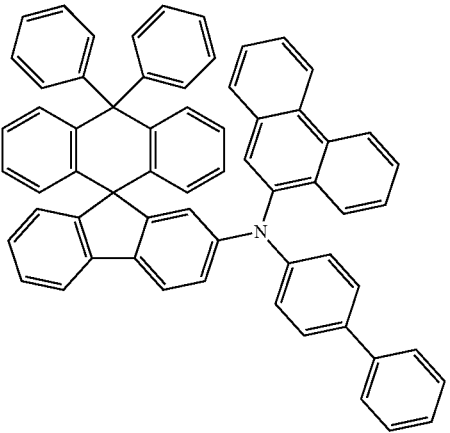
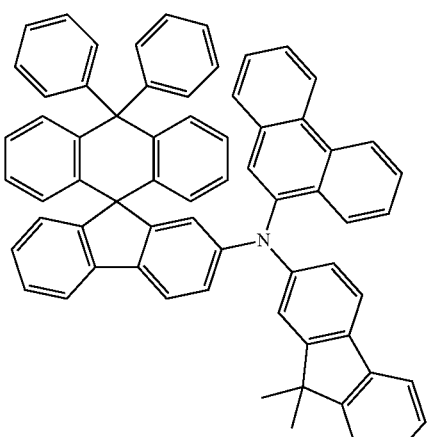
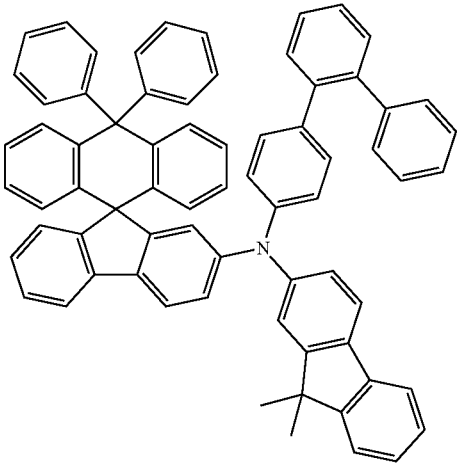

263
-continued
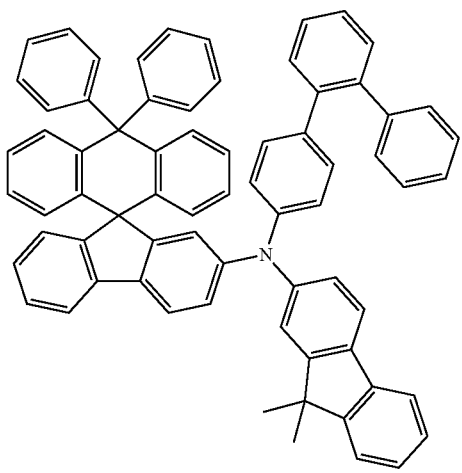 [SMILES: CC1(C)c2ccccc2-c2ccc(N(c3ccc(-c4ccccc4-c4ccccc4)cc3)c3ccc4c(c3)C3(c5ccccc5-4)c4ccccc4C(c4ccccc4)(c4ccccc4)c4ccccc43)cc21]
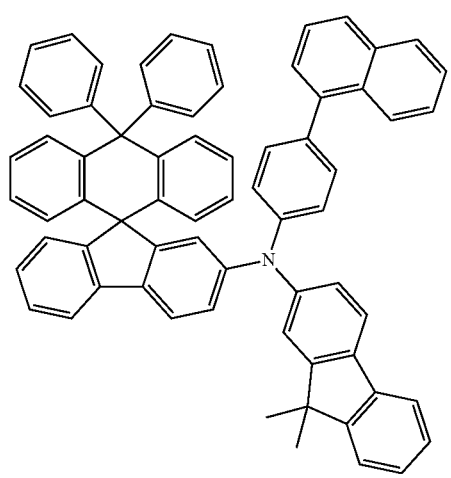
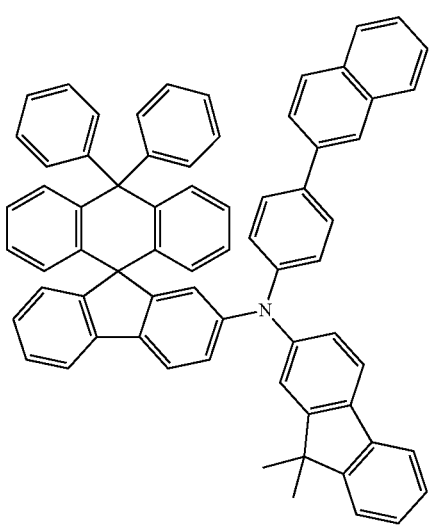
264
-continued
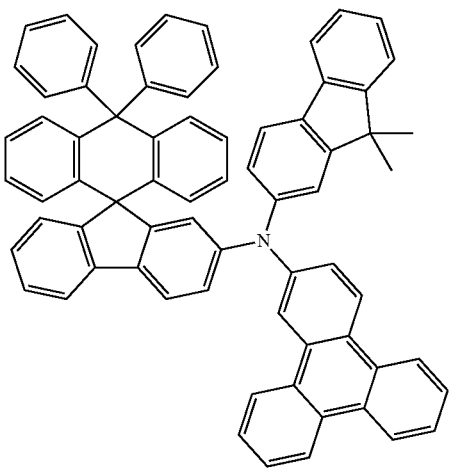
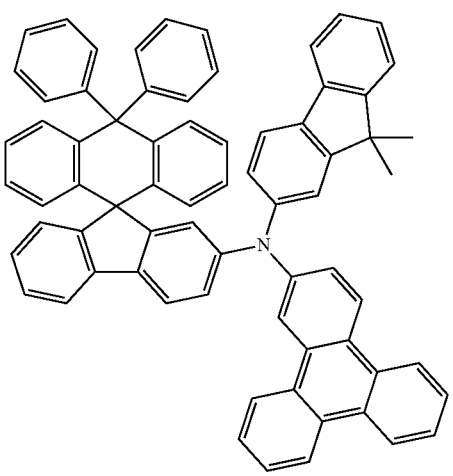 [SMILES: CC1(C)c2ccccc2-c2ccc(N(c3ccc4c(c3)C3(c5ccccc5-4)c4ccccc4C(c4ccccc4)(c4ccccc4)c4ccccc43)c3ccc4c5ccccc5c5ccccc5c4c3)cc21]
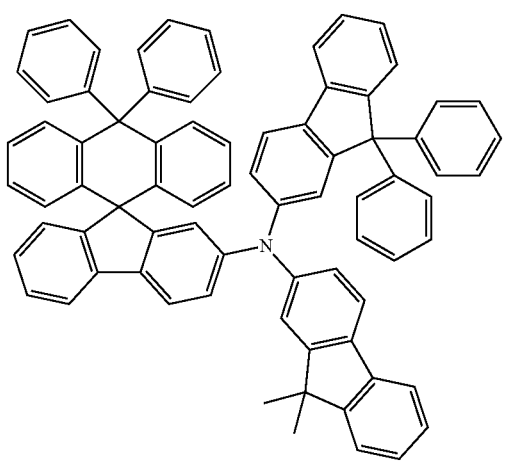

265
-continued
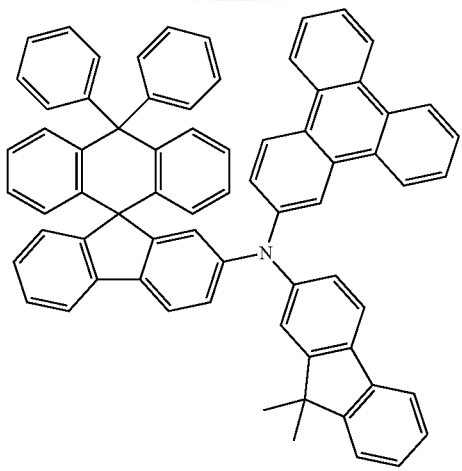
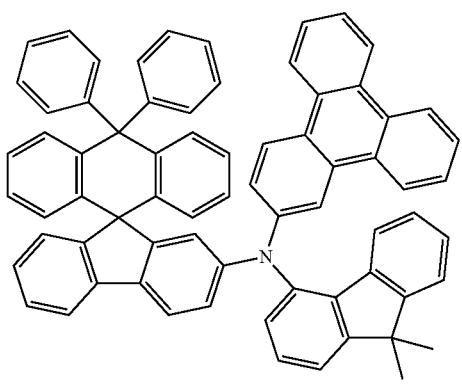 [SMILES: CC1(C)c2ccccc2-c2c(N(c3ccc4c(c3)C3(c5ccccc5-4)c4ccccc4C(c4ccccc4)(c4ccccc4)c4ccccc43)c3ccc4c5ccccc5c5ccccc5c4c3)cccc21]
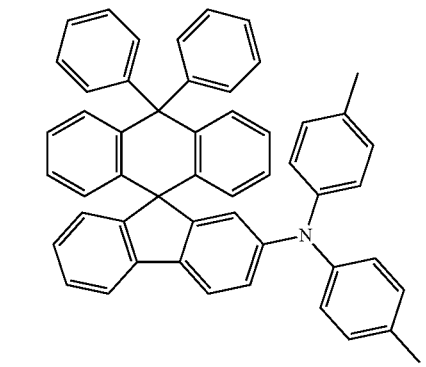
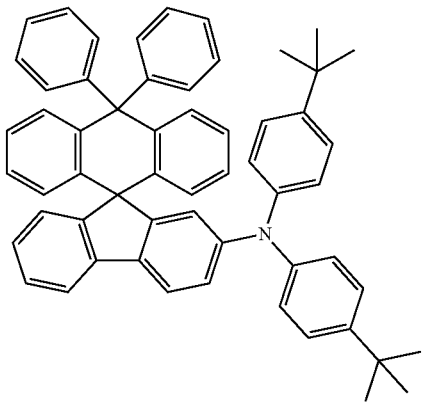
266
-continued
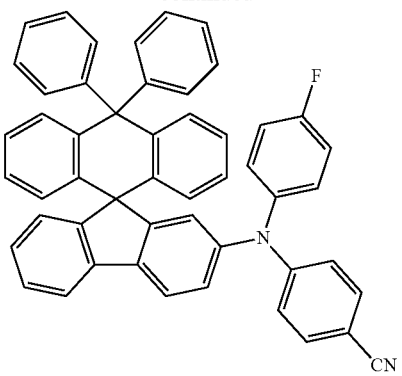
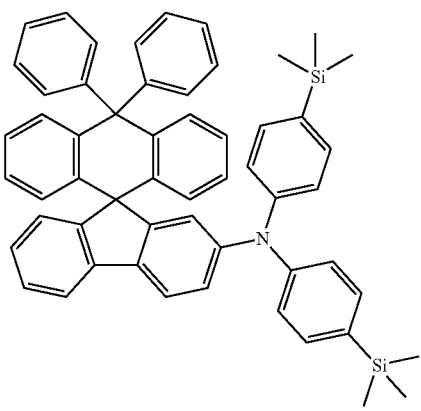
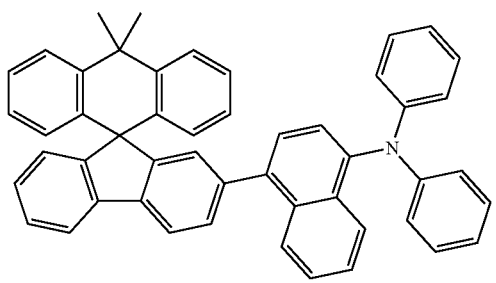
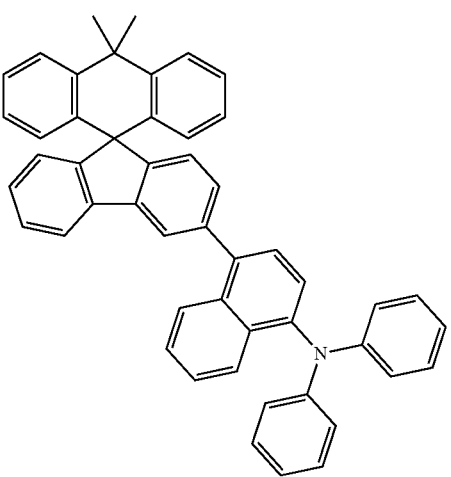

267
-continued
268
-continued
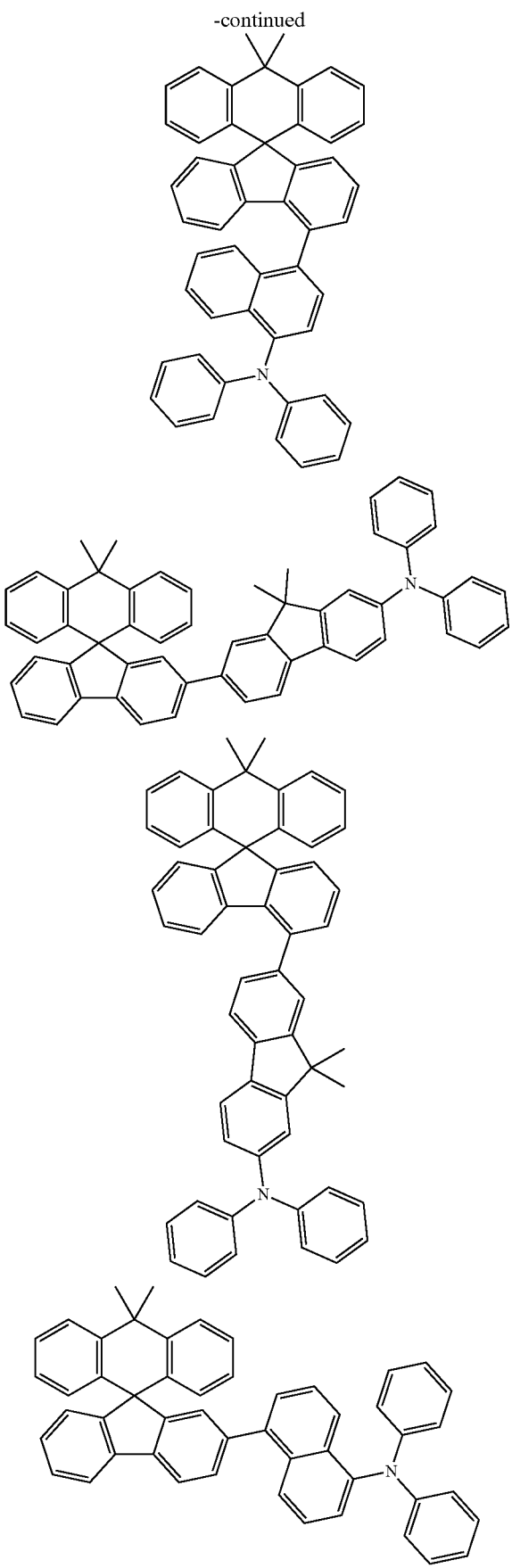
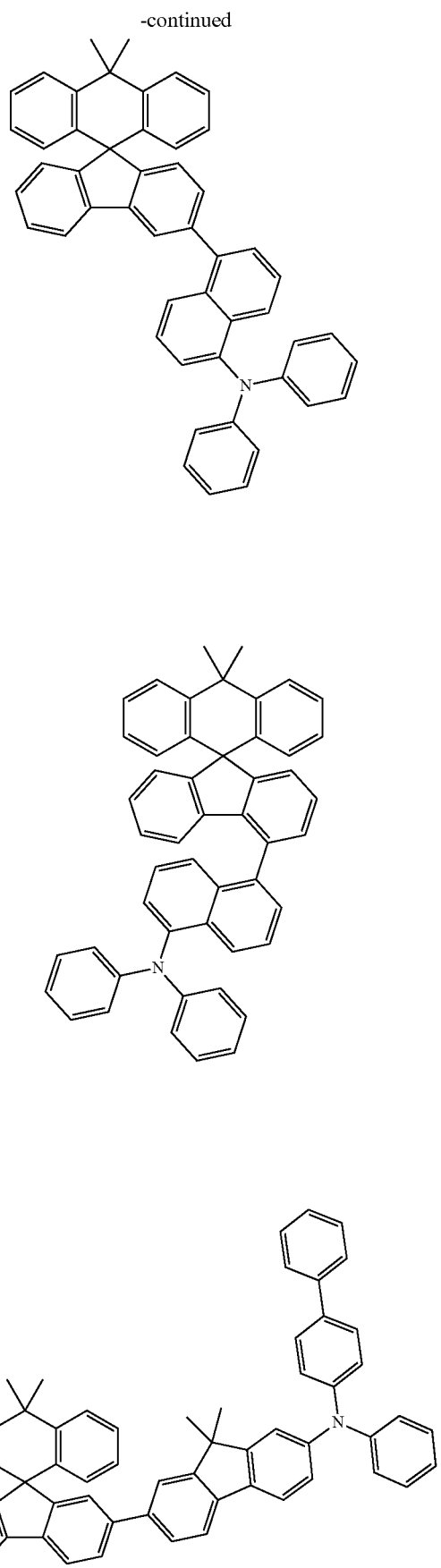

269
-continued
270
-continued
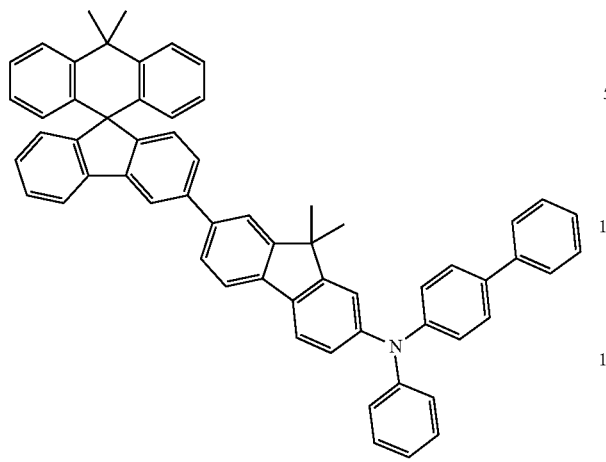
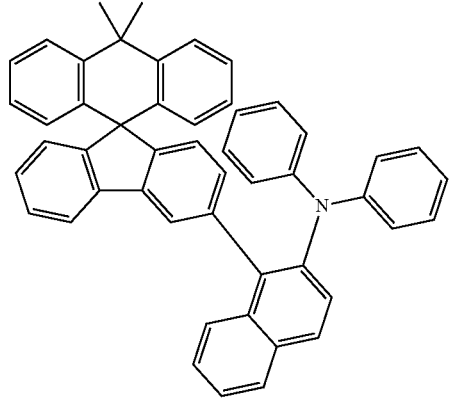
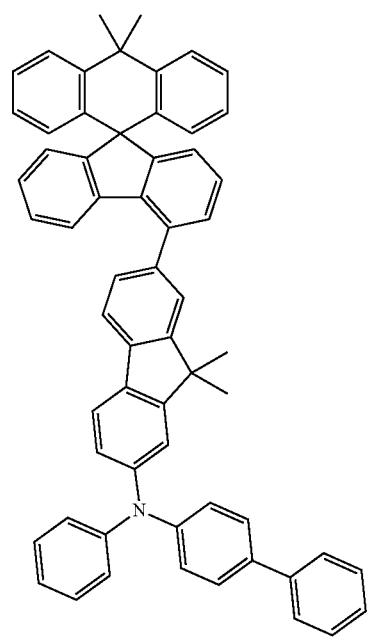
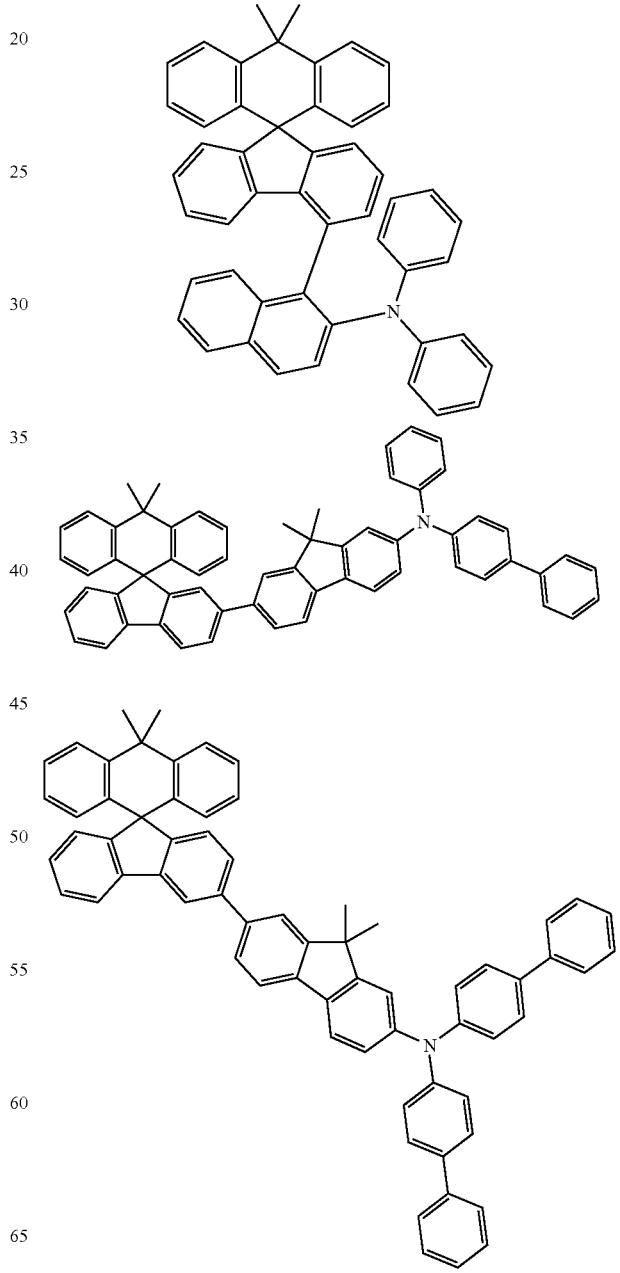

271
-continued
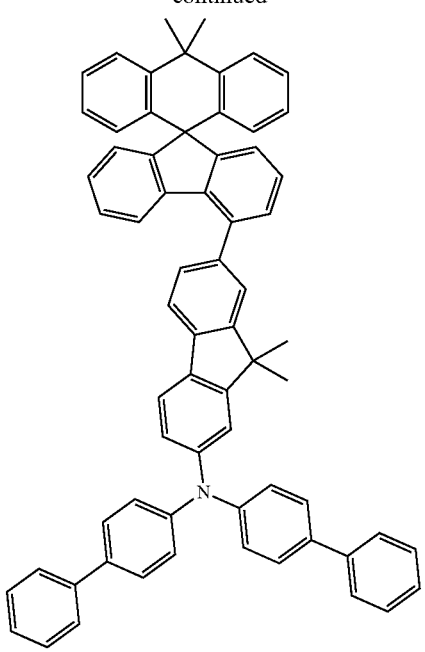
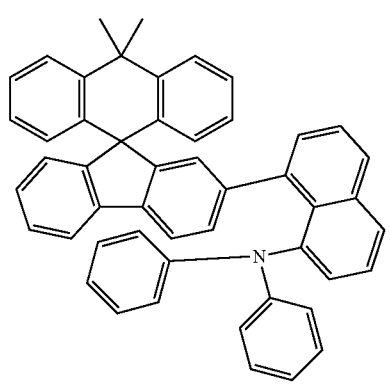
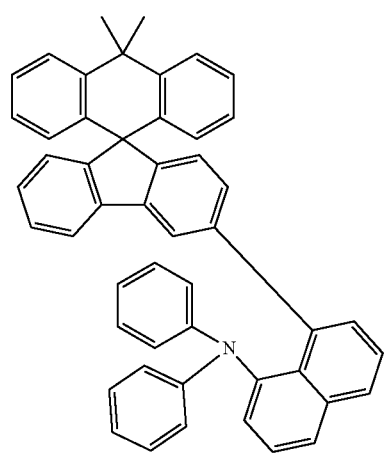
272
-continued
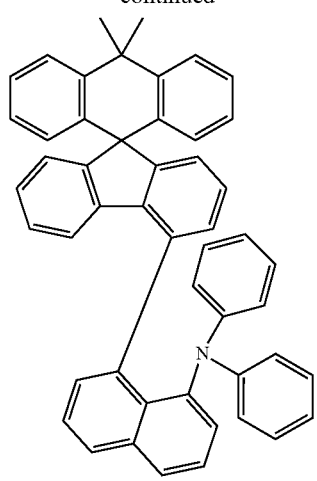
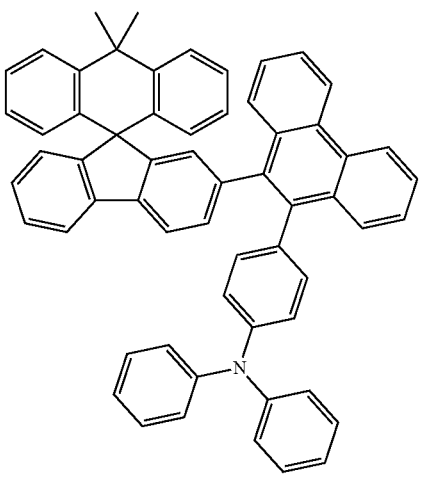
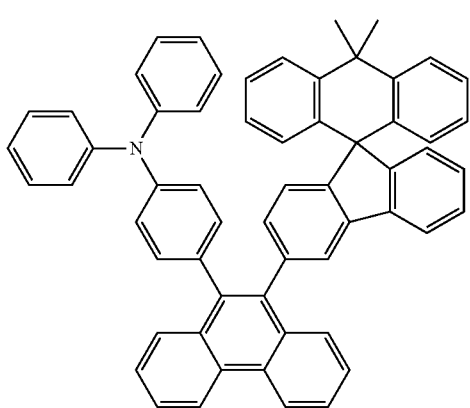

273
-continued
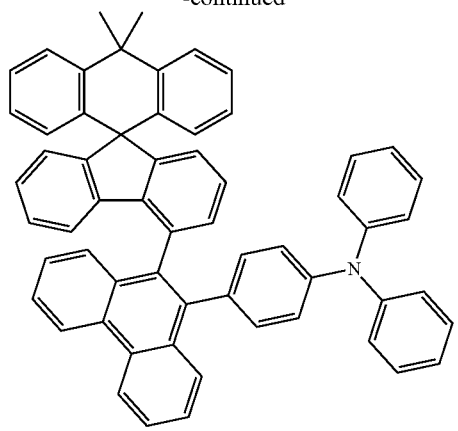
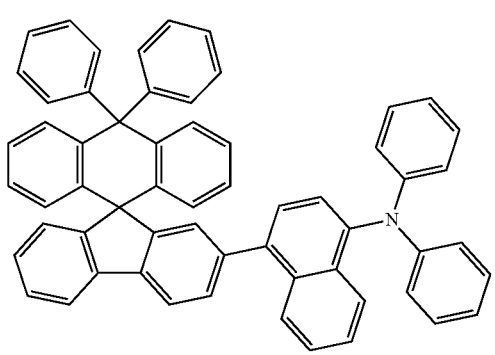
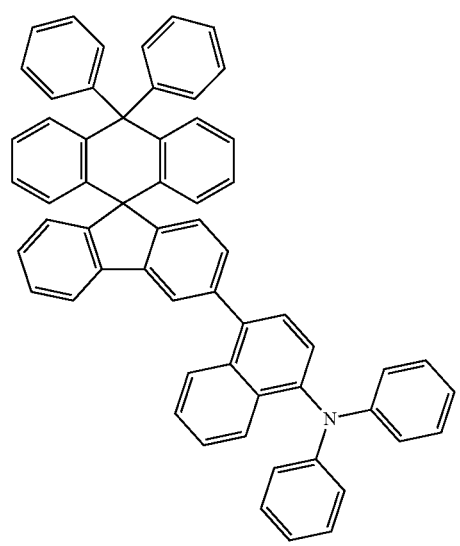
274
-continued
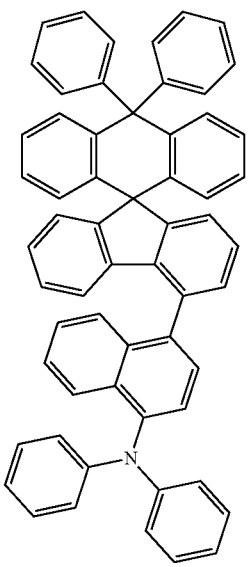
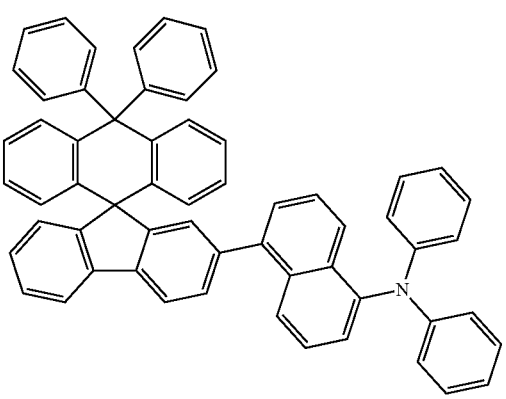
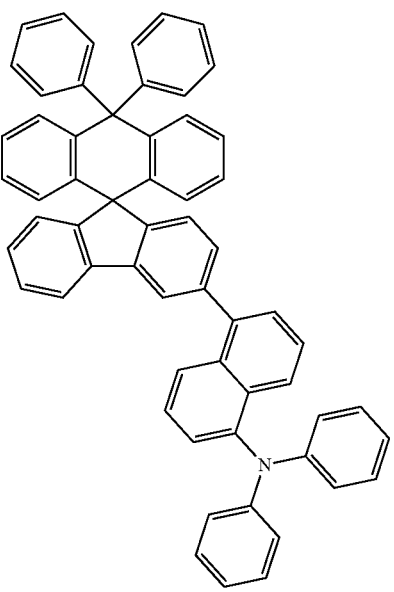

275
-continued
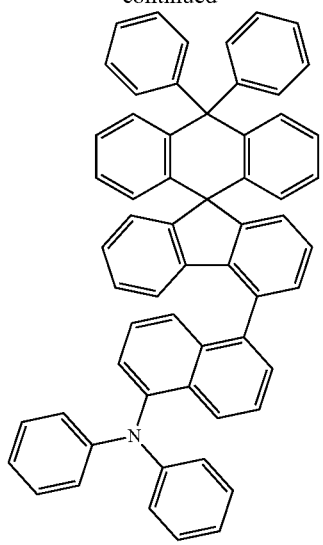
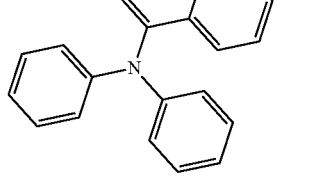
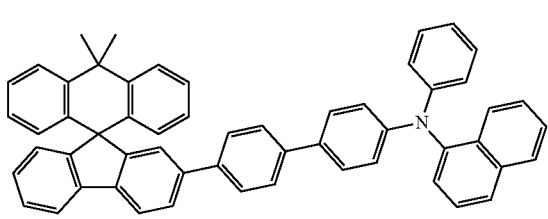
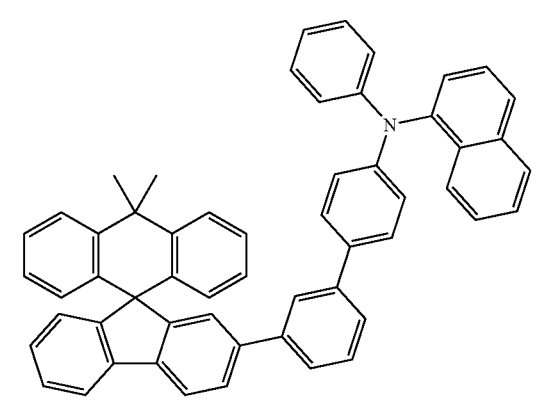
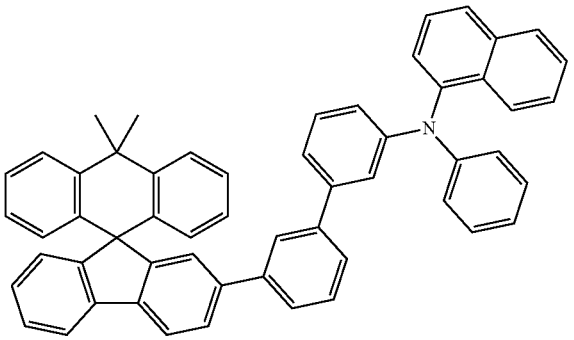
276
-continued
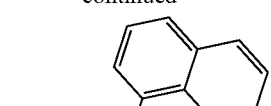
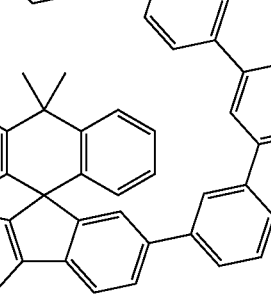
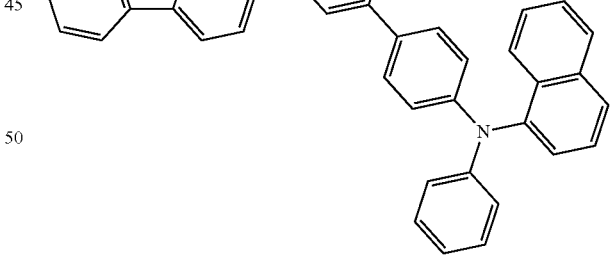
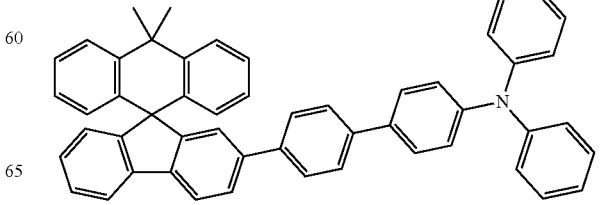

277
-continued
278
-continued
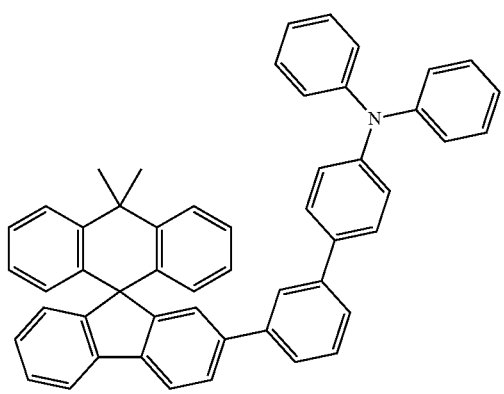
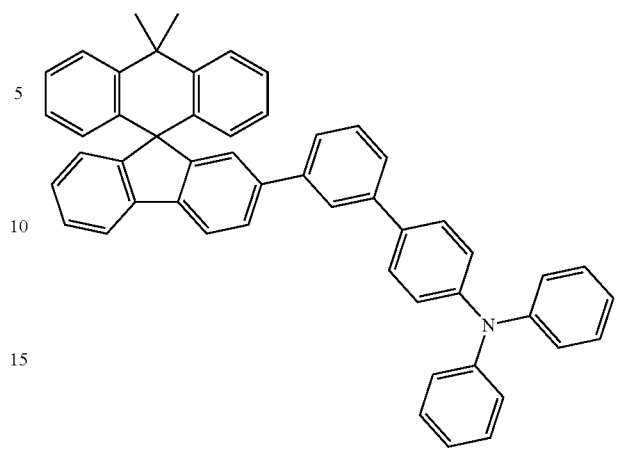
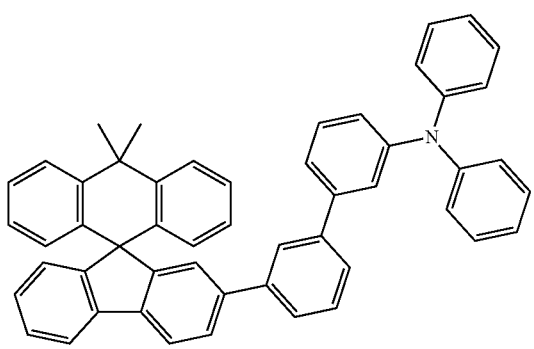
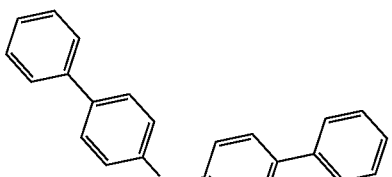
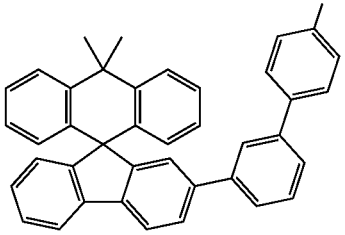
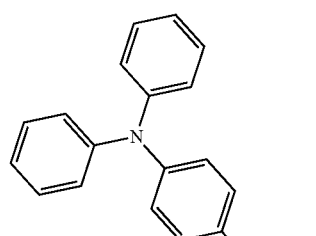
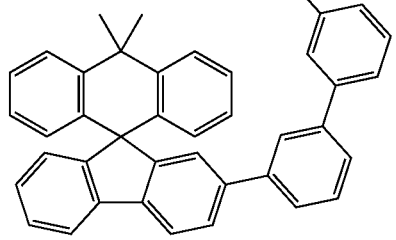
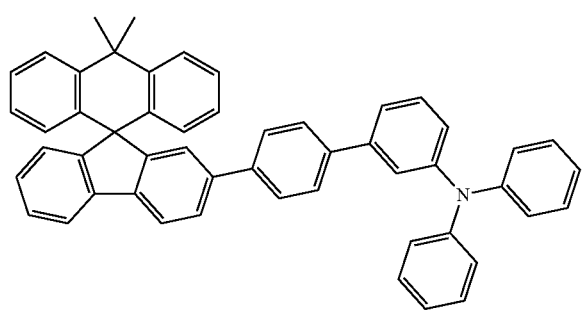
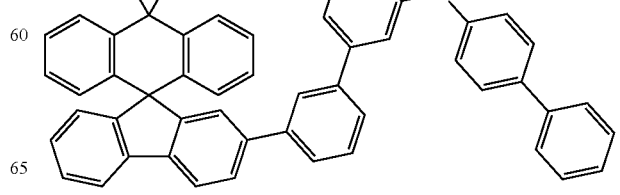

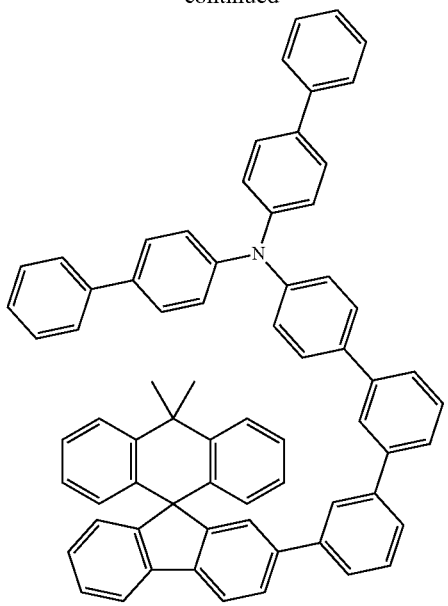
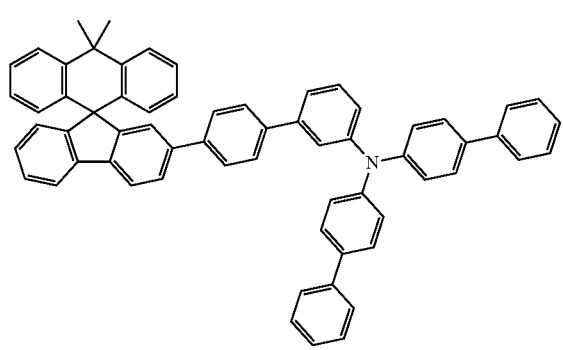
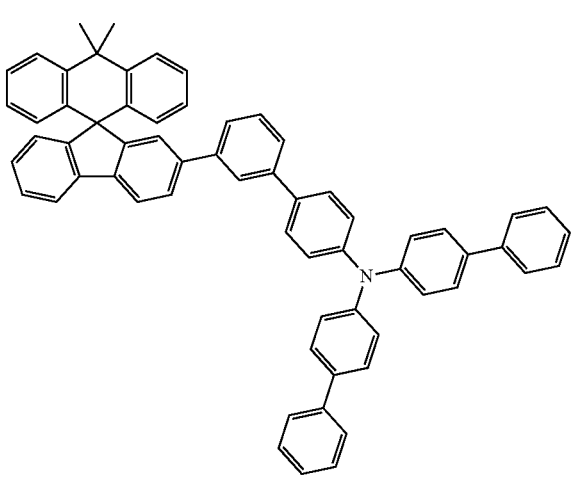
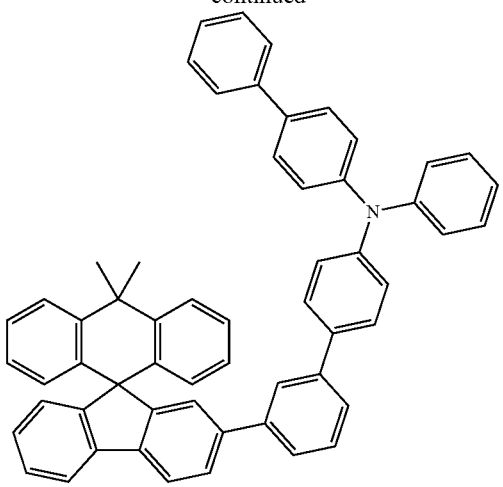
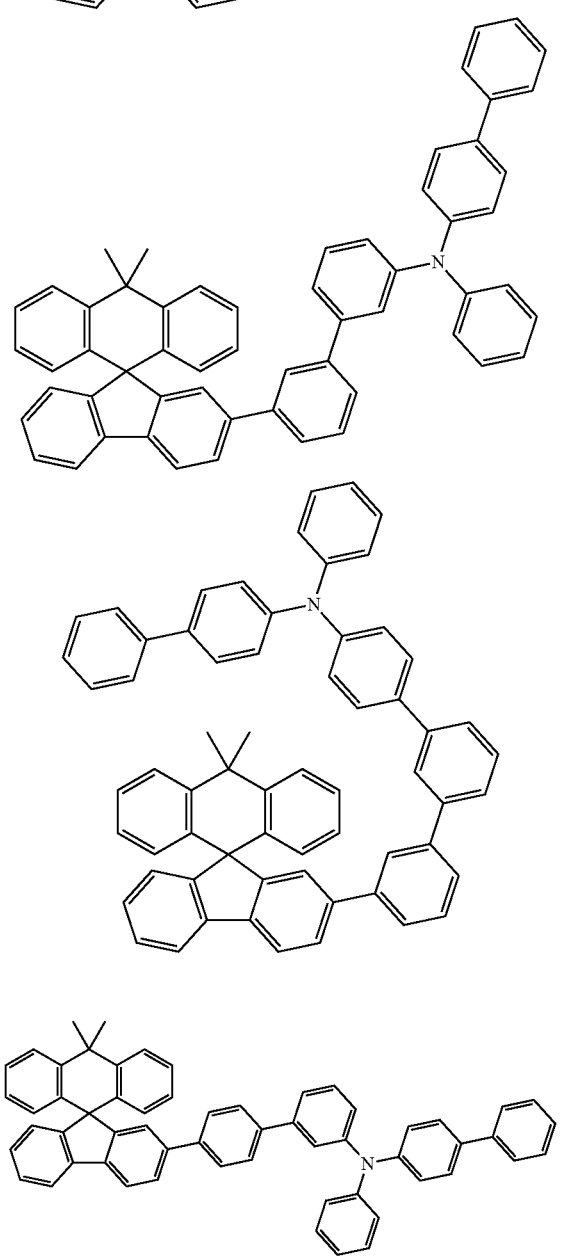

281
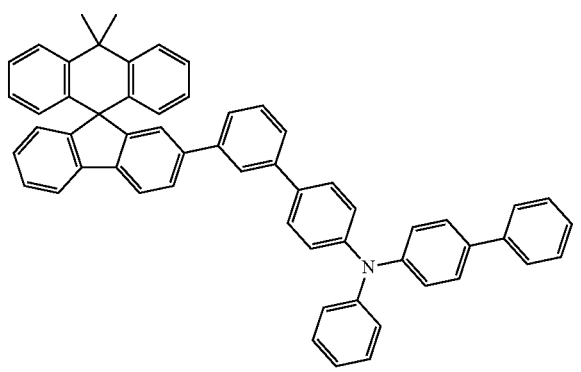
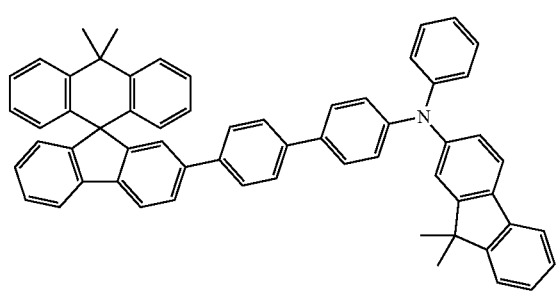
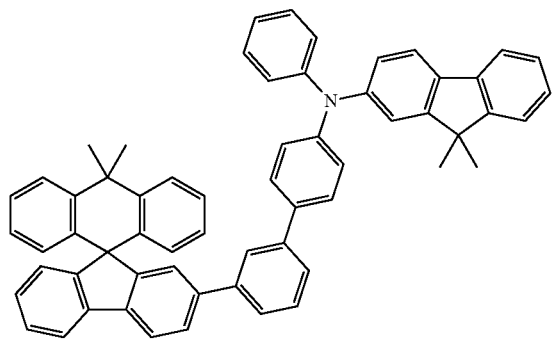
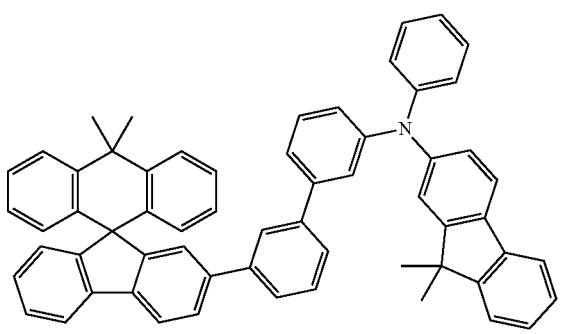
282
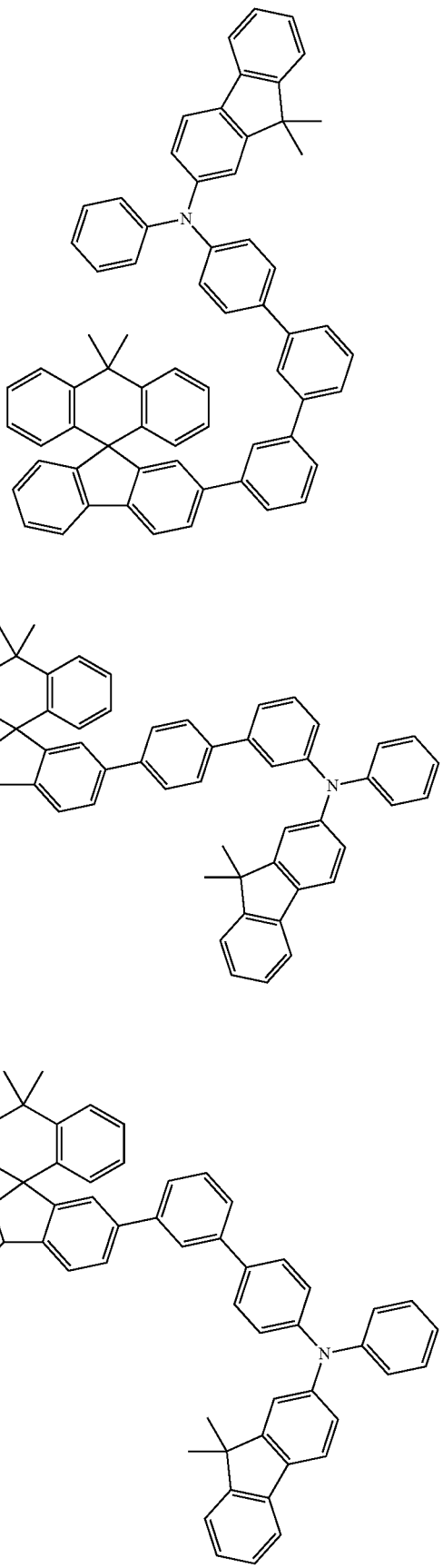

283
-continued
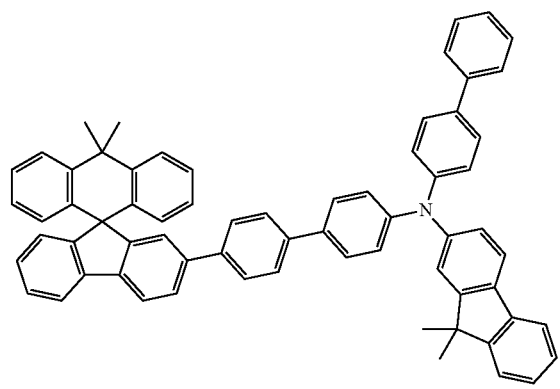
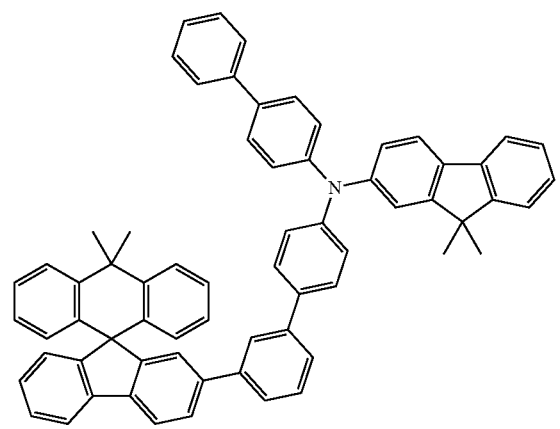
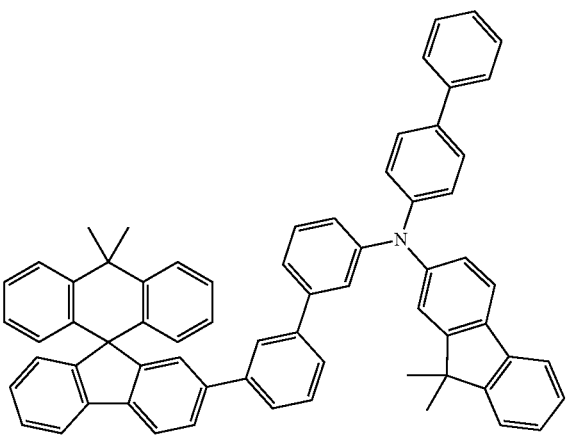
284
-continued
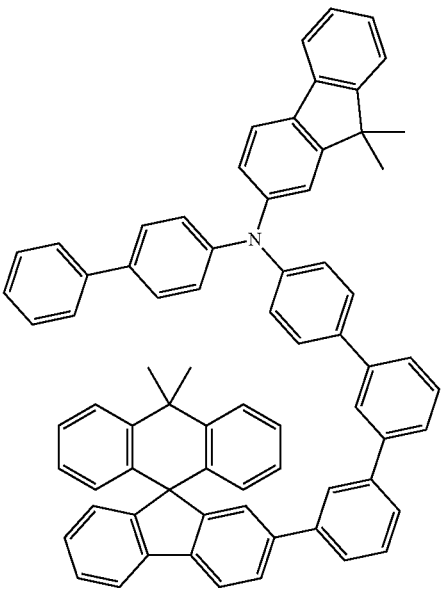
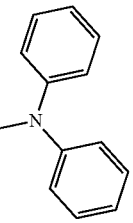

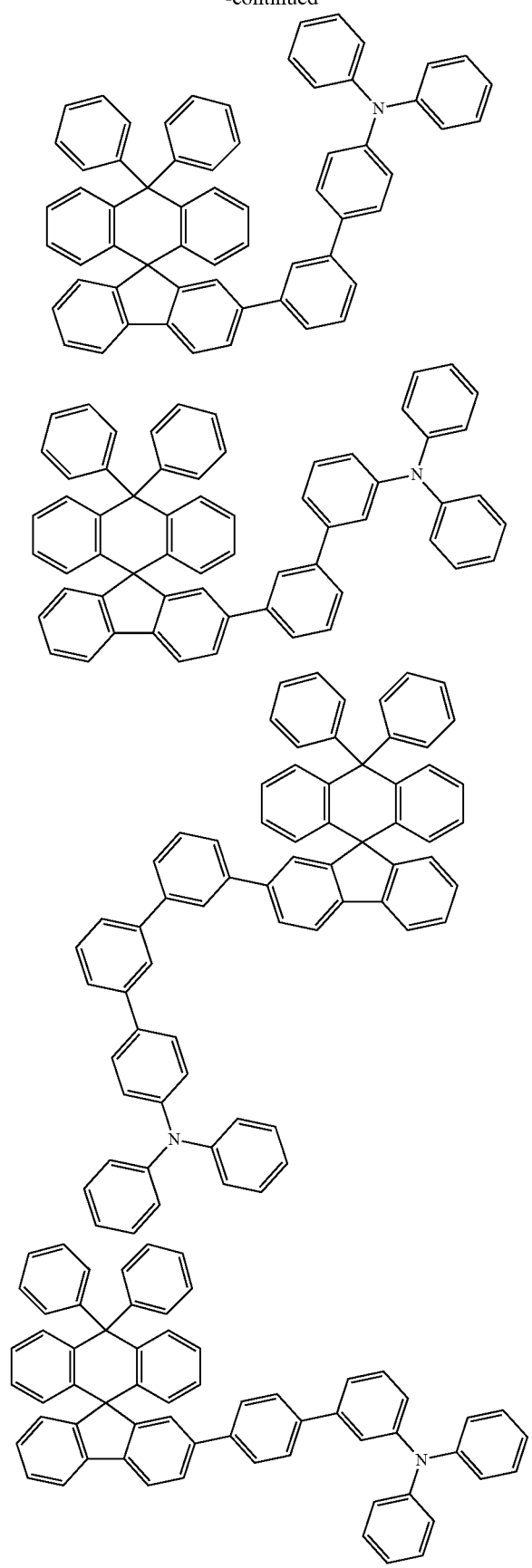
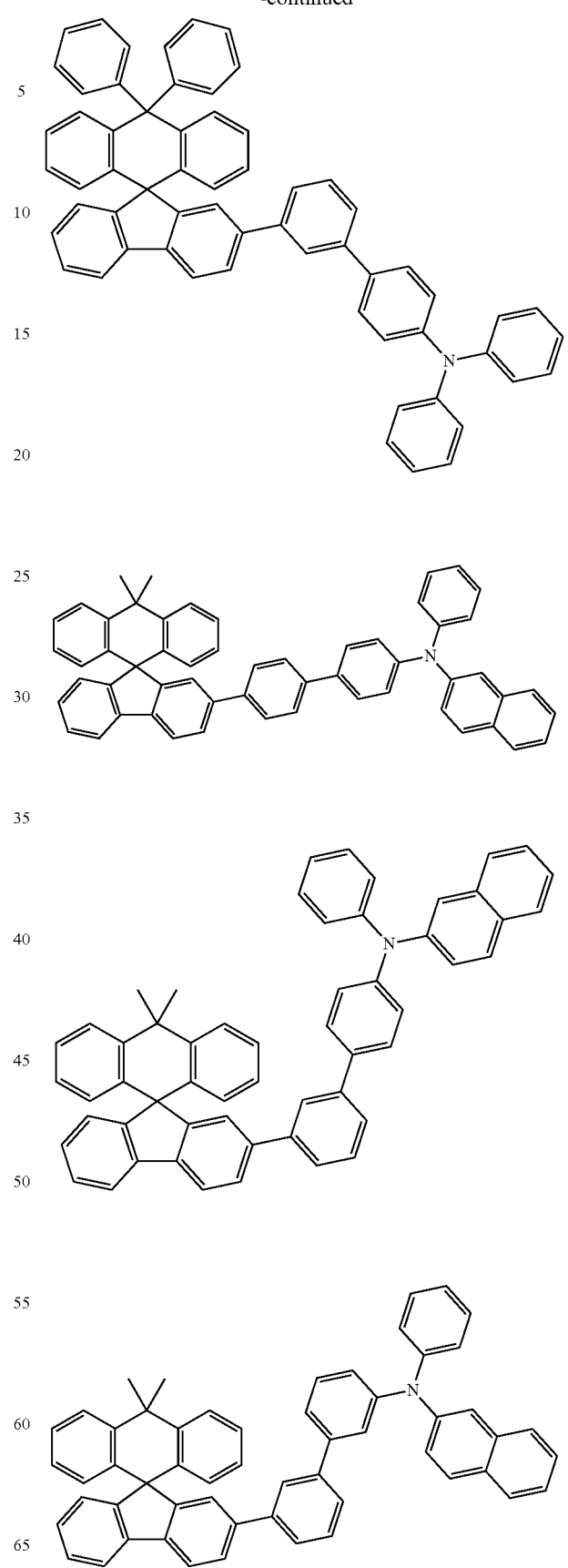

287
-continued
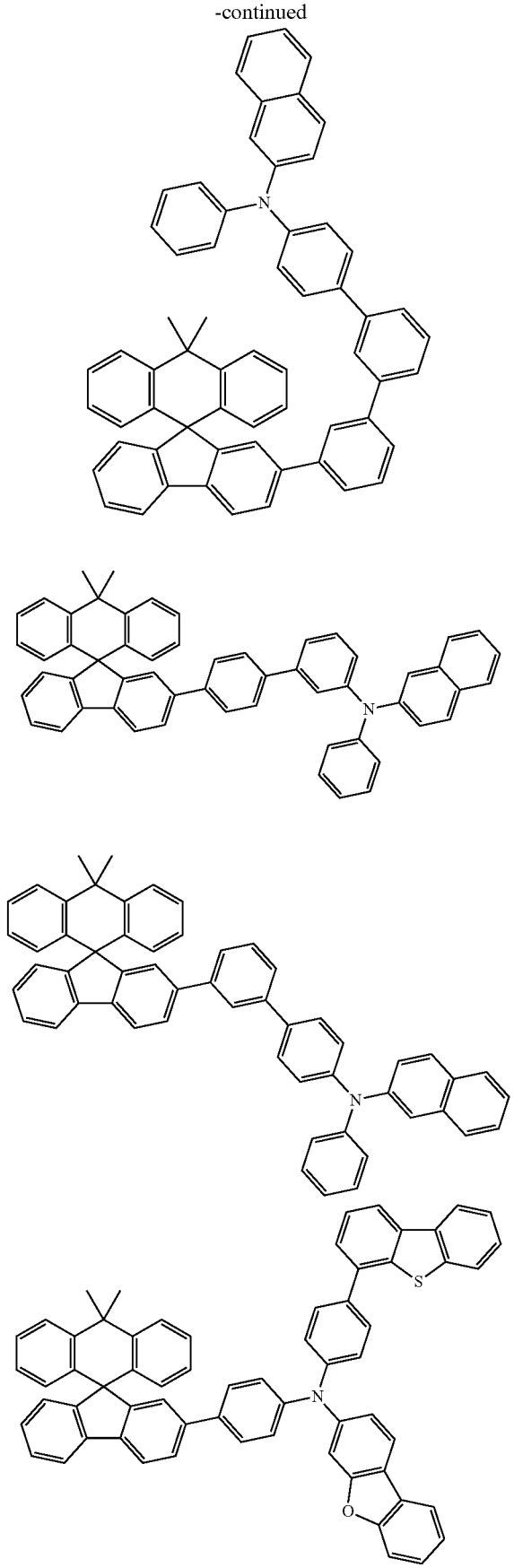
288
-continued
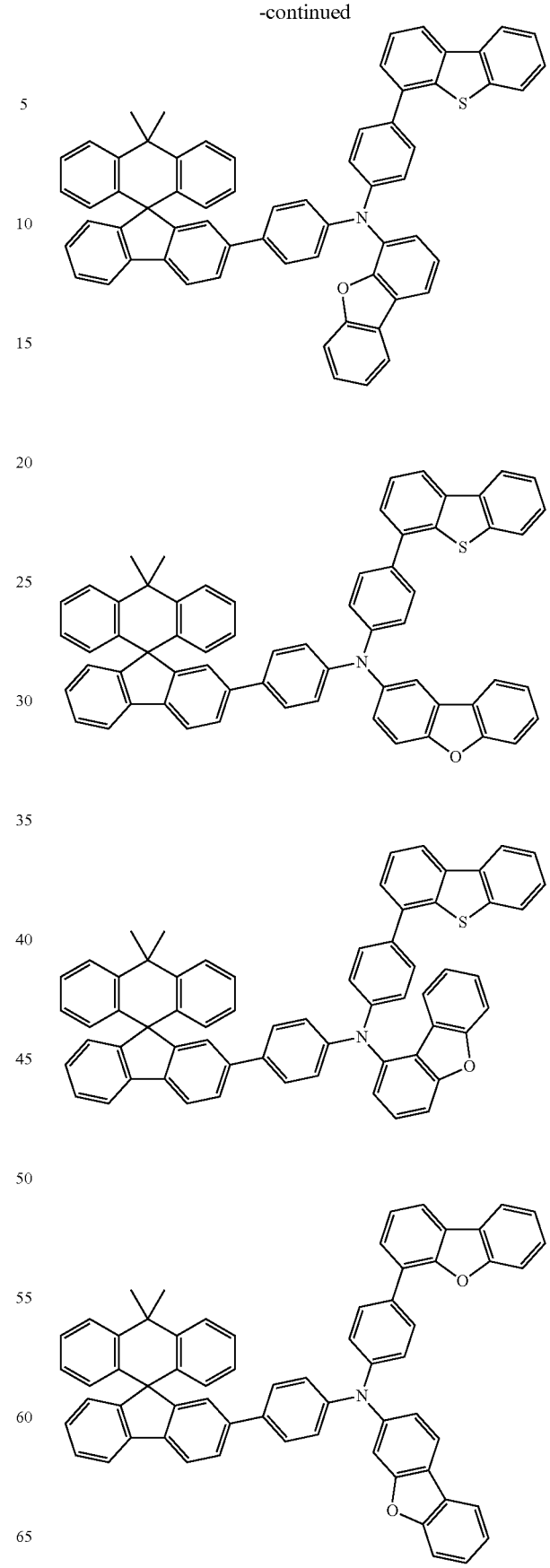

289
-continued
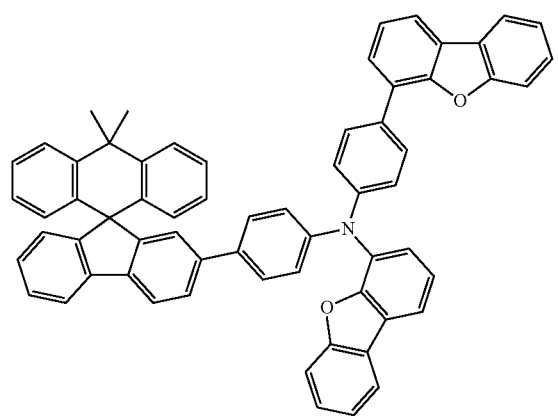
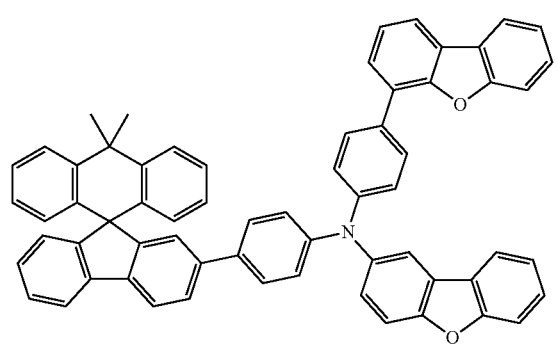
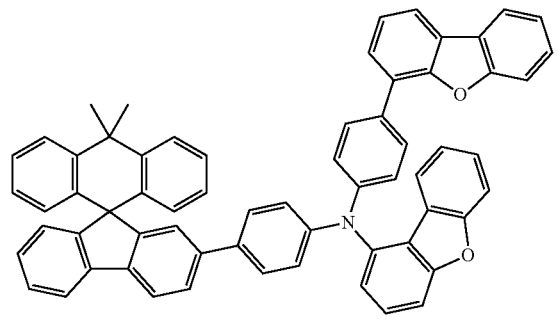
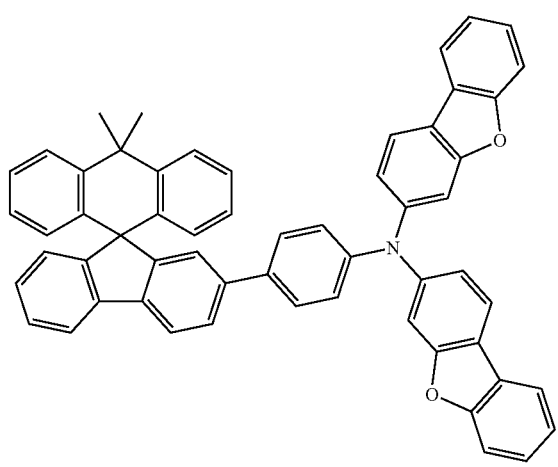
290
-continued
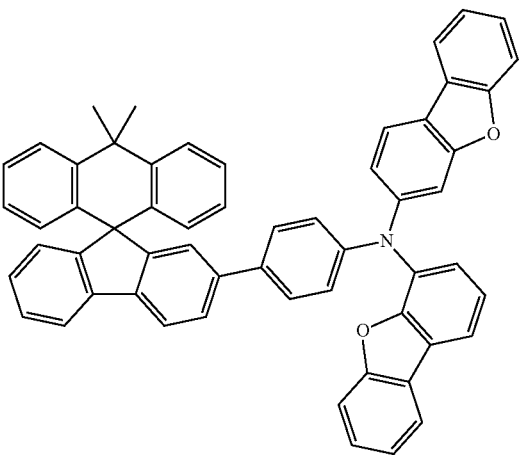
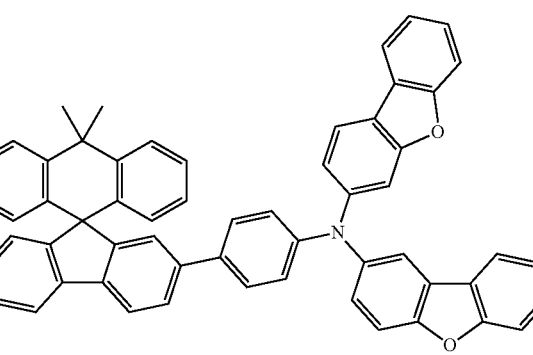
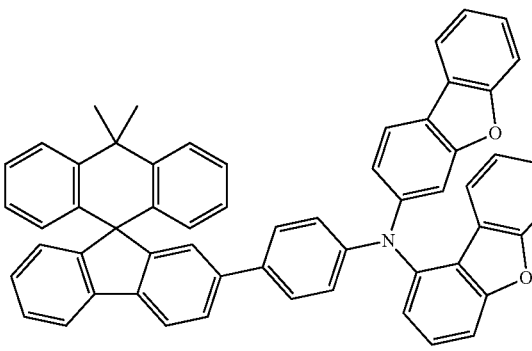
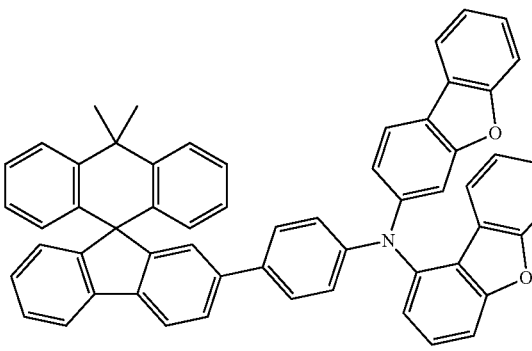

291
-continued
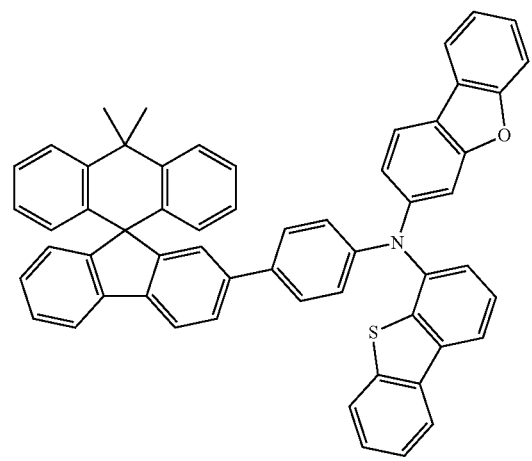
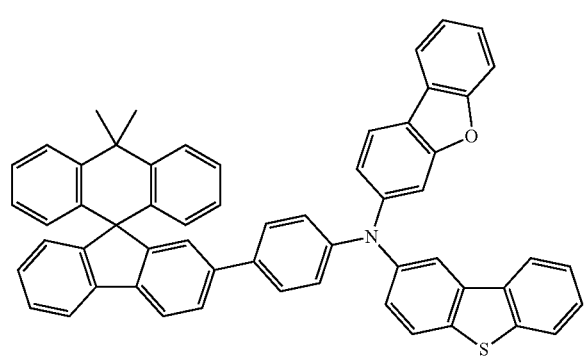
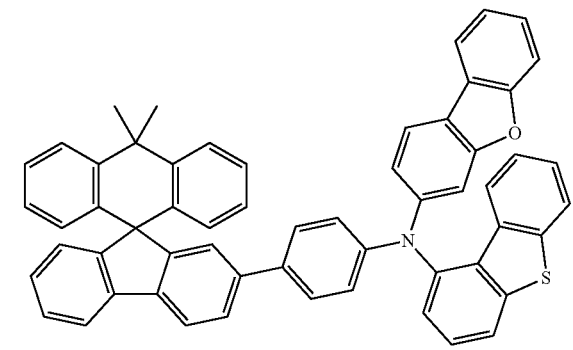
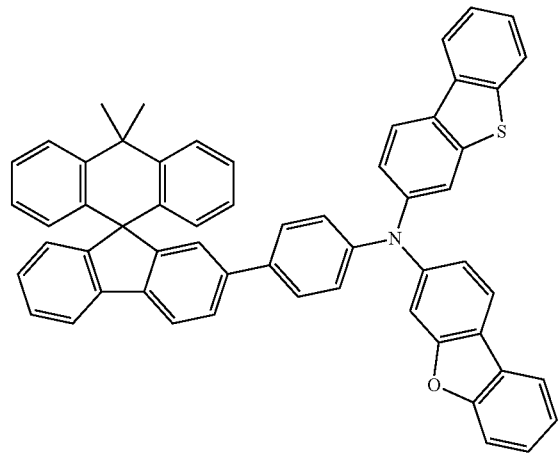
292
-continued
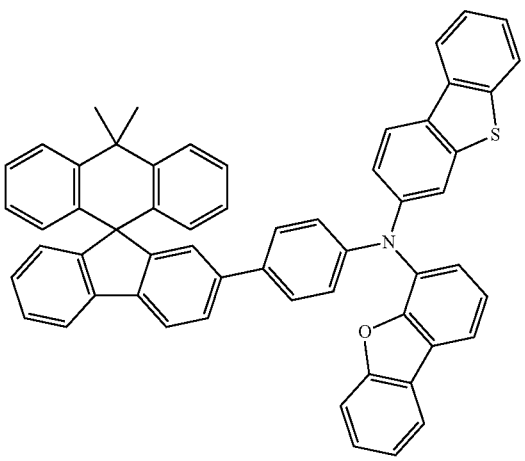
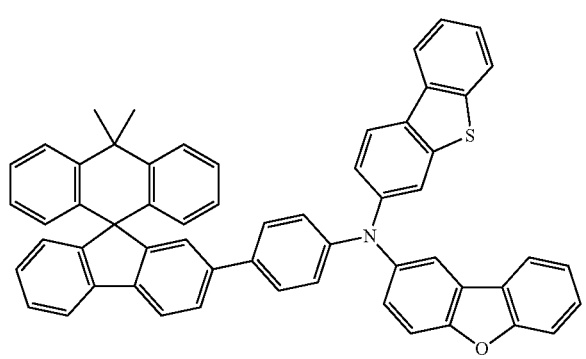
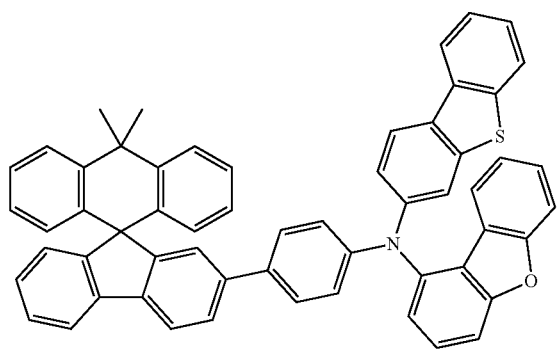
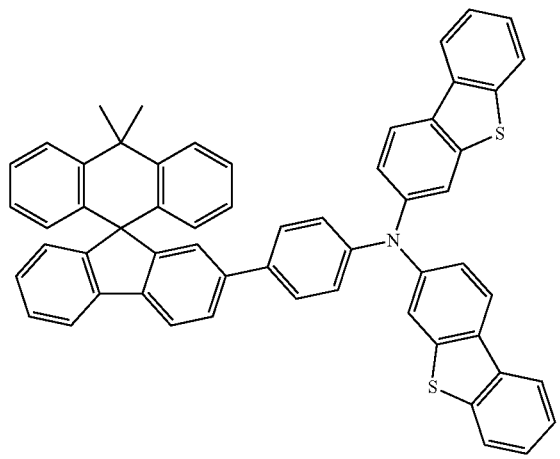

293
-continued
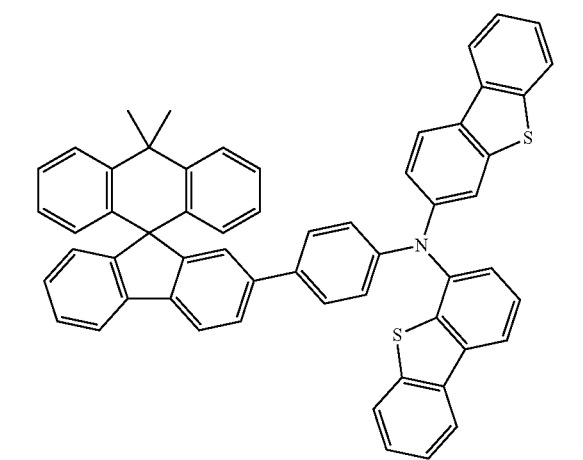
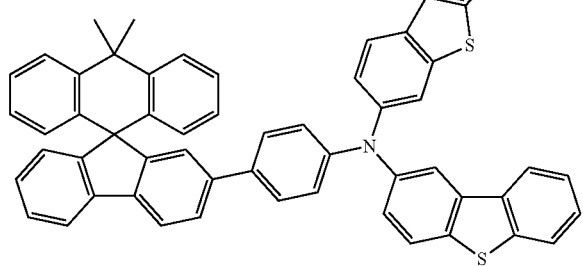
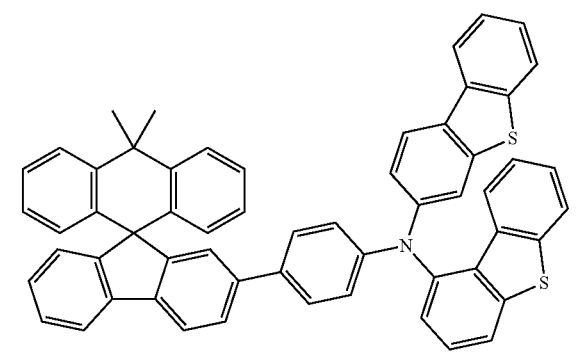
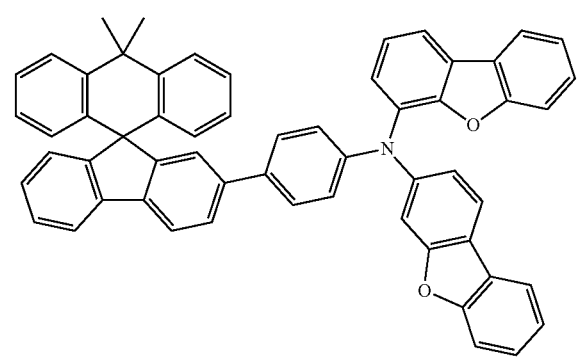
294
-continued
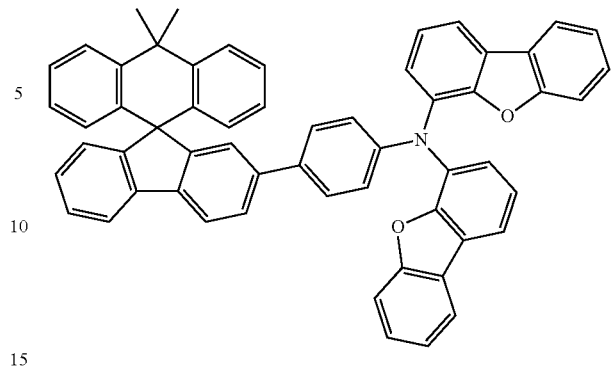
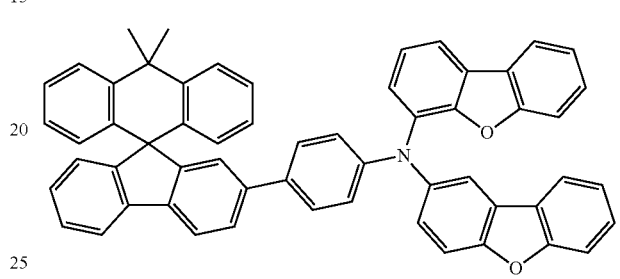
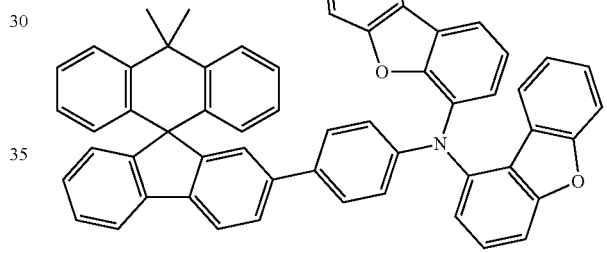
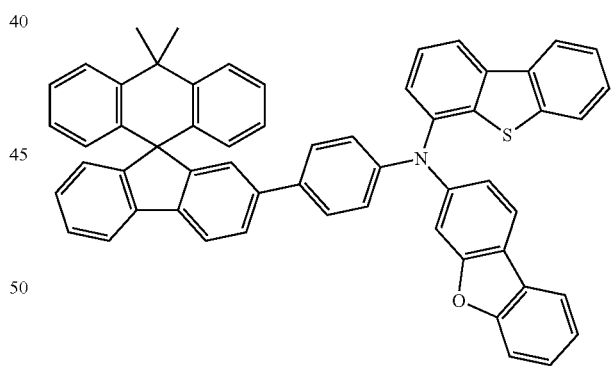
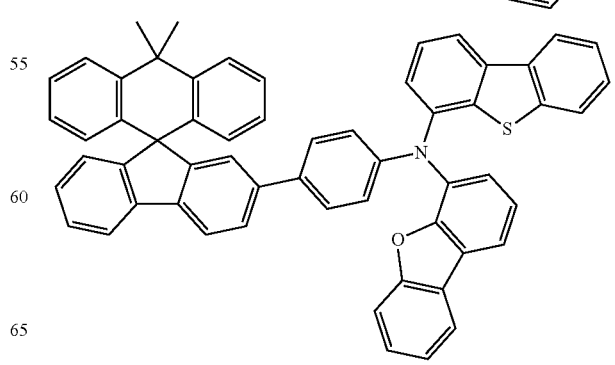

295
-continued
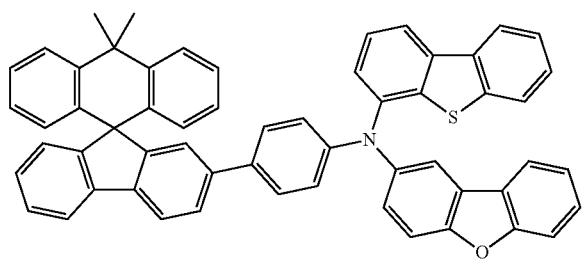
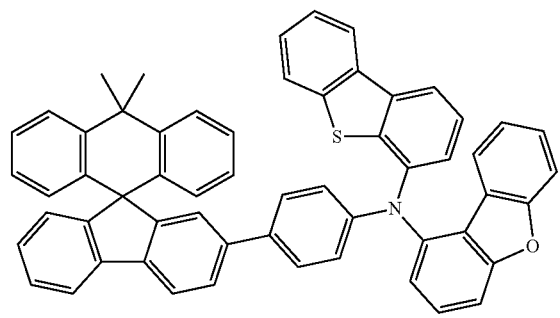
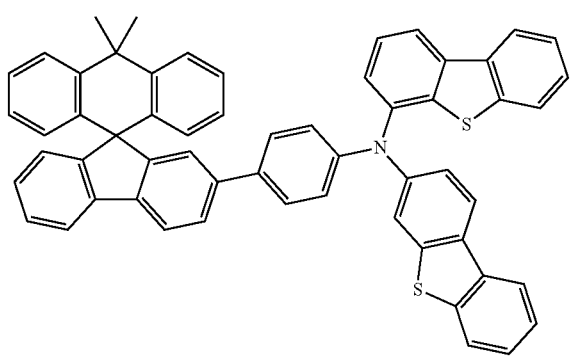
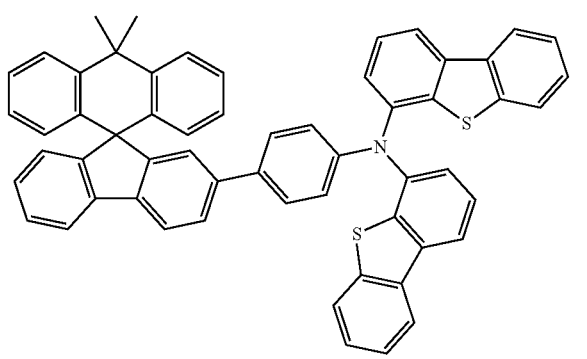
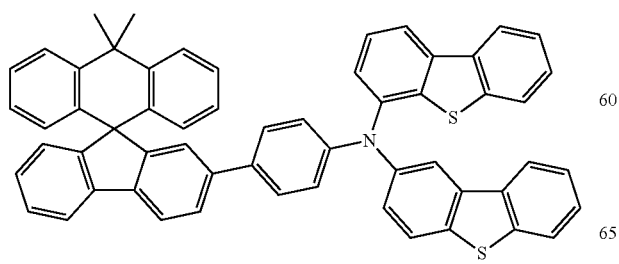
296
-continued
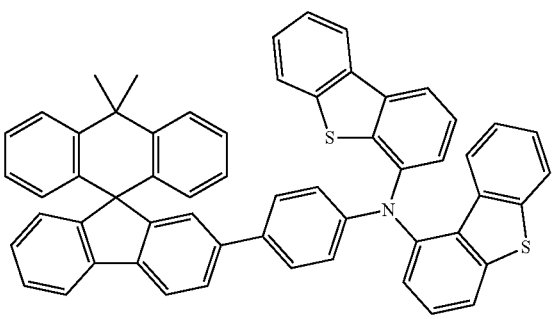
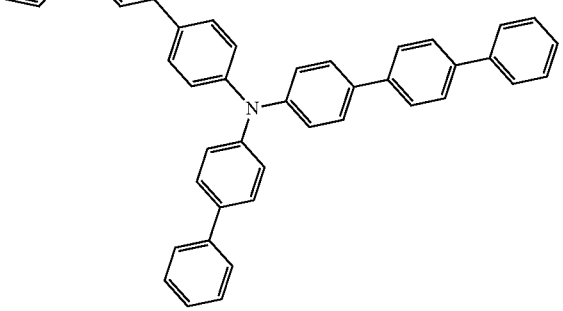

297
-continued
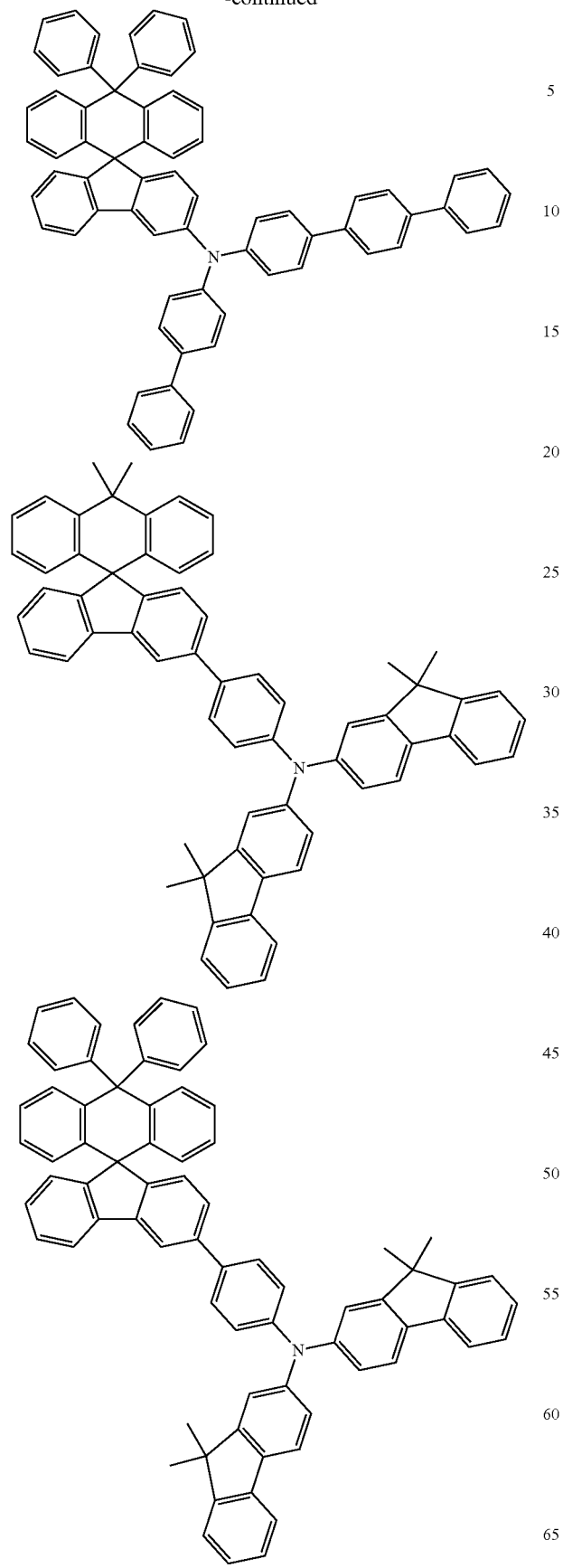
298
-continued

299
-continued
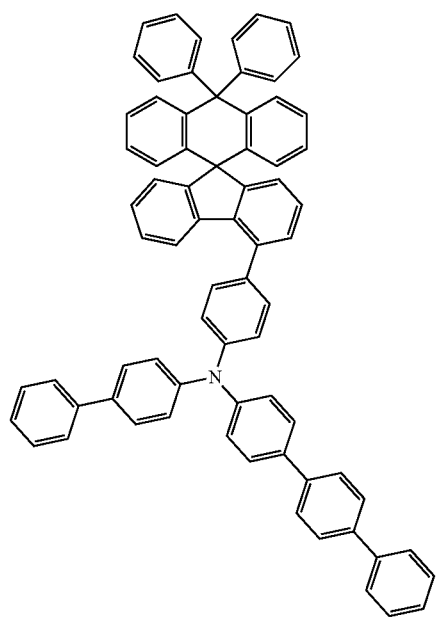
300
-continued
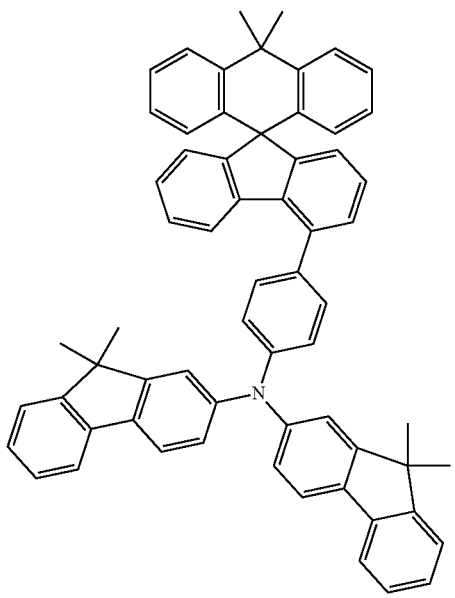
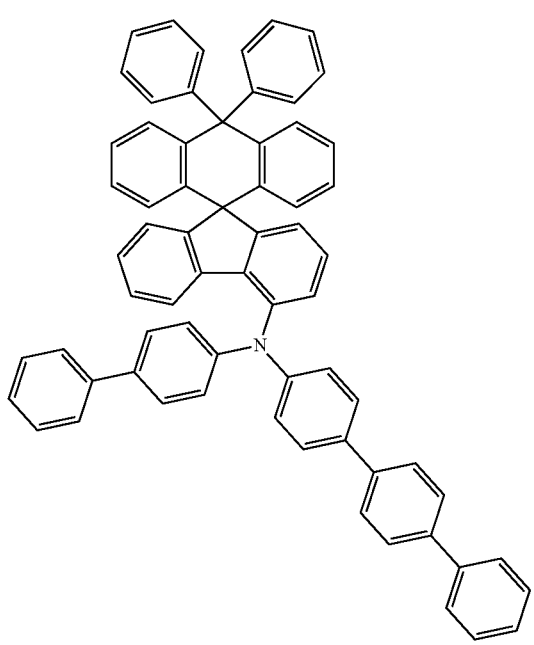
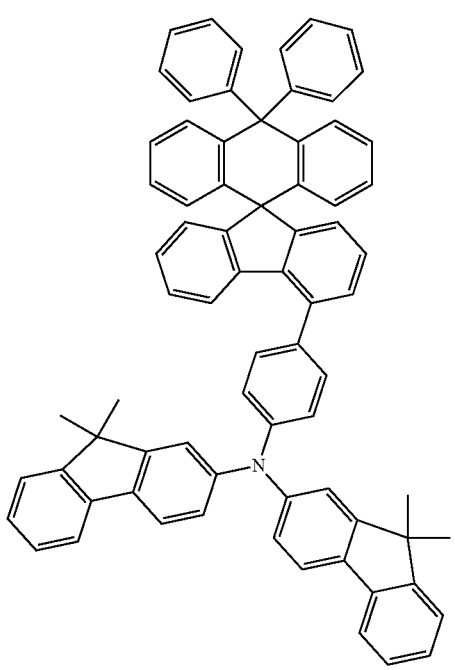

301
-continued
302
-continued
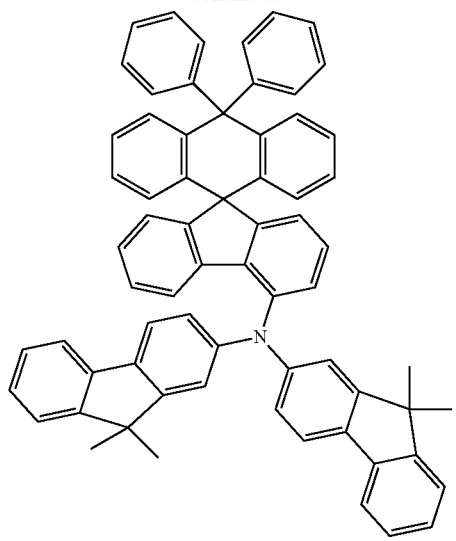
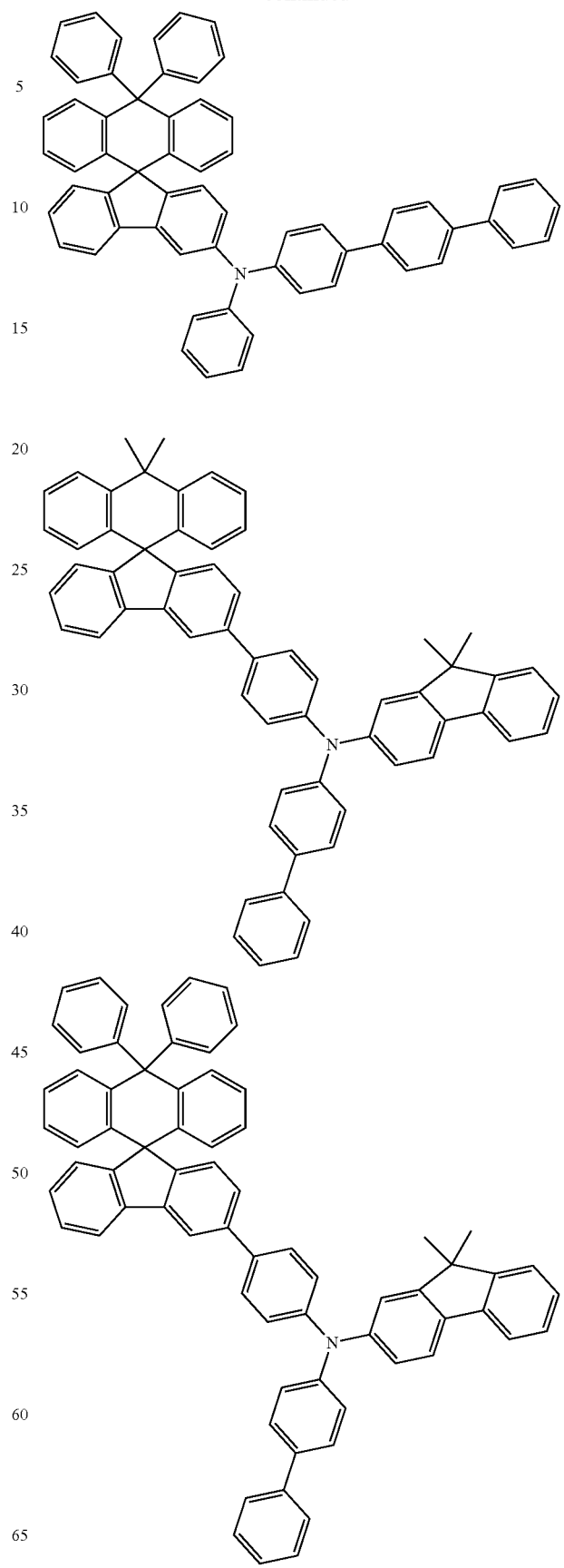

303
-continued
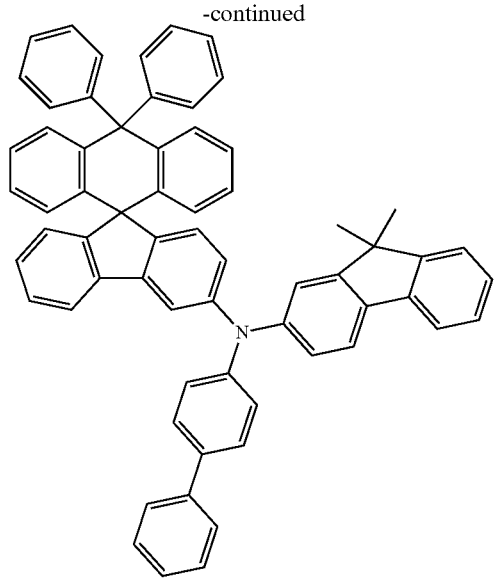
304
-continued
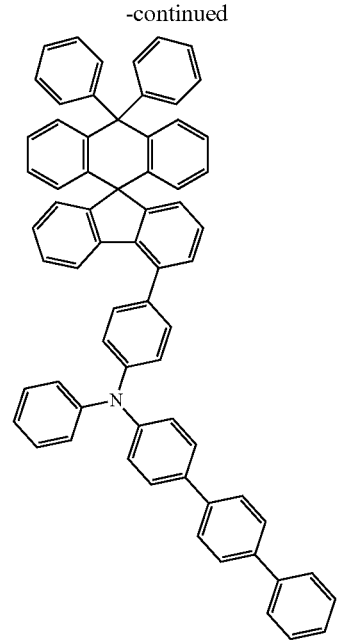
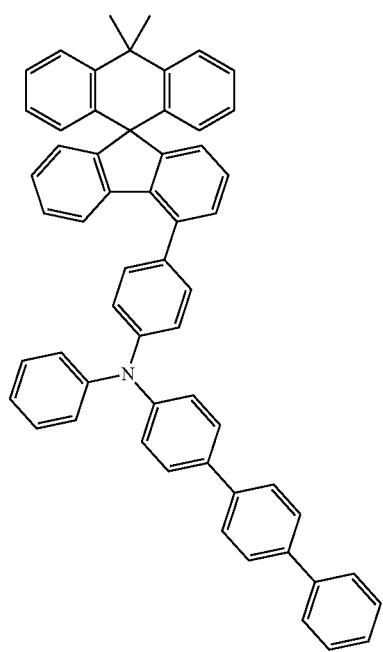
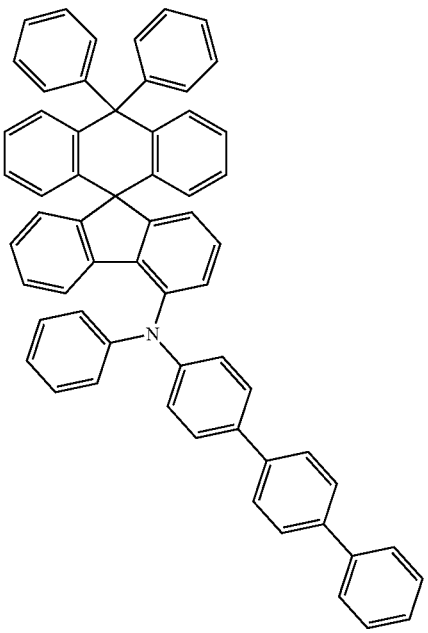

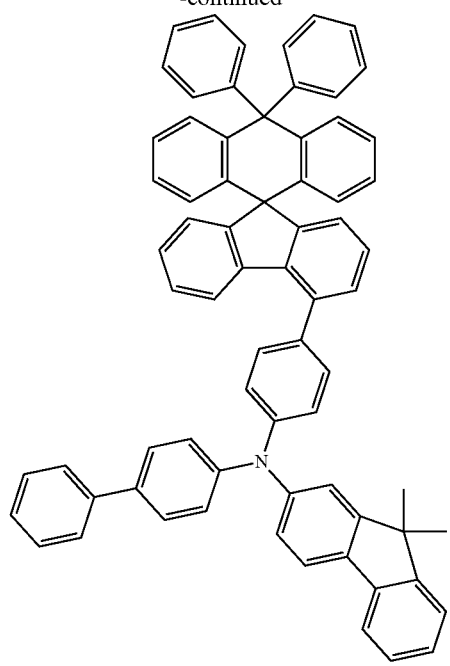
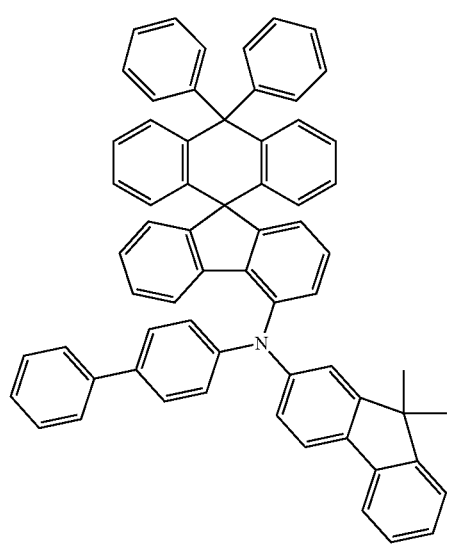
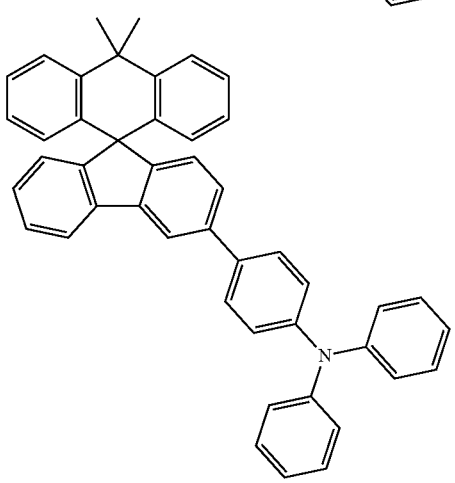
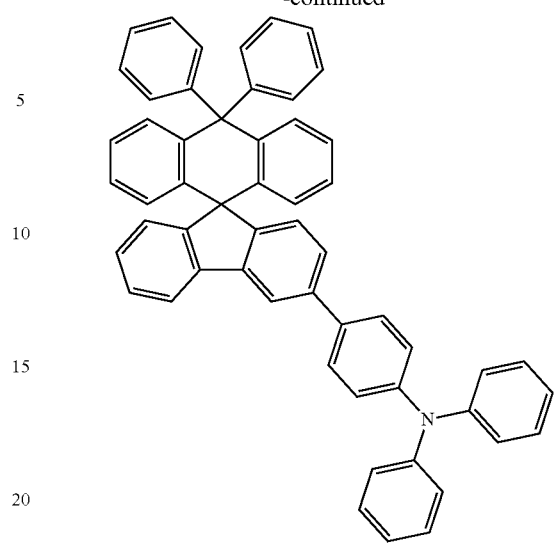
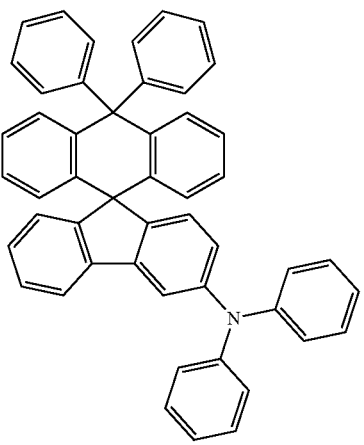
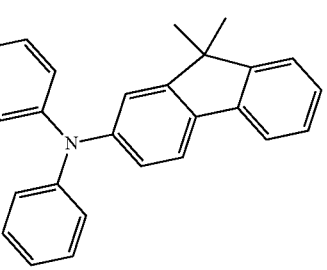

307
-continued
308
-continued
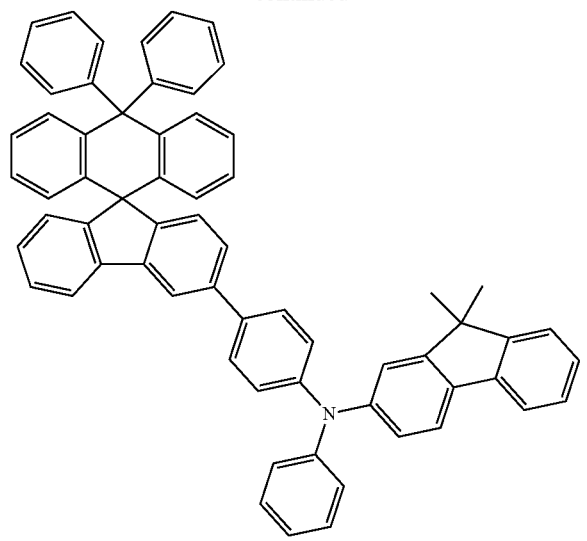
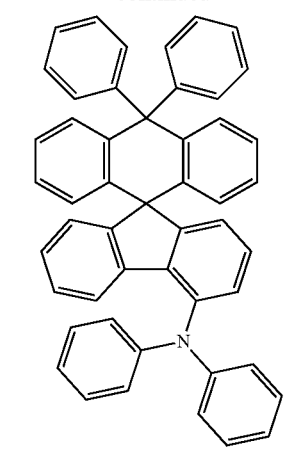
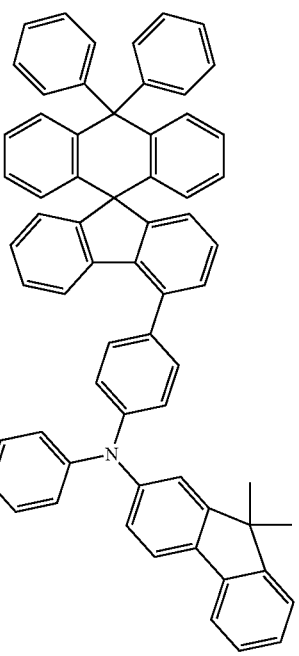
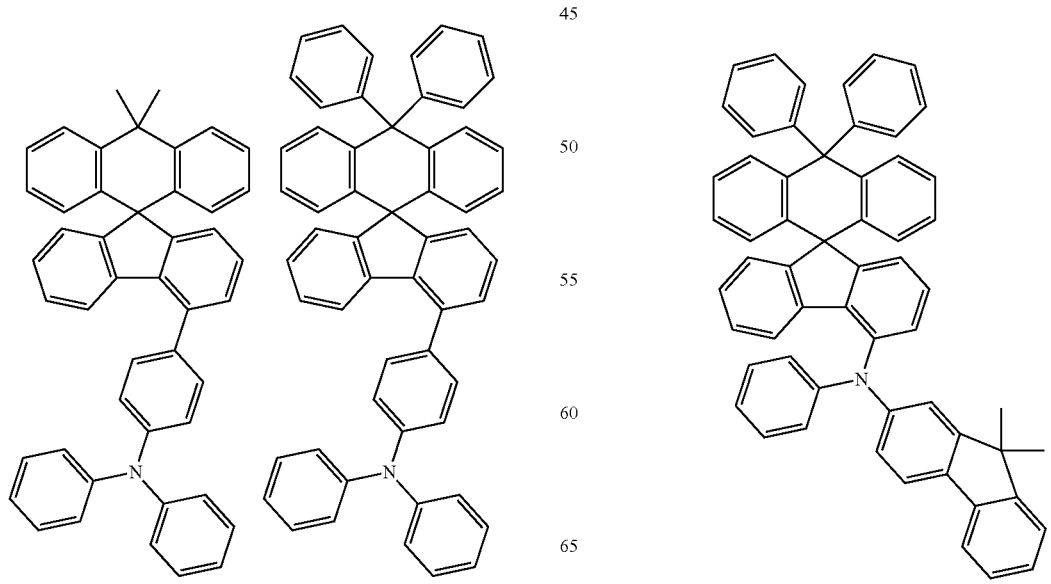

309
-continued
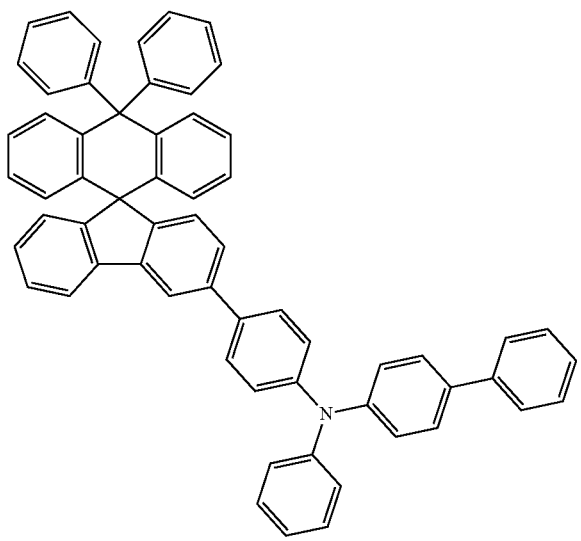
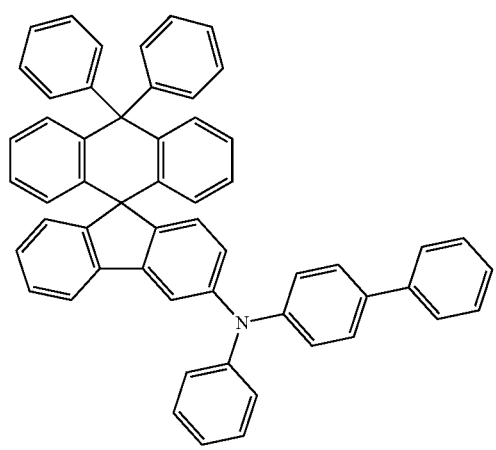
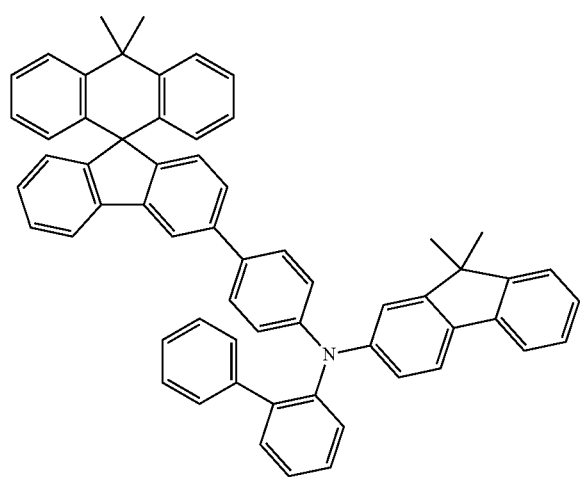
310
-continued
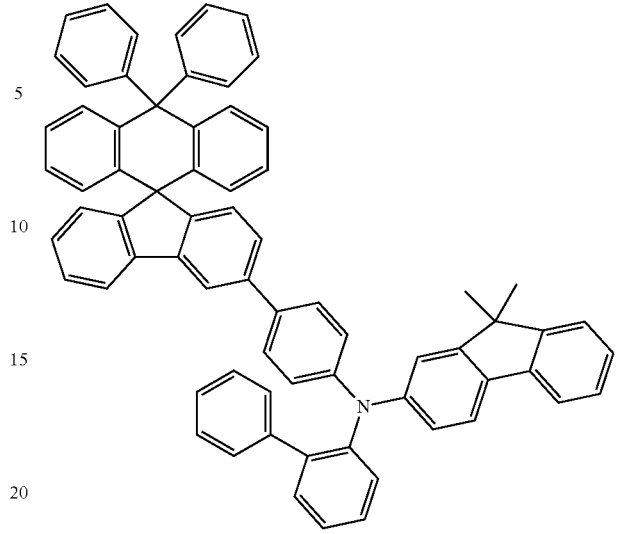
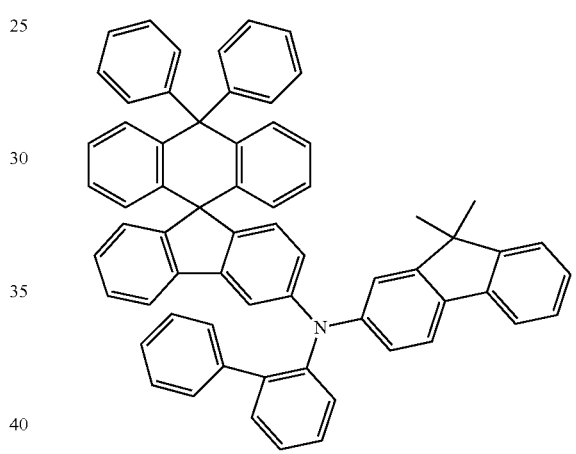
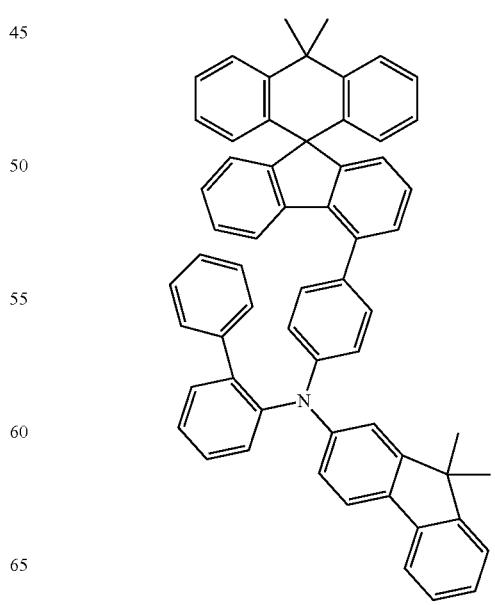

311
-continued
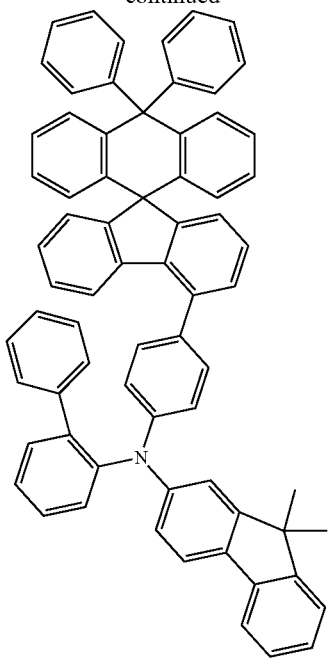
312
-continued
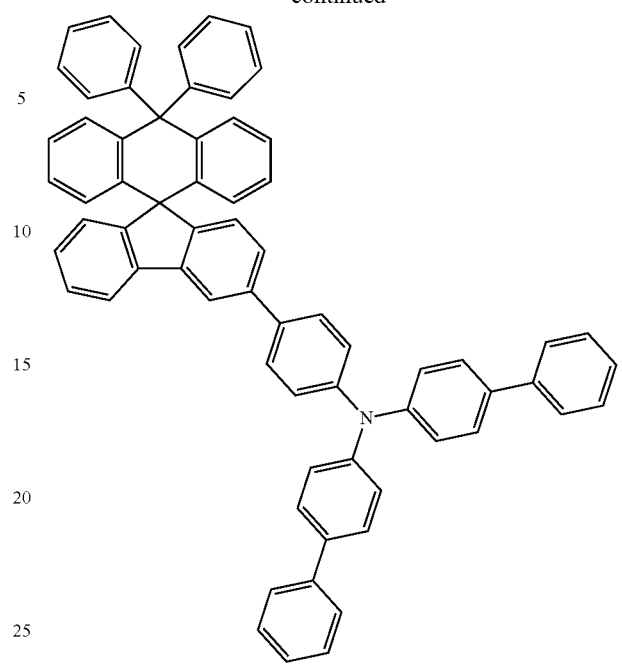
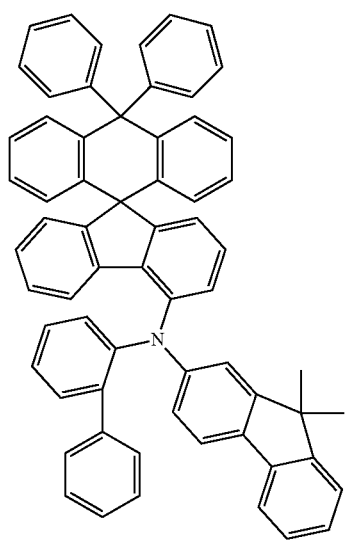 [SMILES: CC1(C)c2ccccc2-c2ccc(N(c3ccccc3-c3ccccc3)c3cccc4c3-c3ccccc3C43c4ccccc4C(c4ccccc4)(c4ccccc4)c4ccccc43)cc21]
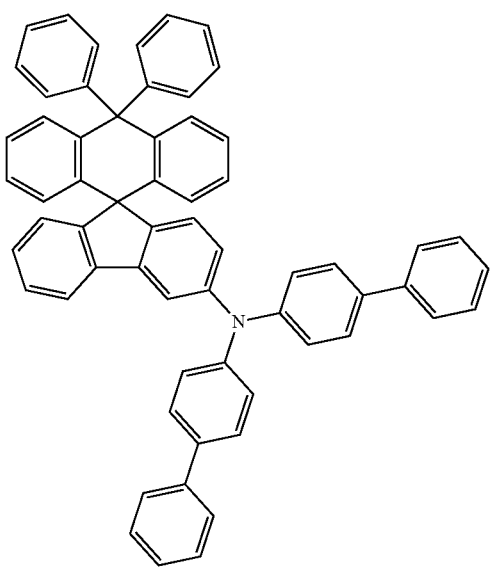

313
-continued
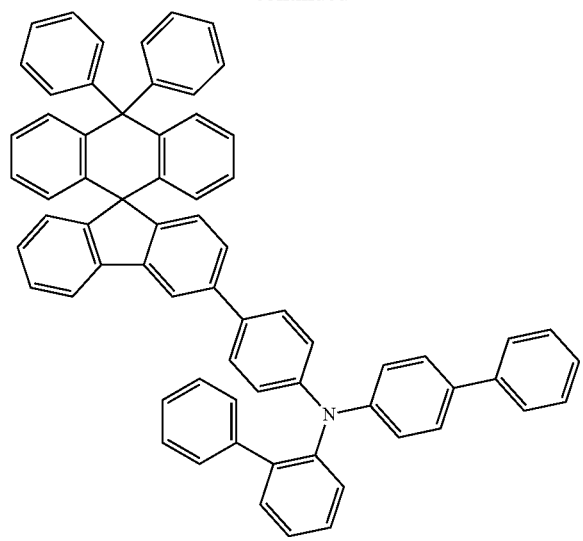
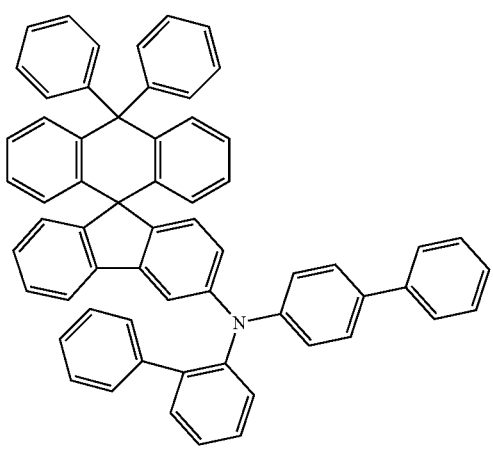
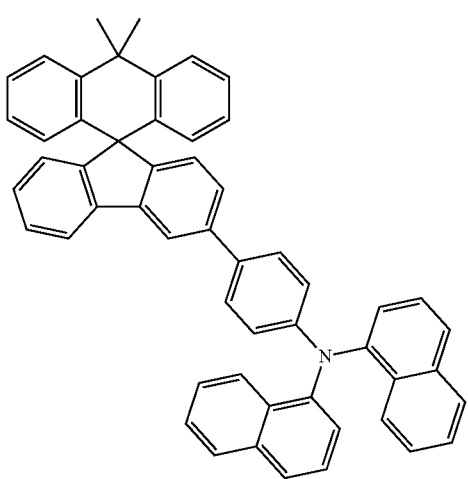 [SMILES: CC1(C)c2ccccc2C2(c3ccccc3-c3cc(-c4ccc(N(c5cccc6ccccc56)c5cccc6ccccc56)cc4)ccc32)c2ccccc21]
314
-continued
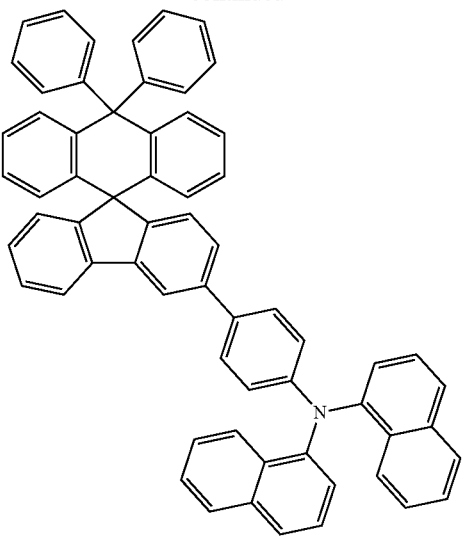
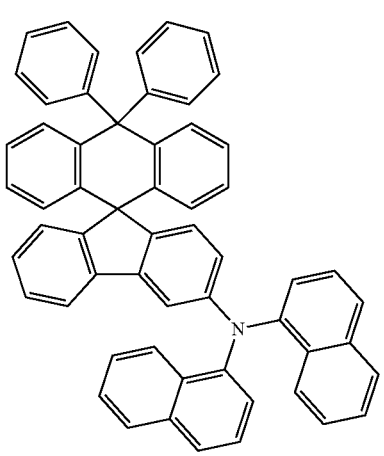
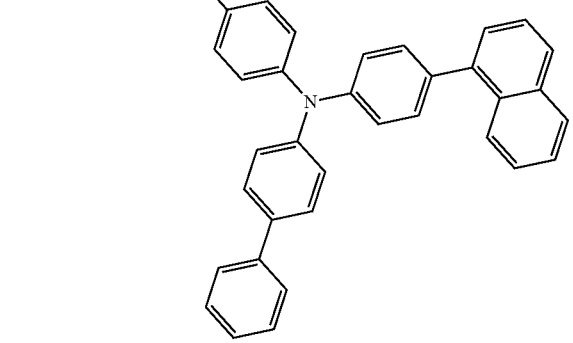

315
-continued
316
-continued
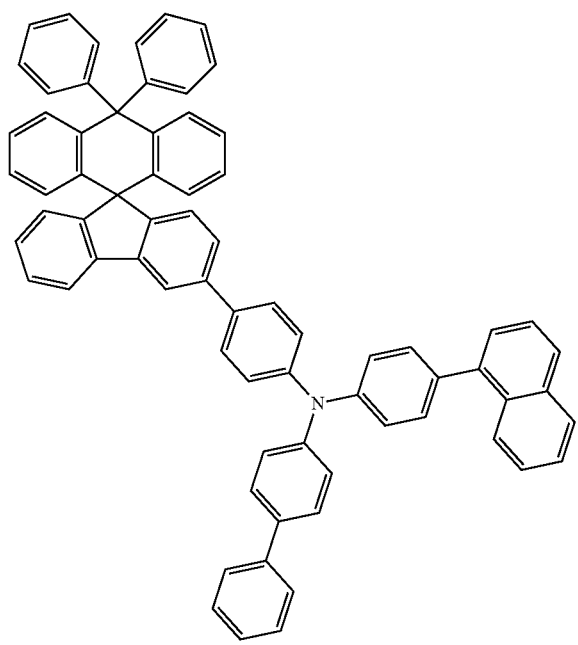
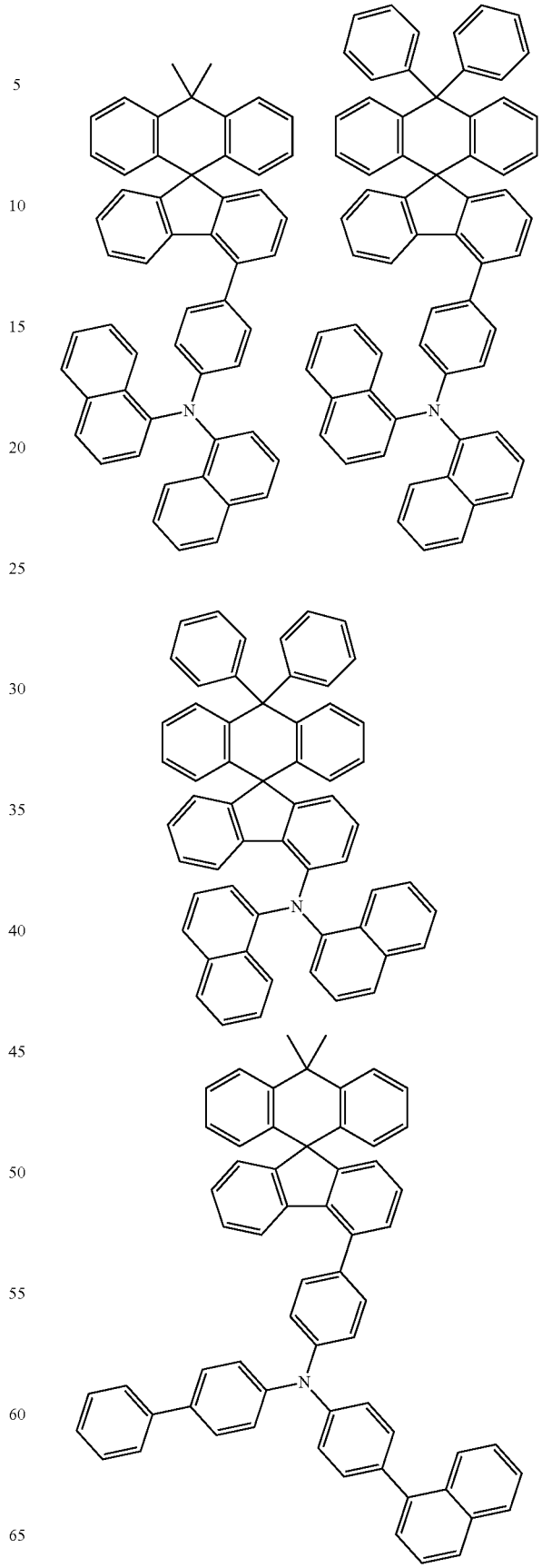

317
-continued
318
-continued
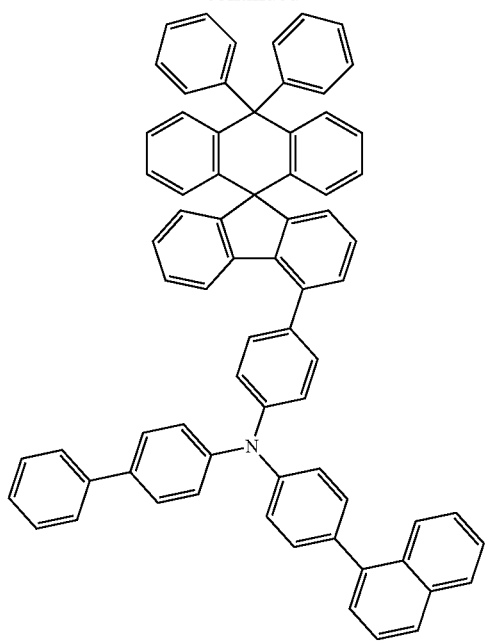
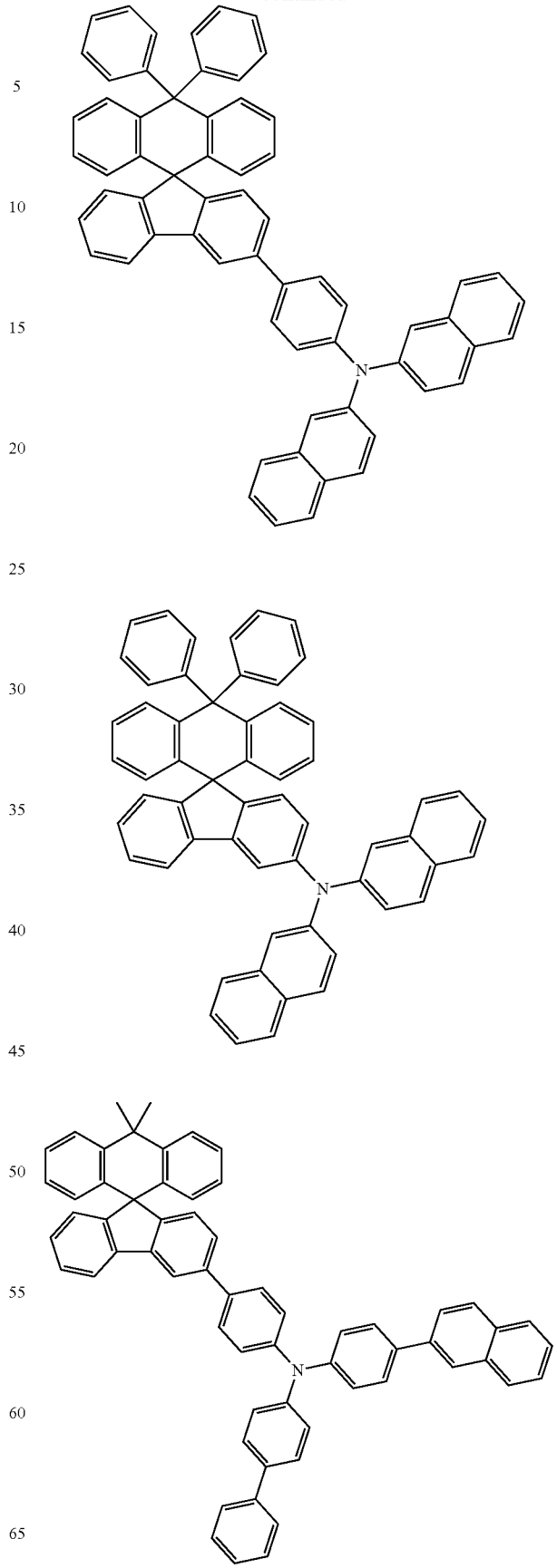

319
-continued
320
-continued
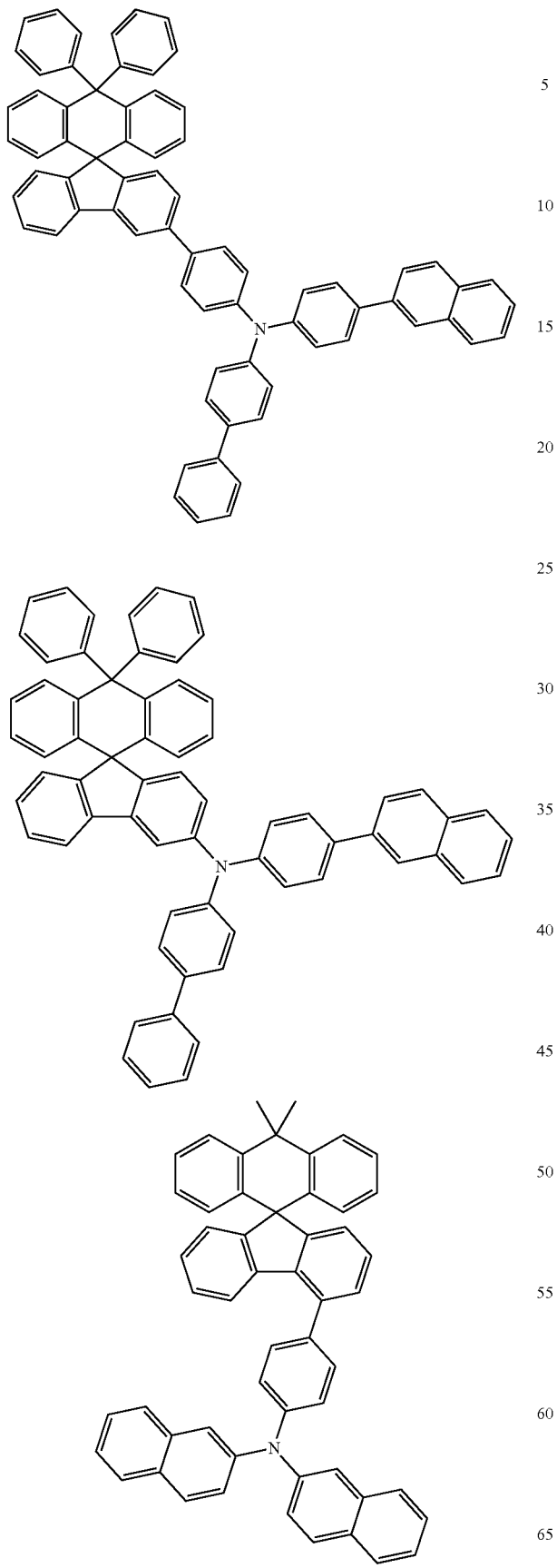
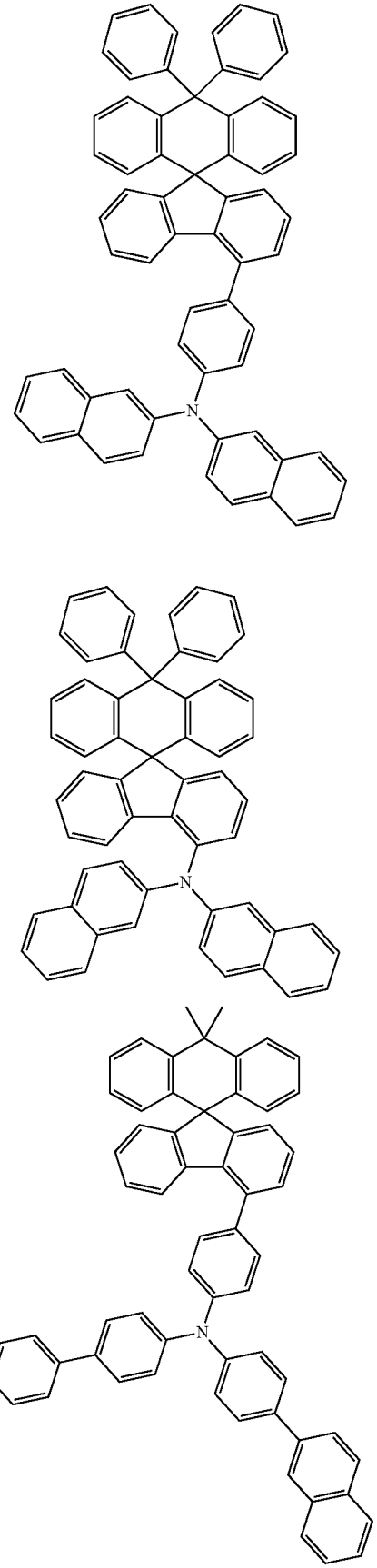

321
-continued
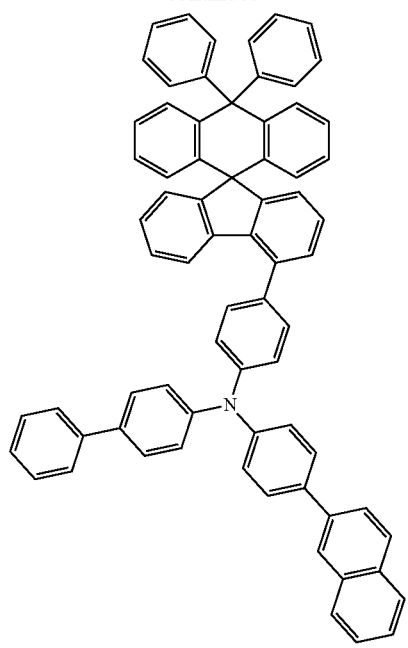
322
-continued
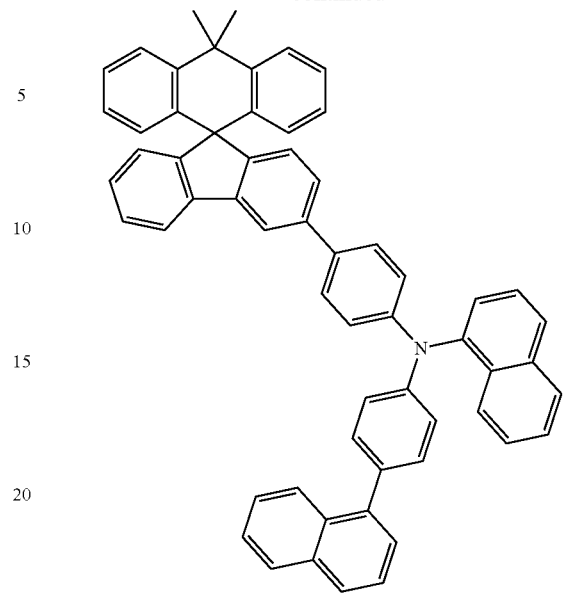
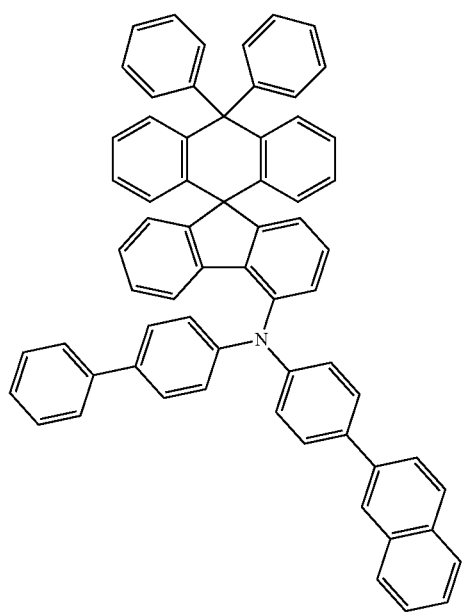
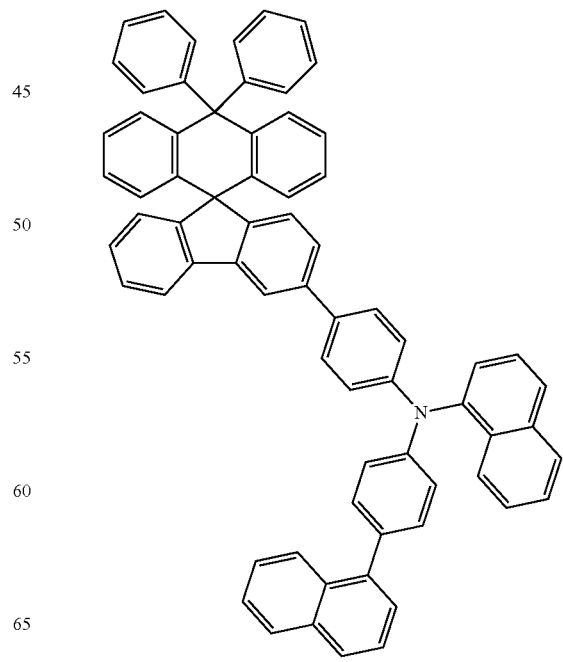

323
-continued
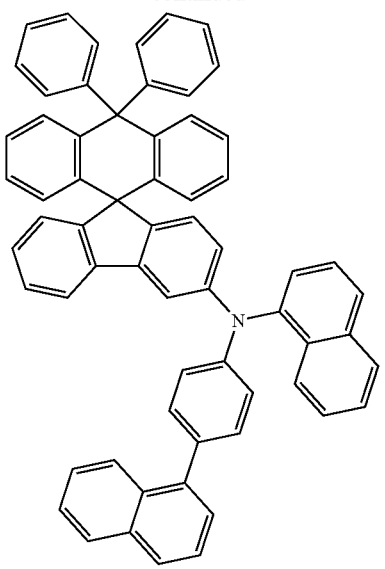
324
-continued
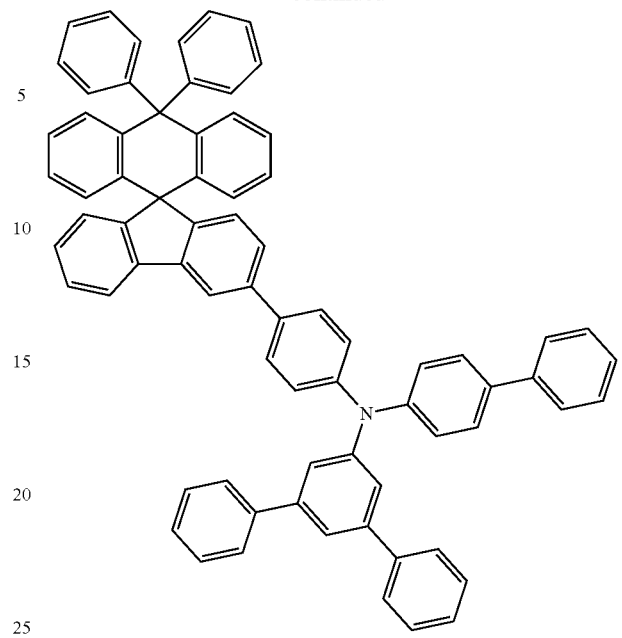
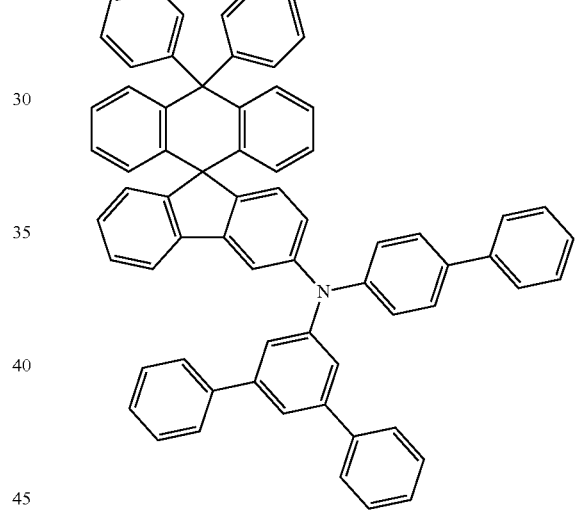
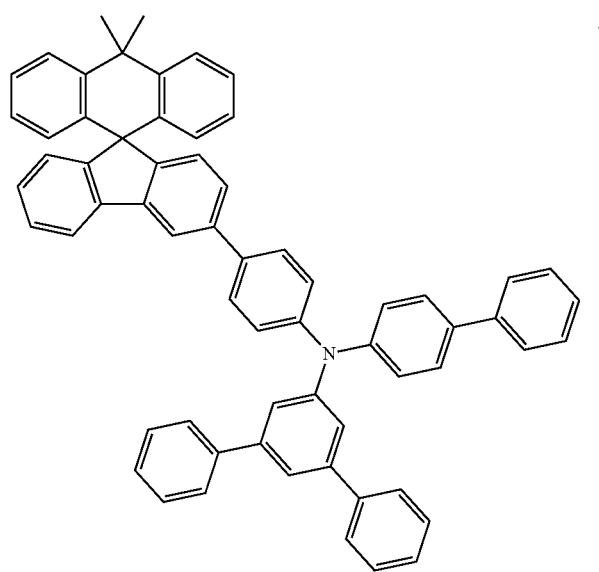
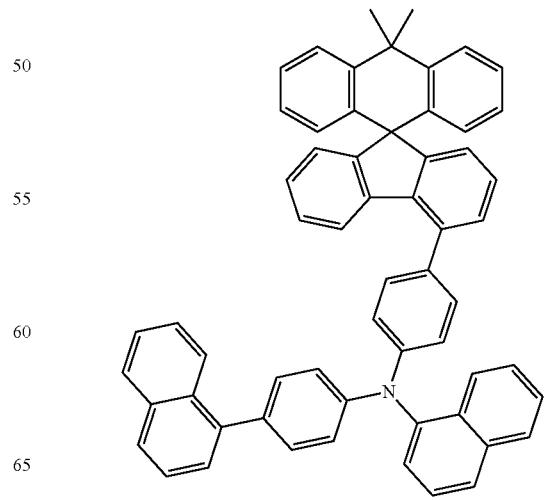

325
-continued
326
-continued
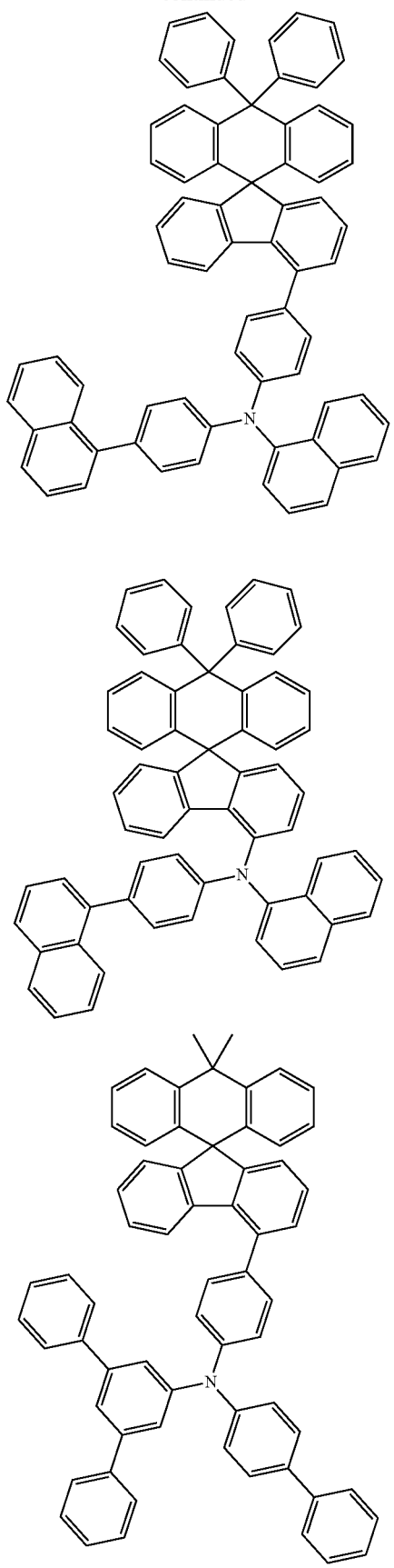

327
-continued
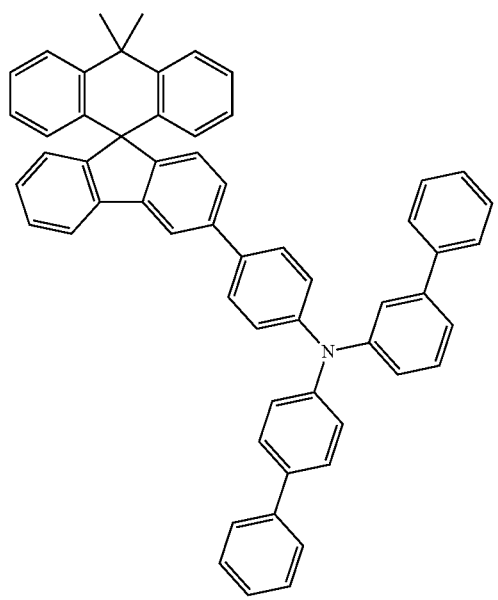
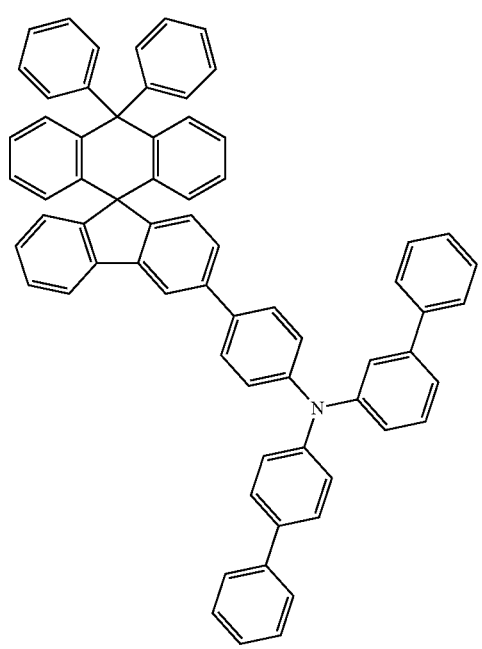
328
-continued
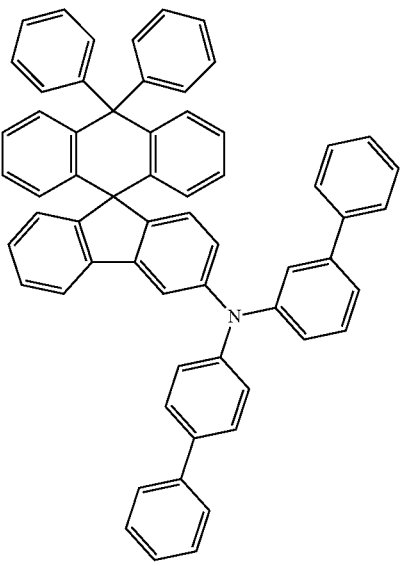
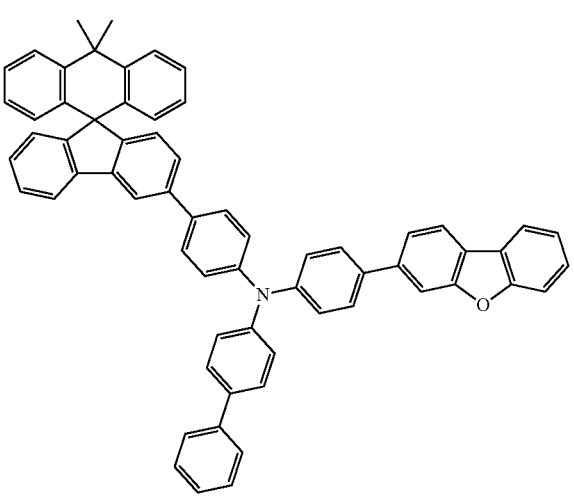
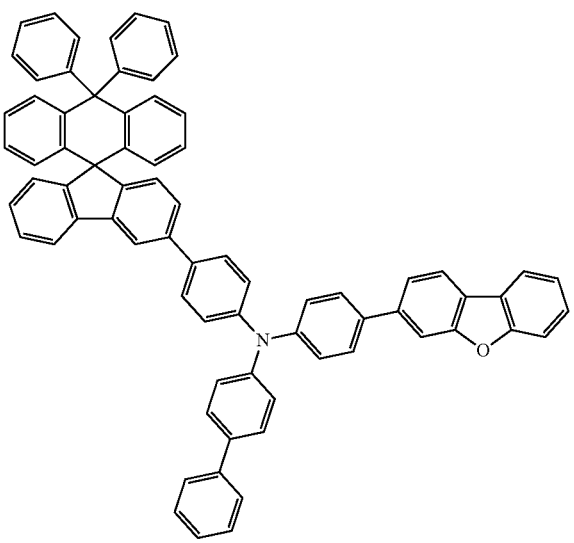

329
-continued
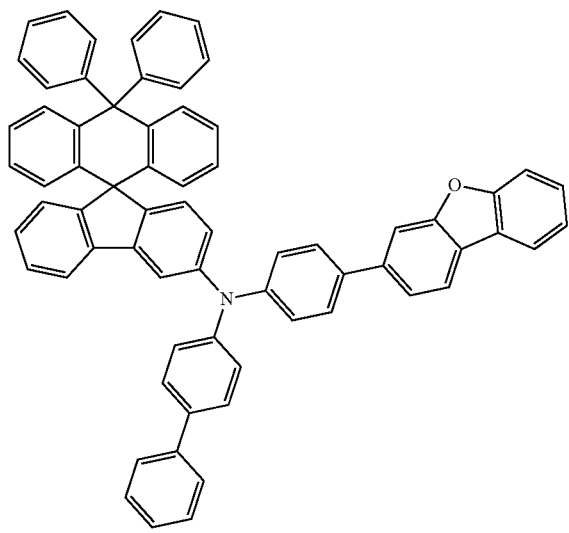 [SMILES: c1ccc(-c2ccc(N(c3ccc(-c4ccc5c(c4)oc4ccccc45)cc3)c3ccc4c(c3)-c3ccccc3C43c4ccccc4C(c4ccccc4)(c4ccccc4)c4ccccc43)cc2)cc1]
330
-continued
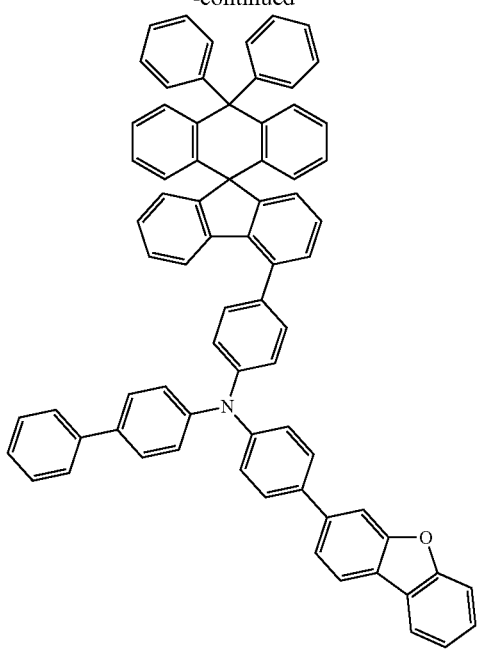
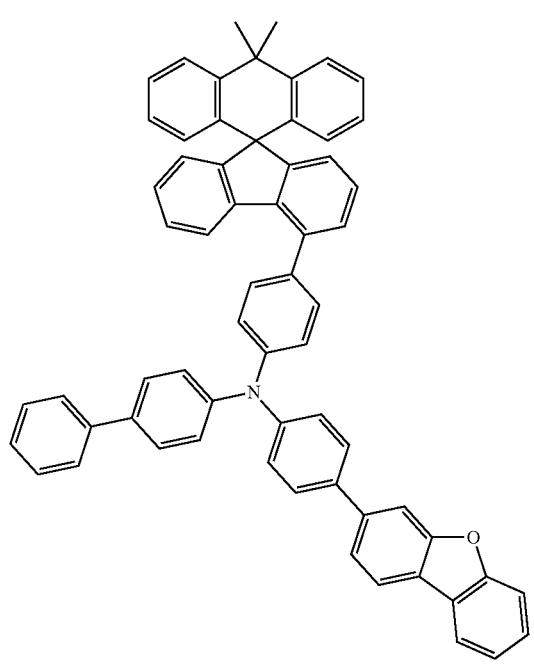
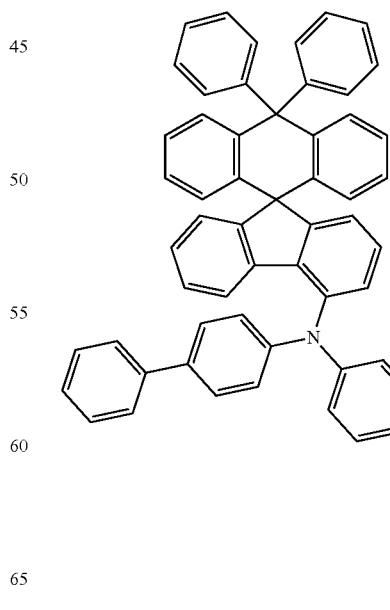

331
-continued
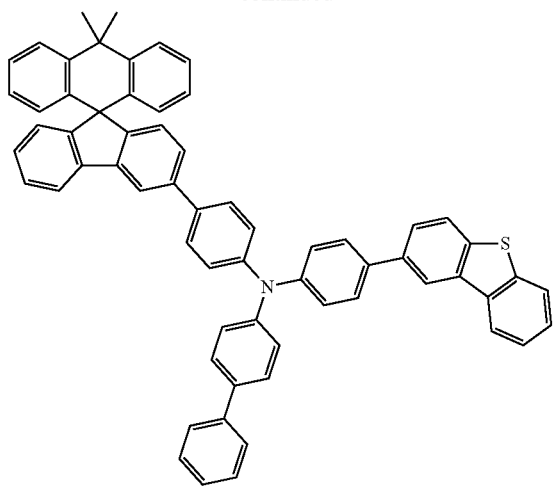
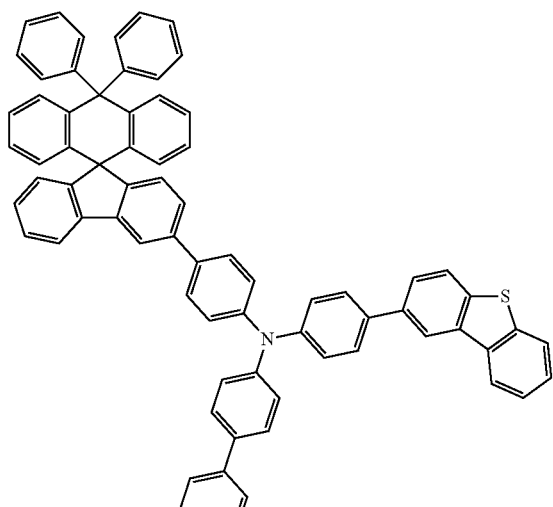
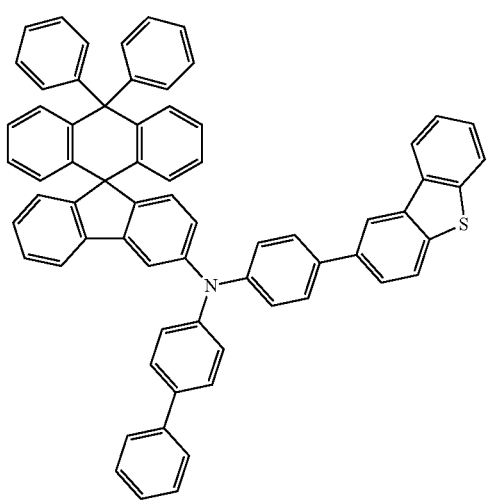
332
-continued
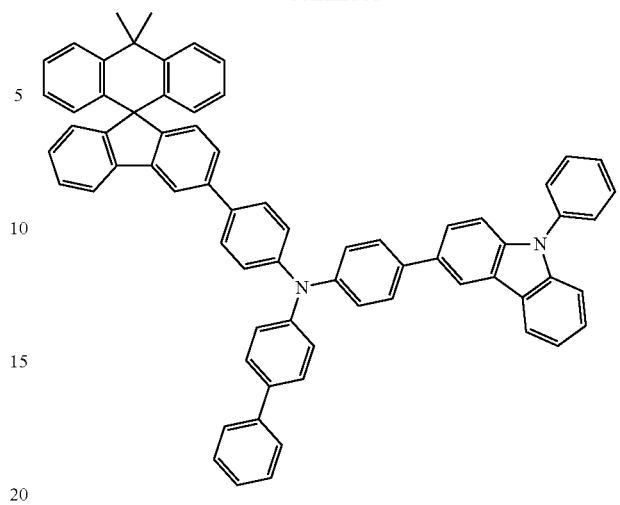
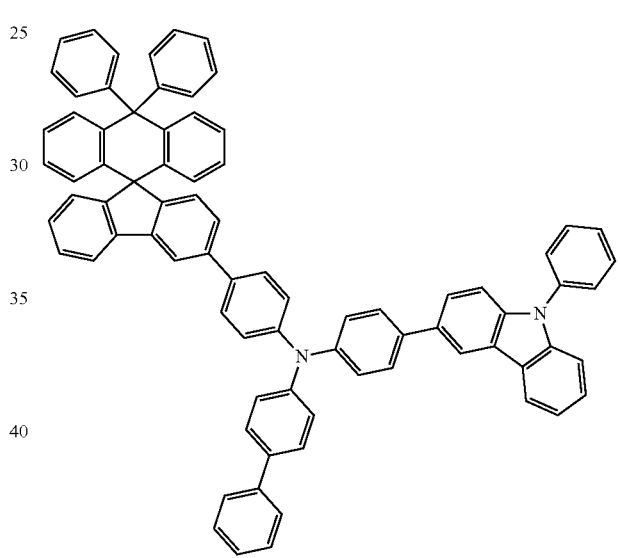
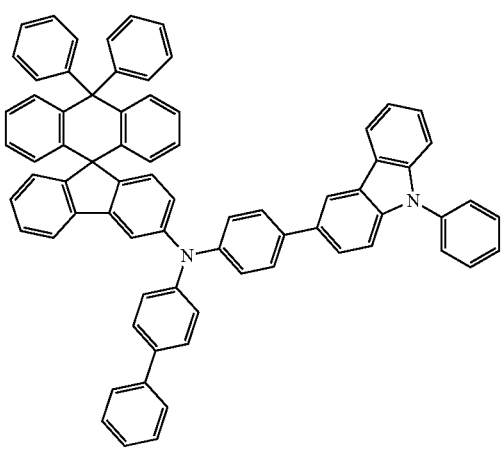

333
-continued
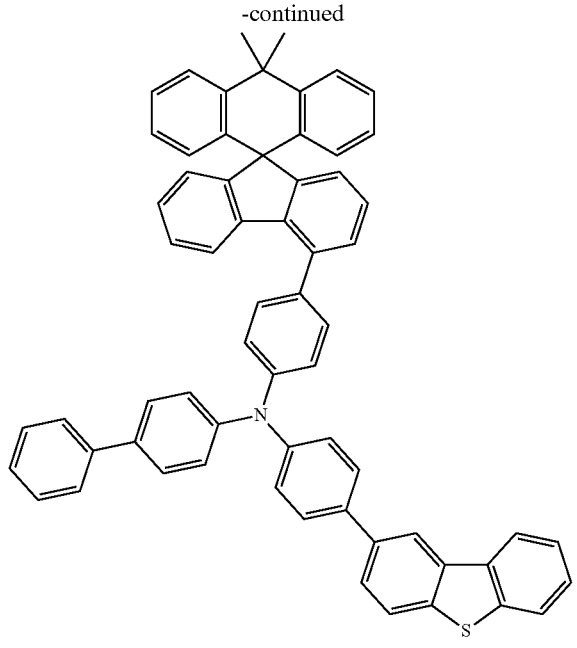
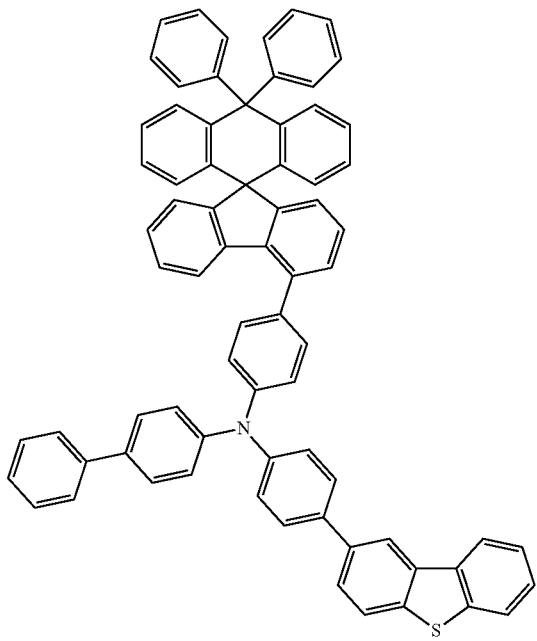
334
-continued
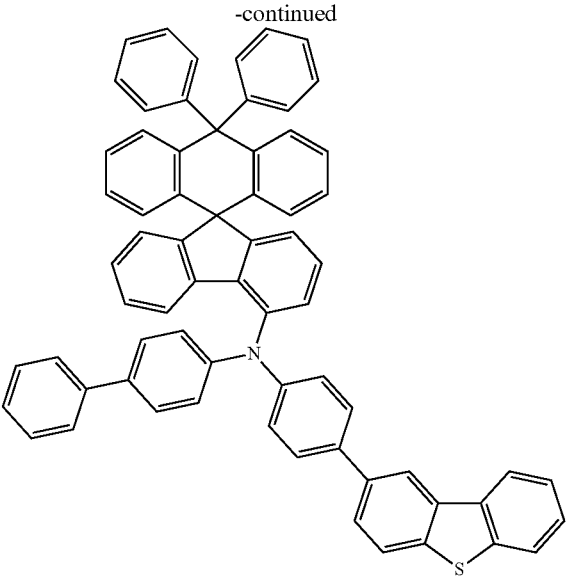
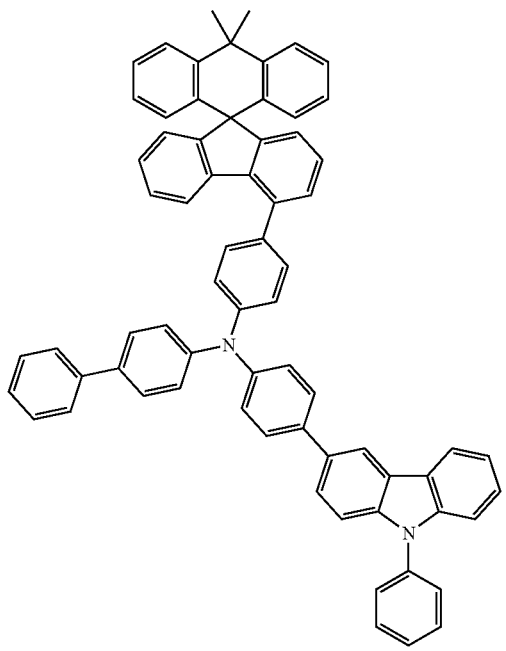

335
-continued
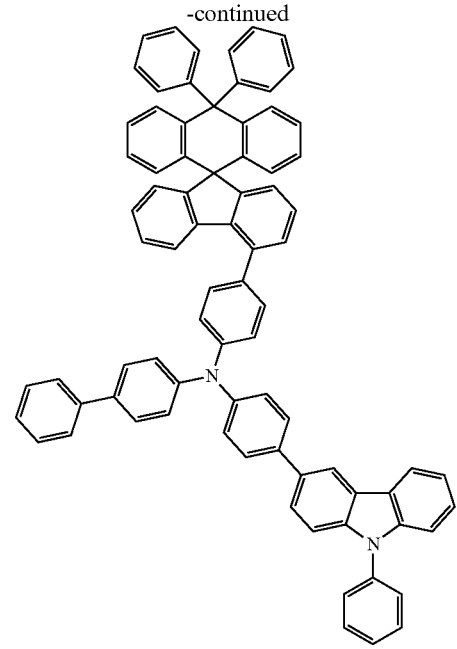
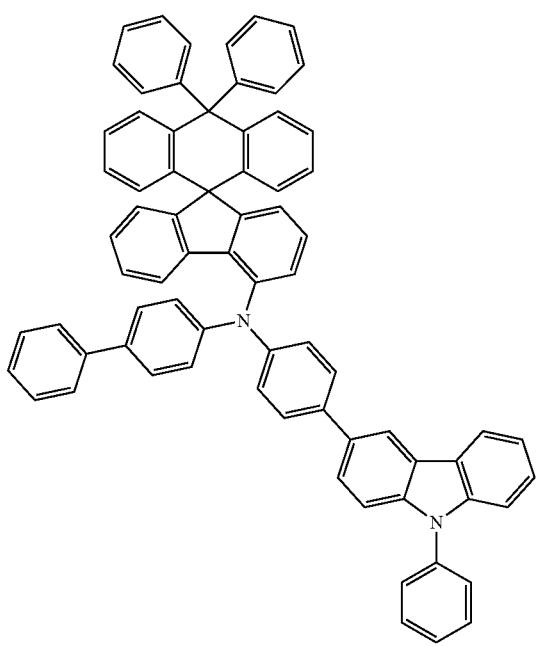
336
-continued
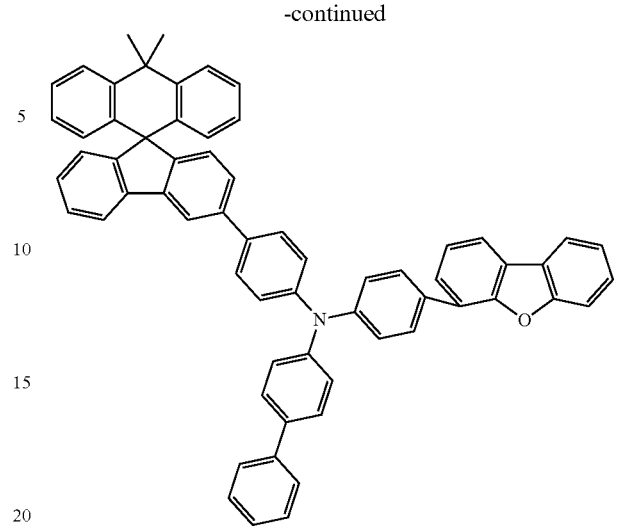
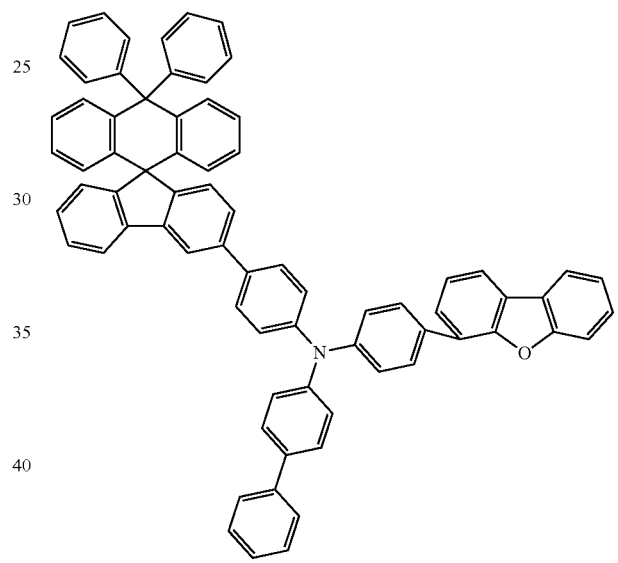
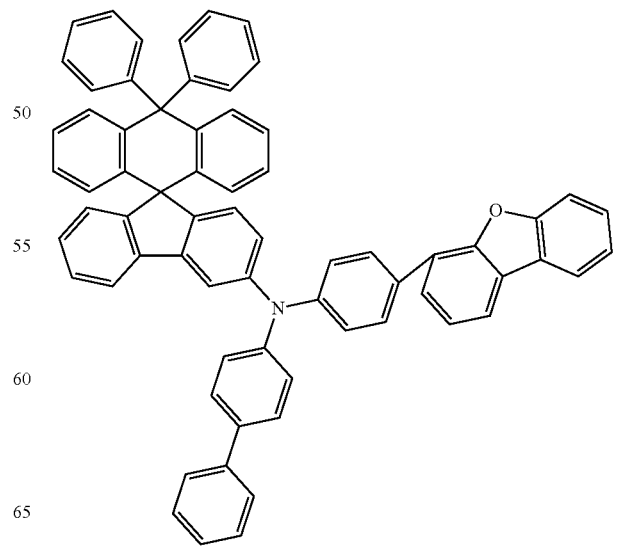

337
-continued
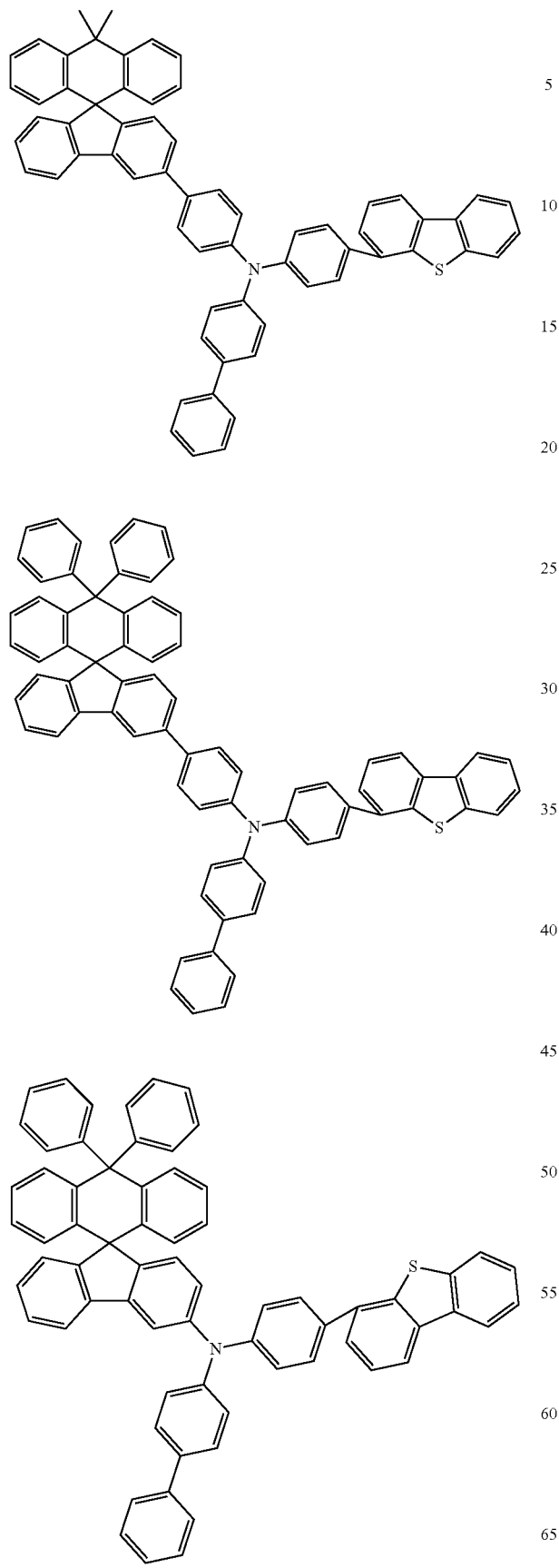
338
-continued
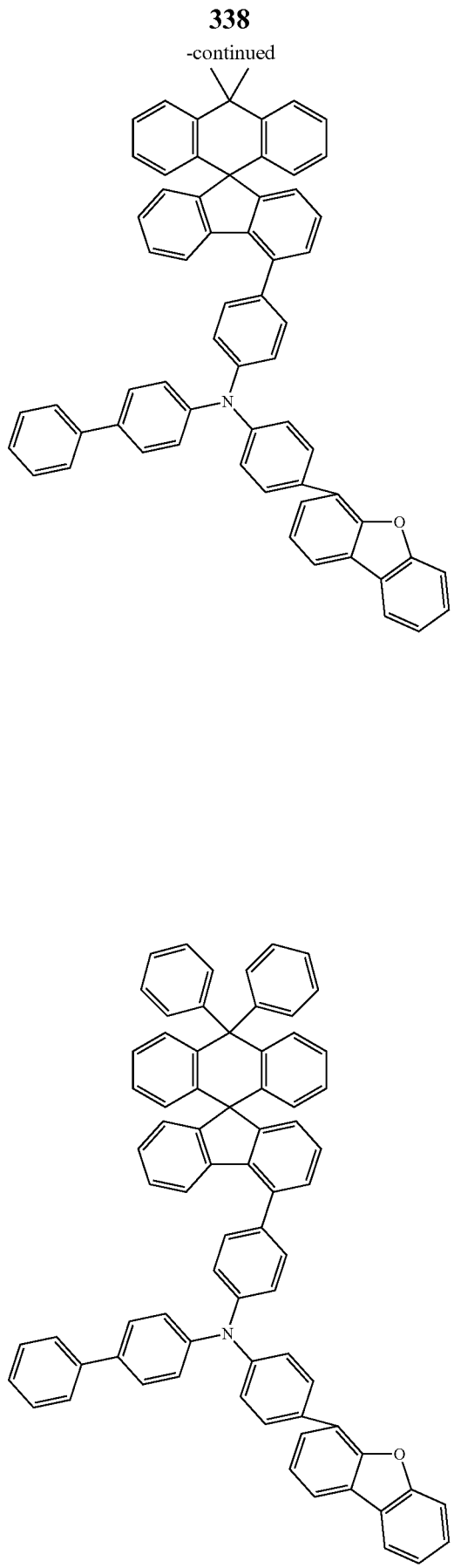

339
-continued

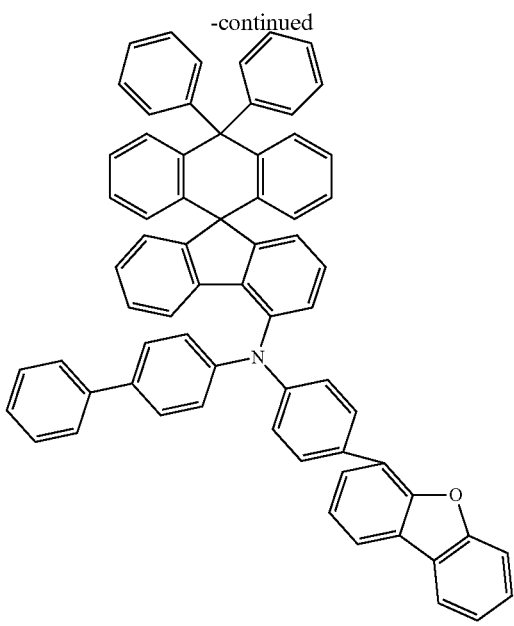

340
-continued

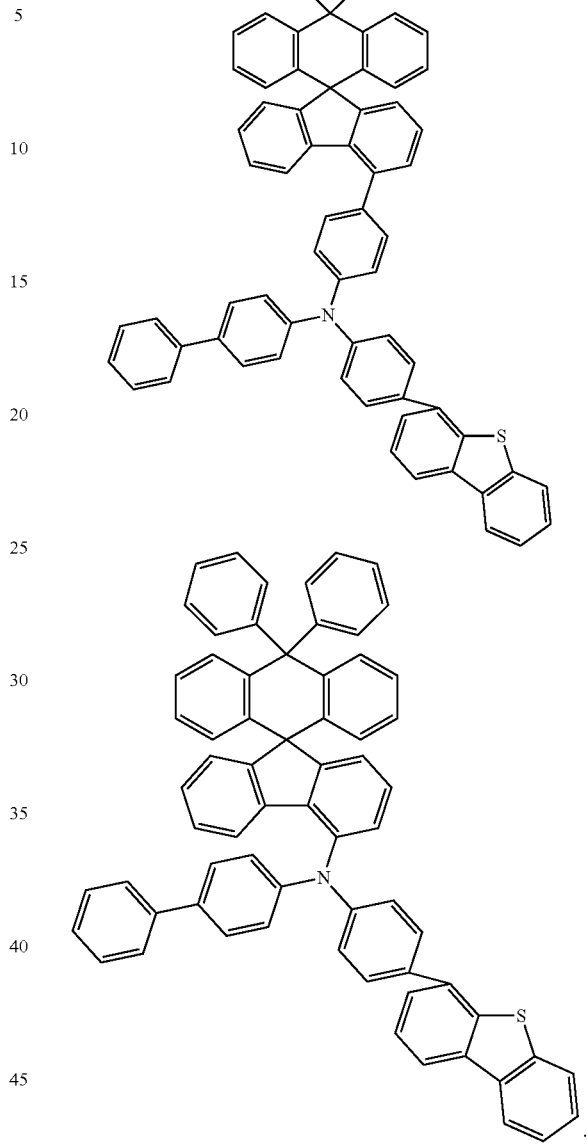

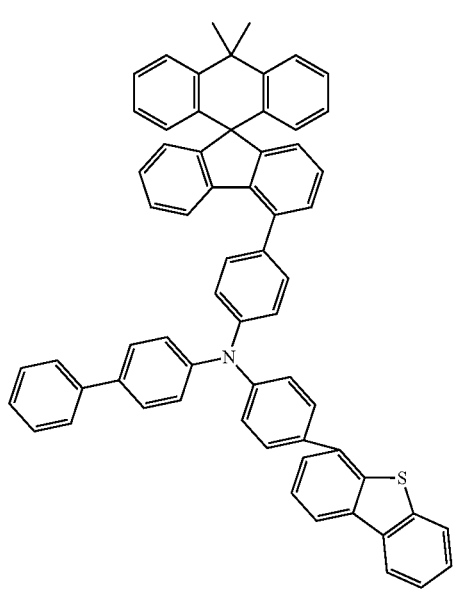

7. An organic light emitting device comprising a first electrode; a second electrode provided to face the first electrode; and at least one layer of organic material layers provided between the first electrode and the second electrode, wherein the at least one layer of the organic material layers comprises the compound according to claim 1.

8. The organic light emitting device of claim 7, wherein the at least one layer of the organic material layers comprises a hole injection layer, wherein the hole injection layer comprises the compound.

9. The organic light emitting device of claim 7, wherein the at least one layer of the organic material layers comprises a hole transport layer, wherein the hole transport layer comprises the compound.

10. The organic light emitting device of claim 7, wherein the at least one layer of the organic material layers comprises an electron blocking layer, wherein the electron blocking layer comprises the compound.

\* \* \* \* \*